(12) United States Patent
Lu et al.

(10) Patent No.: US 12,195,457 B2
(45) Date of Patent: Jan. 14, 2025

(54) AROMATIC RING DERIVATIVE AS IMMUNOREGULATION AND PREPARATION METHOD AND APPLICATION OF AROMATIC RING DERIVATIVE

(71) Applicants: SHANGHAI JEMINCARE PHARMACEUTICALS CO., LTD, Shanghai (CN); JIANGXI JEMINCARE GROUP CO., LTD, Jiangxi (CN)

(72) Inventors: Hongfu Lu, Shanghai (CN); Jianbiao Peng, Shanghai (CN); Weiqiang Xing, Shanghai (CN); Haibing Guo, Shanghai (CN)

(73) Assignees: SHANGHAI JEMINCARE PHARMACEUTICALS CO., LTD;, Shanghai (CN); JIANGXI JEMINCARE GROUP CO., LTD, Nanchang (CN)

( * ) Notice: Subject to any disclaimer, the term of this patent is extended or adjusted under 35 U.S.C. 154(b) by 785 days.

(21) Appl. No.: 17/299,515

(22) PCT Filed: Dec. 6, 2019

(86) PCT No.: PCT/CN2019/123485
§ 371 (c)(1),
(2) Date: Jun. 3, 2021

(87) PCT Pub. No.: WO2020/114475
PCT Pub. Date: Jun. 11, 2020

(65) Prior Publication Data
US 2022/0017513 A1  Jan. 20, 2022

(30) Foreign Application Priority Data

Dec. 6, 2018  (CN) .......................... 201811489503.4
Dec. 21, 2018 (CN) .......................... 201811572313.9
May 15, 2019  (CN) .......................... 201910403277.1
Nov. 22, 2019 (CN) .......................... 201911161764.8

(51) Int. Cl.
| | | |
|---|---|---|
| C07D 471/04 | (2006.01) |
| C07D 209/18 | (2006.01) |
| C07D 235/16 | (2006.01) |
| C07D 263/56 | (2006.01) |
| C07D 277/64 | (2006.01) |
| C07D 401/12 | (2006.01) |
| C07D 405/12 | (2006.01) |

(52) U.S. Cl.
CPC ......... C07D 471/04 (2013.01); C07D 209/18 (2013.01); C07D 235/16 (2013.01); C07D 263/56 (2013.01); C07D 277/64 (2013.01); C07D 401/12 (2013.01); C07D 405/12 (2013.01)

(58) Field of Classification Search
CPC .. C07D 471/04; C07D 209/18; C07D 235/16; C07D 263/56; C07D 277/64; C07D 401/12; C07D 405/12
USPC ........................................................ 514/300
See application file for complete search history.

(56) References Cited

U.S. PATENT DOCUMENTS

| | | |
|---|---|---|
| 5,190,968 A | 3/1993 | Gillard et al. |
| 5,308,850 A | 5/1994 | Gillard et al. |
| 2009/0324581 A1 | 12/2009 | Machinaga et al. |
| 2011/0160243 A1 | 6/2011 | Jones et al. |

FOREIGN PATENT DOCUMENTS

| | | |
|---|---|---|
| EP | 0994095 A1 | 12/1997 |
| EP | 2017263 A1 | 1/2009 |
| JP | H07215966 A | 8/1995 |
| JP | 2007262009 A | 10/2007 |
| JP | 2009263261 A | 11/2009 |
| JP | 2011529049 A | 12/2011 |
| JP | 2012501327 A | 1/2012 |
| WO | WO-9412179 A1 | 6/1994 |
| WO | WO-2007129745 A1 | 11/2007 |
| WO | WO-2010011316 A1 | 1/2010 |

OTHER PUBLICATIONS

JP-2007262009-A, 2007, IP.com, English Machine Translation (Year: 2007).*
Tsai et al., Published Jun. 18, 2016, Drugs, vol. 76, pp. 1067-1079 (Year: 2016).*

(Continued)

*Primary Examiner* — Bahar Craigo
*Assistant Examiner* — Jaret J Crews
(74) *Attorney, Agent, or Firm* — Harness, Dickey & Pierce, P.L.C.

(57) ABSTRACT

Relating to a compound represented by formula (I) and a pharmaceutically acceptable salt of the compound, and an application of the compound as an S1P1 agonist.

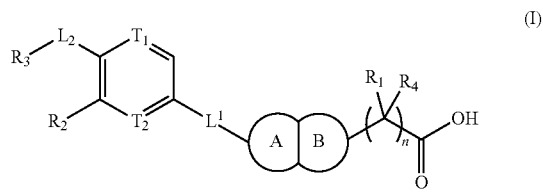

16 Claims, 4 Drawing Sheets

(56) References Cited

OTHER PUBLICATIONS

CDC, Picture of America Prevention, pp. 1-9, https://www.cdc.gov/pictureofamerica/pdfs/picture_of_america_prevention.pdf, accessed Dec. 8, 2023, first published Jul. 2, 2017 (Year: 2017).*

CDC, Picture of America Prevention, p. 1, https://www.cdc.gov/pictureofamerica/pdfs/picture_of_america_prevention.pdf, accessed Dec. 8, 2023, first published Jul. 2, 2017, Wayback Machine (Year: 2017).*

International Search Report and Written Opinion regarding International Application No. PCT/CN2019/123485, dated Mar. 12, 2020.

Jun. 28, 2022 Extended European Search Report issued in European Patent Application No. 19891955.7.

Sep. 9, 2023 Foreign Office Action (Japan) in Japanese Patent Application No. 2021554786.

Nov. 2, 2023 Foreign Office Action (Taiwan) in TW108144658A.

* cited by examiner

AROMATIC RING DERIVATIVE AS IMMUNOREGULATION AND PREPARATION METHOD AND APPLICATION OF AROMATIC RING DERIVATIVE

CROSS-REFERENCE TO RELATED APPLICATIONS

This application is a U.S. National Phase Application under 35 U.S.C. 371 of International Application No. PCT/CN2019/123485, filed on Dec. 6, 2019, which claims the benefit of Chinese Patent Application No. CN 201811489503.4, filed on Dec. 6, 2018, Chinese Patent Application No. CN 201811572313.9, filed on Dec. 21, 2018, Chinese Patent Application No. CN 201910403277.1, filed on May 15, 2019, and Chinese Patent Application No. CN 201911161764.8, filed on Nov. 22, 2019. The entire disclosures of the above applications are incorporated herein by reference.

FIELD OF THE INVENTION

The present disclosure relates to a compound of formula (I) and a pharmaceutically acceptable salt thereof, and a use of the compound as an S1P1 agonist.

BACKGROUND ARTS

Sphingosine-1-phosphate (S1P) is an amphoteric biological signal molecule belonging to lysophospholipid (LP). S1P can activate complex downstream signals by acting on five G protein-coupled receptor subtypes-sphingosine-1-phosphate receptor ($S1PR_{1-5}$), thereby regulating important physiological and biochemical functions. S1P binds to different S1P receptors to regulate different physiological functions and plays an important role in maintaining the health of the body and in the occurrence of diseases.

S1P1 receptor agonists interfere with lymphocyte trafficking, sequestering them in lymph nodes and other secondary lymphoid tissues. This leads to a decrease in peripheral circulating lymphocytes, and the clinical value of lymphocyte isolation is to exclude them from the visual field of inflammation and/or autoimmune response in surrounding tissues. This isolation of lymphocytes (e.g., in lymph nodes) is considered to be the result of the following simultaneous actions: agonist-driven functional antagonism of S1P1 receptors on T cells (thus reducing the ability of S1P to mobilize T cells out of lymph nodes) and continuous agonism of S1P1 receptors on lymph node endothelium (thus enhancing barrier function against lymphocyte migration). Therefore, S1P1 receptor agonists can reduce human autoimmune ability by preventing lymphocyte transportation, so they can be used as immunosuppressants to treat various autoimmune diseases.

Among them, the S1P1 agonist Fingolimod (FTY720) was approved by the FDA for the treatment of Multiple Scleorosis (MS), which had developed a new therapeutic field for the treatment of immune diseases. Although FTY720 has clinical efficacy, it is a non-selective S1P receptor agonist. The combination of FTY720 with S1P3 in vivo often leads to a series of important side effects, such as bradycardia, which greatly limits its use in the treatment of immune diseases. Therefore, the discovery of second-generation of highly selective S1P1 agonists with better efficacy, less side effects and wider range of uses in the treatment of immune diseases has become one of the hot topics in drug research.

In addition to improving target selectivity, shortening the half-life of S1P1 receptor agonist in vivo is also the goal of discovering the second-generation S1P agonist. As an immunosuppressive drug, a longer half-life will lead to the continuous inhibition of lymphocyte transportation and the decrease of the number of peripheral blood lymphocytes, thus will lead to low immune function and increase the risk of viral infection. In the case of infection, it is often necessary to stop drugs to restore the number of peripheral blood lymphocytes to normal levels as soon as possible, so that the human immune function can be quickly restored. Among them, the half-life of S1P1 receptor agonist such as FTY720 in human body is as long as 6-9 days, so even if the drug is stopped to be taken, it will take a long time for the lymphocyte count to return to normal.

Therefore, there is still a need to develop novel S1P1 agonists with S1P1 receptor selectivity and short half-life to overcome the shortcomings of existing therapies.

CONTENT OF THE INVENTION

The present disclosure provides a compound of formula (I) or a pharmaceutically acceptable salt thereof,

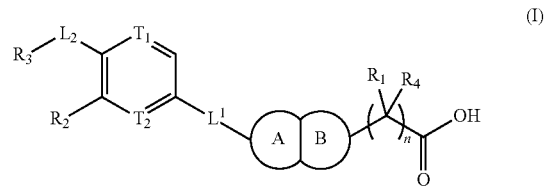

wherein, n is selected from 1, 2 and 3;

$R_1$ is independently selected from H, F, Cl, Br, OH, $NH_2$, CN, $CH_3$, $CH_2CH_3$ and $CF_3$;

$R_4$ is independently selected from H, F, Cl, Br, OH, $NH_2$, CN, $CH_3$, $CH_2CH_3$ and $CF_3$;

or, $R_1$ and $R_4$ are connected together to form a $C_{3-6}$ cycloalkyl; $R_2$ is selected from H, halogen, OH, $NH_2$, CN and $C_{1-3}$ alkyl, the $C_{1-3}$ alkyl is optionally substituted by one, two or three R;

$R_3$ is selected from $C_{3-7}$ cycloalkyl, $C_{3-7}$ cycloalkenyl, $C_{2-6}$ alkenyl and 3-6 membered heterocycloalkyl, the $C_{3-7}$ cycloalkyl, $C_{3-7}$ cycloalkenyl, $C_{2-6}$ alkenyl or 3-6 membered heterocycloalkyl is optionally substituted by one, two or three R;

ring A is selected from phenyl and 6 membered heteroaryl, the phenyl and 6 membered heteroaryl are optionally substituted by one, two or three $R_a$;

ring B is selected from 5 membered heteroaryl, the 5 membered heteroaryl is optionally substituted by $R_b$;

$R_a$ is independently selected from H, halogen, OH, $NH_2$, CN and $C_{1-3}$ alkyl, the $C_{1-3}$ alkyl is optionally substituted by one, two or three R;

$R_b$ is selected from H, halogen, OH, $NH_2$, CN and $C_{1-3}$ alkyl, the $C_{1-3}$ alkyl is optionally substituted by one, two or three R;

R is independently selected from H, F, Cl, Br, OH, $NH_2$, CN, $C_{1-3}$ alkyl and $CF_3$;

$T_1$ is selected from N and CH;

$T_2$ is selected from N and CH;

$L_1$ is selected from

 ;

L₂ is selected from single bond, O and S;

the 5 membered heteroaryl, 6 membered heteroaryl and 3-6 membered heterocycloalkyl contain one, two or three heteroatoms or heteroatom groups independently selected from O, NH, S and N.

In some embodiments of the present disclosure, the R is selected from H, F, Cl, Br, OH, $NH_2$, CN, $CH_3$, $CH_2CH_3$ and $CF_3$, and other variables are as defined in the present disclosure.

In some embodiments of the present disclosure, the $R_2$ is selected from H, F, Cl, Br, OH, $NH_2$, CN, $CH_3$ and $CH_2CH_3$, the $CH_3$ or $CH_2CH_3$ is optionally substituted by one, two or three R, and other variables are as defined in the present disclosure.

In some embodiments of the present disclosure, the $R_2$ is selected from H, F, Cl, Br, OH, $NH_2$, CN, $CH_3$, $CH_2CH_3$ and $CF_3$, and other variables are as defined in the present disclosure.

In some embodiments of the present disclosure, the $R_3$ is selected from $C_{3-6}$ cycloalkyl, $C_{3-6}$ cycloalkenyl, $C_{2-3}$ alkenyl and 3-6 membered heterocycloalkyl, the $C_{3-6}$ cycloalkyl, $C_{3-6}$ cycloalkenyl, $C_{2-3}$ alkenyl or 3-6 membered heterocycloalkyl is optionally substituted by one, two or three R, and other variables are as defined in the present disclosure.

In some embodiments of the present disclosure, the $R_3$ is selected from

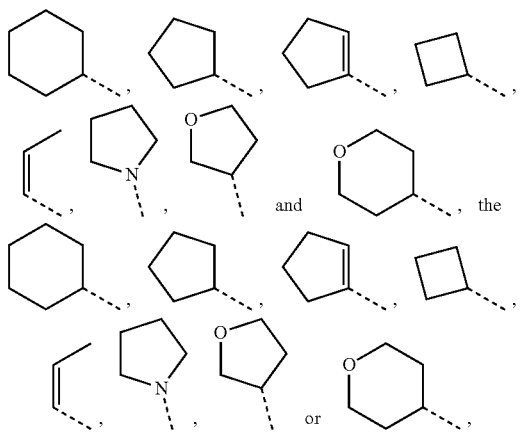

or which are optionally substituted by one, two or three R, and other variables are as defined in the present disclosure.

In some embodiments of the present disclosure, the $R_3$ is selected from

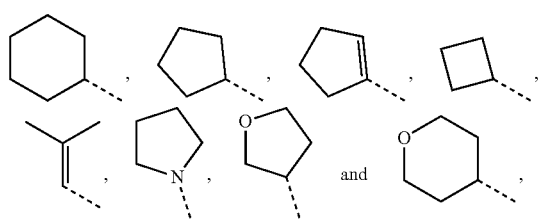

and other variables are as defined in the present disclosure.

In some embodiments of the present disclosure, the moiety

is selected from

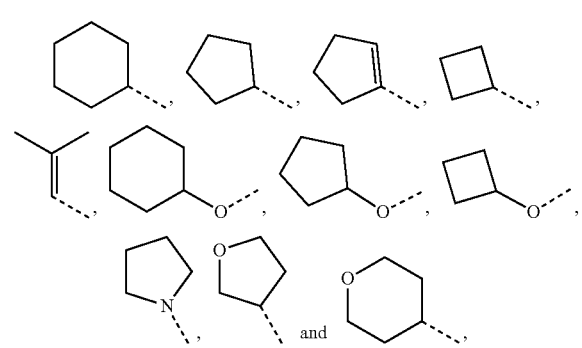

and other variables are as defined in the present disclosure.

In some embodiments of the present disclosure, the $R_a$ is selected from H, F, Cl, Br, OH, $NH_2$, CN, $CH_3$ and $CH_2CH_3$, the $CH_3$ or $CH_2CH_3$ is optionally substituted by one, two or three of R, and other variables are as defined in the present disclosure.

In some embodiments of the present disclosure, the $R_a$ is selected from H, F, Cl, Br, OH, $NH_2$, CN, $CH_3$, $CH_2CH_3$ and $CF_3$, and other variables are as defined in the present disclosure.

In some embodiments of the present disclosure, the $R_b$ is selected from H, F, Cl, Br, OH, $NH_2$, CN, $CH_3$ and $CH_2CH_3$, the $CH_3$ or $CH_2CH_3$ is optionally substituted by one, two or three R, and other variables are as defined in the present disclosure.

In some embodiments of the present disclosure, the $R_b$ is selected from H, F, Cl, Br, OH, $NH_2$, CN, $CH_3$, $CH_2CH_3$ and $CF_3$, and other variables are as defined in the present disclosure.

In some embodiments of the present disclosure, the ring A is selected from phenyl and pyridyl, the phenyl or pyridyl is optionally substituted by one, two or three $R_a$, and other variables are as defined in the present disclosure.

In some embodiments of the present disclosure, the ring B is selected from pyrrolyl, imidazolyl, pyrazolyl, thiazolyl and oxazolyl, the pyrrolyl, imidazolyl, pyrazolyl, thiazolyl or oxazolyl is optionally substituted by $R_b$, and other variables are as defined in the present disclosure.

In some embodiments of the present disclosure, the moiety

is selected from
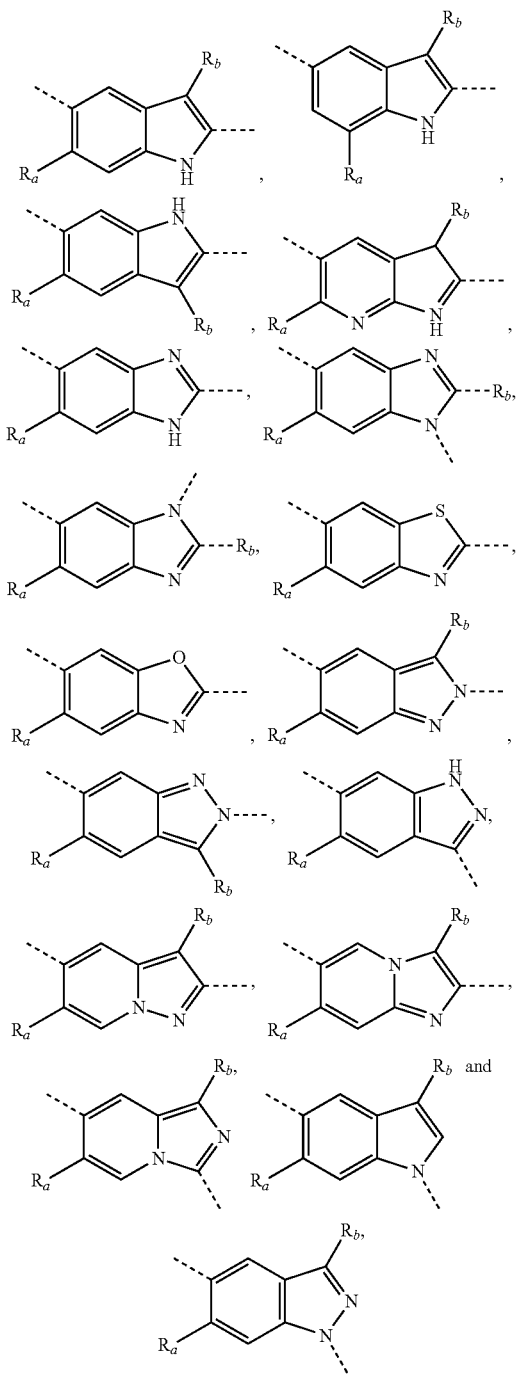
and other variables are as defined in the present disclosure.
In some embodiments of the present disclosure, the moiety
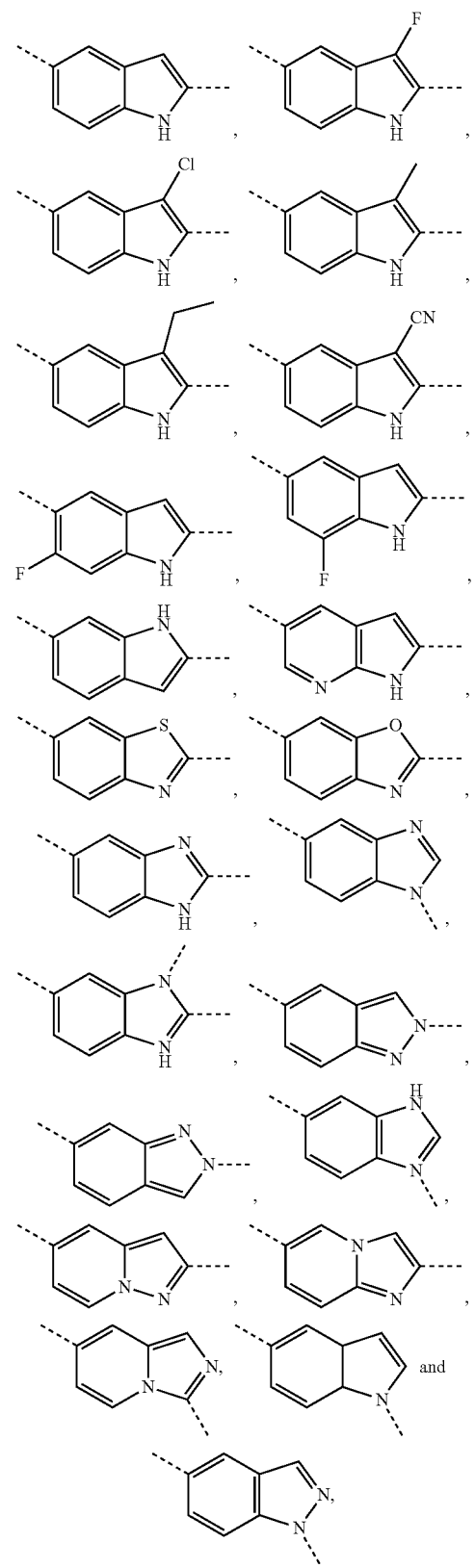
is selected from
and other variables are as defined in the present disclosure.

In some embodiments of the present disclosure, the moiety

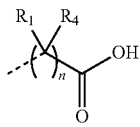

is selected from

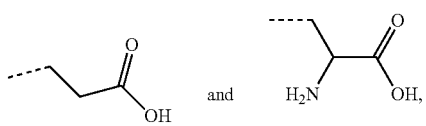

and other variables are as defined in the present disclosure.

In some embodiments of the present disclosure, the compound or the pharmaceutically acceptable salt thereof is selected from, (I-1)

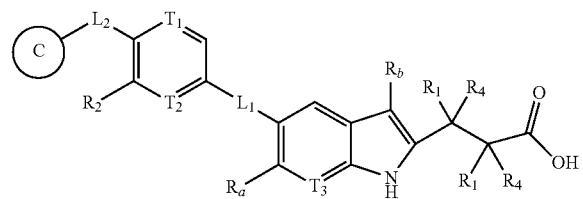

wherein,
T$_1$, T$_2$, L$_1$, L$_2$, R$_1$, R$_2$, R$_4$, R$_a$, R$_b$ are as defined above;
T$_3$ is selected from N and C(R$_a$);
ring C is selected from C$_{3-6}$ cycloalkyl, C$_{3-6}$ cycloalkenyl and 3-6 membered heterocycloalkyl, the C$_{3-6}$ cycloalkyl, C$_{3-6}$ cycloalkenyl or 3-6 membered heterocycloalkyl is optionally substituted by one, two or three R.

In some embodiments of the present disclosure, the ring C is selected from

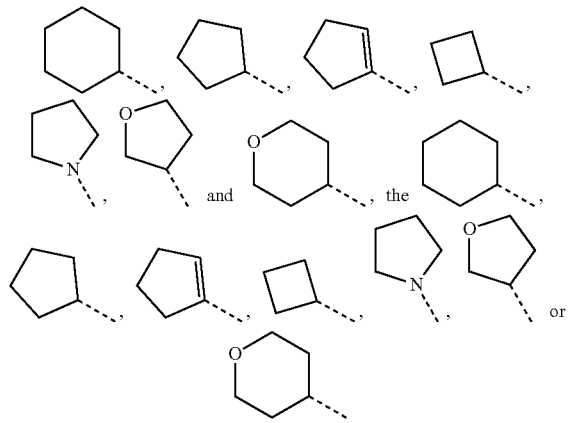

is optionally substituted by one, two or three R.

In some embodiments of the present disclosure, the ring C is selected from

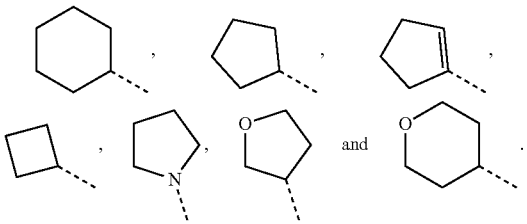

In some embodiments of the present disclosure, the compound or the pharmaceutically acceptable salt thereof is selected from (I-1A)

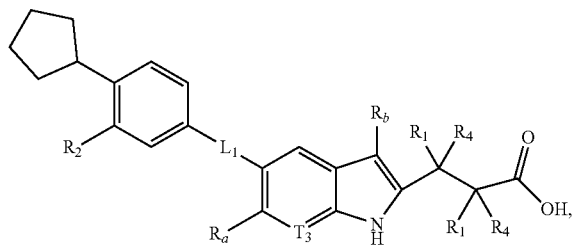

wherein, T$_3$, R$_1$, R$_2$, R$_4$, R$_a$, R$_b$ are as defined above.

The present disclosure provides a compound of the following formula or a pharmaceutically acceptable salt thereof,

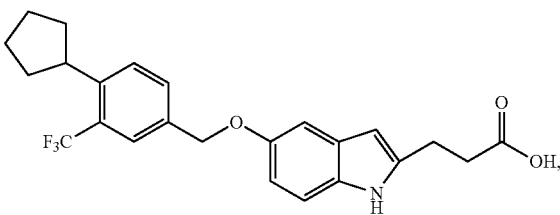

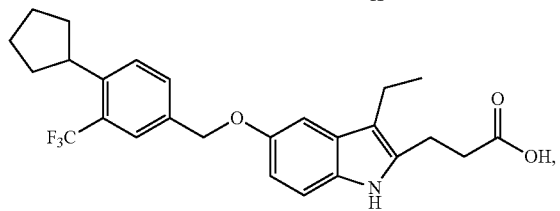

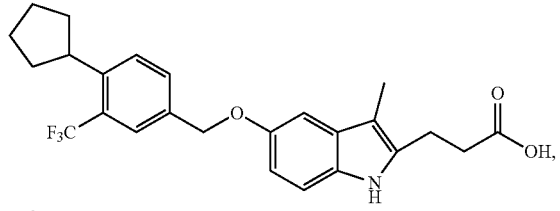

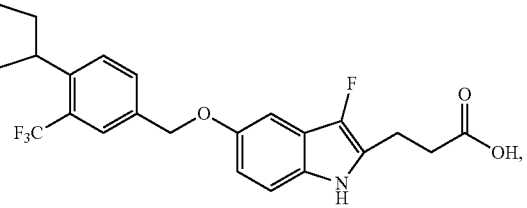

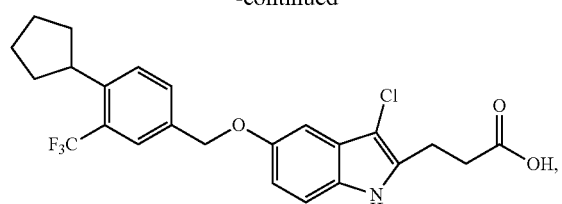
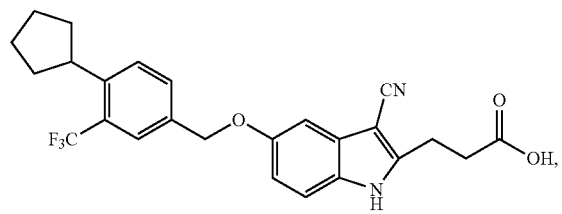
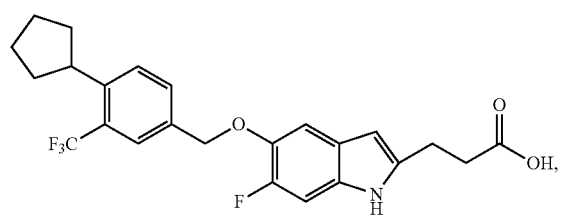
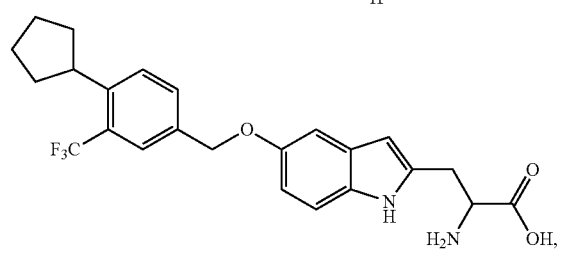
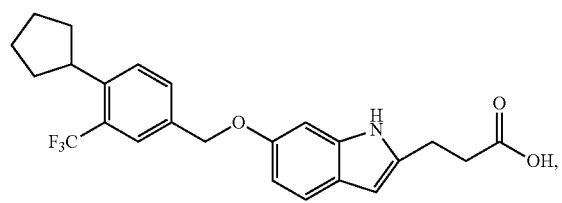
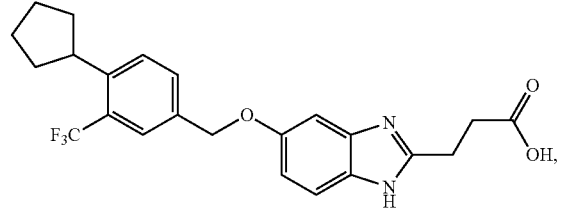
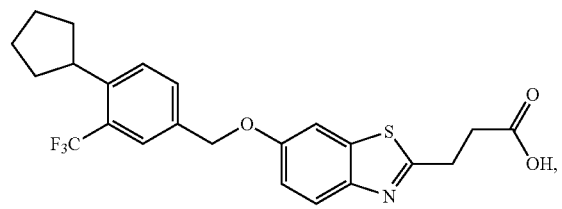
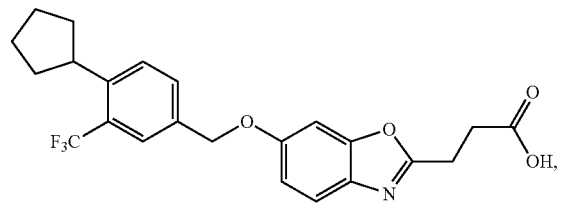
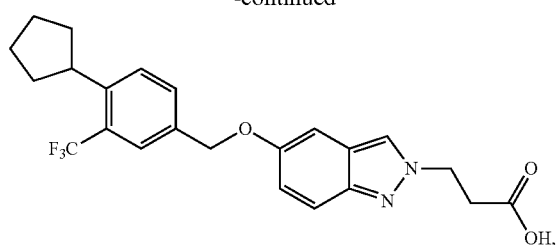
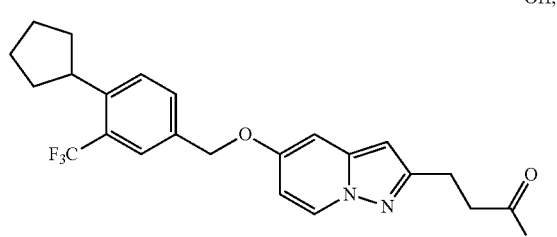
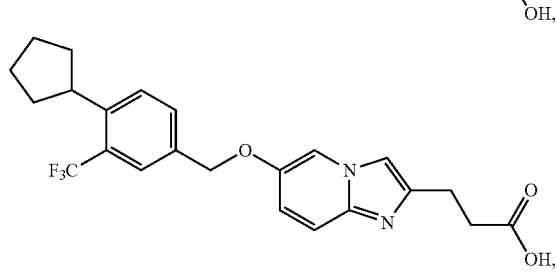
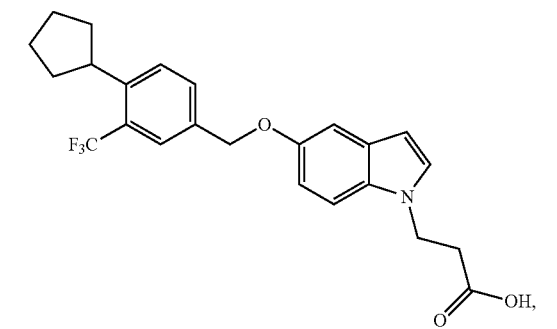
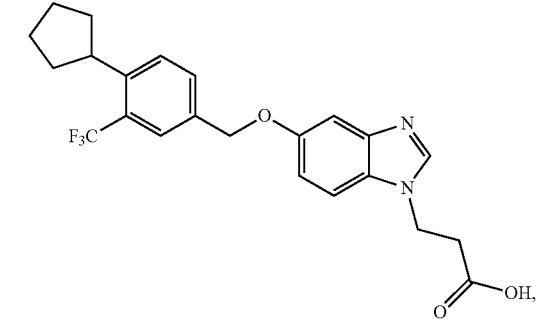
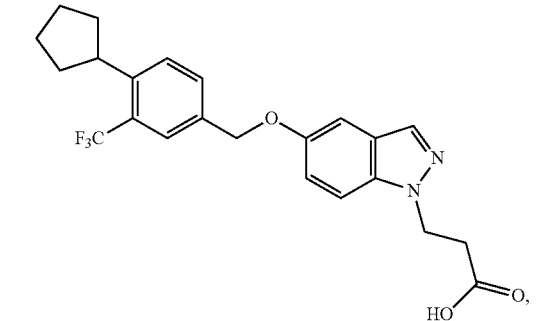

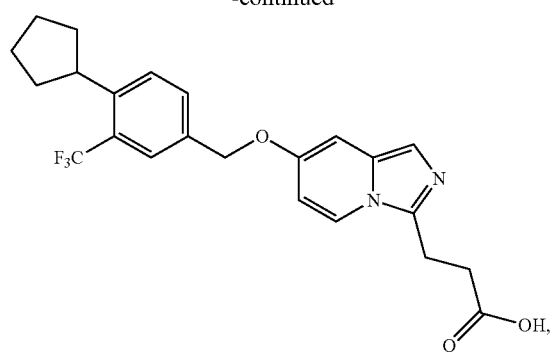
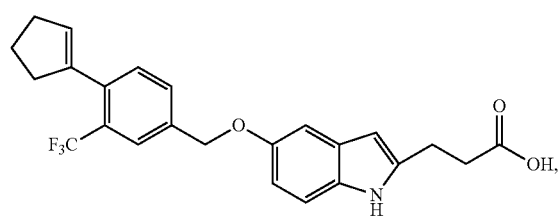
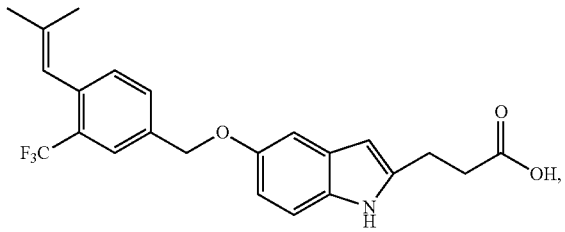
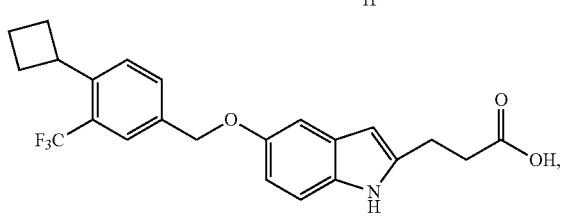
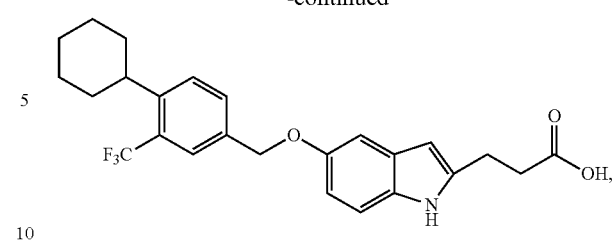
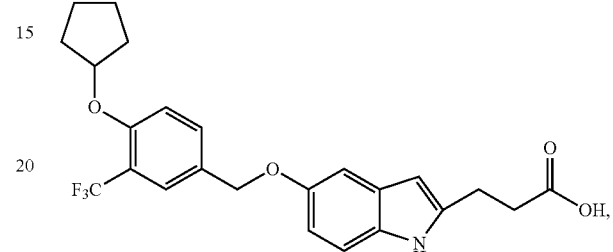
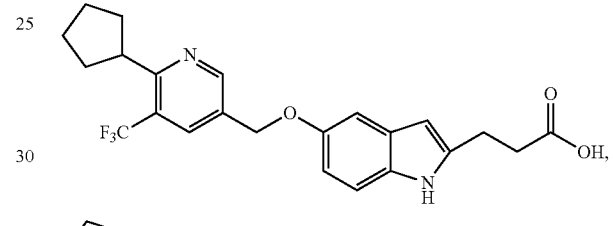
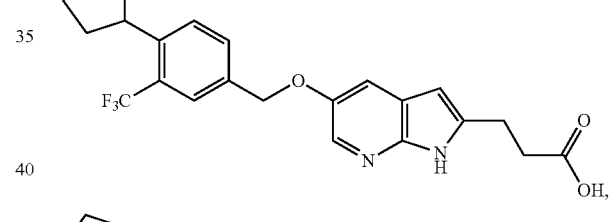
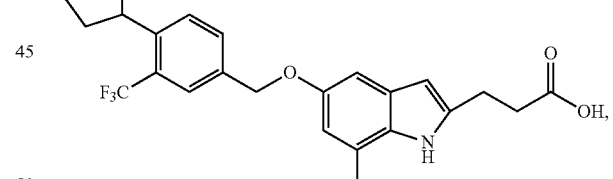
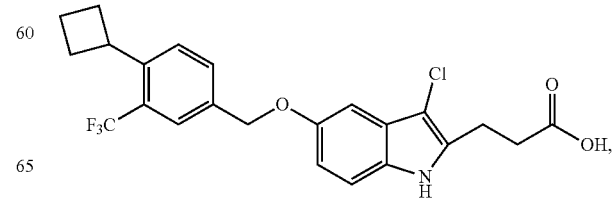

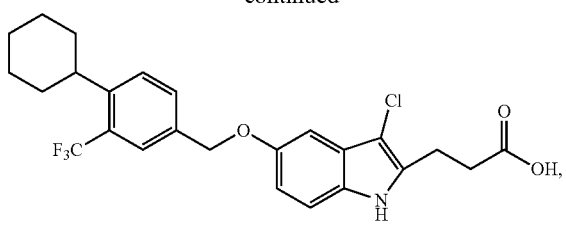
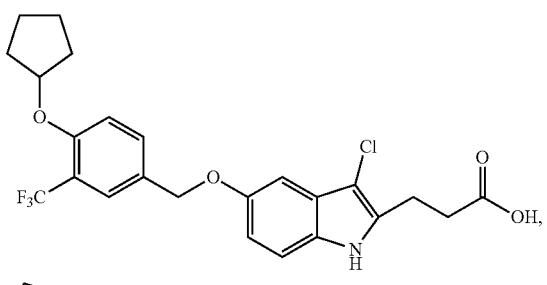
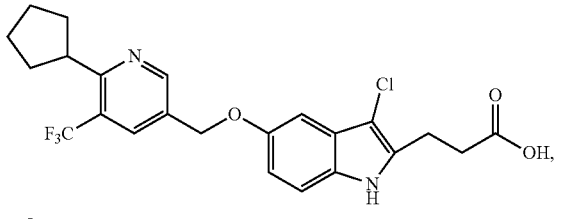
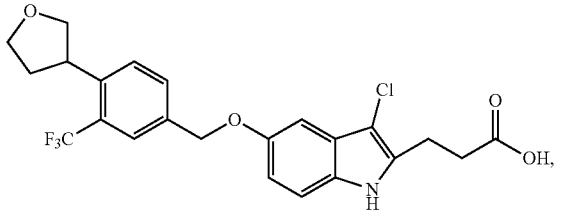
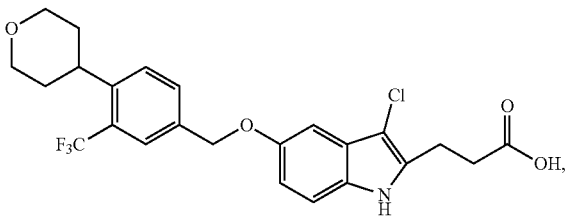
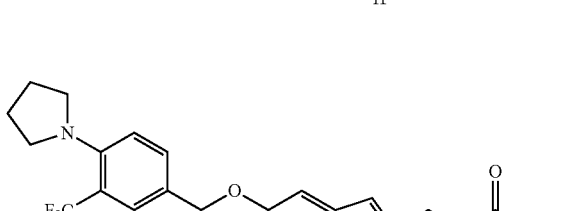
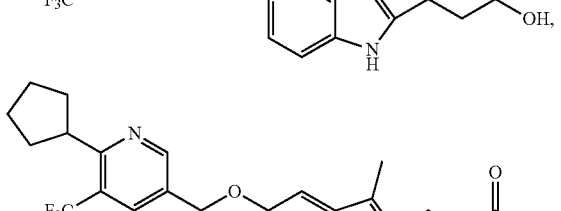
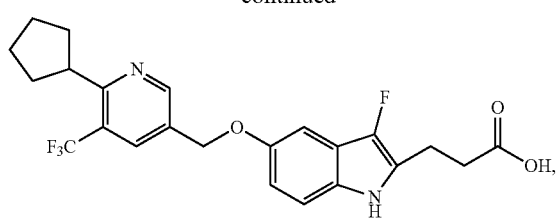
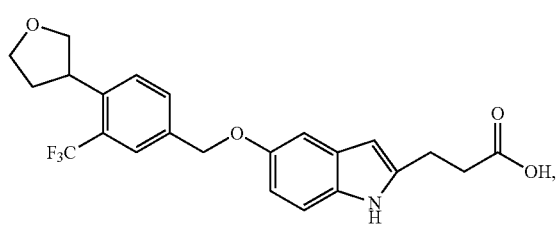
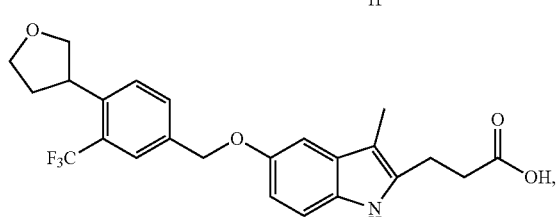
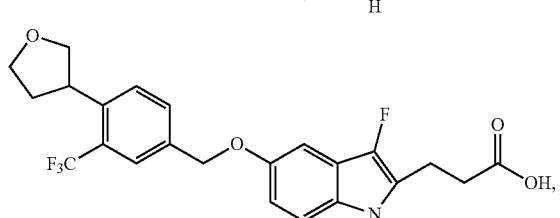
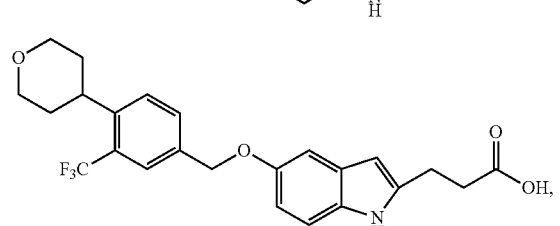
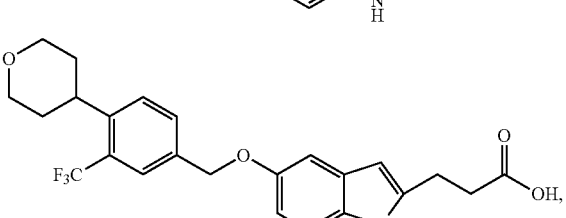
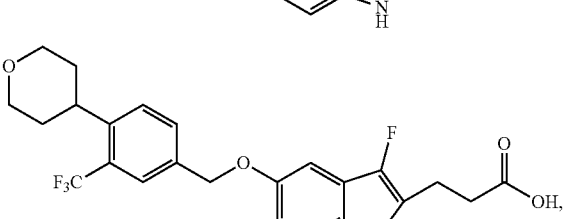

-continued

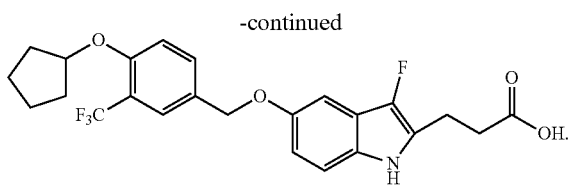

The present disclosure also provides a pharmaceutical composition, which comprises the above compound or the pharmaceutically acceptable salt thereof, and one or more pharmaceutically acceptable carriers, diluents or excipients.

The present disclosure also provides a use of the compound or the pharmaceutically acceptable salt thereof or the pharmaceutical composition in the manufacture of a medicament for preventing and/or treating diseases related to S1P1 receptor-related diseases.

In some embodiments of the present disclosure, the above-mentioned uses, wherein the S1P1 receptor-related diseases are selected from Ulcerative colitis, Crohn's disease, Multiple sclerosis, Systemic lupus erythematosus, Lupus nephritis, Rheumatoid arthritis, Primary Biliary Cholangitis, Atopic Dermatitis, Intracerebral hemorrhage, Graft versus Host Disease, Psoriasis, Type I diabetes, Acne, microbial infections or microbial diseases and viral infections or viral diseases.

DEFINITION AND DESCRIPTION

Unless otherwise indicated, the following terms used in the present disclosure have the following meanings. A specific term or phrase should not be considered indefinite or unclear in the absence of a particular definition, but should be understood in the ordinary sense. When a trade name appears herein, it is intended to refer to its corresponding commodity or active ingredient thereof.

The term "pharmaceutically acceptable" as used herein refers to those compounds, materials, compositions, and/or dosage forms that are suitable for use in contact with human and animal tissues within the scope of reliable medical judgment, with no excessive toxicity, irritation, allergic reaction or other problems or complications, commensurate with a reasonable benefit/risk ratio.

The term "pharmaceutically acceptable salt" refers to a salt of the compound of the present disclosure that is prepared by reacting the compound having a specific substituent of the present disclosure with a relatively non-toxic acid or base. When the compound of the present disclosure contains a relatively acidic functional group, a base addition salt can be obtained by contacting the neutral form of the compound with a sufficient amount of base in a pure solution or a suitable inert solvent. The pharmaceutically acceptable base addition salt includes a salt of sodium, potassium, calcium, ammonium, organic amine or magnesium or similar salts. When the compound of the present disclosure contains a relatively basic functional group, an acid addition salt can be obtained by contacting the neutral form of the compound with a sufficient amount of acid in a pure solution or a suitable inert solvent. Examples of the pharmaceutically acceptable acid addition salt include an inorganic acid salt, wherein the inorganic acid includes, for example, hydrochloric acid, hydrobromic acid, nitric acid, carbonic acid, bicarbonate, phosphoric acid, monohydrogen phosphate, dihydrogen phosphate, sulfuric acid, hydrogen sulfate, hydroiodic acid, phosphorous acid, and the like; and an organic acid salt, wherein the organic acid includes, for example, acetic acid, propionic acid, isobutyric acid, trifluoroacetic acid, maleic acid, malonic acid, benzoic acid, succinic acid, suberic acid, fumaric acid, lactic acid, mandelic acid, phthalic acid, benzenesulfonic acid, p-toluenesulfonic acid, citric acid, tartaric acid, and methanesulfonic acid and the like; and an salt of amino acid (such as arginine and the like), and a salt of an organic acid such as glucuronic acid, and the like. Certain specific compounds of the present disclosure that contain both basic and acidic functional groups can be converted to any base or acid addition salt.

The pharmaceutically acceptable salt of the present disclosure can be prepared from the parent compound that contains an acidic or basic moiety by conventional chemical methods. Generally, such salt can be prepared by reacting the free acid or base form of the compound with a stoichiometric amount of an appropriate base or acid in water or an organic solvent or a mixture thereof.

The compound of the present disclosure may have a specific geometric or stereoisomeric form. The present disclosure contemplates all such compounds, including cis and trans isomer, (−)- and (+)-enantiomer, (R)- and (S)-enantiomer, diastereomer, (D)-isomer, (L)-isomer, and racemic mixture and other mixtures, for example, an enantiomer or diastereomer enriched mixture, all of which are encompassed within the scope of the present disclosure.

The compounds of the present disclosure may be present in particular. Unless otherwise indicated, the term "tautomer" or "tautomeric form" refer to the fact that the isomers with different functional groups are in dynamic equilibrium at room temperature and can be rapidly converted into each other. If tautomers are possible (e.g., in solution), the chemical equilibrium of the tautomers can be achieved. For example, proton tautomer (also known as prototropic tautomer) includes interconversion by proton migration, such as keto-enol isomerization and imine-enamine isomerization. Valence tautomer include the mutual transformation caused by bonding electrons transfer. A specific example of keto-enol tautomerization is the tautomerization between two tautomers of pentane-2,4-dione and 4-hydroxypent-3-en-2-one.

The compound of the present disclosure may contain an unnatural proportion of atomic isotope on one or more atoms that constitute the compound. For example, the compound can be labeled with a radioisotope, such as tritium ($^3$H), iodine-125 ($^{125}$I) or C-14 ($^{14}$C). For another example, hydrogen can be replaced by heavy hydrogen to form a deuterated drug, and the bond formed by deuterium and carbon atoms is stronger than the bond formed by ordinary hydrogen and carbon atoms, compared with undeuterated drugs, deuterated drugs have advantages such as reduced side effects, increased drug stability, enhanced efficacy and prolonged biological half-life. All isotopic variations of the compound of the present disclosure, whether radioactive or not, are encompassed within the scope of the present disclosure. "Optional" or "optionally" means that the subsequent event or condition may occur but not requisite, that the term includes the instance in which the event or condition occurs and the instance in which the event or condition does not occur.

The term "substituted" means one or more than one hydrogen atoms on a specific atom are substituted with a substituent, including deuterium and hydrogen variants, as long as the valence of the specific atom is normal and the substituted compound is stable. The term "optionally substituted" means an atom can be substituted with a substituent or not, unless otherwise specified, the type and number of the substituent may be arbitrary as long as being chemically achievable.

When any variable (such as R) occurs in the constitution or structure of the compound more than once, the definition of the variable at each occurrence is independent. Thus, for example, if a group is substituted by 0-2 R, the group can be optionally substituted by up to two R, wherein the definition of R at each occurrence is independent. Moreover, a combination of the substituent and/or the variant thereof is allowed only when the combination results in a stable compound. For example,

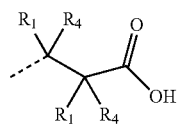

is selected from

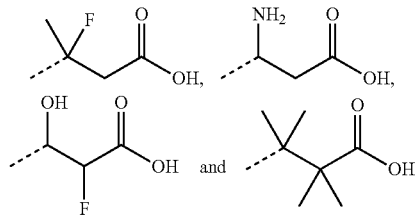

and the like.

When one of the variables is selected from a single bond, it means that the two groups connected are directly connected. For example, when $L_2$ represents a single bond in

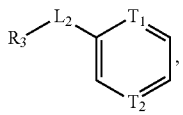

it means that the structure is actually

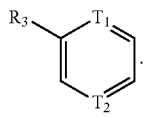

When the listed substituents do not indicate which atom is connected to the substituted group, the substituents can be bonded by any atom. For example, pyridyl as a substituent can be connected to the substituted group by any carbon atom on the pyridine ring.

When an enumerative linking group does not indicate the direction for linking, the direction for linking is arbitrary, for example, the linking group L contained in

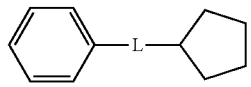

is

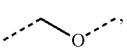

then

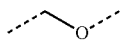

can connect the phenyl and cyclopentyl to form

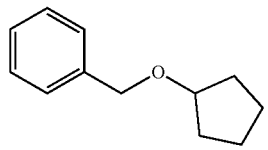 [SMILES: c1ccc(COC2CCCC2)cc1]

in the direction same as left-to-right reading order, and form

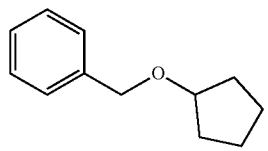 [SMILES: c1ccc(COC2CCCC2)cc1]

in the direction contrary to left-to-right reading order. A combination of linking group, substituents and/or variants thereof is allowed only when such combination can result in a stable compound. Unless otherwise specified, the number of the atom on the ring is usually defined as the member of the ring, for example, a "3-6 membered ring" means that 3 to 6 atoms are arranged on the "ring".

Unless otherwise specified, the term "$C_{1-3}$ alkyl" refers to saturated hydrocarbon groups consisted of 1 to 3 carbon atoms with linear or branched chains. The $C_{1-3}$ alkyl includes $C_{1-2}$ and $C_{2-3}$ alkyl and the like; it can be monovalent (e.g., methyl), divalent (e.g., methylene) or multivalent (e.g., methylidyne). Examples of $C_{1-3}$ alkyl include methyl (Me), ethyl (Et), propyl (such as n-propyl and isopropyl) and the like.

Unless otherwise specified, "$C_{2-6}$ alkenyl" refers to hydrocarbon groups consisted of 2 to 6 carbon atoms containing at least one carbon-carbon double bond with linear or branched chains, and the carbon-carbon double bond can be located at any position of the group. The $C_{2-6}$ alkenyl includes $C_{2-4}$, $C_{2-3}$, $C_4$, $C_3$ and $C_2$ alkenyl, etc; it may be monovalent, divalent or multivalent. Examples of $C_{2-6}$ alkenyl include, but are not limited to, vinyl, propenyl, butenyl, pentenyl, hexenyl, butadienyl, pentadienyl, hexadienyl and the like.

Unless otherwise specified, "$C_{2-3}$ alkenyl" refers to hydrocarbon groups consisted of 2 to 3 carbon atoms containing at least one carbon-carbon double bond with linear or branched chains, and the carbon-carbon double bond can be located at any position of the group. The $C_{2-3}$ alkenyl includes $C_2$ and $C_3$ alkenyl; the $C_{2-3}$ alkenyl may be monovalent, divalent or multivalent. Examples of $C_{2-3}$ alkenyl include, but are not limited to, vinyl, propenyl and the like.

Unless otherwise specified, "$C_{3-7}$ cycloalkyl" refers to saturated cyclic hydrocarbon groups consisted of 3 to 7 carbon atoms with monocyclic and bicyclic systems, the $C_{3-7}$ cycloalkyl including $C_{4-7}$, $C_{5-7}$, $C_{3-5}$, $C_{4-5}$ and $C_{5-6}$ cycloalkyl, etc.; it may be monovalent, divalent or polyvalent. Examples of $C_{3-6}$ cycloalkyl include, but are not limited to cyclopropyl, cyclobutyl, cyclopentyl, cyclohexyl and the like.

Unless otherwise specified, the terms "5-6 membered heteroaromatic ring" and "5-6 membered heteroaryl" in the present disclosure can be used interchangeably, the term "5-6 membered heteroaryl" refers to the ring group with conjugated n electron system composed of 5 to 6 ring atoms, the 1, 2, 3 or 4 ring atoms are heteroatoms independently selected from O, S and N, and the rest are carbon atoms. Among them, the nitrogen atom is optionally quaternized, the nitrogen and sulfur heteroatoms can optionally be oxidized (i.e., NO and $S(O)_p$, p is 1 or 2). The 5-6 membered heteroaryl can be connected to the rest of the molecule via a heteroatom or a carbon atom. The 5-6 membered heteroaryl includes 5 membered heteroaryl and 6 membered heteroaryl. Examples of the 5-6 membered heteroaryl include, but not limited to, pyrrolyl (including A-pyrrolyl, 2-pyrrolyl and 3-pyrrolyl, etc.), pyrazolyl (including 2-pyrazolyl and 3-pyrazolyl, etc.), imidazolyl (including A-imidazolyl, 2-imidazolyl, 4-imidazolyl and 5-imidazolyl, etc.), oxazolyl (including 2-oxazolyl, 4-oxazolyl and 5-oxazolyl, etc.), triazolyl (1H-1,2,3-triazolyl, 2H-1,2,3-triazolyl, 1H-1,2,4-triazolyl and 4H-1,2,4-triazolyl, etc.), tetrazolyl, isoxazolyl (3-isoxazolyl, 4-isoxazolyl and 5-isoxazolyl, etc.), thiazolyl (including 2-thiazolyl, 4-thiazolyl and 5-thiazolyl, etc.), furanyl (including 2-furanyl and 3-furanyl, etc.), thiophenyl (including 2-thiophenyl and 3-thiophenyl, etc.), pyridyl (including 2-pyridyl, 3-pyridyl and 4-pyridyl, etc.), pyrazinyl or pyrimidinyl (including 2-pyrimidinyl and 4-pyrimidinyl, etc.).

Unless otherwise specified, the term "cycloalkenyl" in the present disclosure refers to cyclic alkenyl. "$C_{3-7}$ cycloalkenyl" includes $C_3$, $C_4$, $C_5$, $C_6$ and $C_7$ cycloalkenyl. Examples of cycloalkenyl include, but are not limited to, cyclobutenyl, cyclopentenyl and cyclohexenyl. Unless otherwise specified, $C_{n-n+m}$ or $C_n$–$C_{n+m}$ includes any of the specific cases of n to n+m carbons, for example, $C_{1-12}$ includes $C_1$, $C_2$, $C_3$, $C_4$, $C_5$, $C_6$, $C_7$, $C_8$, $C_9$, $C_{10}$, $C_{11}$, and $C_{12}$, and also any of the ranges from n to n+m, for example, $CH_{1-12}$ includes $C_{1-3}$, $C_{1-6}$, $C_{1-9}$, $C_{3-6}$, $C_{3-9}$, $C_{3-12}$, $C_{6-9}$, $C_{6-12}$, and $C_{9-12}$ and the like. Similarly, n to n+m means that the number of atoms on the ring is n to n+m, for example, 3-12 element rings include 3 membered rings, 4 membered rings, 5 membered rings, 6 membered rings, 7 membered rings, 8 membered rings, 9 membered rings, 10 membered rings, 11 membered rings, and 12 membered rings, but also any of the ranges from n to n+m, for example, 3-12-membered rings include 3-6 membered rings, 3-9 membered rings, 5-6 membered rings, 5-7 membered rings, 6-7 membered rings, 6-8 membered rings, and 6-10 membered rings and the like.

The term "leaving group" refers to a functional group or atom that can be replaced by another functional group or atom by a substitution reaction (for example, an affinity substitution reaction). For example, representative leaving groups include trifluoromethanesulfonate; chlorine, bromine, and iodine; sulfonate groups such as methanesulfonate, toluenesulfonate, p-bromobenzenesulfonate, p-toluenesulfonate and the like; acyloxy groups, such as acetoxy, trifluoroacetoxy and the like.

The term "protecting group" includes, but is not limited to, "amino protecting group", "hydroxyl protecting group" or "thiol protecting group". The term "amino protecting group" refers to a protecting group that is suitable for preventing side reactions at the amino nitrogen position. Representative amino protecting groups include, but are not limited to: formyl; acyl, such as chain alkanoyl (e.g., acetyl, trichloroacetyl or trifluoroacetyl); alkoxycarbonyl, such as tert-butoxycarbonyl (Boc); aryl methoxycarbonyl, such as benzyloxycarbonyl (Cbz) and 9-fluorenylmethoxycarbonyl (Fmoc); arylmethyl, such as benzyl (Bn), trityl (Tr), 1,1-di-(4'-methoxyphenyl) methyl and the like; and methylsilyl, such as trimethylsilyl(TMS) and tert-butyldimethylsilyl (TBS) and the like. The term "hydroxyl protecting group" refers to a protecting group that is suitable for preventing side reactions at hydroxyl. Representative hydroxyl protecting groups include, but are not limited to: alkyl such as methyl, ethyl and tert-butyl; acyl such as chain alkanoyl (e.g., acetyl); arylmethyl such as benzyl (Bn), p-methoxybenzyl (PMB), 9-fluorenylmethyl (Fm) and diphenylmethyl (DPM); methylsilyl such as trimethylsilyl (TMS) and tert-butyldimethylsilyl (TBS) and the like.

The compound of the present disclosure can be prepared by a variety of synthetic methods well known to those skilled in the art, including the following enumerative embodiments, embodiments formed by the following enumerative embodiments in combination with other chemical synthesis methods and equivalent replacements well known to those skilled in the art. The preferred embodiments includes, but not limited to the embodiments of the present disclosure.

The solvent used in the present disclosure is commercially available.

The present disclosure adopts the abbreviating words as follows:

EDCI refers to 1-(3-dimethylaminopropyl)-3-ethylcarbodiimide hydrochloride; $Pd(PPh_3)_4$ refers to tetrakis(triphenylphosphine)palladium; AntPhos refers to 4-(anthracen-9-yl)-3-(tert-butyl)-2,3-dihydrobenzo [d][1,3] oxaphosphole; DMF refers to N,N-dimethylformamide; EA refers to ethyl acetate.

Compounds are named according to common naming principles in the field or using ChemDraw® software, and commercially available compounds are named using supplier catalog names.

DETAILED DESCRIPTION OF THE INVENTION

Figure 1:
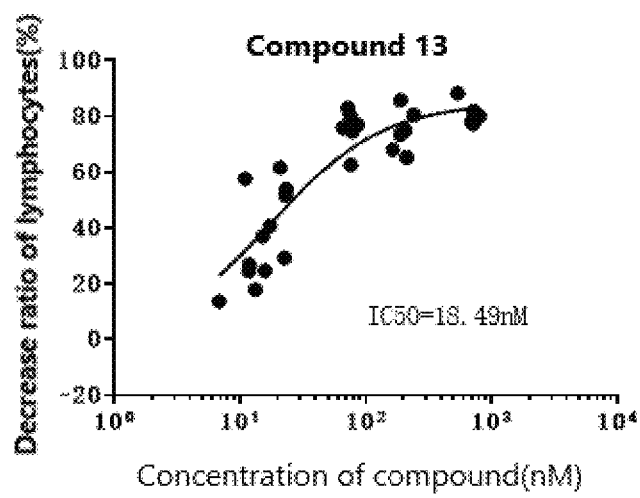
FIG. 1 shows the effects of compounds 13 and 16 in the peripheral blood lymphocyte (PBL) reduction test in mice.
Figure 1:
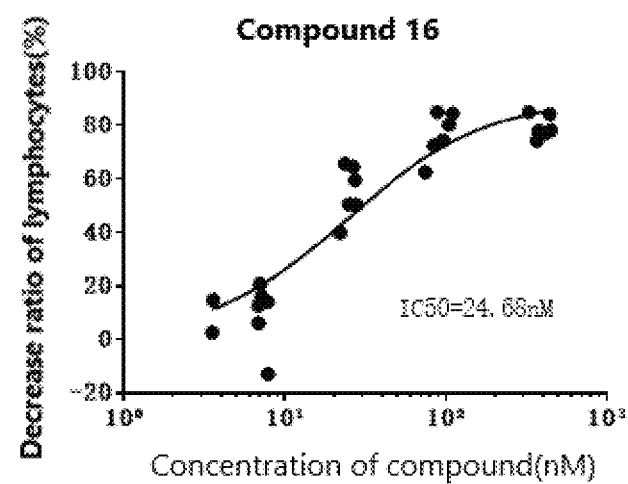
Figure 1:
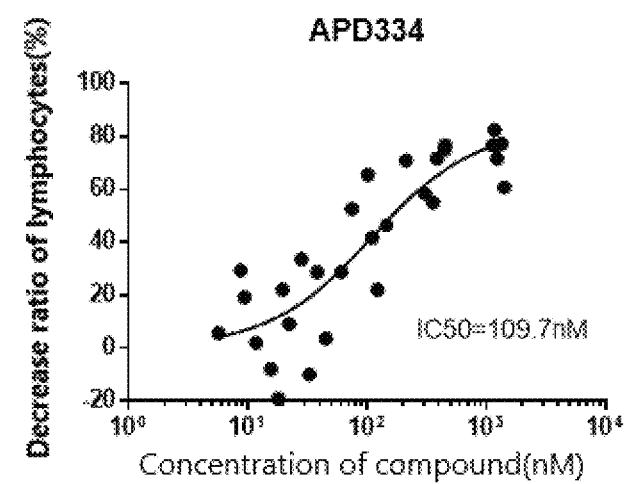

The following embodiments further illustrate the present disclosure, but it does not mean that there are any unfavorable restrictions on this application. The present disclosure has been described in detail herein, and specific embodiments thereof have also been disclosed. It will be apparent to those skilled in the art that various changes and modifications can be made to the specific embodiments of the present disclosure without departing from the spirit and scope of the present disclosure.

PREPARATION OF INTERMEDIATES

Reference Embodiment 1: Preparation of Intermediate I-1

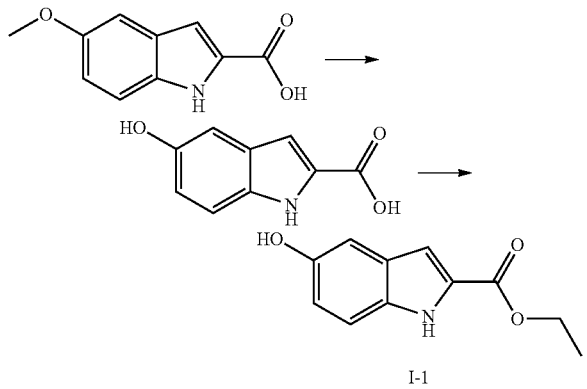

A solution of 5-methoxy-1H-indole-2-carboxylic acid (1.6 g, 8.37 mmol) in dichloromethane (20 mL) was slowly added dropwise to a solution of boron tribromide (6.3 g, 25.1 mmol) in dichloromethane (100 mL). The mixture was stirred at 0° C. for one hour, and quenched by the continuously addition of 100 mL of ethanol and 200 mL of water at 0° C. The organic solvent was removed under reduced pressure and the aqueous layer was extracted with ethyl acetate (50 mL×3), and the combined organic layers were washed with saturated saline, dried with anhydrous sodium sulfate, filtered and concentrated to obtain a residue. The residue was dissolved in 100 mL of ethanol, 2 mL of sulfuric acid was added and the mixture was stirred at 70° C. for 16 hours. The pH of the reaction solution was adjusted to pH=6 with saturated sodium bicarbonate aqueous solution, and 100 mL of water and 50 mL of ethyl acetate were added to extract, and the organic layer was separated. The aqueous layer was continuously extracted with ethyl acetate (50 mL×2). The combined organic layers were washed with saturated saline continuously, dried with anhydrous sodium sulfate, then filtered and concentrated to obtain a residue. The residue was purified by silica gel chromatography to obtain intermediate I-1.

LC-MS (ESI) [M+H]$^+$ 206.1.

Reference Embodiment 2: Preparation of Intermediate I-2

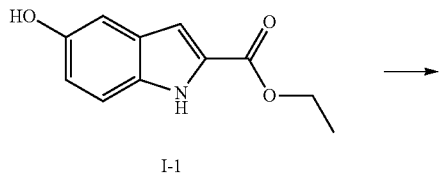

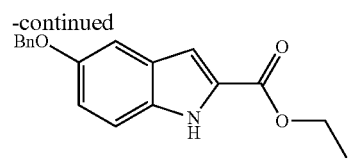

Benzyl bromide (1.0 g, 5.85 mmol) and potassium carbonate (1.35 g, 9.74 mmol) were added to a solution of intermediate I-1 (1.0 g, 4.87 mmol) in acetone (50 mL), and the reaction solution was stirred at room temperature for 16 hours. 100 mL of water and 50 mL of ethyl acetate were added to the reaction solution, and the organic layer was separated by extraction. The aqueous layer was continuously extracted with ethyl acetate (50 mL×2). The combined organic layer was washed with saturated saline, dried with anhydrous sodium sulfate, then filtered and concentrated to obtain a residue. The residue was purified by silica gel chromatography to obtain intermediate I-2.

LC-MS (ESI) [M+H]$^+$ 296.1.

$^1$H NMR (400 MHz, DMSO-d$_6$) δ 11.72 (s, 1H), 7.48-7.41 (m, 2H), 7.40-7.26 (m, 4H), 7.18 (s, 1H), 7.05-6.94 (m, 2H), 5.06 (s, 2H), 4.35-4.24 (m, 2H), 1.36-1.25 (m, 3H).

Reference Embodiment 3: Preparation of Intermediate I-3

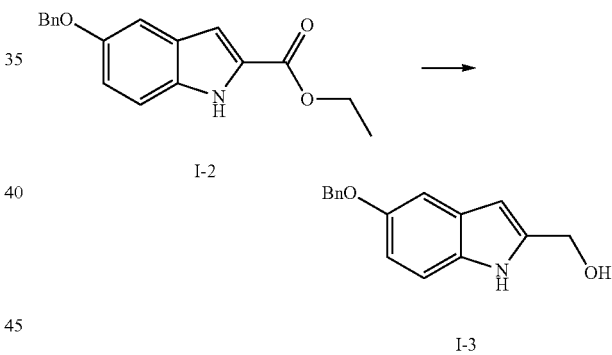

A solution of diisobutylaluminum hydride in n-hexane (1.5 mol/L, 4.1 mL, 6.1 mmol) was slowly added dropwise to a solution of intermediate I-2 (600 mg, 2.03 mmol) in tetrahydrofuran (50 mL) at −40° C. After the dropwise addition, the reaction solution was slowly raised to room temperature and stirred for 16 hours. The reaction solution was quenched with 100 mL of water at 0° C. and 50 mL of ethyl acetate was added, and the organic layer was separated by extraction. The aqueous layer was continuously extracted with ethyl acetate (50 mL×2). The combined organic layer was washed with saturated saline, dried with anhydrous sodium sulfate, then filtered and concentrated to obtain a residue. The residue was purified by silica gel chromatography to obtain intermediate I-3.

LC-MS (ESI) [M+H]$^+$ 254.1.

$^1$H NMR (400 MHz, DMSO-d$_6$) δ 10.82 (s, 1H), 7.49-7.42 (m, 2H), 7.42-7.35 (m, 2H), 7.34-7.27 (m, 1H), 7.21 (d, J=8.7 Hz, 1H), 7.07-7.02 (m, 1H), 6.78-6.71 (m, 1H), 6.17 (s, 1H), 5.17 (m, 1H), 5.06 (s, 2H), 4.56 (d, J=4.0 Hz, 2H).

Reference Embodiment 4: Preparation of Intermediate I-4

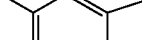

Manganese dioxide (1.13 g, 13.0 mmol) was added to a solution of intermediate I-3 (330 mg, 1.30 mmol) in 1,2-dichloroethane (50 mL) and stirred at 70° C. for 3 hours under the protection of argon. The reaction solution was filtered, and the filtrate was evaporated under reduced pressure to remove the solvent to obtain a residue. The residue was purified by silica gel chromatography to obtain intermediate I-4.

LC-MS (ESI) [M+H]$^+$ 252.0.

$^1$H NMR (400 MHz, DMSO-$d_6$) δ 11.85 (s, 1H), 9.80 (s, 1H), 7.50-7.44 (m, 2H), 7.42-7.32 (m, 4H), 7.31-7.26 (m, 2H), 7.08 (dd, J=9.0, 2.2 Hz, 1H), 5.11 (s, 2H).

Reference Embodiment 5: Preparation of Intermediate I-5

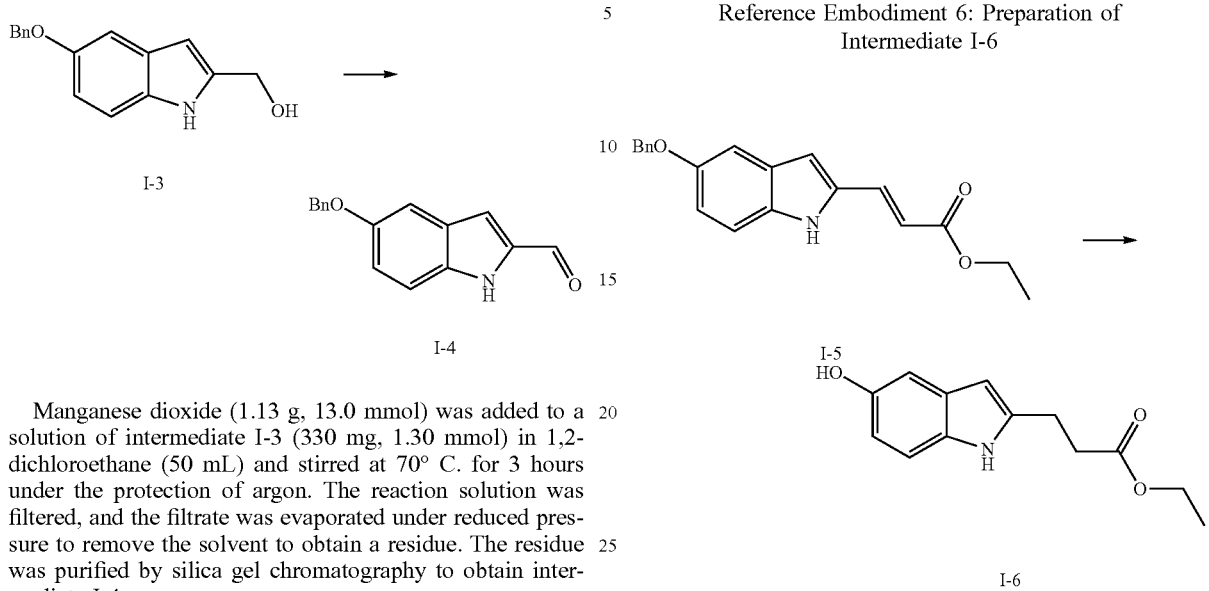

Ethoxyformylmethylene triphenylphosphine (581.8 mg, 1.67 mmol) was added to a solution of intermediate I-4 (280 mg, 1.12 mmol) in tetrahydrofuran (10 mL) and the mixture was stirred at 80° C. for 16 hours. 20 mL of water and 20 mL of ethyl acetate were added to the reaction solution, and the organic layer was separated by extraction. The aqueous layer was continuously extracted with ethyl acetate (20 mL×2). The combined organic layer was washed with saturated saline, dried with anhydrous sodium sulfate, then filtered and concentrated to obtain a residue. The residue was purified by silica gel chromatography to obtain intermediate I-5.

LC-MS (ESI) [M+H]$^+$ 322.1.

$^1$H NMR (400 MHz, DMSO-$d_6$) δ 11.46 (s, 1H), 7.58 (d, J=16.0 Hz, 1H), 7.50-7.42 (m, 2H), 7.42-7.35 (m, 2H), 7.35-7.26 (m, 2H), 7.13 (d, J=1.6 Hz, 1H), 6.93 (dd, J=8.8, 2.2 Hz, 1H), 6.81 (s, 1H), 6.50 (d, J=16.0 Hz, 1H), 5.09 (s, 2H), 4.18 (q, J=7.1 Hz, 2H), 1.26 (t, J=7.1 Hz, 3H).

Reference Embodiment 6: Preparation of Intermediate I-6

Palladium carbon (30 mg, w/w=10%) was added to a solution of intermediate I-5 (190 mg, 0.59 mmol) in ethanol (20 mL), and the reaction solution was stirred at room temperature under hydrogen for 16 hours. The reaction solution was filtered, and the filtrate was concentrated to obtain a residue. The residue was purified by silica gel chromatography to obtain intermediate I-6.

LC-MS (ESI) [M+H]$^+$ 234.1.

$^1$H NMR (400 MHz, DMSO-$d_6$) δ 10.55 (s, 1H), 8.46 (s, 1H), 7.02 (d, J=8.5 Hz, 1H), 6.70 (s, 1H), 6.48 (dd, J=8.5, 2.1 Hz, 1H), 5.93 (s, 1H), 4.05 (q, J=7.1 Hz, 2H), 2.90 (t, J=7.5 Hz, 2H), 2.67 (t, J=7.5 Hz, 2H), 1.15 (t, J=7.1 Hz, 3H).

Reference Embodiment 7: Preparation of Intermediate I-7

Methyl 4-bromo-3-trifluoromethylbenzoate (6.32 g, 22.32 mmol) was dissolved in dioxane/water (4:1, 30 mL) and cyclopentyl-1-ene-1-boric acid (3.0 g, 26.79 mmol), palladium tetrakis(triphenylphosphine) (1.3 g, 1.12 mmol) and potassium carbonate (9.2 g, 66.7 mmol) were added. The reaction solution was stirred at 110° C. for 15 hours under the protection of argon. After cooling to room temperature, the solvent was concentrated and evaporated to dryness to obtain a residue. The residue was purified by silica gel chromatography to obtain intermediate I-7.

$^1$H NMR (400 MHz, CDCl$_3$) δ 8.32 (d, J=1.5 Hz, 1H), 8.11 (dd, J=8.0, 1.5 Hz, 1H), 7.37 (d, J=8.0 Hz, 1H), 5.83-5.77 (m, 1H), 3.95 (s, 3H), 2.74-2.63 (m, 2H), 2.58-2.51 (m, 2H), 2.08-1.99 (m, 2H).

Reference Embodiment 8: Preparation of Intermediate I-8

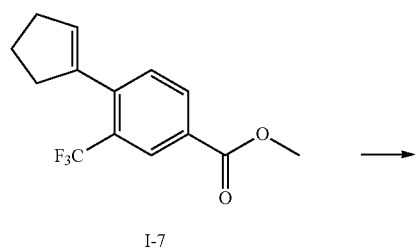

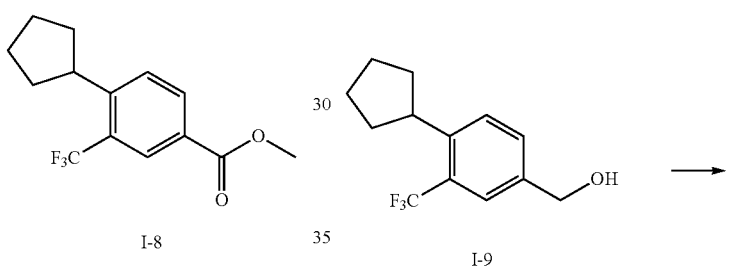

Intermediate I-7 (1.0 g, 3.7 mmol) was dissolved in 20 mL of methanol, and palladium carbon (50 mg, w/w=10%) was added. The reaction mixture was stirred under hydrogen atmosphere at room temperature for 24 hours. The reaction solution was filtered, and the filtrate was concentrated to obtain a crude product of intermediate I-8. The crude product was directly used in the next reaction without purification.

$^1$H NMR (400 MHz, CDCl$_3$) δ 8.27 (d, J=1.3 Hz, 1H), 8.13 (dd, J=8.3, 1.3 Hz, 1H), 7.54 (d, J=8.3 Hz, 1H), 3.93 (s, 3H), 3.47-3.36 (m, 1H), 2.16-2.07 (m, 2H), 1.93-1.82 (m, 2H), 1.82-1.70 (m, 2H), 1.69-1.55 (m, 2H).

Reference Embodiment 9: Preparation of Intermediate I-9

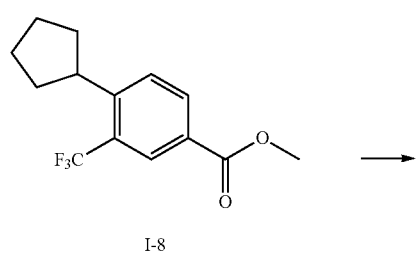

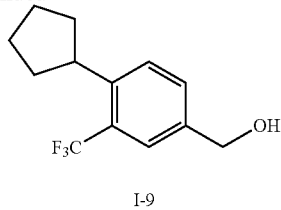

Intermediate I-8 (950 mg) was dissolved in 15 mL of tetrahydrofuran, and a solution of tetrahydrolithium aluminum in tetrahydrofuran (1.5 M, 7 mL, 10.5 mmol) was added dropwise at −20° C. under the protection of argon. After the dropwise addition, the reaction solution was stirred at −20° C. for one hour. After the temperature of the reaction solution was raised to 0° C., saturated ammonium chloride aqueous solution (4 mL) and ethyl acetate (5 mL) were added. The reaction solution was filtered, and the filtrate was concentrated to obtain intermediate I-9. The crude product was directly used in the next reaction without purification.

Reference Embodiment 10: Preparation of Intermediate I-10

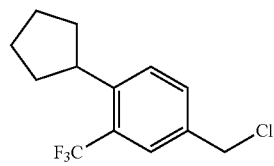

Intermediate I-9 (2.5 g) was dissolved in 10 mL of thionyl chloride, and the mixture was heated and stirred at 50° C. for 2 hours. After cooling to room temperature, the reaction solution was concentrated to obtain a residue. The residue was dissolved in ethyl acetate (10 mL) and washed with saturated sodium bicarbonate aqueous solution (10 mL) and saline (10 mL) successively. After drying with anhydrous sodium sulfate, intermediate I-10 was obtained by filtration and concentration.

$^1$H NMR (400 MHz, CDCl$_3$) δ 7.53 (s, 1H), 7.49-7.36 (m, 2H), 4.50 (s, 2H), 3.35-3.23 (m, 1H), 2.07-1.95 (m, 2H), 1.84-1.72 (m, 2H), 1.71-1.59 (m, 2H), 1.57-1.44 (m, 2H).

Reference Embodiment 11: Preparation of Intermediate I-11

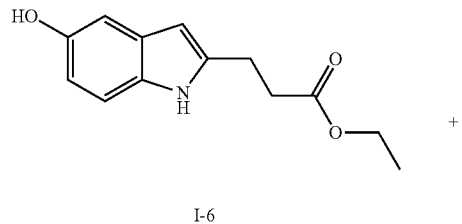

I-6

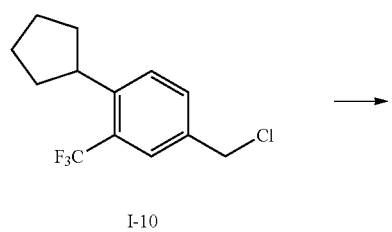

I-10

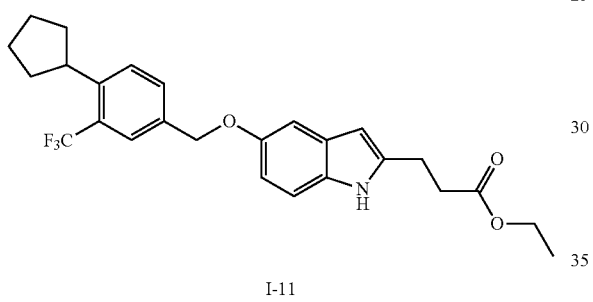

I-11

Intermediate I-10 (101.5 mg), potassium carbonate (71.2 mg, 0.52 mmol) and cesium carbonate (168.2 mg, 0.52 mmol) were added to a solution of intermediate I-6 (60 mg, 0.26 mmol) in acetonitrile (15 mL), and the mixture was stirred at room temperature for 3 hours. 50 mL of water and 20 mL of ethyl acetate were added to the reaction solution, the organic phase was separated by extraction, and the aqueous phase was continuously extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-11.

LC-MS (ESI) [M+H]$^+$ 460.1.

Reference Embodiment 12: Preparation of Intermediate I-12

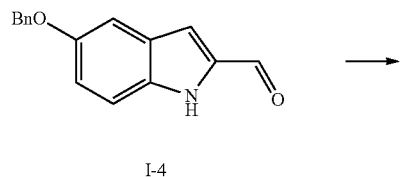

I-4

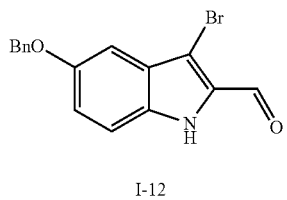

I-12

At 0° C., a solution of liquid bromine (350.6 mg, 2.19 mmol) in N,N-dimethylformamide (10 mL) was added dropwise to a solution of intermediate I-4 (500.0 mg, 1.99 mmol) in N,N-dimethylformamide (10 mL), after the dropwise addition, the reaction solution was stirred at room temperature for 16 hours. 30 mL of water and 20 mL of ethyl acetate were added to the reaction solution. After the organic layer was separated by extraction, the aqueous layer was continuously extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-12.

LC-MS (ESI) [M+H]$^+$ 330.0.

Reference Embodiment 13: Preparation of Intermediate I-13

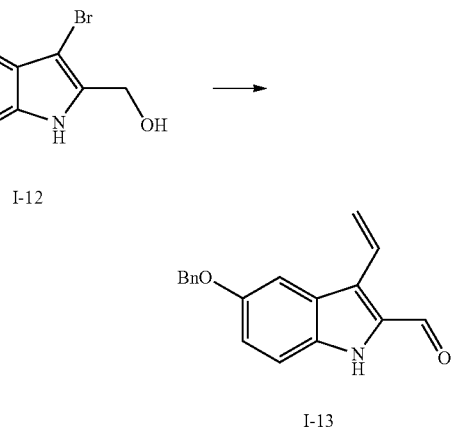

Intermediate I-12 (320.0 mg, 0.97 mmol) was dissolved in a mixed solution of dioxane (10 mL)/water (2 mL), and potassium vinyl trifluoroborate (143.3 mg, 1.07 mmol), potassium carbonate (403 mg, 2.92 mmol) and palladium tetrakis(triphenylphosphine) (11.2 mg, 0.01 mmol) were added. The reaction solution was stirred at 90° C. for 16 hours under the protection of argon. After cooling to room temperature, 50 mL of water and 20 mL of ethyl acetate were added to the reaction solution, the organic layer was separated by extraction, and the aqueous layer was continuously extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-13.

LC-MS (ESI) [M+H]$^+$ 278.0.

Reference Embodiment 14: Preparation of Intermediate I-14

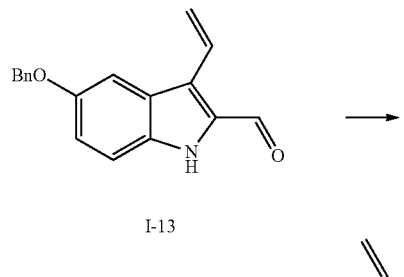

I-13

Ethoxyformylmethylene triphenylphosphine (480.8 mg, 1.38 mmol) was added to a solution of intermediate I-13 (190.0 mg, 0.69 mmol) in tetrahydrofuran (10 mL), and the mixture was stirred at 80° C. for 16 hours. After the reaction solution was cooled to room temperature, 50 mL of water and 20 mL of ethyl acetate were added to separate layers by extraction, and the aqueous phase was continuously extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-14.

LC-MS (ESI) [M+H]$^+$ 348.1.

Reference Embodiment 15: Preparation of Intermediate I-15

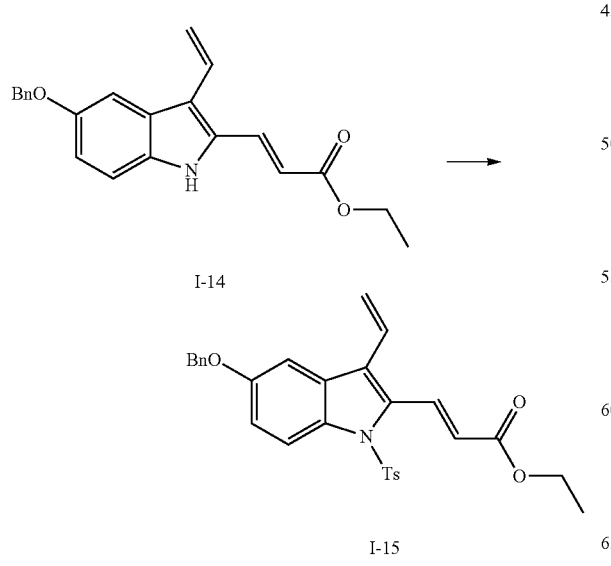

Intermediate I-14 (50.0 mg, 0.14 mmol) was dissolved in tetrahydrofuran (10 mL), and sodium hydride (60% by mass) (7.5 mg, 0.19 mmol) was added to the reaction solution at 0° C., and the mixture was stirred at 0° C. for one hour. 4-Methylbenzenesulfonyl chloride (35.7 mg, 0.19 mmL) was added to the reaction solution, and the mixture was stirred at 60° C. for 2 hours. The reaction solution was cooled to room temperature, and 50 mL of water and 20 mL of ethyl acetate were added, and the organic layer was separated by extraction. The aqueous layer was continuously extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-15.

LC-MS (ESI) [M−H]$^-$ 500.2.

Reference Embodiment 16: Preparation of Intermediate I-16

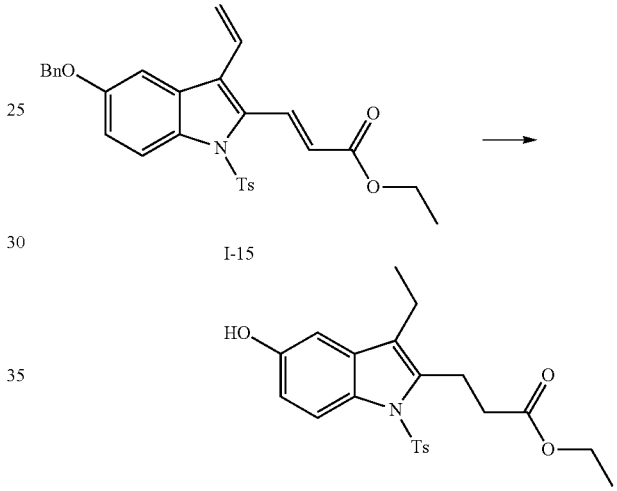

Palladium carbon (15 mg, w/w=10%) was added to a solution of intermediate I-15 (50.0 mg, 0.10 mmol) in methanol (10 mL), and the mixture was stirred at room temperature for 16 hours under hydrogen atmosphere. The reaction solution was filtered, and the filtrate was concentrated to obtain a residue. The residue was purified by silica gel chromatography to obtain intermediate I-16.

LC-MS (ESI) [M+H]$^+$ 416.1.

Reference Embodiment 17: Preparation of Intermediate I-17

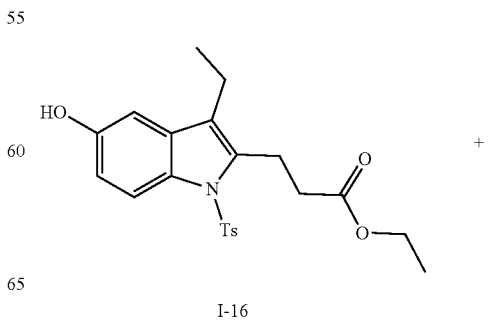

I-16

-continued

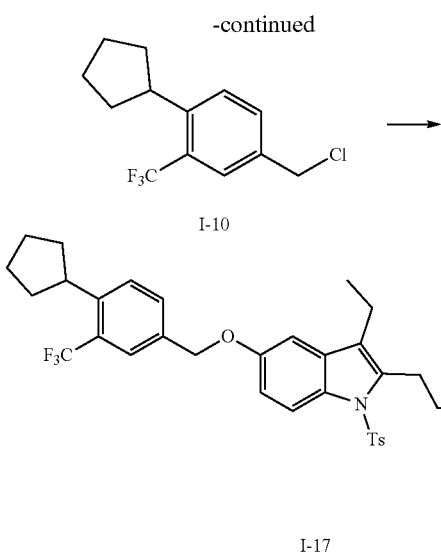

Intermediate I-10 (23.7 mg) and cesium carbonate (59.0 mg, 0.18 mmol) were added to a solution of intermediate I-16 (25.0 mg, 0.06 mmol) in acetonitrile (5 mL), and the reaction solution was stirred at 50° C. for 2 hours. After cooling to room temperature, 10 mL of water and 10 mL of ethyl acetate were added to the reaction solution, the organic layer was separated by extraction, and the aqueous layer was continuously extracted with ethyl acetate (10 mL×2). The combined organic layers were washed with saturated saline, dried with anhydrous sodium sulfate, then filtered and concentrated to obtain a residue. The residue was purified by silica gel chromatography to obtain intermediate I-17.

LC-MS (ESI) [M+H]$^+$ 642.3.

Reference Embodiment 18: Preparation of Intermediate I-18

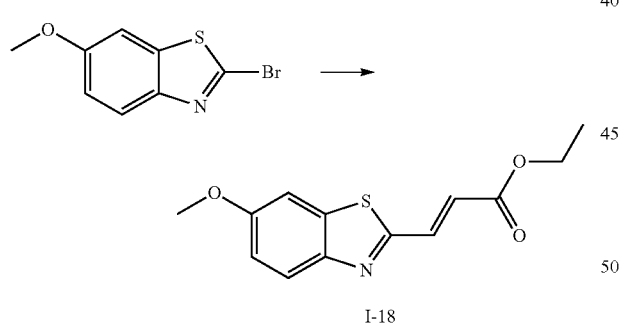

Potassium acetate (402 mg, 4.10 mmol), ethyl 3-(4,4,5,5-tetramethyl-1,3,2-dioxaborolan-2-yl) acrylate (556 mg, 2.46 mmol) and [1,1'-bis(diphenylphosphino)ferrocene]palladium dichloride (150.0 mg, 0.20 mmol) were added to a solution of 2-bromo-6-methoxybenzo[d]thiazole (500.0 mg, 2.05 mmol) in dioxane (10 mL), and the reaction solution was stirred at 100° C. overnight under the protection of argon. After cooling to room temperature, the reaction solution was diluted with 10 mL of water and extracted with ethyl acetate (20 mL×2). The combined organic layers were washed with saturated saline, dried with anhydrous sodium sulfate, then filtered and concentrated to obtain a residue. The residue was purified by silica gel chromatography to obtain intermediate I-18.

$^1$H NMR (400 MHz, CDCl$_3$) δ 7.85 (d, J=8.9 Hz, 1H), 7.24 (d, J=2.6 Hz, 1H), 7.05 (dd, J=9.0, 2.6 Hz, 1H), 6.76 (d, J=18.2 Hz, 1H), 6.62 (d, J=18.2 Hz, 1H), 4.21 (q, J=7.1 Hz, 2H), 3.86 (s, 3H), 1.29 (t, J=7.1 Hz, 3H).

Reference Embodiment 19: Preparation of Intermediate I-19

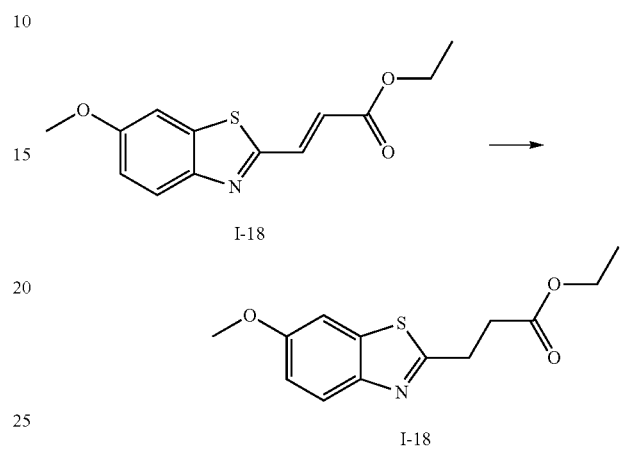

Intermediate I-18 (120 mg, 0.45 mmol) was dissolved in ethanol (5 mL), palladium carbon (20 mg, w/w=10%) was added and the reaction solution was stirred overnight at room temperature under hydrogen atmosphere. The reaction solution was filtered, and the filtrate was concentrated to obtain a residue. The residue was purified by silica gel chromatography to obtain intermediate I-19.

LC-MS (ESI) [M+H]$^+$ 266.0.

Reference Embodiment 20: Preparation of Intermediate I-20

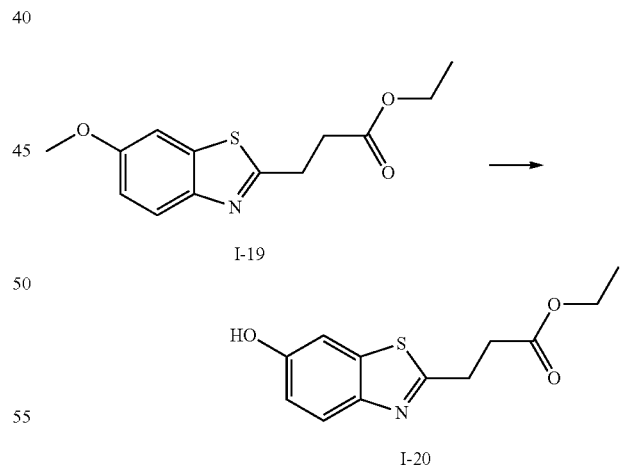

Intermediate I-19 (110 mg, 0.41 mmol) was dissolved in 2 mL of dichloromethane, and then added dropwise to a solution (3 mL) of boron tribromide in dichloromethane (2 mL, 1N, dichloromethane solution) at 0° C. After the dropwise addition, the reaction solution was stirred overnight at room temperature. The reaction solution was cooled to 0° C., ethanol (2 mL) was slowly added dropwise, and after the dropwise addition, the reaction solution was stirred at room temperature for 2 hours. 10 mL of water was added, the aqueous layer was extracted with dichloromethane (20 mL×2), the combined organic layers were washed with saturated saline, dried with anhydrous sodium sulfate, filtered and concentrated to obtain a residue. The residue was purified by silica gel chromatography to obtain intermediate I-20.

LCMS (ESI) [M+H]$^+$ 252.0.

Reference Embodiment 21: Preparation of Intermediate I-21

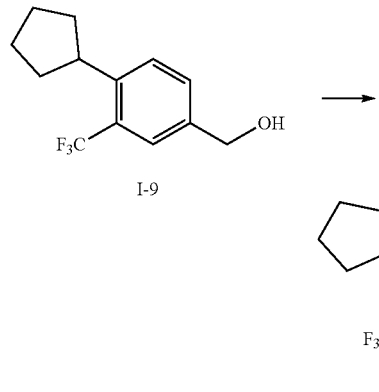

Intermediate I-9 (5.0 g) was dissolved in 10 mL of 40% HBr/H$_2$O solution and heated at 100° C. for 3 hours. After cooling to room temperature, the reaction solution was concentrated to obtain a residue. 100 mL of water was added to the residue, and the mixture was extracted with ethyl acetate (50 mL×3). The combined organic layers were washed with saline (50 mL), dried with anhydrous sodium sulfate, filtered and concentrated to obtain a residue. The residue was purified by silica gel chromatography to obtain intermediate I-21.

$^1$H NMR (400 MHz, MeOH-d$_4$) δ 7.65 (d, J=1.7 Hz, 1H), 7.60 (dd, J=8.2, 1.6 Hz, 1H), 7.53 (d, J=8.2 Hz, 1H), 4.58 (s, 2H), 3.41-3.32 (m, 1H), 2.10-2.01 (m, 2H), 1.94-1.83 (m, 2H), 1.78-1.67 (m, 2H), 1.67-1.57 (m, 2H).

Reference Embodiment 22: Preparation of Intermediate I-22

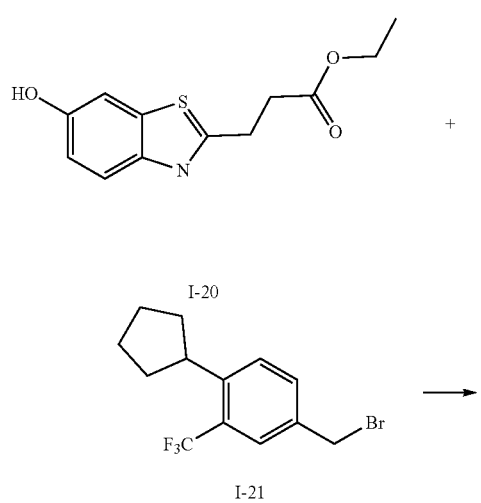

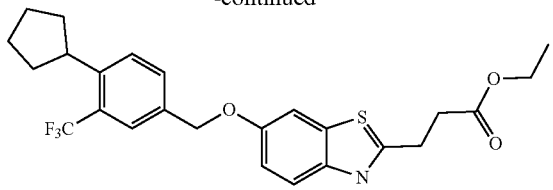

Intermediate I-20 (100.0 mg, 0.40 mmol) and intermediate I-21 (146.0 mg, 0.48 mmol) were dissolved in acetonitrile (5 mL), potassium carbonate (164.1 mg, 1.19 mmol) was added, and the reaction solution was stirred at 80° C. overnight. The reaction solution was cooled to room temperature and filtered, and the filtrate was concentrated to obtain a residue. The residue was purified by silica gel chromatography to obtain intermediate I-22.

LC-MS (ESI) [M+H]$^+$ 478.2.

Reference Embodiment 23: Preparation of Intermediate I-23

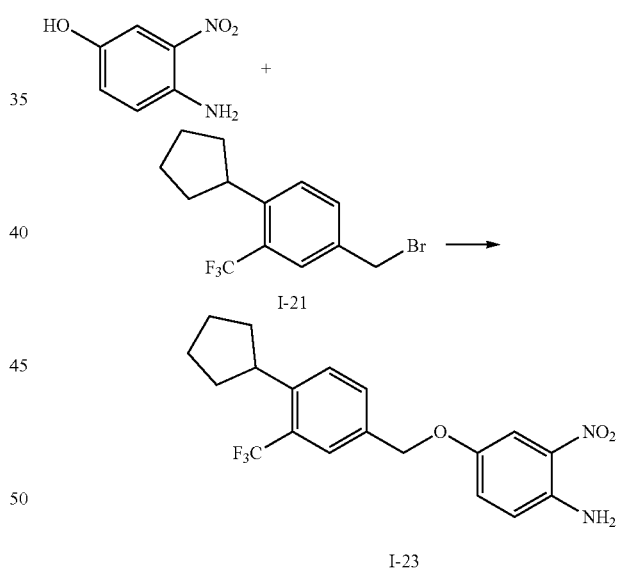

4-Amino-3-nitrophenol (0.66 g, 4.3 mmol) was dissolved in N,N-dimethylformamide (20 mL) and intermediate I-21 (1.50 g, 4.9 mmol) and potassium carbonate (0.65 g, 4.7 mmol) were added. The reaction solution was stirred at 80° C. for 2 hours. After cooling to room temperature, the reaction solution was poured into 100 mL of water and extracted with ethyl acetate (30 mL×3). The combined organic layers were washed with saturated saline, dried with anhydrous sodium sulfate, then filtered and concentrated to obtain a residue. The residue was purified by silica gel chromatography to obtain intermediate I-23.

LC-MS (ESI) [M+H]$^+$ 381.0.

Reference Embodiment 24: Preparation of Intermediate I-24

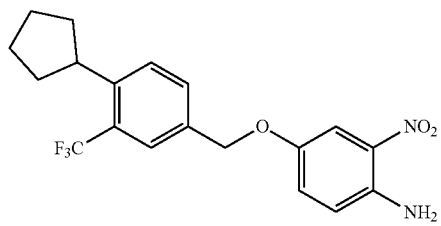

I-23

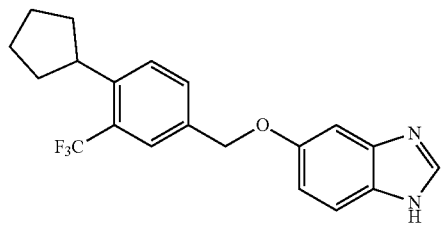

I-24

Intermediate I-23 (500.0 mg, 1.31 mmol) and trimethyl orthoformate (418.0 mg, 3.94 mmol) were dissolved in 15 mL of acetic acid, iron powder (293.0 mg, 5.24 mmol) was added, and the reaction solution was stirred at 100° C. for 10 hours. After cooling to room temperature, the reaction solution was quenched with saturated sodium carbonate aqueous solution (100 mL) and extracted with ethyl acetate (50 mL×3). The combined organic layers were washed with saturated saline, dried with anhydrous sodium sulfate, then filtered and concentrated to obtain a residue. The residue was purified by silica gel chromatography to obtain intermediate I-24.

LC-MS (ESI) [M+H]$^+$ 361.1.

Reference Embodiment 25: Preparation of Intermediate I-25 and Intermediate I-26

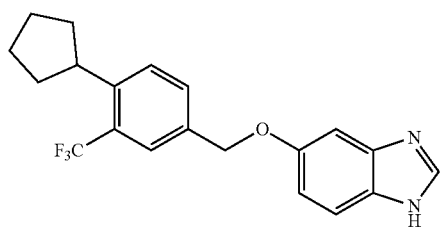

I-24

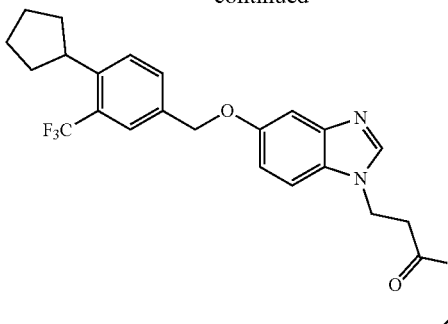

I-24

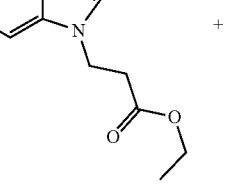

I-26

Intermediate I-24 (200.0 mg, 0.55 mmol) and ethyl 3-bromopropionate (197.0 mg, 1.09 mmol) were dissolved in N,N-dimethylformamide (4 mL), and potassium carbonate (150.0 mg, 1.09 mmol) and potassium iodide (8.9 mg, 0.05 mmol) were added. The reaction solution was stirred at 120° C. for 10 hours. After cooling to room temperature, the reaction solution was poured into 20 mL of water and extracted with ethyl acetate (5 mL×3). The combined organic layers were washed with saturated saline, dried with anhydrous sodium sulfate, then filtered and concentrated to obtain a residue. The residue was purified by silica gel chromatography to obtain a mixture of intermediates I-25 and I-26.

LC-MS (ESI) [M+H]$^+$ 461.2.

Reference Embodiment 26: Preparation of Intermediate I-27

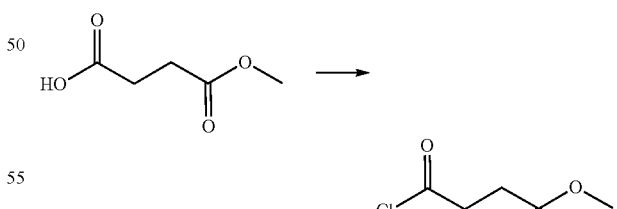

I-27

Thionyl chloride (0.5 mL) was added to a solution of 4-methoxy-4-oxobutyric acid (100 mg, 0.76 mmol) in dichloromethane (2 mL), and the reaction solution was stirred at room temperature overnight. The reaction solution was concentrated under reduced pressure to obtain a crude product of intermediate I-27.

Reference Embodiment 27: Preparation of Intermediate I-28

Reference Embodiment 28: Preparation of Intermediate I-29

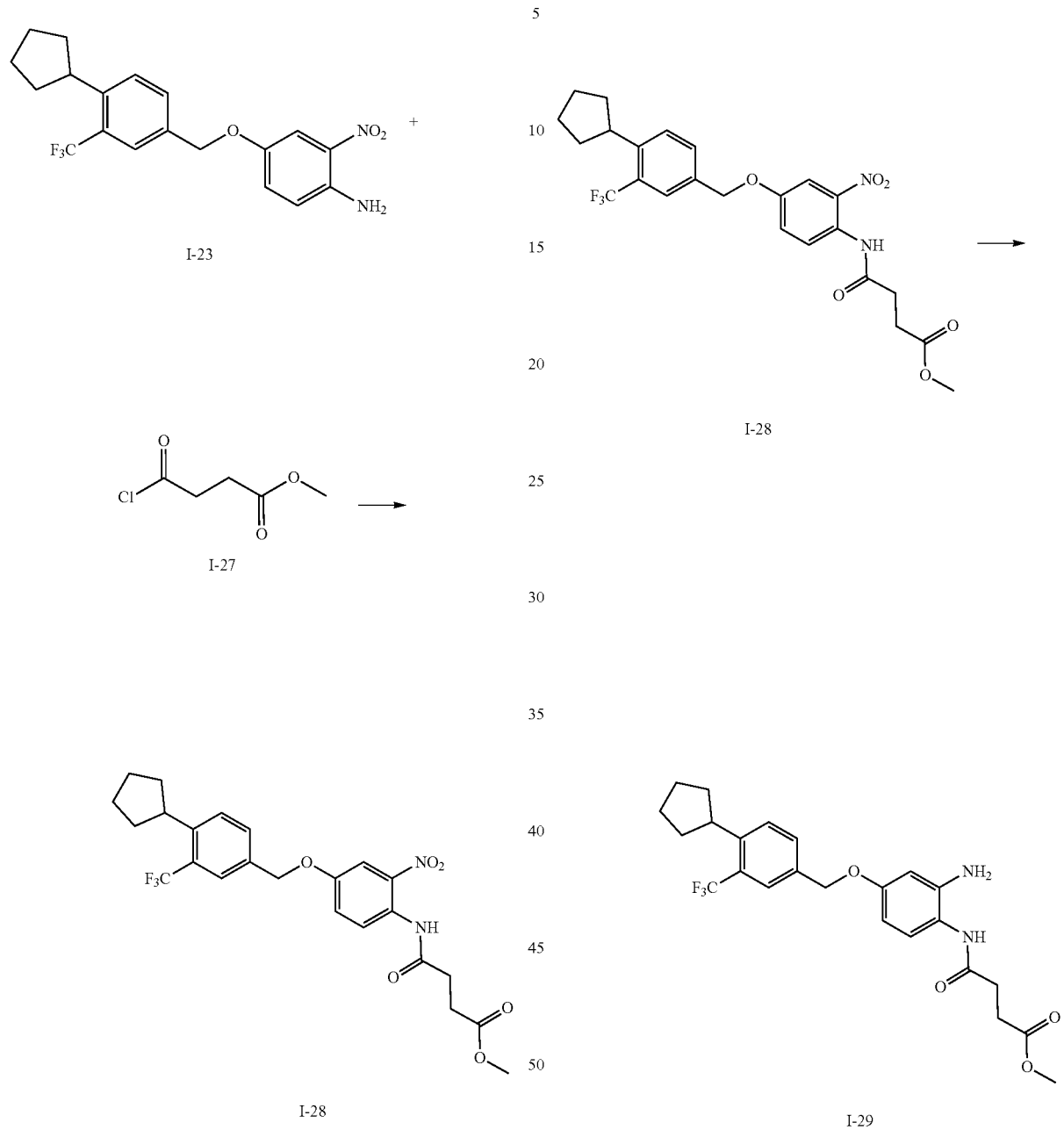

Intermediate I-23 (200 mg, 0.53 mmol) and N,N-dimethylethylamine (136 mg, 0.05 mmol) were dissolved in tetrahydrofuran (4 mL), and intermediate I-27 (104 mg, dissolved in 1 mL tetrahydrofuran) was added at 0° C. The reaction solution was stirred at room temperature overnight. The solvent was removed under reduced pressure, 50 mL of water was added to the residue, and the mixture was extracted with ethyl acetate (15 mL×2). The combined organic layers were washed with saturated saline, dried with anhydrous sodium sulfate, then filtered and concentrated to obtain a residue. The residue was purified by silica gel chromatography to obtain intermediate I-28.

LC-MS (ESI) [M+Na]$^+$ 517.1.

Intermediate I-28 (120 mg, 0.24 mmol) was dissolved in ethanol (5 mL), Raney nickel (10 mg) was added and the reaction solution was stirred for one hour at room temperature under hydrogen atmosphere. The reaction solution was filtered, and the concentrated filtrate was diluted with 30 mL of water and extracted with ethyl acetate (10 mL×2). The combined organic layers were washed with saturated saline, dried with anhydrous sodium sulfate, filtered and concentrated to obtain a crude product of intermediate I-29. The crude product was directly used in the next reaction without purification.

LC-MS (ESI) [M+H]$^+$ 465.3.

Reference Embodiment 29: Preparation of Intermediate I-30

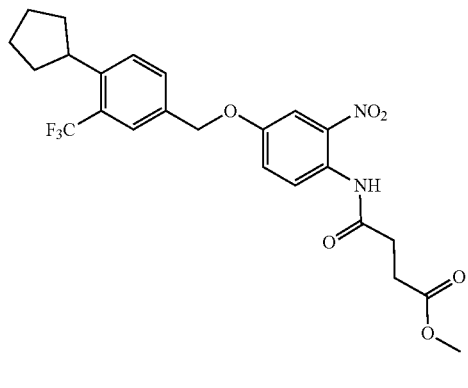

I-29

Intermediate I-29 (60 mg) was dissolved in acetic acid (3 mL) and stirred at 60° C. overnight. The solvent was removed under reduced pressure, and the residue was diluted with 20 mL of water and extracted with ethyl acetate (10 mL×2). The combined organic layers were washed with saturated sodium bicarbonate aqueous solution and saturated saline, dried with anhydrous sodium sulfate, filtered and concentrated to obtain residue. The residue was purified by silica gel chromatography to obtain intermediate I-30.

LC-MS (ESI) [M+H]$^+$ 447.1.

Reference Embodiment 30: Preparation of Intermediate I-31

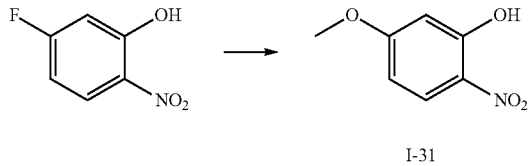

I-31

5-Fluoro-2-nitrophenol (8.0 g, 50.9 mmol) was dissolved in dimethyl sulfoxide (100 mL), and sodium methoxide (11.0 g, 204 mmol) was added. The reaction solution was stirred at 70° C. for 3 hours. The reaction solution was quenched with 300 mL of saturated ammonium chloride aqueous solution, and 100 mL of water and 200 mL of ethyl acetate were added. The organic layer was separated by extraction, and the aqueous layer was continuously extracted with ethyl acetate (200 mL×2). The combined organic layers were washed with saturated saline, dried with anhydrous sodium sulfate, then filtered and concentrated to obtain a residue. The residue was purified by silica gel chromatography to obtain intermediate I-31.

LC-MS (ESI) [M−H]$^−$168.2.

$^1$H NMR (400 MHz, DMSO-d$_6$) δ 10.92 (s, 1H), 7.94 (d, J=9.3 Hz, 1H), 6.61-6.53 (m, 2H), 3.81 (s, 3H).

Reference Embodiment 31: Preparation of Intermediate I-32

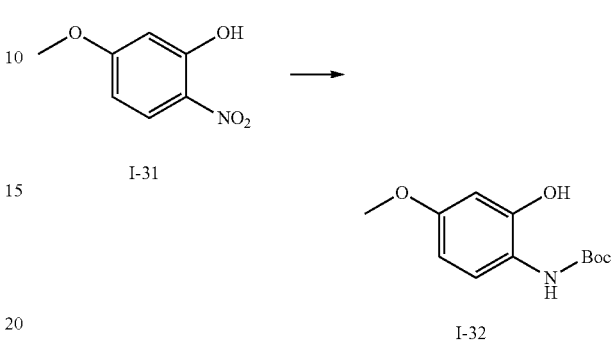

Intermediate I-31 (6.3 g, 37.3 mmol) was dissolved in 100 mL of methanol, palladium carbon (1.5 g, w/w=10%) and di-tert-butyl dicarbonate (20.3 g, 93.2 mmol) were added, and the mixture was stirred at room temperature for 16 hours in hydrogen atmosphere. The reaction solution was filtered, and the filtrate was concentrated under reduced pressure to obtain a residue. The residue was purified by silica gel chromatography to obtain intermediate I-32.

LC-MS (ESI) [M+H-56]$^+$184.0.

$^1$H NMR (400 MHz, DMSO-d$_6$) δ 9.58 (s, 1H), 7.71 (s, 1H), 7.28 (d, J=7.9 Hz, 1H), 6.37 (d, J=2.8 Hz, 1H), 6.30 (dd, J=8.8, 2.8 Hz, 1H), 3.63 (s, 3H), 1.40 (s, 9H).

Reference Embodiment 32: Preparation of Intermediate I-33

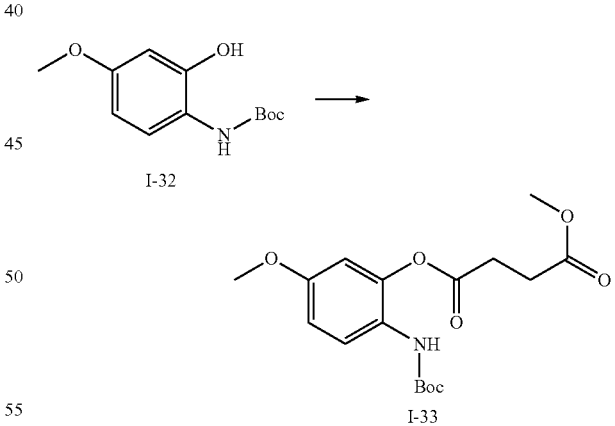

Intermediate I-32 (200 mg, 0.84 mmol) was dissolved in 15 mL of N,N-dimethylformamide and 4-methoxy-4-oxobutyric acid (133 mg, 1.01 mmol), 4-dimethylaminopyridine (133 mg, 1.09 mmol) and 1-(3-dimethylaminopropyl)-3-ethylcarbodiimide hydrochloride (209 mg, 1.09 mmol) were added. The reaction solution was stirred at room temperature for 16 hours. 50 mL of water and 30 mL of ethyl acetate were added to the reaction solution, and the organic phase was separated by extraction. The aqueous phase was continuously extracted with ethyl acetate (30 mL×2). The combined organic layers were washed with saturated saline, dried with anhydrous sodium sulfate, then filtered and concentrated to obtain a residue. The residue was purified by silica gel chromatography to obtain intermediate I-33.

LC-MS (ESI) [M+Na]⁺376.0.

$^1$H NMR (400 MHz, DMSO-d$_6$) δ 8.45 (s, 1H), 7.45 (d, J=8.9 Hz, 1H), 6.75 (dd, J=9.0, 2.9 Hz, 1H), 6.63 (d, J=2.9 Hz, 1H), 3.68 (s, 3H), 3.60 (s, 3H), 2.80 (t, J=6.8 Hz, 2H), 2.64 (t, J=6.8 Hz, 2H), 1.40 (s, 9H).

Reference Embodiment 33: Preparation of Intermediate I-34

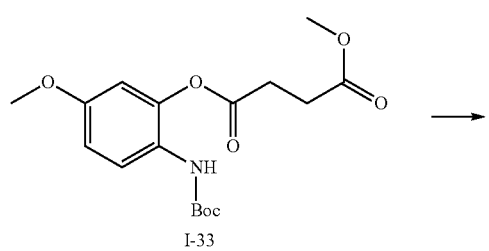

4-Methylbenzenesulfonic acid (monohydrate, 206.2 mg, 1.08 mmol) was added to a solution of intermediate I-33 (1.9 g, 5.38 mmol) in toluene (30 mL), and the reaction solution was stirred at 110° C. for 16 hours. After cooling to room temperature, 100 mL of ethyl acetate was added to the reaction solution, the organic phase was washed with saturated saline, dried with anhydrous sodium sulfate, filtered and concentrated to obtain a residue. The residue was purified by silica gel chromatography to obtain intermediate I-34.

LC-MS (ESI) [M+H]⁺ 236.1.

$^1$H NMR (400 MHz, DMSO-d$_6$) δ 7.51 (d, J=8.7 Hz, 1H), 7.26 (d, J=2.4 Hz, 1H), 6.89 (dd, J=8.7, 2.4 Hz, 1H), 3.77 (s, 3H), 3.58 (s, 3H), 3.12 (t, J=7.0 Hz, 2H), 2.85 (t, J=7.0 Hz, 2H).

Reference Embodiment 34: Preparation of Intermediate I-35

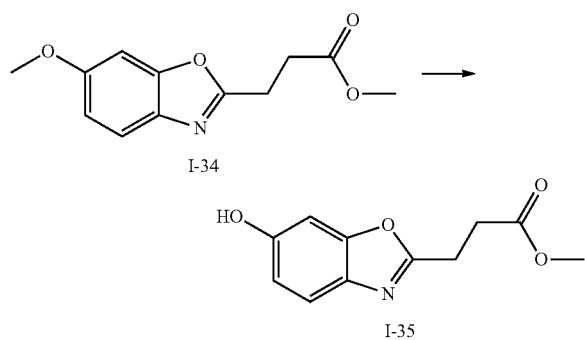

A solution of intermediate I-34 (450 mg, 1.91 mmol) in dichloromethane (10 mL) was slowly added dropwise to a solution containing boron tribromide (1 M dichloromethane solution, 3.83 mL, 3.83 mmol) in dichloromethane (20 mL) at 0° C. After the dropwise addition, the reaction solution was stirred at 0° C. for 5 hours. The reaction solution was quenched with 100 mL of water, and 30 mL of ethyl acetate was added, and the organic layer was separated by extraction. The aqueous layer was continuously extracted with ethyl acetate (30 mL×2). The combined organic layers were washed with saturated saline, dried with anhydrous sodium sulfate, then filtered and concentrated to obtain a residue. The residue was purified by silica gel chromatography to obtain intermediate I-35.

LC-MS (ESI) [M+H]⁺ 222.1.

$^1$H NMR (400 MHz, DMSO-d$_6$) δ 9.67 (s, 1H), 7.42 (d, J=8.6 Hz, 1H), 6.97 (d, J=2.2 Hz, 1H), 6.76 (dd, J=8.6, 2.3 Hz, 1H), 3.61 (s, 3H), 3.12 (t, J=7.0 Hz, 2H), 2.86 (t, J=7.0 Hz, 2H).

Reference Embodiment 35: Preparation of Intermediate I-36

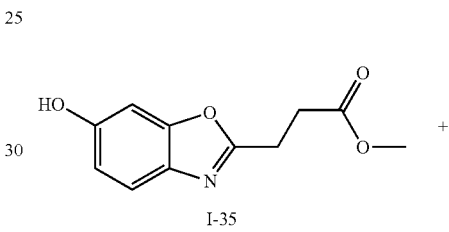

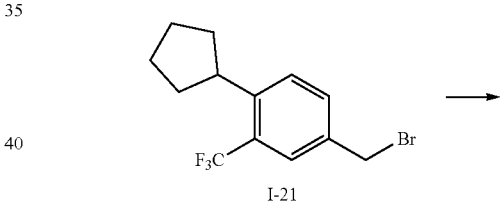

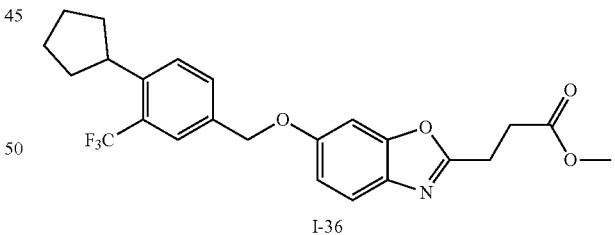

Intermediate I-35 (150 mg, 0.68 mmol) was dissolved in acetonitrile (30 mL), intermediate I-21 (313.1 mg, 1.02 mmol) and cesium carbonate (665.0 mg, 2.04 mmol) were added, and the reaction solution was stirred at room temperature for 16 hours. The reaction solution was quenched with 100 mL of water, and extracted with ethyl acetate (30 mL×3). The combined organic layers were washed with saturated saline, dried with anhydrous sodium sulfate, then filtered and concentrated to obtain a residue. The residue was purified by silica gel chromatography to obtain intermediate I-36.

LC-MS (ESI) [M+H]⁺ 448.3.

Reference Embodiment 36: Preparation of Intermediate I-37

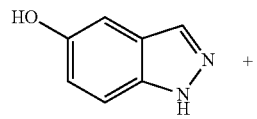

+

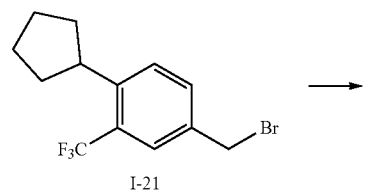

→

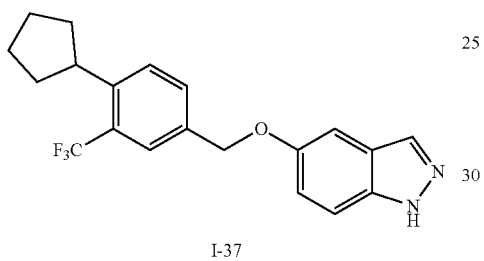

Potassium carbonate (2.06 g, 14.91 mmol) was added to a solution of 1-hydro-indazole-5-ol (1 g, 7.46 mmol) and intermediate I-21 (2.52 g, 8.20 mmol) in acetonitrile (25 mL), and the mixture was stirred at 0° C. for 2 hours and then stirred at 25° C. for 10 hours. The reaction solution was diluted with 200 mL of water and extracted with ethyl acetate (300 mL×2). The combined organic layers were washed with saturated saline, dried with anhydrous sodium sulfate, then filtered and concentrated to obtain a residue. The residue was purified by silica gel chromatography to obtain intermediate I-37.

$^1$H NMR (400 MHz, DMSO-$d_6$) δ 12.95 (s, 1H), 7.95 (s, 1H), 7.77-7.70 (m, 2H), 7.65 (d, J=8.0 Hz, 1H), 7.47 (d, J=9.0 Hz, 1H), 7.28 (d, J=2.1 Hz, 1H), 7.09 (dd, J=9.0, 2.3 Hz, 1H), 5.17 (s, 2H), 3.30-3.19 (m, 1H), 2.03-1.95 (m, 2H), 1.89-1.80 (m, 2H), 1.71-1.55 (m, 4H).

Reference Embodiment 37: Preparation of Intermediate I-38 and Intermediate I-39

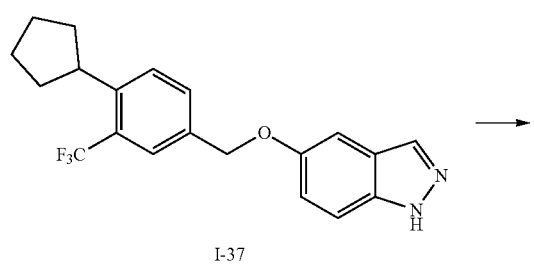

→

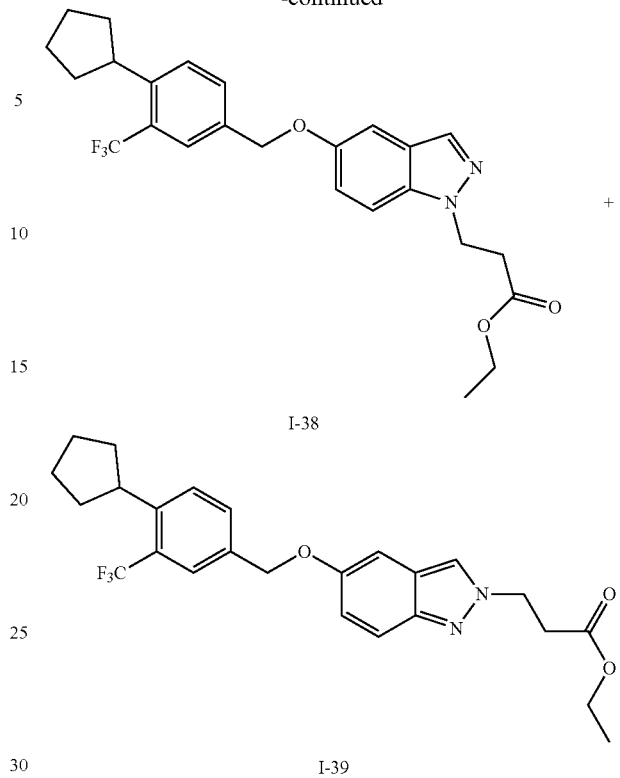

Potassium carbonate (575.24 mg, 4.16 mmol) was added to a solution of intermediate I-37 (500 mg, 1.39 mmol) and ethyl 3-bromopropionate (376.75 mg, 2.08 mmol) in N,N-dimethylformamide (10 mL), and the mixture was stirred at 80° C. for 10 hours. After cooling to room temperature, 230 mL of saturated saline was added to dilute, and the mixture was extracted with ethyl acetate (200 mL×2). The combined organic layers were dried with anhydrous sodium sulfate, then filtered and concentrated to obtain a residue. The residue was purified by silica gel chromatography to obtain intermediate I-38 and intermediate I-39.

Intermediate I-38

$^1$H NMR (400 MHz, CDCl$_3$) δ 7.91 (d, J=0.5 Hz, 1H), 7.69 (s, 1H), 7.61-7.56 (m, 1H), 7.49 (d, J=8.1 Hz, 1H), 7.42 (d, J=9.0 Hz, 1H), 7.16 (dd, J=9.0, 2.3 Hz, 1H), 7.14-7.11 (m, 1H), 5.08 (s, 2H), 4.65 (t, J=6.8 Hz, 2H), 4.09 (q, J=7.2 Hz, 2H), 3.43-3.33 (m, 1H), 2.96 (t, J=6.8 Hz, 2H), 2.14-2.05 (m, 2H), 1.90-1.82 (m, 2H), 1.78-1.69 (m, 2H), 1.65-1.56 (m, 2H), 1.17 (t, J=7.1 Hz, 3H).

Reference Embodiment 38: Preparation of Intermediate I-40

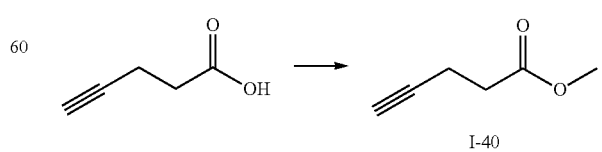

4-Alkynylvaleric acid (2.5 g, 25.5 mmol) and potassium carbonate (14.07 g, 102 mmol) were suspended in 20 mL of N,N-dimethylformamide, and methyl iodide (10.8 g, 76.5 mmol) was added, and the mixture was stirred at room temperature for 10 hours. The reaction solution was poured into 100 mL of water and extracted with ethyl acetate (50 mL×3). The combined organic layers were washed with saturated saline, dried with anhydrous sodium sulfate, then filtered and concentrated to obtain a crude product of intermediate I-40. The crude product was directly used in the next reaction.

$^1$H NMR (400 MHz, DMSO-d$_6$) δ 3.61 (s, 3H), 2.78 (t, J=2.6 Hz, 1H), 2.54-2.50 (m, 2H), 2.43-2.38 (m, 2H).

Reference Embodiment 39: Preparation of Intermediate I-41

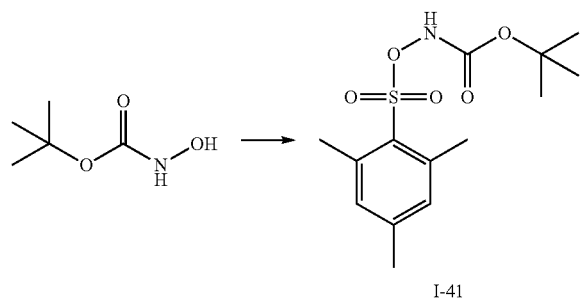

At 0° C., triethylamine (4.6 g, 45.5 mmol) and 2,4,6-trimethylbenzenesulfonyl chloride (9.95 g, 45.6 mmol) were added to a solution of N-tert-butoxy carbonyl hydroxylamine (6.1 g, 45.8 mmol) in N,N-dimethylformamide (60 mL). After stirring at 0° C. for one hour, the reaction solution was poured into 300 mL of water and extracted with dichloromethane (100 mL×3). The combined organic layers were washed with saturated saline, dried with anhydrous sodium sulfate, then filtered and concentrated to obtain a residue. The residue was purified by silica gel chromatography to obtain intermediate I-41.

LC-MS (ESI) [M−H]$^−$ 314.1.

Reference Embodiment 40: Preparation of Intermediate I-42

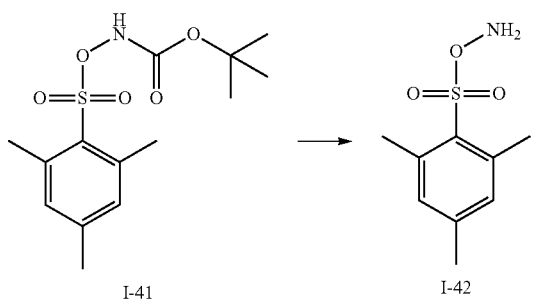

Intermediate I-41 (1.0 g, 3.17 mmol) was added to 6 mL of trifluoroacetic acid at 0° C. After continuously stirring at 0° C. for one hour, the reaction solution was poured into 100 mL of water and filtered. The solid was washed with cold water (10 mL) and dissolved in cold ether solution (30 mL). The organic layer was washed with water, dried with anhydrous sodium sulfate, then filtered and concentrated to obtain intermediate I-42, the crude product of which was directly used in the next reaction.

Reference Embodiment 41: Preparation of Intermediate I-43

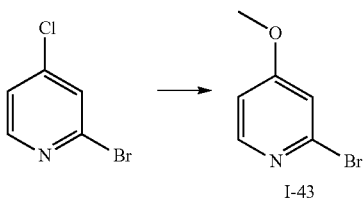

Sodium methoxide (1.7 g, 31.5 mmol) was added to a solution of 2-bromo-4-chloropyridine (5.0 g, 26.0 mmol) in dimethyl sulfoxide (50 mL), and the mixture was stirred at 120° C. for 10 hours. After cooling to room temperature, the reaction solution was poured into 200 mL of water and extracted with ethyl acetate (40 mL×3). The combined organic layers were washed with saturated saline, dried with anhydrous sodium sulfate, then filtered and concentrated to obtain a residue. The residue was purified by silica gel chromatography to obtain intermediate I-43.

LC-MS (ESI) [M+H]$^+$ 187.9.

Reference Embodiment 42: Preparation of Intermediate I-44

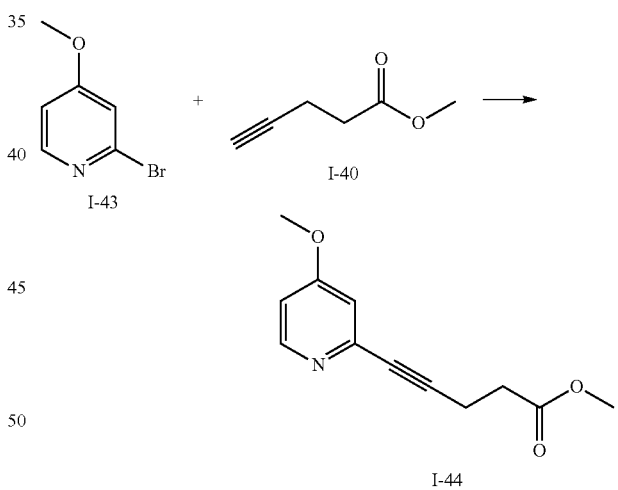

Intermediate I-43 (1.0 g, 5.3 mmol) was dissolved in 30 mL of tetrahydrofuran, and intermediate I-40 (1.0 g), bis(triphenylphosphine)palladium dichloride (371 mg, 0.53 mmol), cuprous iodide (100 mg, 0.53 mmol) and N,N-dimethylethylamine (2.05 g, 15.9 mmol) were added sequentially, the mixture was stirred at room temperature for 3 hours under the protection of argon, and then the reaction solution was poured into 50 mL of water and extracted with ethyl acetate (20 mL×3). The combined organic layers were washed with saturated saline, dried with anhydrous sodium sulfate, then filtered and concentrated to obtain a residue. The residue was purified by silica gel chromatography to obtain intermediate I-44.

¹H NMR (400 MHz, DMSO-d₆) δ 8.31 (d, J=5.8 Hz, 1H), 7.00 (d, J=2.5 Hz, 1H), 6.94 (dd, J=5.8, 2.6 Hz, 1H), 3.82 (s, 3H), 3.64 (s, 3H), 2.73-2.59 (m, 4H).

Reference Embodiment 43: Preparation of Intermediate I-45

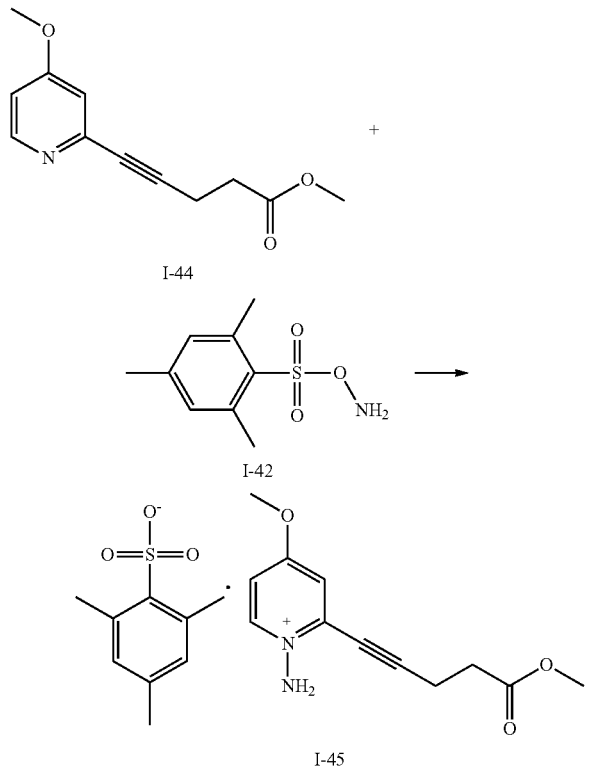

Intermediate I-42 (600 mg) was added to a solution of intermediate I-44 (400 mg, 1.8 mmol) (at 0° C.) in dichloromethane (10 mL), and the reaction solution was stirred at 0° C. for 3 hours. The reaction solution was concentrated to obtain intermediate I-45, and the crude product of which was directly used in the next reaction without purification.

LC-MS (ESI) [M+H]⁺ 235.1.

Reference Embodiment 44: Preparation of Intermediate I-46

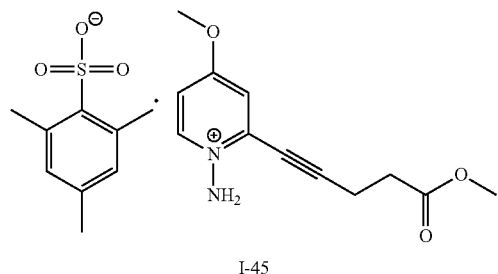

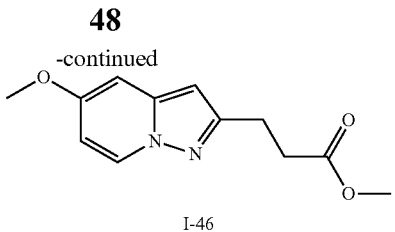

Intermediate I-45 (410 mg) was dissolved in a mixed solution of tetrahydrofuran/N,N-dimethylformamide (4 mL, 3:1), and potassium tert-butoxide (224 mg, 2 mmol) was added. The reaction solution was stirred at room temperature for one hour, then the reaction solution was diluted with 10 mL of water and extracted with ethyl acetate (30 mL×2). The combined organic layers were washed with saturated saline, dried with anhydrous sodium sulfate, then filtered and concentrated to obtain a residue. The residue was purified by silica gel chromatography to obtain intermediate I-46.

¹H NMR (400 MHz, CDCl₃) δ 8.17 (d, J=7.5 Hz, 1H), 6.63 (d, J=2.6 Hz, 1H), 6.37 (dd, J=IN 2.7 Hz, 1H), 6.12 (s, 1H), 3.82 (s, 3H), 3.69 (s, 3H), 3.10 (t, J=7.6 Hz, 2H), 2.77 (t, J=7.6 Hz, 2H).

Reference Embodiment 45: Preparation of Intermediate I-47

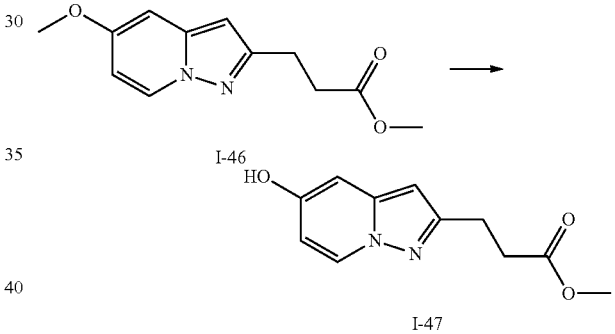

Aluminum trichloride (112.8 mg, 0.85 mmol) was added to a solution of intermediate I-46 (40.0 mg, 0.17 mmol) in 1,2-dichloroethane (5 mL), and the mixture was stirred at room temperature overnight. The reaction solution was diluted with 10 mL and extracted with dichloromethane (10 mL×2). The combined organic layers were washed with saturated saline, dried with anhydrous sodium sulfate, then filtered and concentrated to obtain a residue. The residue was purified by silica gel chromatography to obtain intermediate I-47.

LC-MS (ESI) [M+H]⁺ 221.2.

Reference Embodiment 46: Preparation of Intermediate I-48

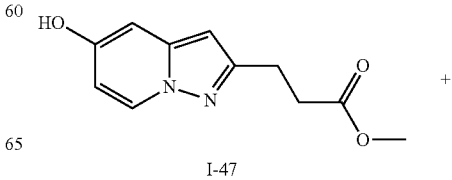

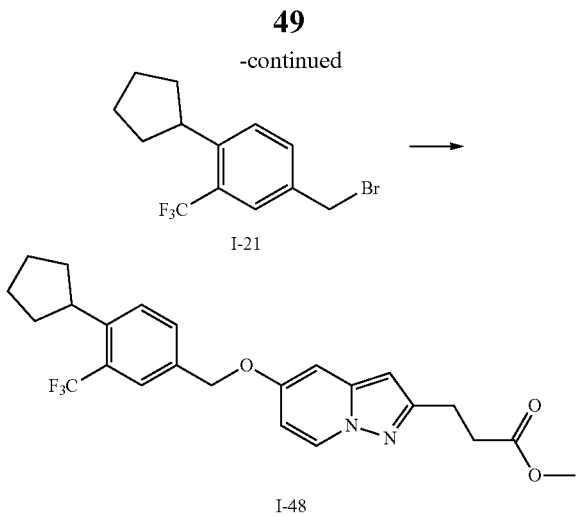

Intermediate I-47 (12.0 mg, 0.05 mmol) and intermediate I-21 (27.9 mg, 0.09 mmol) were dissolved in acetonitrile (10 mL), potassium carbonate (12.6 mg, 0.091 mmol) was added, and the mixture was stirred at 50° C. for 6 hours. The reaction solution was diluted with 20 mL of water and extracted with ethyl acetate (10 mL×2). The combined organic layers were washed with saturated saline, dried with anhydrous sodium sulfate, then filtered and concentrated to obtain intermediate I-48. The crude product of which was directly used in the next reaction without purification.

LC-MS (ESI) [M+H]$^+$ 447.3.

Reference Embodiment 47: Preparation of Intermediate I-49

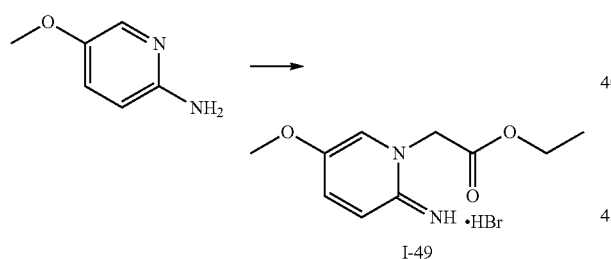

5-Methoxypyridin-2-amine (3.5 g, 28.19 mmol) and ethyl bromoacetate (28.25 g, 169.16 mmol) were mixed and stirred at 25° C. for 8 hours. The mixture was filtered and the obtained solid was washed with ether and dried to obtain a crude product of intermediate I-49, the crude product of which was directly used in the next reaction without purification.

Reference Embodiment 48: Preparation of Intermediate I-50

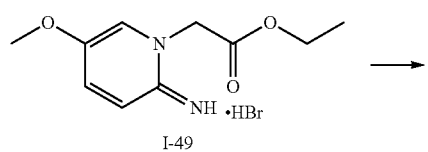

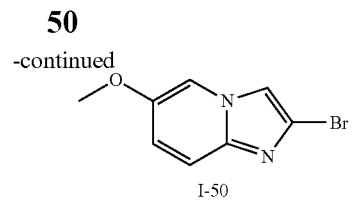

Intermediate I-49 (8.0 g) was added to phosphorus oxybromide (21.51 g, 75.01 mmol) and stirred at 120° C. for 2 hours (externally connected with calcium sulfate drying tube). After cooling to room temperature, 400 mL of ice water was added and the pH of the reaction solution was adjusted to 7-8 with ammonium hydroxide at 0° C. Then the mixture was extracted with chloroform (500 mL×2). The combined organic layers were washed with saturated saline, dried with anhydrous sodium sulfate, then filtered and concentrated to obtain a residue, the residue was purified by silica gel chromatography to obtain intermediate I-50.

LC-MS (ESI) [M+H]$^+$ 227.0

$^1$H NMR (400 MHz, DMSO-d$_6$) δ 8.22 (d, J=2.2 Hz, 1H), 7.97 (s, 1H), 7.46 (d, J=9.7 Hz, 1H), 7.09 (dd, J=9.7, 2.4 Hz, 1H), 3.34 (s, 3H).

Reference Embodiment 49: Preparation of Intermediate I-51

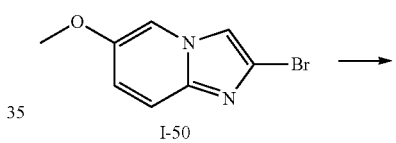

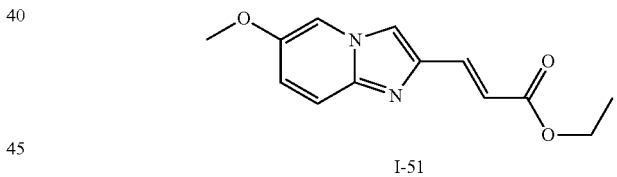

[1,1'-Bis(diphenylphosphino)ferrocene] palladium(II)dichloride dichloromethane complex (179.52 mg, 0.22 mmol) was added to a mixed solution of intermediate I-50 (500 mg, 2.2 mmol), (E)-(3-ethoxy-3-oxopropyl-1-en-1-yl)-boronic acid pinacol ester (1.99 g, 8.81 mmol), sodium carbonate (816.87 mg, 7.71 mmol) in water (3 mL)/dioxane (12 mL). The reaction solution was stirred at 110° C. for 8 hours. After cooling to room temperature, 300 mL of water was added to the reaction solution, and the mixture was extracted with ethyl acetate (250 mL×2). The combined organic layers were washed with saturated saline, dried with anhydrous sodium sulfate, then filtered and concentrated to obtain a residue, the residue was purified by silica gel chromatography to obtain intermediate I-51.

LC-MS (ESI) [M+H]$^+$ 247.1.

$^1$H NMR (400 MHz, MeOH-d$_4$) δ 8.08 (d, J=2.0 Hz, 1H), 8.04 (s, 1H), 7.69 (d, J=15.8 Hz, 1H), 7.43 (d, J=9.8 Hz, 1H), 7.15 (dd, J=9.8, 2.4 Hz, 1H), 6.67 (d, J=15.8 Hz, 1H), 4.27 (q, J=7.1 Hz, 2H), 3.91-3.83 (s, 3H), 1.35 (t, J=7.1 Hz, 3H).

Reference Embodiment 50: Preparation of Intermediate I-52

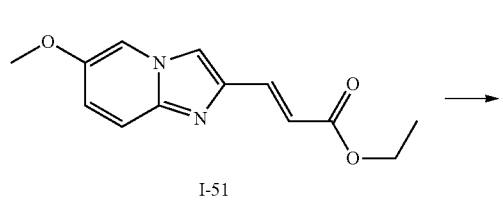

Palladium carbon (20 mg, w/w=10%) was added to a solution of intermediate I-51 (220 mg, 0.893 mmol) in ethyl acetate (5 mL) under hydrogen atmosphere, and the mixture was stirred at 25° C. for 4 hours. The reaction solution was filtered, and the filtrate was concentrated to obtain intermediate I-52. The intermediate was directly used in the next reaction without purification.

LC-MS (ESI) $[M+H]^+$ 249.1.

Reference Embodiment 51: Preparation of Intermediate I-53

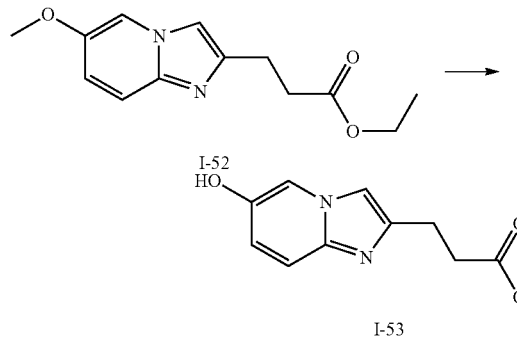

Boron tribromide (1 M, dichloromethane solution, 4.11 mL) was slowly added dropwise to a solution of intermediate I-52 (170 mg, 0.685 mmol) in dichloromethane (5 mL) at 0° C. After the dropwise addition, the reaction solution was stirred at 25° C. for 2 hours under the protection of nitrogen. The reaction solution was quenched by adding methanol (3 mL) and water (10 mL), and extracted with dichloromethane (30 mL). The organic layer was washed with saturated saline, dried with anhydrous sodium sulfate, then filtered and concentrated to obtain intermediate I-53. The intermediate was directly used in the next reaction without purification.

LC-MS (ESI) $[M+H]^+$ 235.1.

Reference Embodiment 52: Preparation of Intermediate I-54

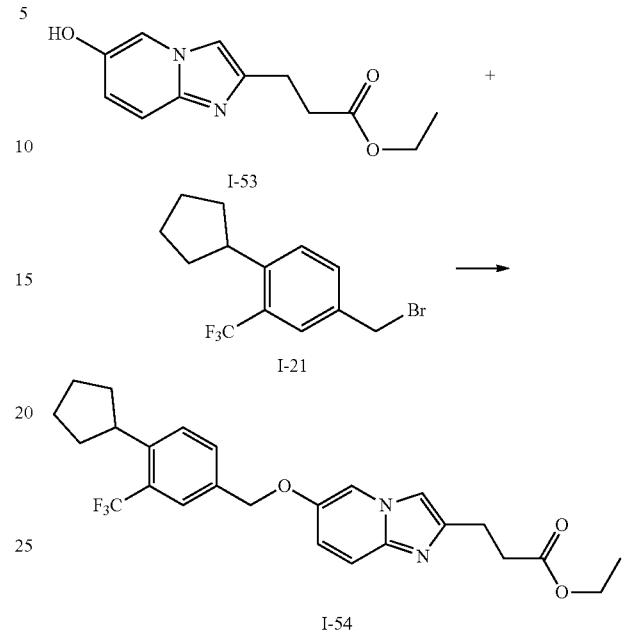

Intermediate I-21 (127.19 mg, 0.414 mmol) and potassium carbonate (171.68 mg, 1.24 mmol) were added to a solution of intermediate I-53 (97 mg, 0.414 mmol) in acetonitrile (5 mL). The reaction solution was stirred at 80° C. for 4 hours. After cooling to room temperature, 8 mL of water was added to the reaction solution, and the mixture was extracted with ethyl acetate (15 mL). The organic layer was washed with saturated saline, dried with anhydrous sodium sulfate, then filtered and concentrated to obtain intermediate I-54. The intermediate was directly used in the next reaction without purification.

LC-MS (ESI) $[M+H]^+$ 461.2.

Reference Embodiment 53: Preparation of Intermediate I-55

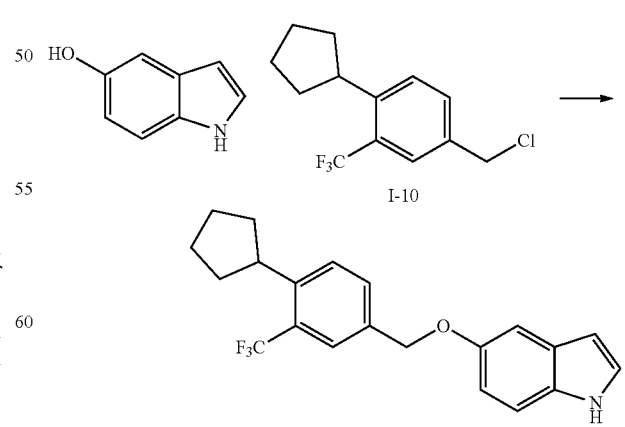

5-Hydroxyindole (266 mg, 2 mmol) was dissolved in acetonitrile (5 mL), and cesium carbonate (1.3 g, 4 mmol) and intermediate I-10 (789 mg, 3 mmol) were added successively. The reaction solution was stirred at room temperature for 3 hours. The reaction solution was filtered, and the solid was washed with ethyl acetate (20 mL), and the filtrate was evaporated to obtain a residue, the residue was purified by silica gel chromatography to obtain intermediate I-55.

LC-MS (ESI) [M+H]+ 360.1.

Reference Embodiment 54: Preparation of Intermediate I-56

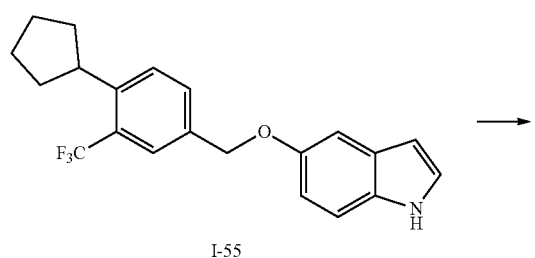

I-55

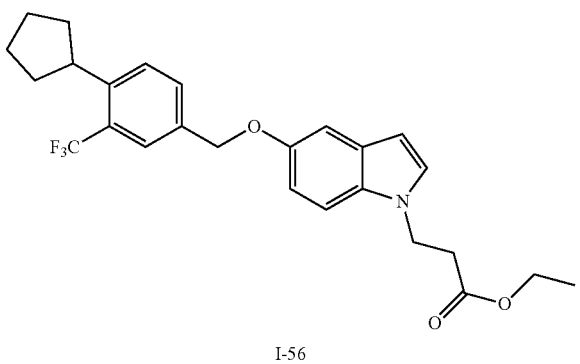

I-56

Sodium hydride (80 mg, 2 mmol, 60% mass fraction) was suspended in N,N-dimethylformamide (4 mL), and a solution of intermediate I-55 (359 mg, 1 mmol) in N,N-dimethylformamide (2 mL) was added under the protection of nitrogen at 0° C. The reaction solution was stirred at 0° C. for one hour, then ethyl 3-bromopropionate (272 mg, 1.5 mmol) was added dropwise, and continuously stirred for 2 hours. The reaction solution was quenched with water (10 mL) and extracted with ethyl acetate (10 mL). The organic layer was washed with water (3 mL×3) and saline (3 mL) successively, dried with anhydrous sodium sulfate, then filtered and concentrated to obtain a crude product of intermediate I-56, the crude product directly was used in the next reaction without purification.

LC-MS (ESI) [M+H]+ 460.3.

Reference Embodiment 55: Preparation of Intermediate I-57

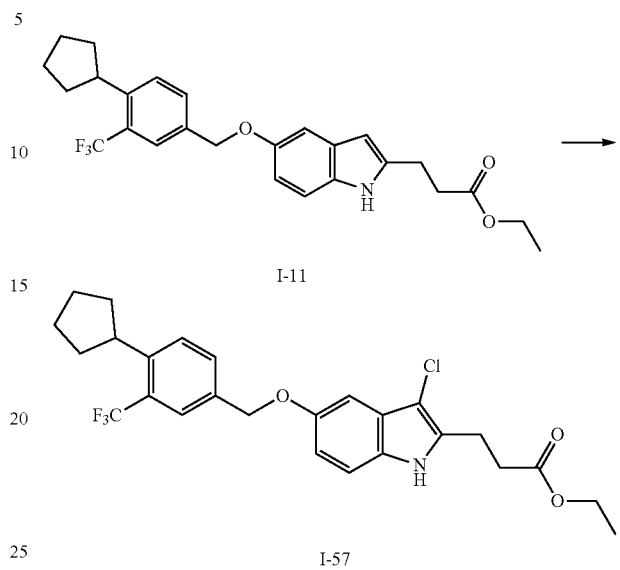

Intermediate I-11 (100 mg, 0.22 mmol) was dissolved in dichloromethane (9 mL) at room temperature. The reaction mixture was cooled to −70° C., and a solution of N-chlorosuccinimide (29 mg, 0.22 mmol) in dichloromethane (1 mL) was slowly added dropwise to the reaction system. After the dropwise addition, the reaction solution was stirred at −70° C. for half an hour, then raised to room temperature and the reaction was continuously stirred at room temperature for 2 hours. The reaction solution was concentrated under reduced pressure to remove the organic solvent to obtain a crude product. The crude product was purified by silica gel chromatography to obtain intermediate I-57.

LC-MS (ESI) [M+H]+ 494.1.

$^1$H NMR (400 MHz, CDCl$_3$) δ 8.69 (s, 1H), 7.71 (s, 1H), 7.61 (d, J=8.1 Hz, 1H), 7.49 (d, J=8.1 Hz, 1H), 7.20 (d, J=8.8 Hz, 1H), 7.06 (d, J=2.4 Hz, 1H), 6.90 (dd, J=8.8, 2.5 Hz, 1H), 5.10 (s, 2H), 4.18 (q, J=7.1 Hz, 2H), 3.43-3.33 (m, 1H), 3.12-3.05 (m, 2H), 2.75-2.67 (m, 2H), 2.14-2.05 (m, 2H), 1.91-1.82 (m, 2H), 1.78-1.69 (m, 2H), 1.67-1.58 (m, 2H), 1.26 (t, J=7.2 Hz, 3H).

Reference Embodiment 56: Preparation of Intermediate I-58

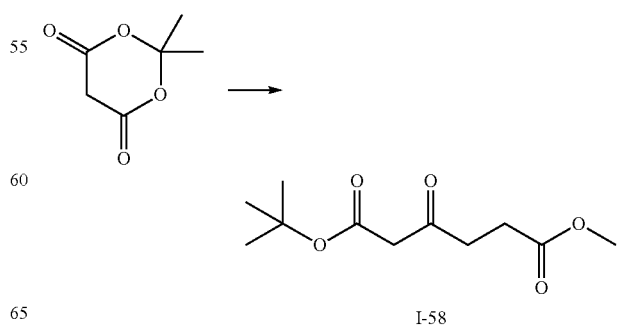

I-58

Cycloisopropylidene malonate (15.7 g, 109 mmol) was dissolved in dichloromethane (50 mL) at room temperature. After the reaction temperature was cooled to 0° C., pyridine (17.2 g, 218 mmol) was added. The internal temperature was controlled not more than 0° C., a solution of methyl succinyl chloride (18.0 g, 120 mmol) in dichloromethane (50 mL) was slowly added dropwise to the reaction system. After the dropwise addition, the reaction temperature was slowly raised to room temperature and the reaction was stirred at room temperature for 16 hours. Dilute hydrochloric acid (30 mL) was added to the reaction solution. The separated organic phase was washed with dilute hydrochloric acid (30 mL×2), saline (10 mL), dried with anhydrous sodium sulfate, filtered, and the filtrate was concentrated under reduced pressure to remove the organic solvent to obtain a residue. The crude product was dissolved in tert-butanol (100 mL) and the mixture was stirred at 80° C. for 16 hours. The reaction solution was cooled to room temperature and concentrated under reduced pressure to obtain a residue. The residue was purified by silica gel chromatography to obtain intermediate I-58.

$^1$H NMR (400 MHz, DMSO-d$_6$) δ 3.56 (s, 3H), 3.47 (s, 2H), 2.78 (t, J=6.5 Hz, 2H), 2.46 (t, J=9.1, 2.8 Hz, 2H), 1.39 (s, 9H).

Reference Embodiment 57: Preparation of Intermediate I-59

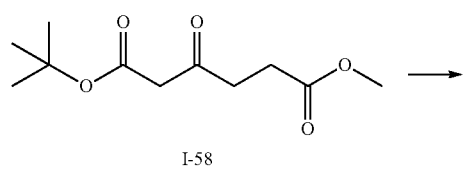

I-58

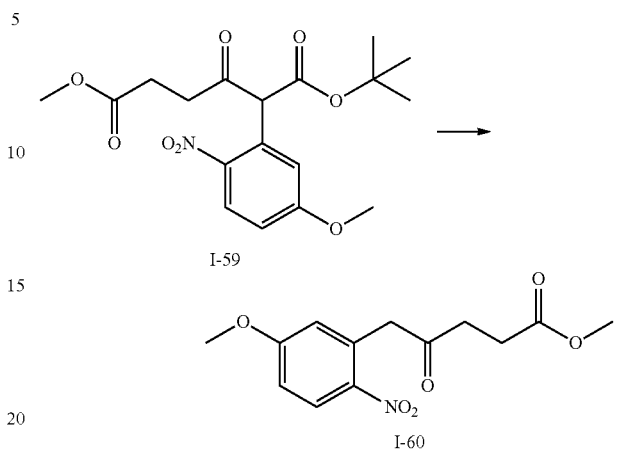

Sodium hydride (60% mass fraction, 6.22 g, 156 mmol) was added to N,N-dimethylformamide (100 mL) at room temperature. The mixture was cooled to 0° C. and 2-fluoro-4-methoxynitrobenzene (13.3 g, 77.8 mmol) and intermediate I-58 (19.7 g, 85.6 mmol) were added sequentially and slowly under the protection of argon. After the addition, the reaction mixture was raised to 60° C. and the reaction was stirred at 60° C. for 16 hours. The reaction mixture was cooled to 0° C., and saturated ammonium chloride aqueous solution (200 mL) and ethyl acetate (100 mL) were added for separation by extraction. The organic phase was separated and the aqueous phase was extracted with ethyl acetate (100 mL×2). The organic phases were combined, washed with saturated saline, dried with anhydrous sodium sulfate, filtered, and concentrated under reduced pressure to obtain a residue. The residue was purified by silica gel chromatography to obtain intermediate I-59.

LC-MS (ESI) [M−H]$^-$ 380.2.

Reference Embodiment 58: Preparation of Intermediate I-60

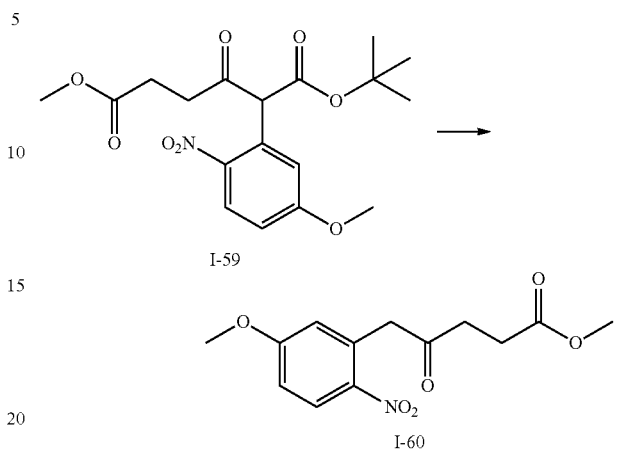

At room temperature, intermediate I-59 (31 g, 81.4 mmol) was dissolved in anhydrous dichloromethane (300 mL), and trifluoroacetic acid (108 mL) and triethylsilane (36.5 mL, 230 mmol) were added to the reaction solution successively. The reaction solution was stirred at room temperature for one hour and then diluted with dichloromethane (200 mL). Water (100 mL) was added for separation by extraction. The organic phase was washed with saturated saline, dried with anhydrous sodium sulfate, filtered, and concentrated under reduced pressure to remove the organic solvent to obtain a residue. The residue was purified by silica gel chromatography to obtain intermediate I-60.

LC-MS (ESI) [M+H]$^+$ 282.0.

Reference Embodiment 59: Preparation of Intermediate I-61

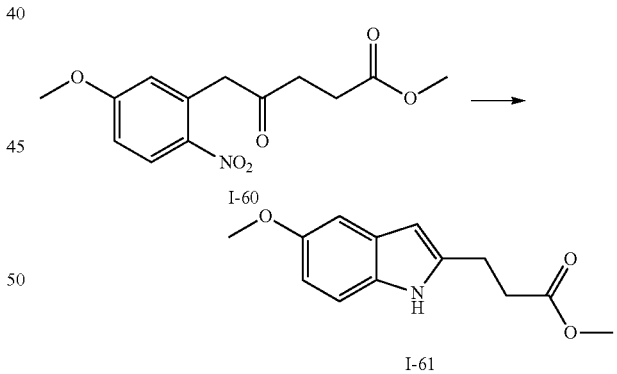

At room temperature, intermediate I-60 (13.1 g, 46.62 mmol) was dissolved in glacial acetic acid (150 mL), and reduced iron powder (15.7 g, 0.28 mol) was added. Under the protection of argon, the reaction mixture was stirred at 95° C. for 2 hours and then cooled to room temperature. Ethyl acetate (100 mL) was added to dilute, then the mixture was filtered, and the filtrate was washed with saturated saline (200 mL). The organic phase was dried with anhydrous sodium sulfate, filtered with suction, and the filtrate was concentrated under reduced pressure to obtain a residue. The residue was purified by silica gel chromatography to obtain intermediate I-61.

LC-MS (ESI) [M+H]$^+$ 234.2.

¹H NMR (400 MHz, DMSO-d₆) δ 10.74 (s, 1H), 7.15 (d, J=8.7 Hz, 1H), 6.91 (d, J=2.4 Hz, 1H), 6.63 (dd, J=8.7, 2.5 Hz, 1H), 6.05 (s, 1H), 3.71 (s, 3H), 3.60 (s, 3H), 2.95 (t, J=7.5 Hz, 2H), 2.73 (t, J=7.5 Hz, 2H).

Reference Embodiment 60: Preparation of Intermediate I-62

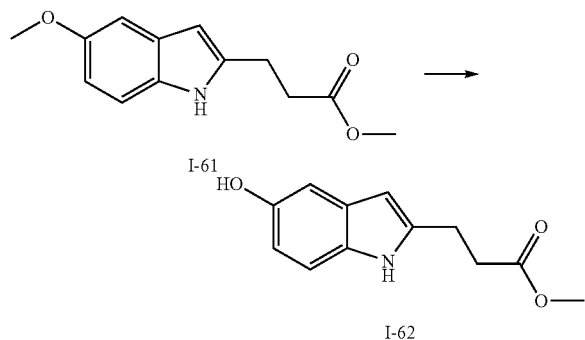

Intermediate I-61 (3.9 g, 16.7 mmol) was dissolved in 1,2-dichloroethane (200 mL) at room temperature, and aluminum trichloride (8.9 g, 66.9 mmol) was added. Under the protection of argon, the reaction solution was stirred and reacted at 55° C. for 16 hours. The reaction solution was cooled to 0° C., and water (300 mL) and dichloromethane (200 mL) were added for separation by extraction, the aqueous phase was extracted with dichloromethane (200 mL×2). The organic phases were combined, washed with saturated saline (100 mL), dried with anhydrous sodium sulfate, filtered, and concentrated under reduced pressure to obtain a residue. The residue was purified by silica gel chromatography to obtain intermediate I-62.

LC-MS (ESI) [M+H]⁺ 220.0.

¹H NMR (400 MHz, DMSO-d₆) δ 10.55 (s, 1H), 8.46 (s, 1H), 7.01 (d, J=8.5 Hz, 1H), 6.69 (d, J=2.3 Hz, 1H), 6.47 (dd, J=8.6, 2.3 Hz, 1H), 5.91 (d, J=1.1 Hz, 1H), 3.57 (s, 3H), 2.89 (t, J=7.6 Hz, 2H), 2.69 (t, J=7.6 Hz, 2H).

Reference Embodiment 61: Preparation of Intermediate I-63

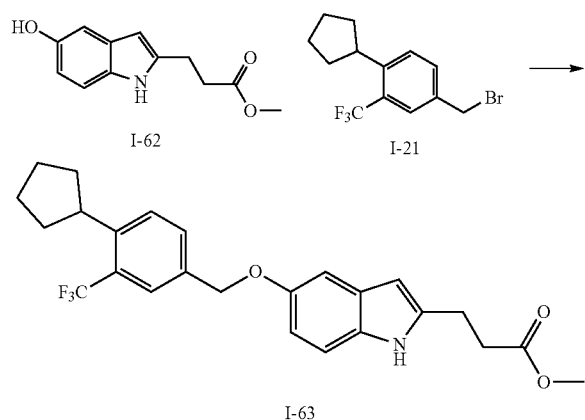

At room temperature, intermediate I-62 (3.0 g, 13.7 mmol) was dissolved in acetonitrile (150 mL). 1-21 (4.62 g, 15.1 mmol) and anhydrous potassium carbonate (5.67 g, 41.1 mmol) were added successively. The reaction solution was stirred and reacted at 45° C. for 16 hours. Water (250 mL) and ethyl acetate (200 mL) were added for separation by extraction, the aqueous phase was extracted with ethyl acetate (200 mL×2), then the organic phases were combined, washed with saturated saline (50 mL), dried with anhydrous sodium sulfate and filtered, and the filtrate was concentrated under reduced pressure to obtain a residue. The residue was purified by silica gel chromatography to obtain intermediate I-63.

LC-MS (ESI) [M+H]⁺ 446.1.

¹H NMR (400 MHz, DMSO-d₆) δ 10.76 (s, 1H), 7.67 (d, J=9.0 Hz, 2H), 7.59 (d, J=8.0 Hz, 1H), 7.14 (d, J=8.7 Hz, 1H), 6.99 (d, J=2.3 Hz, 1H), 6.70 (dd, J=8.7, 2.4 Hz, 1H), 6.03 (d, J=0.9 Hz, 1H), 5.08 (s, 2H), 3.58 (s, 3H), 3.25-3.18 (m, 1H), 2.92 (t, J=7.5 Hz, 2H), 2.70 (t, J=7.6 Hz, 2H), 1.97 (dd, J=7.4, 3.6 Hz, 2H), 1.81 (dd, J=7.4, 5.1 Hz, 2H), 1.70-1.52 (m, 4H).

Reference Embodiment 62: Preparation of Intermediate I-64

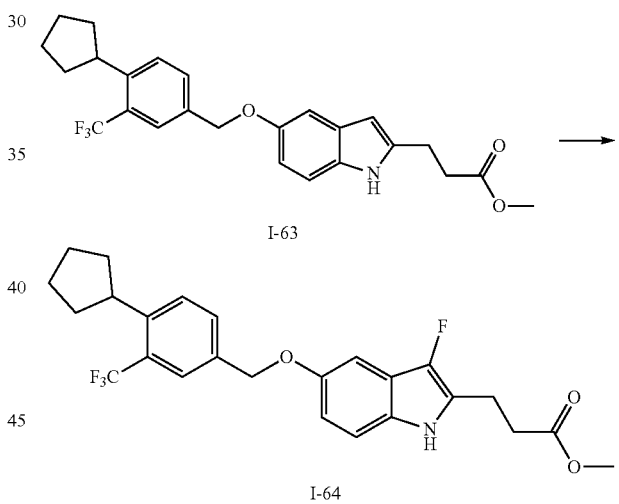

Intermediate I-63 (100 mg, 0.22 mmol) was dissolved in a mixed solvent of acetonitrile (3 mL) and saturated sodium carbonate aqueous solution (0.5 mL) under ice bath. 1-Chloromethyl-4-fluoro-1,4-diazoniabicyclo [2.2.2] octane bis (tetrafluoroborate) (selectfluor, 95 mg, 0.27 mmol) was added. The reaction solution was stirred under ice bath for 0.5 hour and then raised to room temperature, and the reaction was continuously stirred at room temperature for 3 hours. Water (20 mL) and ethyl acetate (5 mL) were added to the reaction solution for separation by extraction, and the aqueous phase was extracted with ethyl acetate (5 mL). The organic phases were combined, washed with saturated saline (5 mL), dried with anhydrous sodium sulfate, filtered, and the filtrate was concentrated under reduced pressure to obtain a residue. The residue was purified by silica gel chromatography to obtain intermediate I-64.

LC-MS (ESI) [M+H]⁺ 464.2.

Reference Embodiment 63: Preparation of Intermediate I-65

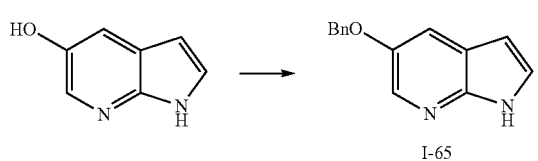

1H-pyrrolo[2,3-b]pyridin-5-ol (5.0 g, 37.3 mmol) was dissolved in N,N-dimethylformamide (60 mL). Benzyl bromide (9.6 g, 55.9 mmol) and potassium phosphate (15.8 g, 74.6 mmol) were added to the reaction system successively. The reaction mixture was stirred at room temperature for 4 hours. The reaction mixture was slowly poured into water (300 mL) and extracted with ethyl acetate (50 mL×4). The combined organic phases were washed with saturated saline, dried with anhydrous sodium sulfate, filtered, and concentrated under reduced pressure to remove the organic solvent to obtain a residue. The residue was purified by silica gel chromatography to obtain intermediate I-65.

$^1$H NMR (400 MHz, CDCl$_3$) δ 9.26 (s, 1H), 8.16 (d, J=2.6 Hz, 1H), 7.51 (d, J=2.6 Hz, 1H), 7.50-7.43 (m, 2H), 7.43-7.37 (m, 2H), 7.37-7.28 (m, 2H), 6.48-6.39 (m, 1H), 5.14 (s, 2H).

Reference Embodiment 64: Preparation of Intermediate I-66

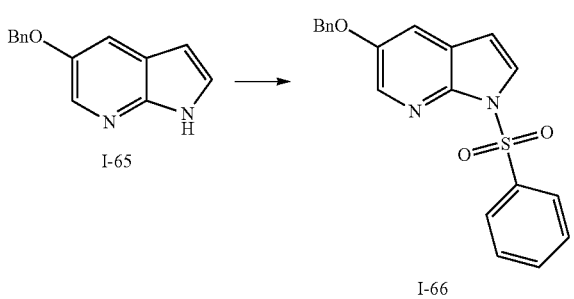

Intermediate I-65 (800 mg, 3.57 mmol) was dissolved in tetrahydrofuran (13 mL). The reaction system was cooled to 0° C., and sodium hydride (60%, 214 mg, 5.35 mmol) was added under the protection of nitrogen. After the addition, the reaction mixture was stirred at 0° C. for 20 minutes. At 0° C., benzenesulfonyl chloride (761 mg, 4.30 mmol) was added to the reaction system continuously. After the addition, the reaction mixture was stirred and reacted at 0° C. for 4 hours. The reaction mixture was slowly poured into water (30 mL) and extracted with ethyl acetate (10 mL×5), the combined organic phases were washed with saturated saline, dried with anhydrous sodium sulfate, filtered and concentrated under reduced pressure to remove the organic solvent to obtain a residue. The residue was purified by silica gel chromatography to obtain intermediate I-66.

LC-MS (ESI) [M+H]$^+$ 365.0.

Reference Embodiment 65: Preparation of Intermediate I-67

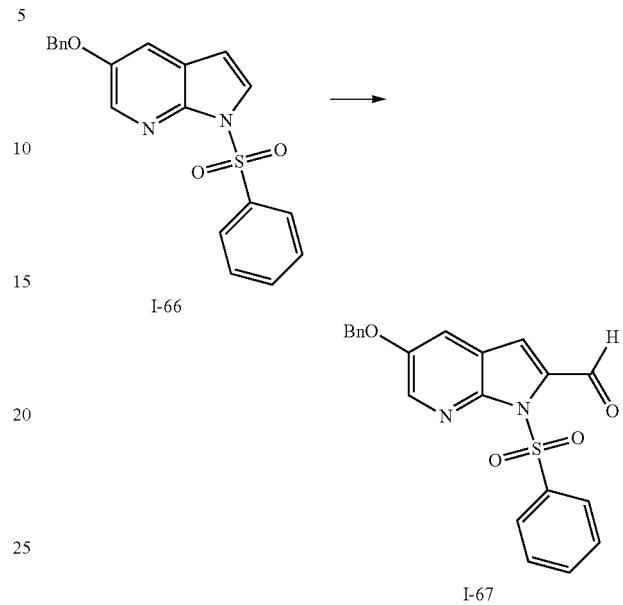

Intermediate I-66 (800 mg, 2.20 mmol) was dissolved in anhydrous tetrahydrofuran (10 mL). After the reaction solution was cooled to −60° C., a mixed solution of LDA in tetrahydrofuran/n-heptane/ethylbenzene (2.0 M, 1.65 mL, 3.3 mmol) was added dropwise under the protection of nitrogen. After the dropwise addition, the reaction mixture was continuously stirred at −60° C. for 30 minutes. DMF (241 mg, 3.3 mmol) was slowly added dropwise to the reaction system at −60° C. After the dropwise addition, the reaction mixture was continuously stirred at −60° C. for 2 hours. The reaction mixture was slowly poured into saturated NH$_4$Cl (100 mL), extracted with ethyl acetate (50 mL×4), the combined organic phases were washed with saturated saline, dried with anhydrous sodium sulfate, filtered, and concentrated under reduced pressure to remove the organic solvent to obtain a residue. The residue was purified only by silica gel chromatography to obtain intermediate I-67.

LC-MS (ESI) [M+H]$^+$ 393.0.

Reference Embodiment 66: Preparation of Intermediate I-68

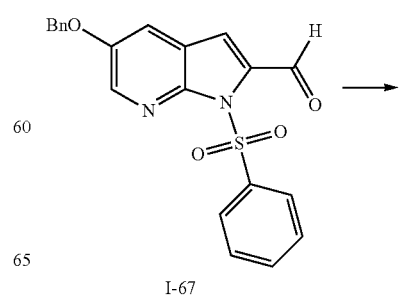

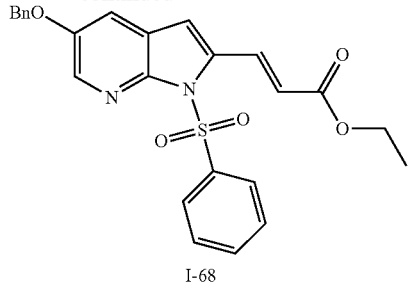

I-68

Intermediate I-67 (500 mg, 1.27 mmol) was dissolved in tetrahydrofuran (10 mL), and ethoxymethylene triphenylphosphine (665 mg, 1.91 mmol) was added at 15° C. The reaction mixture was stirred at 50° C. for 3 hours. The reaction mixture was purified by silica gel chromatography to obtain intermediate I-68.

LC-MS (ESI) [M+H]$^+$ 463.1.

Reference Embodiment 67: Preparation of Intermediate I-69

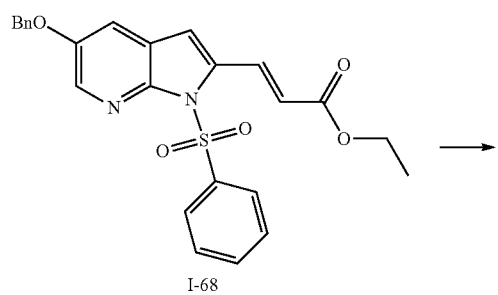

I-68

↓

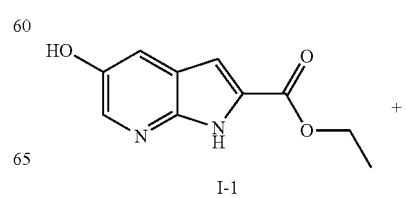

I-69

Intermediate I-68 (500 mg, 1.08 mmol) was dissolved in a mixed solvent of methanol/tetrahydrofuran (10 mL, 4:1), and palladium carbon (w/w=10%, 20 mg) was added. The reaction mixture was stirred and reacted at 30° C. for 40 hours under hydrogen atmosphere. The reaction system was filtered, and the filtrate was concentrated under reduced pressure to obtain a residue. The residue was purified by silica gel chromatography to obtain intermediate I-69.

LC-MS (ESI) [M+H]$^+$ 375.1.

Reference Embodiment 68: Preparation of Intermediate I-70

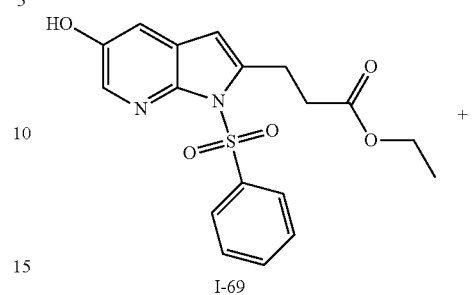

I-69

+

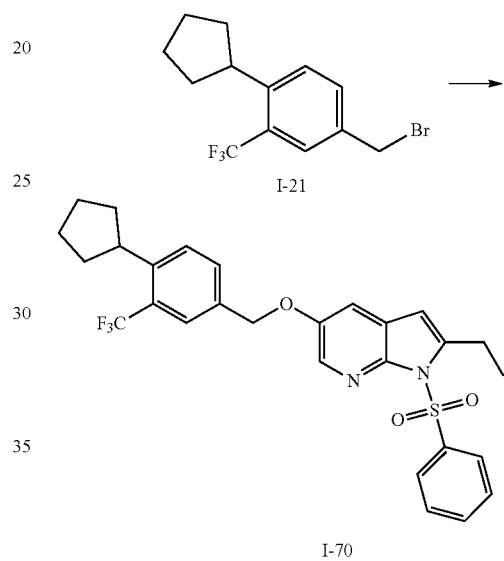

I-21

→

I-70

Intermediate I-69 (160 mg, 0.43 mmol) and intermediate I-21 (156.6 mg, 0.51 mmol) were dissolved in DMF (5 mL). Potassium phosphate (274 mg, 1.29 mmol) was added at 10° C. The reaction mixture was stirred at 30° C. for 3 hours. The reaction mixture was poured into water (20 mL), extracted with ethyl acetate (10 mL×4), the combined organic phases were washed with saturated saline, dried with anhydrous sodium sulfate, filtered, and concentrated under reduced pressure to remove the organic solvent to obtain a residue. The residue was purified by silica gel chromatography to obtain intermediate I-70.

LC-MS (ESI) [M+H]$^+$ 601.2.

Reference Embodiment 69: Preparation of Intermediate I-71

I-1

+

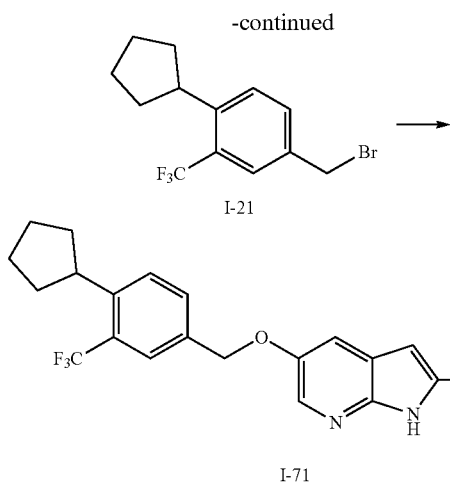

I-21

I-71

Intermediate I-1 (4.8 g, 23.4 mmol) was dissolved in acetonitrile (50 mL), and intermediate I-21 (7.2 g, 23.4 mmol) and potassium carbonate (9.7 g, 70.2 mmol) were added successively. After the addition, the reaction mixture was stirred and reacted at 50° C. overnight. The reaction mixture was cooled to room temperature, filtered, and the filtrate was concentrated under reduced pressure to obtain a residue. The residue was purified by silica gel chromatography to obtain intermediate I-71.

LC-MS (ESI) [M−H]− 430.0.

Reference Embodiment 70: Preparation of Intermediate I-72

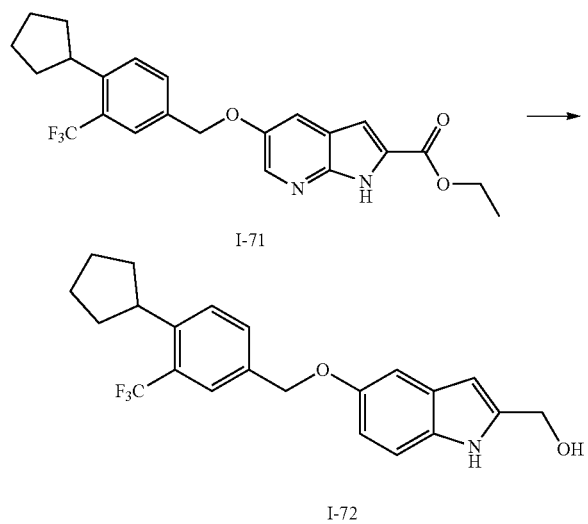

I-71

I-72

Intermediate I-71 (7.27 g, 16.85 mmol) was dissolved in tetrahydrofuran (60 mL). Under the protection of argon, the reaction solution was cooled to −40° C., and then a solution of DIBAL-H in toluene (1.5 M in toluene, 33.7 mL, 50.55 mmol) was slowly added dropwise. After the dropwise addition, the reaction mixture was continuously stirred at −40° C. for 2 hours. Saturated ammonium chloride aqueous solution (10 mL) was slowly added at 0° C., and the internal temperature of the reaction system was controlled below 20° C. After the addition, the reaction system was raised to room temperature and stirred for 30 minutes. The reaction solution was filtered with celite. The filtrate was dried with anhydrous sodium sulfate, filtered and concentrated under reduced pressure to obtain a crude product of intermediate I-72, the crude product was directly used for the next reaction without purification.

LC-MS (ESI) [M+H]+ 390.1.

Reference Embodiment 71: Preparation of Intermediate I-73

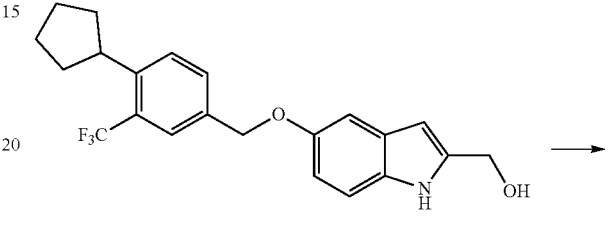

I-72

I-73

Intermediate I-72 (6.5 g) was dissolved in 1,2-dichloroethane (50 mL), and MnO$_2$ (7.27 g, 83.55 mmol) was added. Under the protection of argon, the reaction mixture was stirred and reacted at 60° C. for 6 hours. The mixture was filtered while hot, and the filter cake was washed with dichloromethane. The filtrate was concentrated under reduced pressure to obtain a residue. The crude product was purified by silica gel chromatography to obtain intermediate I-73.

LC-MS (ESI) [M+H]+ 388.3.

Reference Embodiment 72: Preparation of Intermediate I-74

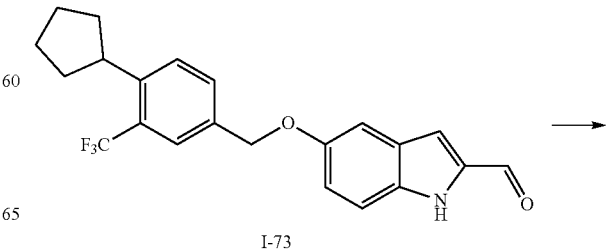

I-73

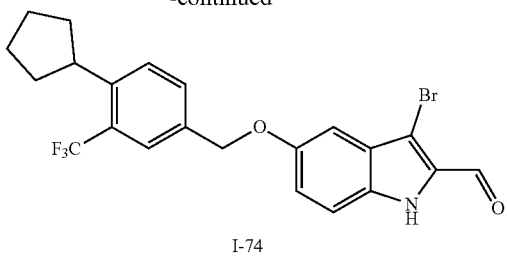

I-74

Intermediate I-73 (4.3 g) was dissolved in dichloromethane (30 mL). The reaction solution was cooled to −40° C. and a solution of N-bromosuccinimide (NBS, 1.98 g, 11.1 mmol) in dichloromethane (50 mL) was slowly added dropwise. After the dropwise addition, the reaction mixture was raised to 0° C. and stirred at 0° C. for 2 hours. The reaction mixture was washed with water (20 mL), and the organic phase was separated, dried with anhydrous sodium sulfate, filtered and concentrated under reduced pressure to obtain a residue. The residue was purified by silica gel chromatography to obtain intermediate I-74.

LC-MS (ESI) [M−H]− 464.

Reference Embodiment 73: Preparation of Intermediate I-75

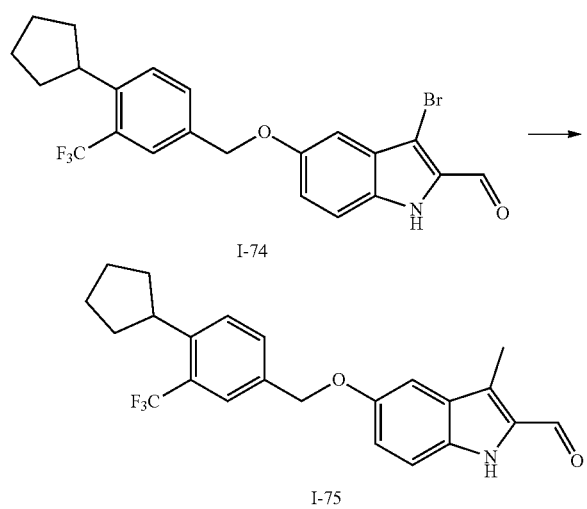

At room temperature, intermediate I-74 (1.0 g, 2.15 mmol) was dissolved in a mixed solvent of 1,4-dioxane and water (10 mL, 4:1), and then methylboronic acid (1.29 g, 21.46 mmol), potassium carbonate (0.89 g, 6.44 mmol) and tetrakis(triphenylphosphine)palladium (1.29 g, 21.46 mmol) were added successively. Under the protection of argon, the reaction mixture was stirred at 90° C. for 7 hours. The reaction mixture was cooled to room temperature, filtered and concentrated under reduced pressure to obtain a residue. The residue was dissolved in dichloromethane (20 mL), and water (10 mL) was added. The separated aqueous phase was extracted with dichloromethane (20 mL×2). The organic phases were combined, dried with anhydrous sodium sulfate and concentrated under reduced pressure to obtain a residue. The residue was purified by silica gel chromatography to obtain intermediate I-75.

LC-MS (ESI) [M−H]− 400.0.

Reference Embodiment 74: Preparation of Intermediate I-76

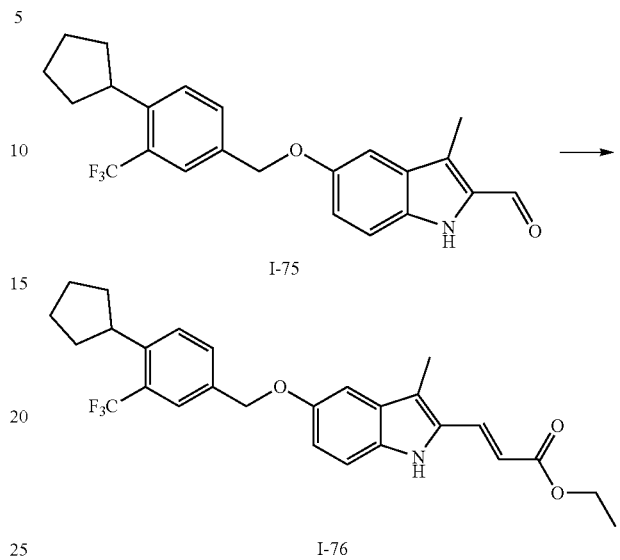

At room temperature, intermediate I-75 (470 mg, 1.17 mmol) was dissolved in tetrahydrofuran (10 mL), and ethoxycarbonylmethylene triphenylphosphorus (490 mg, 1.41 mmol) was added. The reaction mixture was stirred at 80° C. for 15 hours. The reaction solution was cooled to room temperature, and then concentrated under reduced pressure to remove the organic solvent to obtain a residue. The residue was purified by reversed-phase preparative liquid chromatography to obtain intermediate I-76.

LC-MS (ESI) [M−H]− 470.2.

Reference Embodiment 75: Preparation of Intermediate I-77

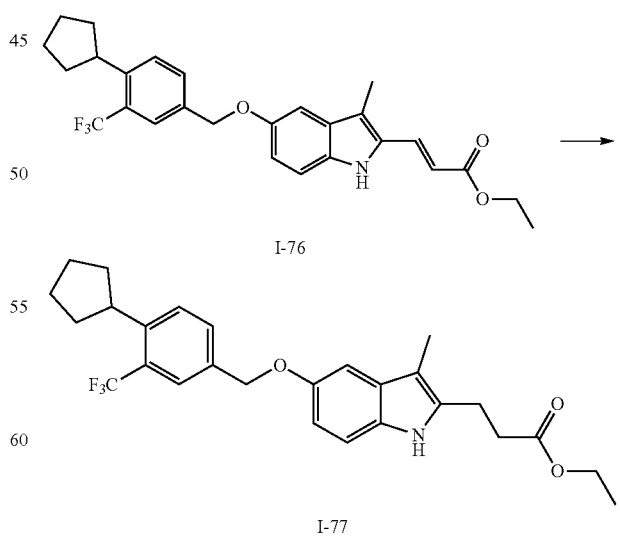

Intermediate I-76 (110 mg, 0.23 mmol) was dissolved in ethyl acetate (2 mL), and PtO₂ (50 mg) was added. The reaction mixture was stirred for 2 hours at room temperature under hydrogen atmosphere. The filtrate was filtered and concentrated under reduced pressure to obtain intermediate I-77.

LC-MS (ESI) [M+H]⁺ 474.2.

Reference Embodiment 76: Preparation of Intermediate I-78

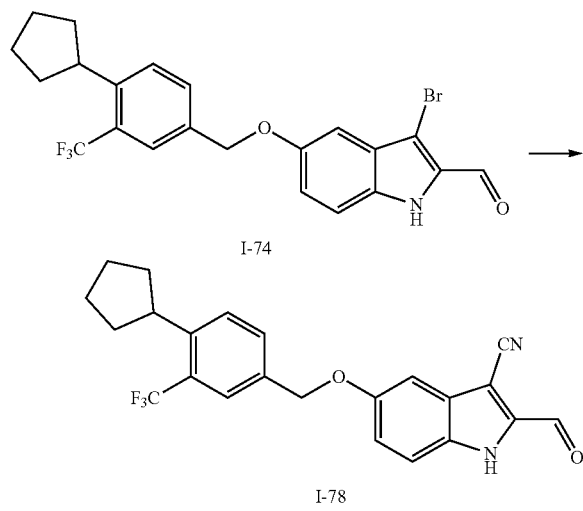

Intermediate I-74 (500 mg, 1.07 mmol) was dissolved in N,N-dimethylformamide (10 mL), and zinc cyanide (377 mg, 3.21 mmol) and tetrakis(triphenylphosphine)palladium (127 mg, 0.11 mmol) were added to the reaction system successively. Under the protection of argon, the reaction mixture was stirred at 100° C. for 3 hours. The reaction mixture was cooled to room temperature and water (100 mL) and ethyl acetate (50 mL) were added. The organic phase was separated and the aqueous phase was extracted with ethyl acetate (50 mL×2). The organic phases were combined, washed with saturated saline, dried with anhydrous sodium sulfate, filtered, and the filtrate was concentrated under reduced pressure to obtain a residue. The residue was purified by silica gel chromatography to obtain intermediate I-78.

LC-MS (ESI) [M−H]⁻ 411.1.

¹H NMR (400 MHz, CDCl₃) δ 10.07 (s, 1H), 9.45 (s, 1H), 7.71 (d, J=1.0 Hz, 1H), 7.60 (d, J=8.2 Hz, 1H), 7.53-7.51 (m, 1H), 7.46 (d, J=9.0 Hz, 1H), 7.29 (d, J=2.2 Hz, 1H), 7.26-7.23 (m, 1H), 5.13 (s, 2H), 3.43-3.35 (m, 1H), 2.15-2.08 (m, 2H), 1.91-1.85 (m, 2H), 1.78-1.72 (m, 2H), 1.67-1.59 (m, 2H).

Reference Embodiment 77: Preparation of Intermediate I-79

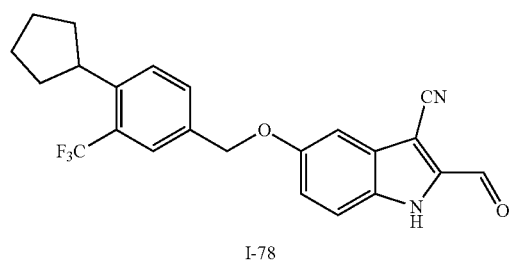

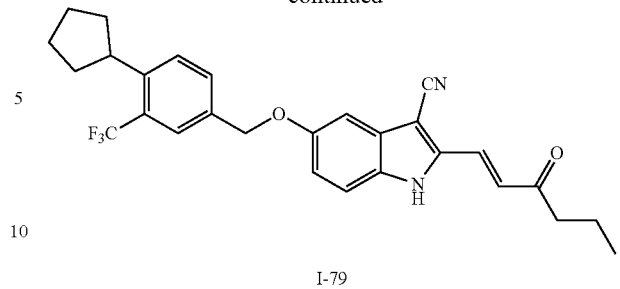

Intermediate I-78 (322 mg, 0.78 mmol) was dissolved in tetrahydrofuran (10 mL), and ethoxyformylmethylene triphenylphosphine (543 mg, 1.56 mmol) was added. Under the protection of argon, the reaction mixture was stirred at 70° C. for 16 hours. The residue was obtained by concentration under reduced pressure. The residue was purified by silica gel chromatography to obtain intermediate I-79.

LC-MS (ESI) [M−H]⁻ 481.3.

¹H NMR (400 MHz, CDCl₃) δ 8.98 (s, 1H), 7.76 (d, J=16.2 Hz, 1H), 7.70 (s, 1H), 7.60 (d, J=8.1 Hz, 1H), 7.51 (d, J=8.2 Hz, 1H), 7.35 (d, J=8.9 Hz, 1H), 7.22 (d, J=2.3 Hz, 1H), 7.10 (dd, J=8.9, 2.4 Hz, 1H), 6.65 (d, J=16.2 Hz, 1H), 5.11 (s, 2H), 4.33 (q, J=7.1 Hz, 2H), 3.43-3.34 (m, 1H), 2.14-2.06 (m, 2H), 1.90-1.83 (m, 2H), 1.78-1.70 (m, 2H), 1.68-1.59 (m, 2H), 1.37 (t, J=7.1 Hz, 3H).

Reference Embodiment 78: Preparation of Intermediate I-80

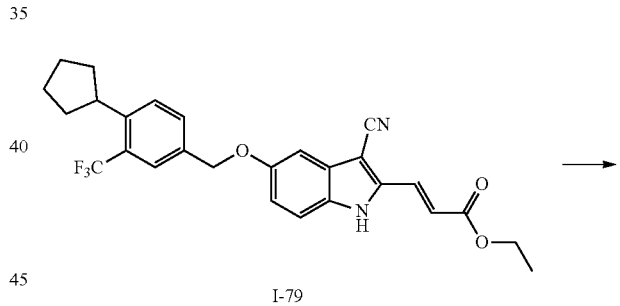

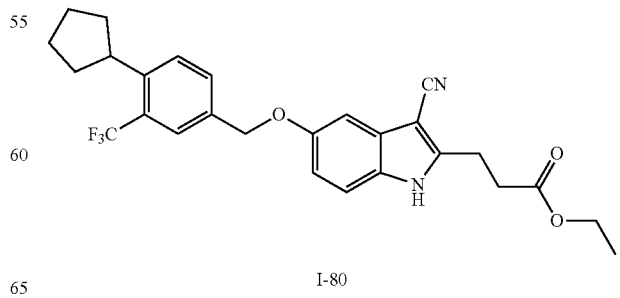

Intermediate I-79 (294 mg, 0.61 mmol) was dissolved in anhydrous ethyl acetate (30 mL), and platinum dioxide (20 mg) was added. The reaction mixture was stirred at room temperature for 4 hours under hydrogen atmosphere. The reaction mixture was filtered with suction, and the filtrate was concentrated under reduced pressure to obtain a residue. The residue was purified by silica gel chromatography to obtain intermediate I-80.

LC-MS (ESI) [M−H]⁻ 483.1

$^1$H NMR (400 MHz, CDCl$_3$) δ 9.49 (s, 1H), 7.70 (s, 1H), 7.59 (d, J=8.2 Hz, 1H), 7.49 (d, J=8.1 Hz, 1H), 7.29 (s, 1H), 7.18 (d, J=2.3 Hz, 1H), 6.97 (dd, J=8.8, 2.4 Hz, 1H), 5.09 (s, 2H), 4.21 (q, J=7.2 Hz, 2H), 3.42-3.34 (m, 1H), 3.22-3.18 (m, 2H), 2.80-2.78 (m, 2H), 2.13-2.07 (m, 2H), 1.89-1.83 (m, 2H), 1.77-1.71 (m, 2H), 1.65-1.59 (m, 2H), 1.29 (t, J=7.2 Hz, 3H).

Reference Embodiment 80: Preparation of Intermediate I-82

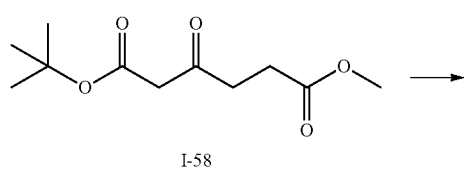

I-58

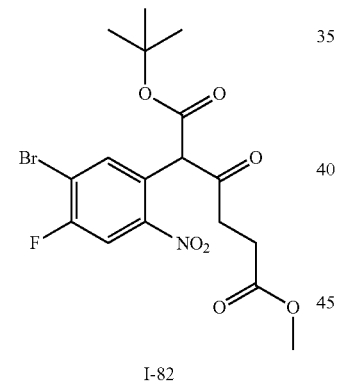

I-82

Sodium hydride (60% mass fraction, 1.26 g, 31.62 mmol) was added to anhydrous N,N-dimethylformamide (40 mL). After the reaction solution was cooled to 0° C. 1-bromo-2,5-difluoro-4-nitrobenzene (3.76 g, 15.81 mmol) was added, and then intermediate I-58 (4.0 g, 17.39 mmol) was slowly added dropwise. Under the protection of argon, the reaction mixture was stirred at 60° C. for 16 hours. The reaction solution was cooled to room temperature and quenched with saturated ammonium chloride aqueous solution (200 mL), the mixture was extracted with ethyl acetate (50 mL×4), the organic phases were combined, washed with saturated saline, dried with anhydrous sodium sulfate and filtered. The filtrate was concentrated under reduced pressure to remove the organic solvent to obtain a residue. The residue was separated and purified by silica gel chromatography to obtain intermediate I-82.

LC-MS (ESI) [M−H]⁻ 446.1.

Reference Embodiment 81: Preparation of Intermediate I-83

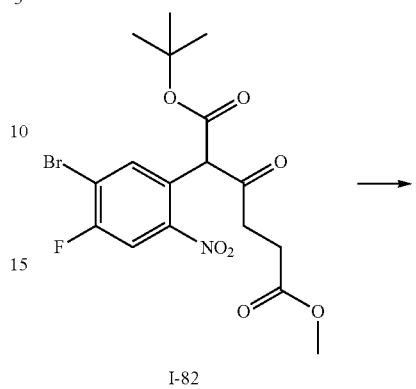

I-82

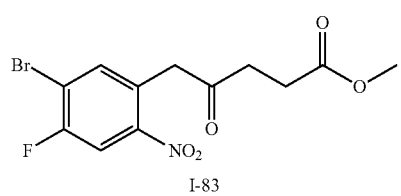

I-83

Intermediate I-82 (2.685 g, 5.99 mmol) was dissolved in dichloromethane (40 mL). Trifluoroacetic acid (4 mL) and triethylsilane (3.47 g, 29.95 mmol) were added dropwise successively. After the dropwise addition, the reaction mixture was stirred at 40° C. for 16 hours. Water (60 mL) was added and the aqueous phase was extracted with dichloromethane (40 mL×2). The organic phases were combined, washed with saturated saline, dried with anhydrous sodium sulfate, filtered, and the filtrate was concentrated under reduced pressure to remove the organic solvent to obtain a residue. The residue was separated and purified by silica gel chromatography to obtain intermediate I-83.

Reference Embodiment 82: Preparation of Intermediate I-84

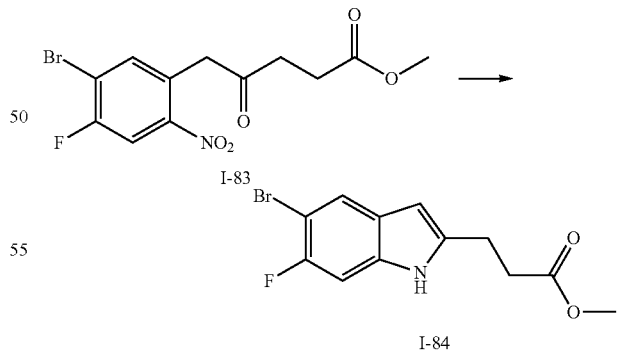

Intermediate I-83 (1.63 g, 4.68 mmol) was dissolved in acetic acid (20 mL) and iron powder (1.31 g, 23.42 mmol) was added. The reaction mixture was stirred at 115° C. for 1.5 hours and then cooled to room temperature. The mixture was filtered with suction, water (100 mL) was added to the filtrate, and the aqueous phase was extracted with ethyl acetate (30 mL×3). The organic phases were combined, washed with saturated saline, dried with anhydrous sodium sulfate, filtered, and the filtrate was concentrated under reduced pressure to remove the organic solvent to obtain a residue. The residue was separated and purified by silica gel chromatography to obtain intermediate I-84.

LC-MS (ESI) [M+H]$^+$ 300.1.

Reference Embodiment 83: Preparation of Intermediate I-85

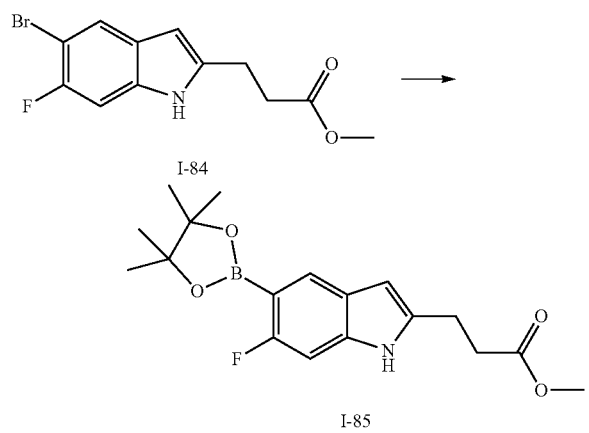

Intermediate I-84 (1.3 g, 4.3 mmol) was dissolved in 1,4-dioxane (20 mL), and bis(pinacolato)diboron (2.18 g, 8.6 mmol), potassium acetate (1.27 g, 12.9 mmol) and 1,1'-bis(diphenylphosphino)ferrocene palladium(II)dichloride dichloromethane complex (351 mg, 0.43 mmol) were added successively. Under the protection of argon, the reaction mixture was stirred at 110° C. overnight and then cooled to room temperature. The mixture was filtrated with suction, and the filtrate was separated by extraction with adding ethyl acetate (90 mL) and water (30 mL). The aqueous phase was extracted with ethyl acetate (90 mL×2). The organic phases were combined, washed with saturated saline, dried with anhydrous sodium sulfate, filtered, and the filtrate was concentrated under reduced pressure to remove the organic solvent to obtain a residue. The residue was separated and purified by silica gel chromatography to obtain intermediate I-85.

LC-MS (ESI) [M+H]$^+$ 348.3.

Reference Embodiment 84: Preparation of Intermediate I-86

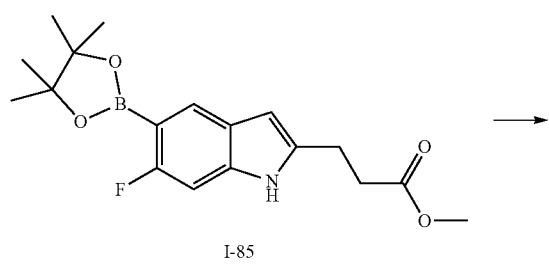

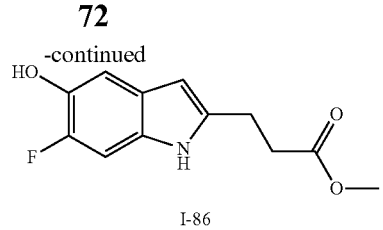

Intermediate I-85 (360 mg, 1.04 mmol) was dissolved in tetrahydrofuran (9 mL) and water (3 mL), and sodium perborate tetrahydrate (801 mg, 5.20 mmol) was added. The reaction mixture was stirred at 40° C. for one hour, and then water (50 mL) was added. The mixture was extracted with ethyl acetate (30 mL×3). The organic phases were combined, washed with saturated saline, dried with anhydrous sodium sulfate, filtered, and the filtrate was concentrated under reduced pressure to remove the organic solvent to obtain a residue. The residue was separated and purified by silica gel chromatography to obtain intermediate I-86.

LC-MS (ESI) [M+H]$^+$ 238.0.

Reference Embodiment 85: Preparation of Intermediate I-87

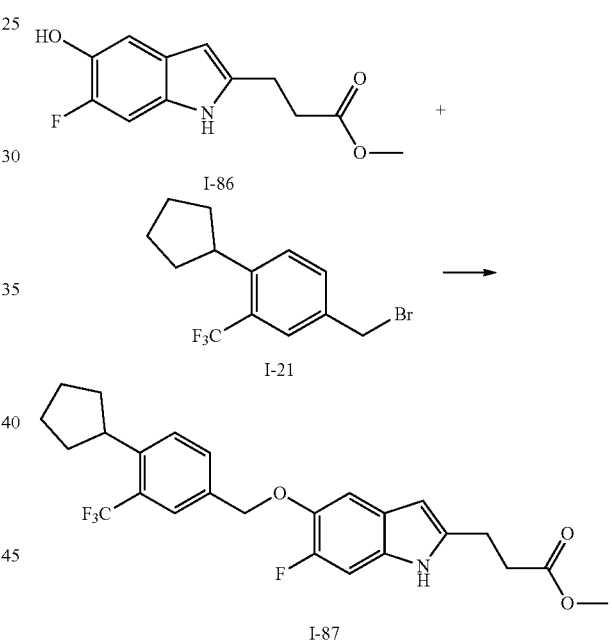

Intermediates I-86 (101 mg, 0.426 mmol) and I-21 (196 mg, 0.639 mmol) were dissolved in acetonitrile (8 mL), and cesium carbonate (417 mg, 1.278 mmol) was added. The reaction mixture was stirred and reacted at room temperature for one hour and then filtered with suction. The filtrate was concentrated under reduced pressure to remove the organic solvent to obtain a residue.

Another batch: Intermediates 1-86 (137 mg, 0.578 mmol) and 1-21 (266 mg, 0.867 mmol) were dissolved in acetonitrile (5 mL), and cesium carbonate (565 mg, 1.734 mmol) was added. The reaction mixture was stirred and reacted at room temperature for one hour and then filtered with suction. The filtrate was concentrated under reduced pressure to remove the organic solvent to obtain a residue.

The two residues were combined, separated and purified by preparative liquid chromatography to obtain intermediate I-87.

LC-MS (ESI) [M+H]$^+$ 464.3.

Reference Embodiment 86: Preparation of Intermediate I-88

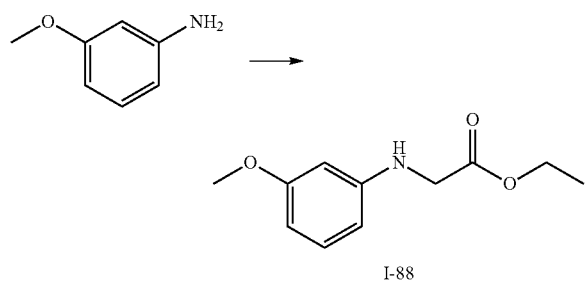

M-aminoanisole (10 g, 81.2 mmol) and ethyl bromoacetate (13.6 g, 81.2 mmol) were dissolved in acetone (100 mL) at room temperature. Potassium carbonate (16.8 g, 121.8 mmol) was added to the reaction system, and then the reaction mixture was stirred at 60° C. for 16 hours. The reaction mixture was filtered and the filtrate was diluted with water (150 mL) and extracted with ethyl acetate (150 mL×2). The organic phases were combined, washed with saturated saline (100 mL), dried with anhydrous sodium sulfate, and filtered. The filtrate was concentrated under reduced pressure to remove the organic solvent to obtain a crude product. The crude product was separated and purified by silica gel chromatography to obtain intermediate I-88.

LC-MS (ESI) [M+H]$^+$ 210.1.

Reference Embodiment 87: Preparation of Intermediate I-89

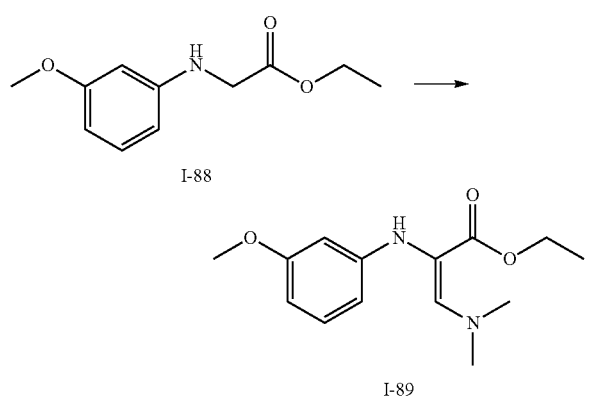

Intermediate I-88 (14.2 g, 67.9 mmol) was dissolved in N,N-dimethylformamide dimethyl acetal (16.2 g, 135.8 mmol) at room temperature, and then the reaction mixture was stirred at reflux for 48 hours. After the reaction solution was cooled to room temperature, water (50 mL) was added, and the mixture was extracted with ethyl acetate (50 mL×3). The organic phases were combined, washed with saturated saline (50 mL), dried with anhydrous sodium sulfate, and filtered. The filtrate was concentrated under reduced pressure to remove the organic solvent to obtain a crude product. The crude product was separated and purified by silica gel chromatography to obtain intermediate I-89.

LC-MS (ESI) [M+H]$^+$ 265.2

Reference Embodiment 88: Preparation of Intermediate I-90

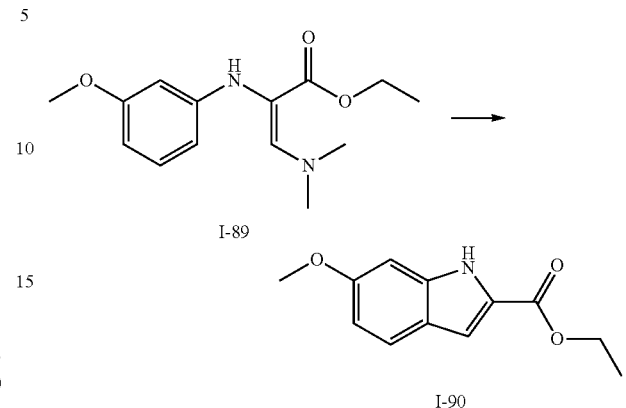

Intermediate I-89 (11 g) was dissolved in dichloromethane (50 mL) at room temperature, and then anhydrous aluminum trichloride (5.5 g, 41.6 mmol) was added at 0° C. The reaction mixture was stirred at room temperature for 16 hours. The reaction solution was cooled to 0° C. and quenched with saturated ammonium chloride solution (10 mL), the organic phase was separated, the aqueous phase was extracted with dichloromethane (60 mL×3). The organic phases were combined, washed with saturated saline (50 mL), dried with anhydrous sodium sulfate and filtered. The filtrate was concentrated under reduced pressure to remove the organic solvent to obtain a crude product. The crude product was separated and purified by silica gel chromatography to obtain intermediate I-90.

LC-MS (ESI) [M+H]$^+$ 220.1

Reference Embodiment 89: Preparation of Intermediate I-91

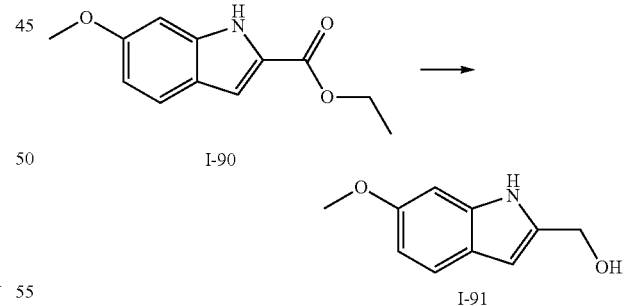

Intermediate I-90 (8.8 g) was dissolved in tetrahydrofuran (80 mL) at room temperature, and then lithium aluminum tetrahydride (3.05 g, 80.26 mmol) was slowly added at 0° C. The reaction mixture was raised to room temperature, and the reaction was stirred at room temperature for 4 hours. The reaction solution was cooled to 0° C., quenched with water (10 mL), filtered and separated. The aqueous phase was extracted with ethyl acetate (80 mL×2), the organic phases were combined, washed with saturated saline (80 mL), dried with anhydrous sodium sulfate, and filtered. The filtrate was concentrated under reduced pressure to remove organic solvent to obtain intermediate I-91, and the crude product was directly used for the next reaction step without purification.

LC-MS (ESI) [M+H]+ 178.

Reference Embodiment 90: Preparation of Intermediate I-92

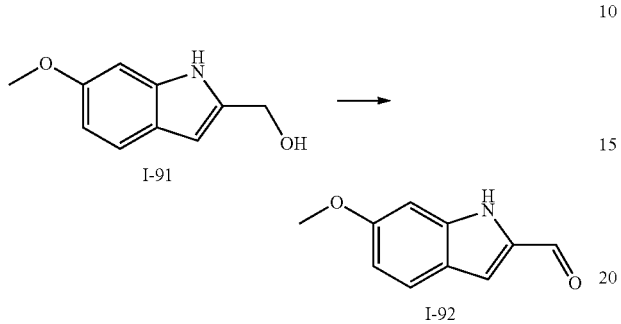

At room temperature, intermediate I-91 (3.5 g, 19.8 mmol) was dissolved in tetrahydrofuran (40 mL), and manganese dioxide (17.2 g, 198 mmol) was added under the protection of nitrogen. After stirring the reaction mixture at 60° C. for 16 hours, the reaction mixture was filtered. The filtrate was concentrated under reduced pressure to obtain a crude product. The crude product was separated and purified by silica gel column chromatography (ethyl acetate/petroleum ether=0-40%) to obtain a target compound I-92.

LC-MS (ESI) [M+H]+ 176.1.

Reference Embodiment 91: Preparation of Intermediate I-93

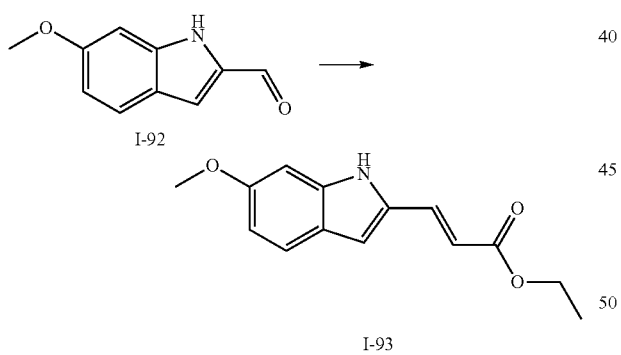

At room temperature, ethoxyformylmethylene triphenylphosphine (2.4 g, 6.85 mmol) was dissolved in tetrahydrofuran (20 mL), and sodium hydride (356.4 mg, 8.91 mmol) was added at 0° C. The reaction mixture was stirred at 0° C. for 30 minutes, and then intermediate I-92 (1 g, 5.71 mmol) was added. The reaction mixture was raised to room temperature, and the reaction was continuously stirred at room temperature for 4 hours. The reaction mixture was cooled to 0° C., quenched with saturated ammonium chloride solution (5 mL), extracted with ethyl acetate (20 mL×3). The organic phases were combined, washed with saturated saline (30 mL), dried with anhydrous sodium sulfate and filtered. The filtrate was concentrated under reduced pressure to remove the organic solvent to obtain a crude product.

The crude product was separated and purified by silica gel chromatography to obtain intermediate I-93.

LC-MS (ESI) [M+H]+ 246.0.

Reference Embodiment 92: Preparation of Intermediate I-94

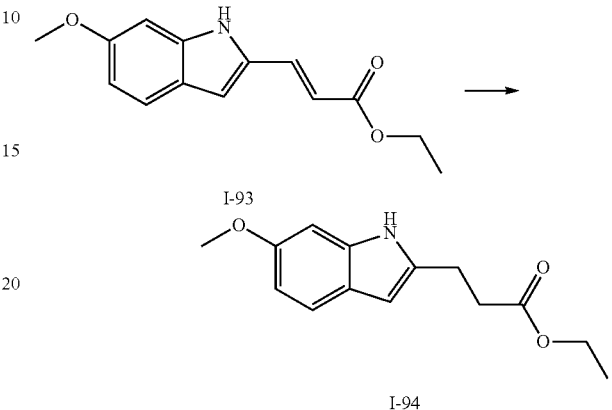

At room temperature, intermediate I-93 (2.2 g, 8.97 mmol) was dissolved in ethanol (20 mL), and then Pd/C (400 mg, 10% w/w) was added. The reaction mixture was stirred and reacted at room temperature for 6 hours under hydrogen atmosphere. The reaction mixture was filtered, and the filtrate was concentrated under reduced pressure to obtain a crude product of intermediate I-94, the crude product was directly used for the next reaction without purification.

LC-MS (ESI) [M+H]+ 248.0.

Reference Embodiment 93: Preparation of Intermediate I-95

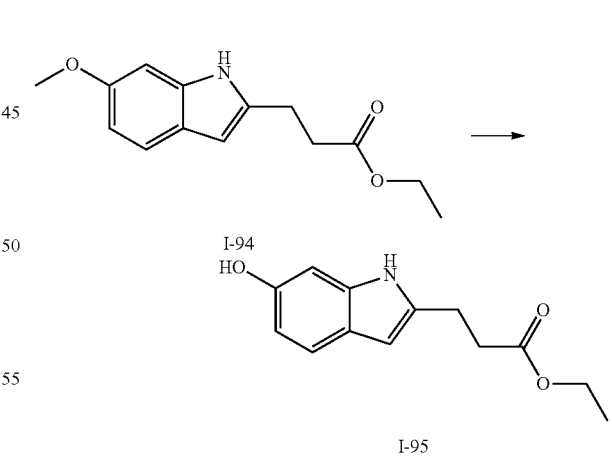

Boron tribromide (10.1 mL, 1 M in DCM, 10.1 mmol) was added to dichloromethane (10 mL) at 0° C., and intermediate I-94 (500 mg, 2.02 mmol) was added to the above solution at 0° C. The reaction mixture was stirred at room temperature for 2 hours. The reaction was quenched with ethanol (10 mL) at 0° C., diluted with water (20 mL), the organic phase was separated, and the aqueous phase was extracted with dichloromethane (20 mL×3). The organic phases were combined, washed with saturated saline (20 mL), dried with anhydrous sodium sulfate, and filtered. The filtrate was concentrated under reduced pressure to remove the organic solvent to obtain a crude product. The crude product was separated and purified by silica gel chromatography to obtain intermediate I-95.

LC-MS (ESI) [M+H]+ 234.1.

Reference Embodiment 94: Preparation of Intermediate I-96

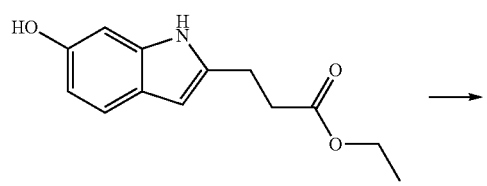

I-95

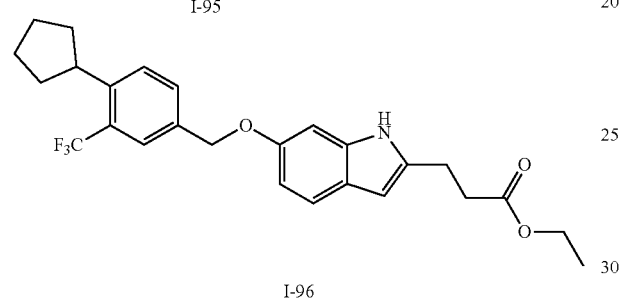

I-96

Intermediate I-95 (55 mg, 0.24 mmol) was dissolved in acetonitrile (8 mL), and intermediate I-10 (126 mg, 0.48 mmol), potassium carbonate (66.3 mg, 0.48 mmol) and cesium carbonate (235 mg, 0.72 mmol) were added successively. The reaction mixture was stirred at room temperature for 16 hours, then water (10 mL) was added, and the mixture was extracted with ethyl acetate (15 mL×3). The organic phases were combined, washed with saturated saline (20 mL), dried with anhydrous sodium sulfate, and filtered. The filtrate was concentrated under reduced pressure to remove the organic solvent to obtain a crude product. The crude product was separated and purified by silica gel chromatography to obtain intermediate I-96.

LC-MS (ESI) [M+H]+ 460.1.

Reference Embodiment 95: Preparation of Intermediate I-97

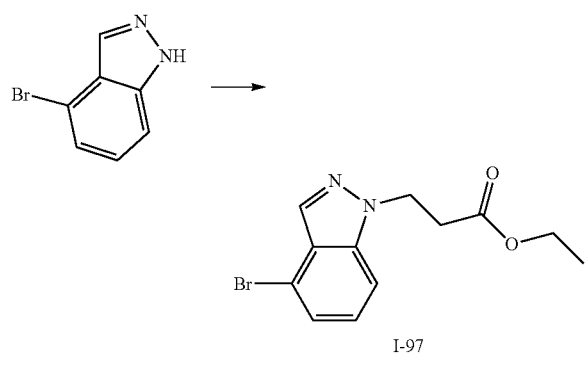

I-97

4-Bromo-1H-indazole (1.0 g, 5.1 mmol) and ethyl bromopropionate (1.1 g, 6.1 mmol) were dissolved in DMF (10 mL), and potassium carbonate (2.1 g, 15.3 mmol) was added. The reaction mixture was stirred at 80° C. for 5 hours and then cooled to room temperature. EA (20 mL) and water (100 mL) were added for separation by extraction. The organic solvent was removed by concentration under reduced pressure to obtain a crude product. The crude product was separated and purified by silica gel chromatography to obtain intermediate I-97.

LC-MS (ESI) [M+H]+ 297.0.
$^1$H NMR (400 MHz, DMSO-d$_6$) δ 8.05 (s, 1H), 7.75 (d, J=8.0 Hz, 1H), 7.40-7.30 (m, 2H), 4.66 (t, J=6.5 Hz, 2H), 3.98 (q, J=7.1 Hz, 2H), 2.95 (t, J=6.5 Hz, 2H), 1.07 (t, J=7.1 Hz, 3H).

Reference Embodiment 96: Preparation of Intermediate I-98

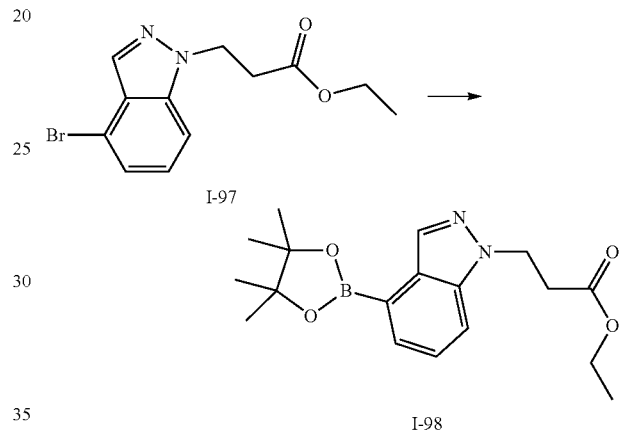

I-98

Intermediate I-97 (1.2 g, 4 mmol) was dissolved in 1,4-dioxane (12 mL), bis(pinacolato)diboron (1.2 g, 4.8 mmol), [1,1'-bis(diphenylphosphino)ferrocene]dichloropalladium (293 mg, 0.4 mmol) and potassium acetate (1.18 g, 12 mmol) were added successively. Under the protection of argon, the reaction mixture was stirred at 100° C. for 4 hours. The reaction mixture was cooled to 30° C., filtered, and the filtrate was concentrated under reduced pressure to obtain a crude product. The crude product was dissolved in ethyl acetate (20 mL), and water (10 mL) was added for separation by extraction. The organic phase was washed with saturated saline (10 mL), dried with anhydrous sodium sulfate, filtered, and the filtrate was concentrated under reduced pressure to obtain a target intermediate I-98, the intermediate was directly used in the next reaction without further purification.

LC-MS (ESI) [M+H]+ 345.0.

Reference Embodiment 97: Preparation of Intermediate I-99

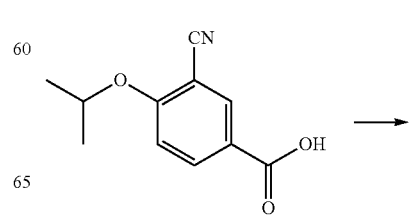

-continued

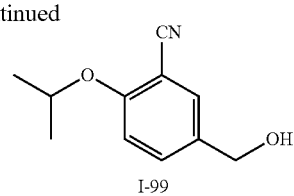

I-99

3-Cyano-4-isopropoxybenzoic acid (1 g, 4.87 mmol) was dissolved in dichloromethane (20 mL), and after adding one drop of N,N-dimethylformamide, oxalyl chloride (0.6 mL, 7.31 mmol) was added dropwise at 0° C. The reaction solution was stirred at room temperature for one hour and then concentrated. The obtained residue was dissolved in tetrahydrofuran (10 mL) and cooled to 0° C., and sodium borohydride (461 mg, 12.18 mmol) and methanol (2 mL) were added successively. The reaction solution was stirred at 0° C. for 30 minutes and then stirred at room temperature for 2 hours. The reaction system was acidified to pH=3 with 1N hydrochloric acid, and extracted twice with ethyl acetate, 10 mL each time. The organic layers were combined, dried with anhydrous sodium sulfate, filtered, and the filtrate was concentrated under reduced pressure to obtain a residue. The residue was separated and purified by silica gel chromatography to obtain intermediate I-99.

$^1$H NMR (400 MHz, CDCl$_3$) δ 7.54 (d, J=2.0 Hz, 1H), 7.52-7.47 (dd, J=8.8, 2.0 Hz, 1H), 6.95 (d, J=8.8 Hz, 1H), 4.70-4.60 (m, 3H), 1.39 (d, J=6.0 Hz, 6H).

Reference Embodiment 98: Preparation of Intermediate I-100

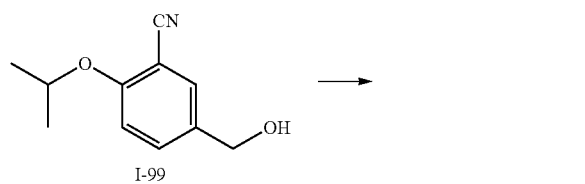

Intermediate I-99 (300 mg, 1.57 mmol) was dissolved in toluene (5 mL), and thionyl chloride (1.12 g, 9.41 mmol) was added. The reaction solution was stirred at 75° C. for 20 minutes. The reaction solution was diluted with ethyl acetate (15 mL), washed with sodium bicarbonate (twice, 20 mL each time), and then the organic layer was washed with saturated saline (20 mL), dried with anhydrous sodium sulfate and filtered. The filtrate was concentrated under reduced pressure to remove the organic solvent to obtain a crude product of intermediate I-100, the crude product was directly used in the next reaction without purification.

Reference Embodiment 99: Preparation of Intermediate I-101

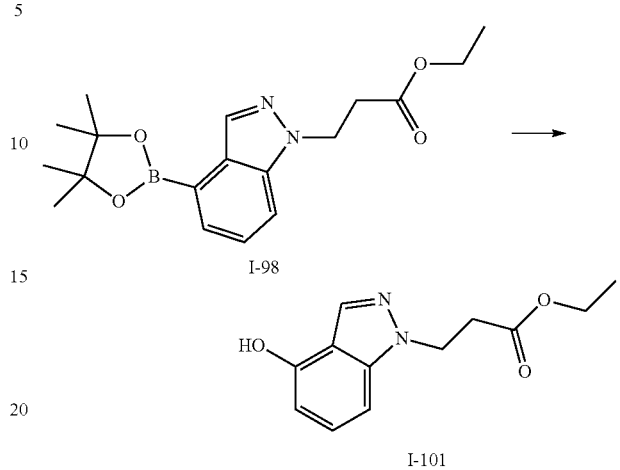

Intermediate I-98 (400 mg, 1.16 mmol) was dissolved in a mixed solution of ethanol (10 mL)/water (5 mL), and m-chloroperoxybenzoic acid (85% purity, 260 mg, 1.28 mmol) was added and stirred at room temperature for 2 hours. Part of the organic solvent was evaporated under reduced pressure, and the residue was diluted with water (15 mL) and extracted with ethyl acetate (twice, 10 mL each time). The organic layer was washed with saturated saline (20 mL), dried with anhydrous sodium sulfate, and filtered. The filtrate was concentrated under reduced pressure to remove the organic solvent to obtain a residue. The residue was separated and purified by silica gel chromatography to obtain intermediate I-101.

LC-MS (ESI) [M+H]$^+$ 235.1.

Reference Embodiment 100: Preparation of Intermediate I-102

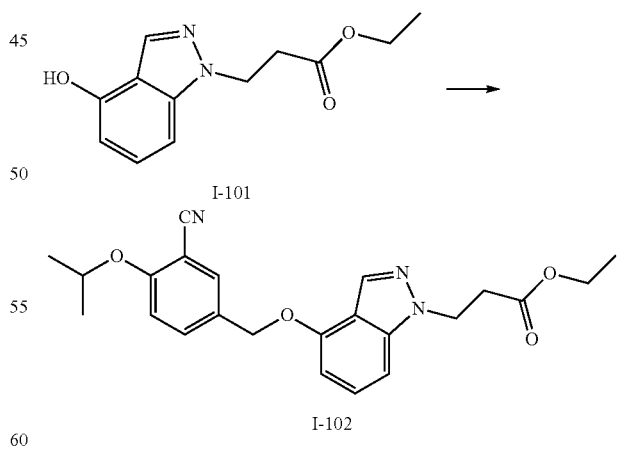

Intermediates I-101 (87 mg, 0.37 mmol) and I-100 (92 mg, 0.44 mmol) were dissolved in acetonitrile (4 mL), and potassium carbonate (102 mg, 0.74 mmol) was added, and the mixture was stirred overnight at 80° C. and then stirred overnight at room temperature. The reaction solution was filtered, and the filtrate was concentrated to obtain a residue.

The residue was separated and purified by silica gel chromatography to obtain intermediate I-102.

Reference Embodiment 101: Preparation of Intermediate I-103

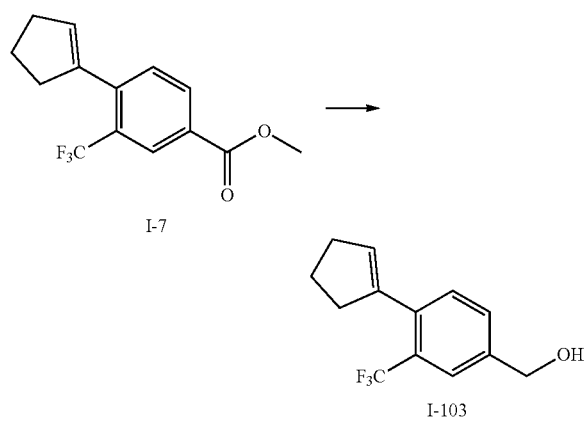

The intermediate I-7 (900 mg, 3.33 mmol) was dissolved in tetrahydrofuran (10.0 mL), the mixture was cooled to −20° C., and a solution of diisobutyl aluminum hydride (1.0 M, 9.99 mL, 9.99 mmol) in toluene was slowly added dropwise under the protection of argon, after the dropwise addition, the reaction solution was stirred at 0° C. for 2 hours. The reaction solution was poured into 1M ice hydrochloric acid aqueous solution (50 mL). The mixture was extracted with ethyl acetate (50 mL×3). The organic phases were combined and concentrated under reduced pressure to remove the organic solvent to obtain intermediate I-103. The crude product was directly used in the next step without purification.

Reference Embodiment 102: Preparation of Intermediate I-104

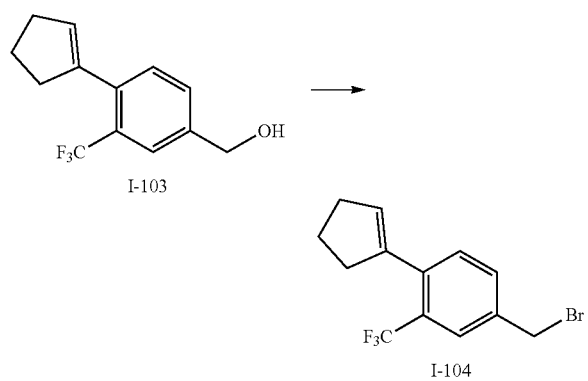

Hydrobromic acid aqueous solution (40% w/w, 5 mL) was added to intermediate I-103 (400 mg), and the reaction mixture was heated to 100° C. and stirred for 2 hours. After the reaction solution was cooled to room temperature, it was extracted with ethyl acetate (30 mL×3). The organic phases were combined, washed with saturated saline (30 mL), dried with anhydrous sodium sulfate, filtered, and the filtrate was concentrated to dryness under reduced pressure. The residue was separated and purified by silica gel chromatography to obtain intermediate I-104.

$^1$H NMR (400 MHz, Chloroform-d) δ 7.66 (s, 1H), 7.50 (d, J=7.9 Hz, 1H), 7.27 (d, J=8.1 Hz, 1H), 5.74 (t, J=2.3 Hz, 1H), 4.50 (s, 2H), 2.64 (m, 2H), 2.52 (m, 2H), 2.02 (m 2H).

Reference Embodiment 103: Preparation of Intermediate I-105

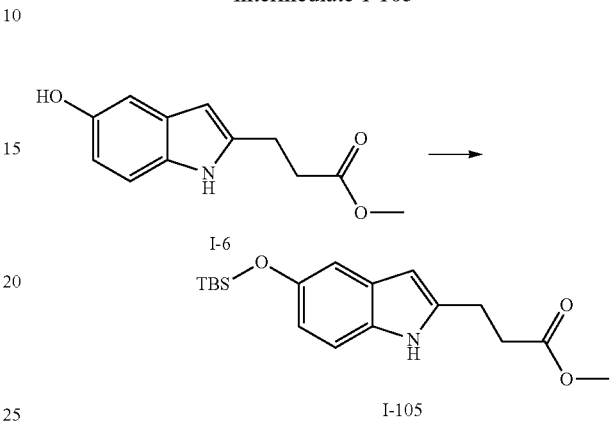

Intermediate I-6 (200 mg, 0.912 mmol) and imidazole (112 mg, 1.64 mmol) were dissolved in N,N-dimethylformamide (15 mL), and tert-butyl dimethylchlorosilane (144 mg, 0.958 mmol) was added at 10° C. The reaction mixture was stirred at 10° C. for 2 hours. The reaction solution was poured into water (150 mL), extracted with ethyl acetate (20 mL×2). The organic phases were combined, washed with saturated saline (50 mL), dried with anhydrous sodium sulfate and filtered. The filtrate was concentrated under reduced pressure to remove the organic solvent to obtain a crude product. The crude product was separated and purified by silica gel chromatography to obtain intermediate I-105. LC-MS (ESI) [M+H]$^+$ 333.9.

Reference Embodiment 104: Preparation of Intermediate I-106

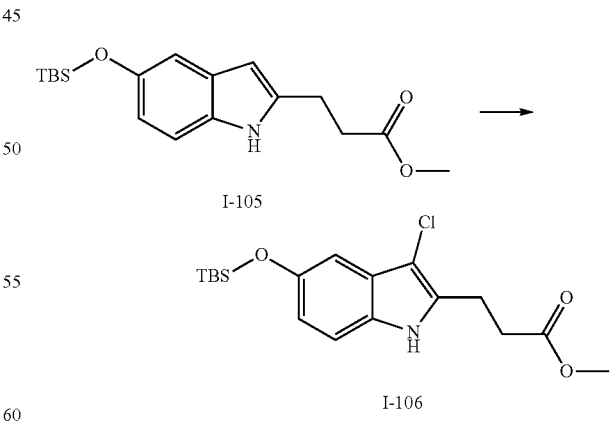

Intermediate I-105 (90.0 mg, 0.270 mmol) was dissolved in dichloromethane (5 mL), the reaction system was cooled to −70° C., and N-chlorosuccinimide (36.1 mg, 0.270 mmol) was added. The reaction mixture was stirred at −70° C. for half an hour, then heated to 10° C., and stirred at 10° C. for half an hour. The mixture was poured into water (10 mL), separated and the aqueous phase was extracted with dichloromethane (5 mL). The organic phases were combined, dried with anhydrous sodium sulfate, and filtered. The filtrate was concentrated under reduced pressure to remove organic solvent to obtain intermediate I-106.

LC-MS (ESI) [M+H]$^+$ 367.8.

Reference Embodiment 105: Preparation of Intermediate I-107

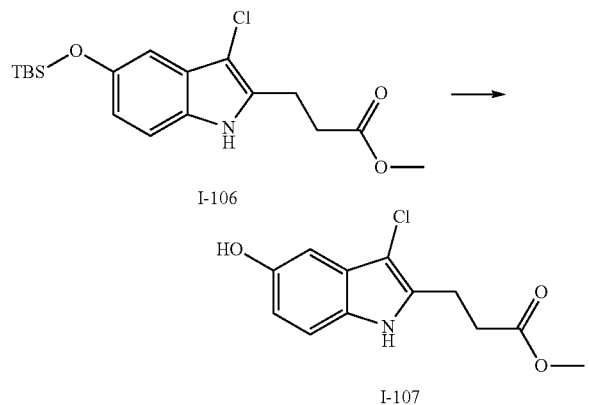

Intermediate I-106 (90.0 mg, 0.245 mmol) was dissolved in tetrahydrofuran (1 mL), and 1M tetrabutylammonium fluoride solution in tetrahydrofuran (0.294 mL, 0.294 mmol) was added at 10° C. The reaction mixture was stirred at 10° C. for one hour. The mixture was concentrated under reduced pressure to remove the organic solvent to obtain a crude product. The crude product was separated and purified by silica gel chromatography to obtain intermediate I-107.

LC-MS (ESI) [M+H]$^+$ 254.0.

Reference Embodiment 106: Preparation of Intermediate I-108

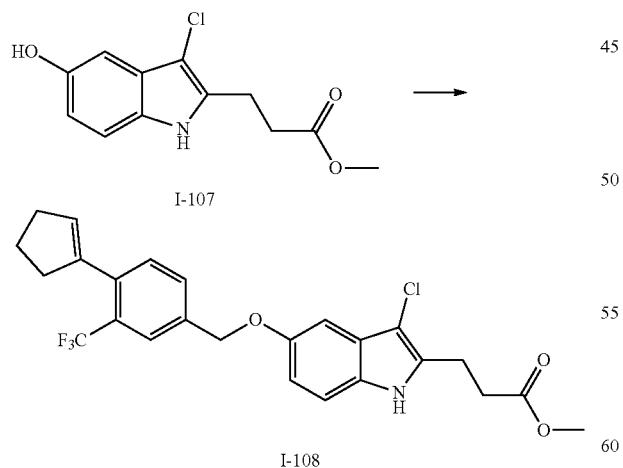

Intermediate I-104 (67.1 mg, 0.220 mmol) and intermediate I-107 (50.7 mg, 0.200 mmol) were dissolved in acetonitrile (3 mL), and cesium carbonate (195 mg, 0.600 mmol) was added. The reaction solution was heated to 30° C. and stirred and reacted for 2 hours, then filtered, the filtrate was concentrated under vacuum and reduced pressure, and the residue was separated and purified by silica gel chromatography to obtain intermediate I-108.

LC-MS. (ESI) [M−H]-476.0.

Reference Embodiment 107: Preparation of Intermediate I-109

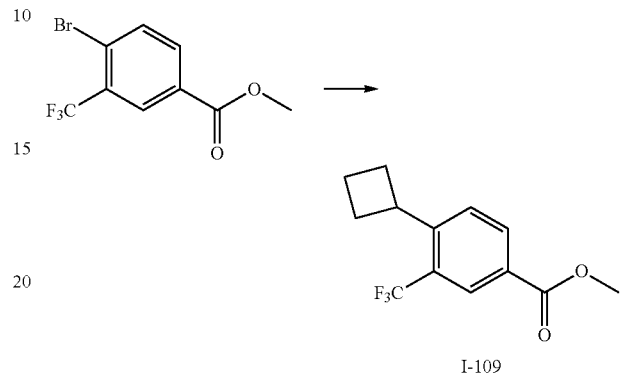

At room temperature, methyl 4-bromo-3-(trifluoromethyl) benzoate (100 mg, 0.35 mmol) and cyclobutylboric acid (70 mg, 0.70 mmol) were dissolved in xylene (4 mL), then palladium acetate (4.5 mg, 0.02 mmol), Antphos (11.1 mg, 0.03 mmol) and potassium phosphate (297 mg, 1.40 mmol) were added to the above system. The reaction system was replaced with argon for three times and reacted at 140° C. for 16 hours under the protection of argon. The reaction solution was cooled to room temperature and water (15 mL) was added. The mixture was extracted with ethyl acetate (15 mL×2). The organic phases were combined, washed with saturated saline (20 mL), dried with anhydrous sodium sulfate, and filtered. The filtrate was concentrated under reduced pressure to remove the organic solvent to obtain a crude product. The crude product was purified by silica gel chromatography to obtain intermediate I-109.

$^1$H NMR (400 MHz, CDCl$_3$) δ 8.26 (s, 1H), 8.18 (d, J=8.1 Hz, 1H), 7.66 (d, J=8.2 Hz, 1H), 4.11-3.81 (m, 4H), 2.46-2.32 (m, 2H), 2.28-2.15 (m, 2H), 2.12-1.98 (m, 1H), 1.93-1.84 (m, 1H).

Reference Embodiment 108: Preparation of Intermediate I-110

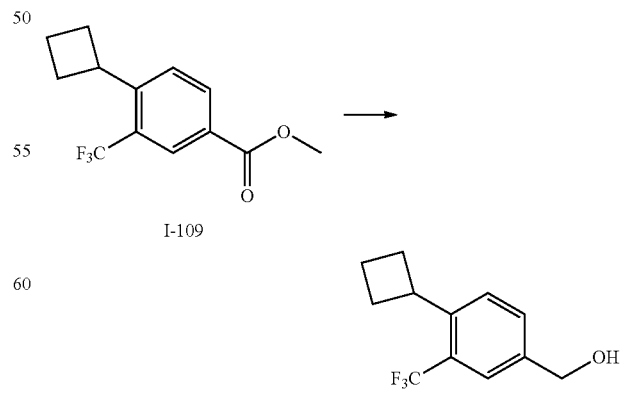

At 0° C., lithium aluminum tetrahydride (291.4 mg, 7.68 mmol) was added to a solution of intermediate I-109 (660 mg) in tetrahydrofuran (15 mL) in batches. The reaction mixture was reacted at room temperature for 16 hours. The reaction solution was cooled to 0° C., and water (2 mL) was added to quench the reaction. The reaction solution was filtered, and the filtrate was concentrated under reduced pressure to remove the organic solvent to obtain a crude product. The crude product was separated and purified by reverse phase preparation chromatography to obtain intermediate I-110.

¹H NMR (400 MHz, CDCl₃) δ 7.64-7.49 (m, 3H), 4.72 (s, 2H), 3.94-3.81 (m, 1H), 2.41-2.29 (m, 2H), 2.25-2.12 (m, 2H), 2.09-1.96 (m, 1H), 1.92-1.80 (m, 1H).

Reference Embodiment 109: Preparation of Intermediate I-111

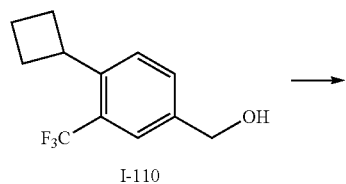

I-110

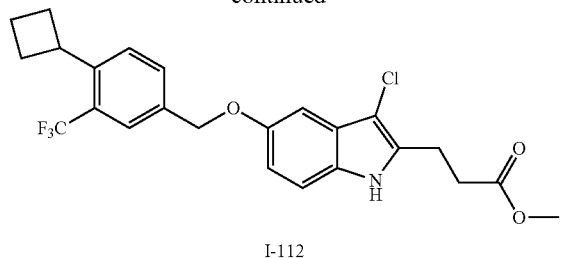

I-112

At room temperature, intermediate I-107 (60.6 mg, 0.239 mmol) was dissolved in acetonitrile (5 mL), and intermediate I-111 (70.0 mg, 0.239 mmol) and cesium carbonate (234 mg, 0.718 mmol) were added successively. The reaction mixture was stirred at 30° C. for one hour. The reaction mixture was filtered, and the filtrate was concentrated under reduced pressure to remove the organic solvent to obtain a crude product. The crude product was separated and purified by silica gel chromatography to obtain intermediate I-112.

LC-MS (ESI) [M+H]⁺ 466.2.

Reference Embodiment 111: Preparation of Intermediate I-113

I-111

At room temperature, intermediate I-110 (70.0 mg, 0.304 mmol) was dissolved in hydrobromic acid aqueous solution (1 mL, 40 wt %). The reaction mixture was stirred at 100° C. for 2 hours. After cooling to room temperature, water (10 mL) was added to the reaction mixture, and the reaction mixture was extracted with ethyl acetate (5 mL×3). The organic phases were combined, washed with saturated saline (5 mL), dried with anhydrous sodium sulfate, and filtered. The filtrate was concentrated under reduced pressure to remove the organic solvent to obtain a crude product. The crude product was separated and purified by silica gel chromatography to obtain intermediate I-111.

¹H NMR (400 MHz, CDCl₃) δ 7.61 (s, 1H), 7.56 (d, J=1.2 Hz, 2H), 4.49 (s, 2H), 3.93-3.81 (m, 1H), 2.39-2.30 (m, 2H), 2.25-2.12 (m, 2H), 2.09-1.96 (m, 1H), 1.91-1.81 (m, 1H).

Reference Embodiment 110: Preparation of Intermediate I-112

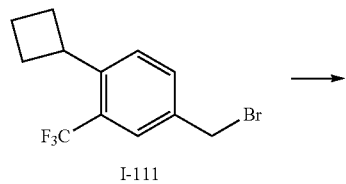

I-111

I-113

At room temperature, methyl-4-bromo-3-(trifluoromethyl) benzoate (2 g, 7.07 mmol), cyclohexen-1-yl boric acid (1.07 g, 8.48 mmol) and potassium carbonate (2.93 g, 21.2 mmol) were dissolved in dioxane (20.0 mL) and water (4.00 mL), and then Pd(PPh₃)₄ (409 mg, 0.354 mmol) was added. Under the protection of nitrogen, the reaction mixture was heated to 110° C., stirred and reacted for 5 hours at this temperature. The reaction solution was cooled to room temperature, added with water (200 mL), and extracted with ethyl acetate (300 mL×2). The organic phases were combined, washed with saturated saline (200 mL), dried with anhydrous sodium sulfate, filtered, and the filtrate was concentrated under reduced pressure to remove the organic solvent to obtain a crude product. The crude product was purified by silica gel chromatography to obtain intermediate I-113.

¹H NMR (400 MHz, CD₃OD) δ 8.30 (d, J=1.7 Hz, 1H), 8.11 (dd, J=8.0, 1.8 Hz, 1H), 7.29 (d, J=8.0 Hz, 1H), 5.62-5.58 (m, 1H), 3.94 (s, 3H), 2.24-2.12 (m, 4H), 1.79-1.65 (m, 4H).

Reference Embodiment 112: Preparation of Intermediate I-114

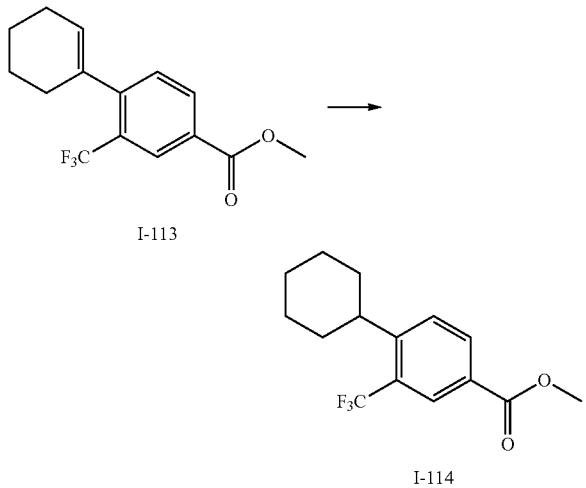

At room temperature, intermediates 1-113 (900 mg, 3.17 mmol) and Pd/C (10% w/w, 90 mg) were added to a 100 mL stainless steel reactor, and then methanol (10.0 mL) was added. The gas in the cylinder was replaced with hydrogen, and the system was pressurized with hydrogen to 40 atmospheres. The reaction mixture was heated to 50° C. under this pressure, and the mixture was stirred and reacted at this temperature for 10 hours. After the reaction solution was cooled to room temperature, it was filtered with celite, and the filtrate was concentrated under reduced pressure to remove the organic solvent to obtain the target compound 1-114, the compound was directly used in the next reaction without purification.

$^1$H NMR (400 MHz, CD$_3$OD) δ 8.28 (d, J=1.4 Hz, 1H), 8.13 (dd, J=8.3, 1.8 Hz, 1H), 7.53 (d, J=8.2 Hz, 1H), 3.93 (s, 3H), 3.03-2.93 (m, 1H), 1.89-1.76 (m, 5H), 1.52-1.37 (m, 4H), 1.35-1.25 (m, 1H).

Reference Embodiment 113: Preparation of Intermediate I-115

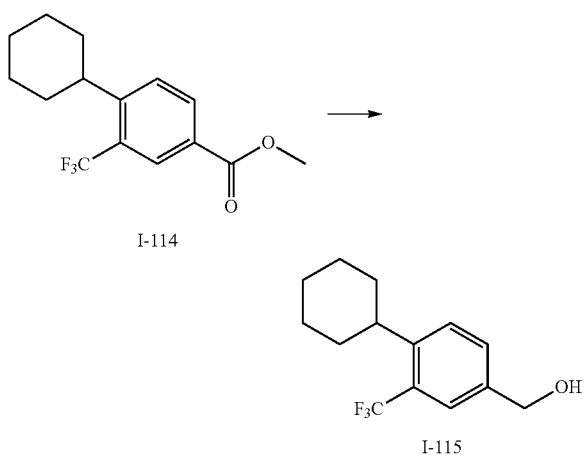

At room temperature, intermediate I-114 (700 mg) was dissolved in anhydrous tetrahydrofuran (10.0 mL). After the reaction solution was cooled to 0° C. under the protection of nitrogen, and lithium aluminum tetrahydride (1 M in THF) (6.13 mL, 6.13 mmol) was slowly added dropwise. After the dropwise addition, the reaction solution was raised to room temperature and stirred at room temperature for 10 hours. Ether (10.0 mL) was added to the reaction mixture, and the mixture was cooled to 0° C., water (4.00 mL) was added, and then sodium hydroxide aqueous solution (6.00 mL, 10% w/w) was added. Water (18.0 mL) was added and stirred for 10 minutes. Anhydrous sodium sulfate was added to the system and continuously stirred for 10 minutes. Then the mixture was filtered, concentrated under reduced pressure to remove the organic solvent to obtain a crude product. The crude product separated and purified by silica gel chromatography to obtain intermediate I-115.

$^1$H NMR (400 MHz, CD$_3$OD) δ 7.60 (d, J=1.9 Hz, 1H), 7.49 (dd, J=8.1 Hz, 1.8 Hz, 1H), 7.44 (d, J=8.1 Hz, 1H), 4.69 (s, 2H), 2.97-2.87 (m, 1H), 1.91-1.74 (m, 5H), 1.50-1.36 (m, 4H), 1.34-1.26 (m, 1H).

Reference Embodiment 114: Preparation of Intermediate I-116

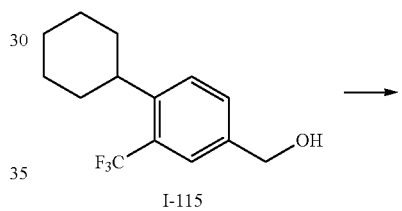

Intermediate I-115 (1.00 g, 3.87 mmol) was mixed with 40% hydrobromic acid aqueous solution (10 mL), and the reaction mixture was stirred at 100° C. for 2 hours. The reaction mixture was cooled to room temperature and extracted with dichloromethane (10 mL×2). The organic phases were combined, washed with saturated sodium bicarbonate aqueous solution (20 mL), saturated saline (20 mL), dried with anhydrous sodium sulfate, filtered, and the filtrate was concentrated to remove the organic solvent to obtain a crude product. The crude product was separated and purified by silica gel chromatography to obtain intermediate I-116.

$^1$H NMR (400 MHz, Chloroform-d) δ 7.61 (d, J=1.9 Hz, 1H), 7.51 (dd, J=8.1, 2.0 Hz, 1H), 7.43 (d, J=8.1 Hz, 1H), 4.48 (s, 2H), 2.98-2.86 (m, 1H), 1.90-1.73 (m, 5H), 1.49-1.25 (m, 5H).

Reference Embodiment 115: Preparation of Intermediate I-117

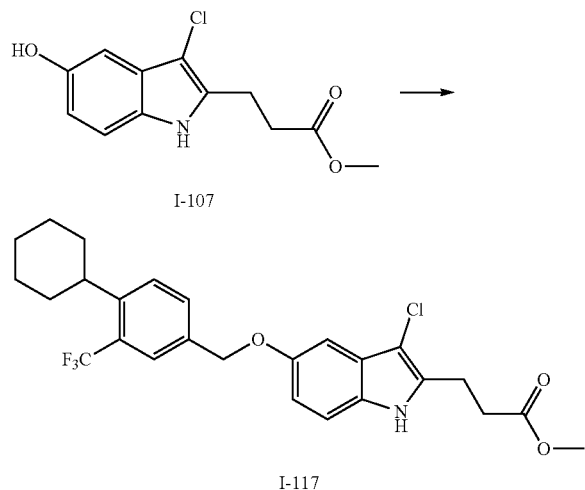

Intermediate I-107 (25.0 mg, 0.0985 mmol), intermediate I-116 (34.7 mg, 0.108 mmol) and potassium carbonate (27.2 mg, 0.197 mmol) were mixed in acetonitrile (1 mL), and the reaction mixture was stirred and reacted at 10° C. overnight, and then heated to 50° C., and stirred at 50° C. for 3 hours. The reaction mixture was filtered, and the filtrate was concentrated to remove the organic solvent to obtain a crude product. The crude product was separated and purified by silica gel chromatography to obtain intermediate I-117.

LC-MS (ESI) [M+H]$^+$ 494.2.

$^1$H NMR (400 MHz, Chloroform-d) δ 8.65 (s, 1H), 7.72 (d, J=1.8 Hz, 1H), 7.60 (d, J=7.8 Hz, 1H), 7.47 (d, J=8.1 Hz, 1H), 7.21 (d, J=8.8 Hz, 1H), 7.06 (d, J=2.4 Hz, 1H), 6.91 (dd, J=8.8, 2.4 Hz, 1H), 5.09 (s, 2H), 3.72 (s, 3H), 3.09 (d, J=6.3 Hz, 2H), 3.01-2.80 (m, 1H), 2.72 (d, J=6.3 Hz, 2H), 1.89-1.74 (m, 5H), 1.51-1.33 (m, 5H).

Reference Embodiment 116: Preparation of Intermediate I-118

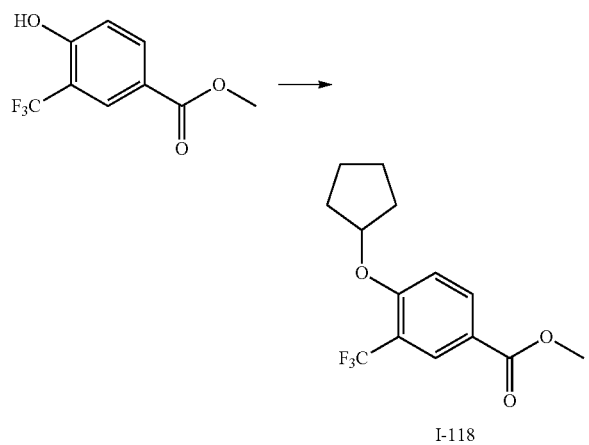

Methyl 4-hydroxy-3-(trifluoromethyl) benzoate (950 mg, 4.32 mmol) was dissolved in N,N-dimethylformamide (15 mL), and iodocyclopentane (1270 mg, 6.48 mmol) and cesium carbonate (4223 mg, 12.96 mmol) were added to the reaction successively. The reaction mixture was heated to 45° C., and the reaction was stirred and reacted at this temperature for 16 hours. The reaction solution was cooled to room temperature, water (50 mL) and ethyl acetate (50 mL) were added successively, and the organic phase was separated by extraction. The aqueous phase was extracted with ethyl acetate (50 mL×2), and the organic phases were combined, washed with saturated saline (20 mL), dried with anhydrous sodium sulfate and filtered. The filtrate was concentrated under reduced pressure to obtain a crude product. The crude product was purified by silica gel chromatography to obtain intermediate I-118.

LC-MS (ESI) [M+H]$^+$ 289.1.

$^1$H NMR (400 MHz, CDCl$_3$) δ 8.24 (d, J=2.0 Hz, 1H), 8.15 (dd, J=8.7, 2.1 Hz, 1H), 7.01 (d, J=8.9 Hz, 1H), 4.96-4.92 (m, 1H), 3.91 (s, 3H), 1.95-1.92 (m, 2H), 1.92-1.88 (m, 2H), 1.87-1.79 (m, 2H), 1.70-1.63 (m, 2H).

Reference Embodiment 117: Preparation of Intermediate I-119

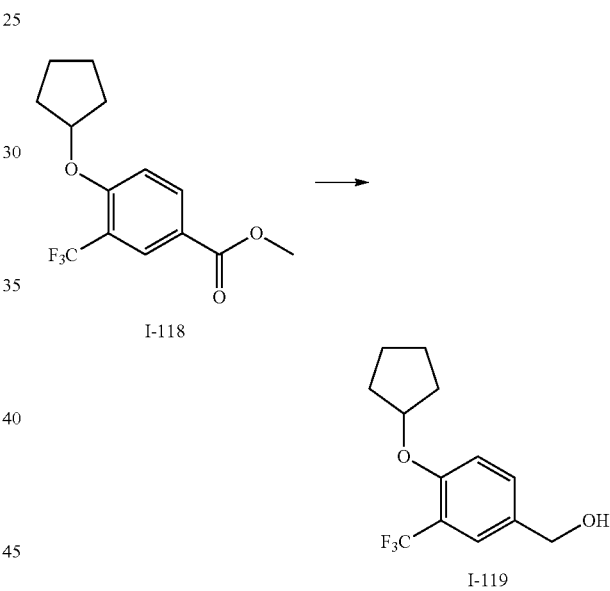

Intermediate I-118 (1.19 g, 4.13 mmol) was dissolved in anhydrous tetrahydrofuran (50 mL), DIBAL-H (5.51 mL, 8.26 mmol, 1.5M in toluene) was added dropwise to the reaction mixture at −40° C. After the dropwise addition, the reaction mixture was raised to room temperature, and the reaction was stirred at this temperature for 16 hours. Water (100 mL) and ethyl acetate (50 mL) were added successively, and the organic phase was separated by extraction. The aqueous phase was extracted with ethyl acetate (50 mL×2), and the organic phases were combined, washed with saturated saline (20 mL), dried with anhydrous sodium sulfate and filtered. The filtrate was concentrated under reduced pressure to obtain a crude product. The crude product was purified by silica gel chromatography to obtain intermediate I-119.

$^1$H NMR (400 MHz, CDCl$_3$) δ 7.55 (d, J=1.8 Hz, 1H), 7.45 (dd, J=8.5, 1.8 Hz, 1H), 6.97 (d, J=8.5 Hz, 1H), 4.89-4.85 (m, 1H), 4.64 (s, 2H), 1.92-1.89 (m, 2H), 1.88-1.84 (m, 2H), 1.84-1.76 (m, 2H), 1.65-1.61 (m, 2H).

Reference Embodiment 118: Preparation of Intermediate I-120

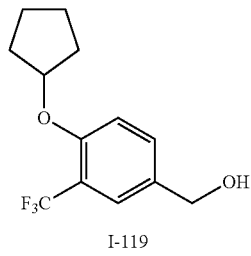

I-119

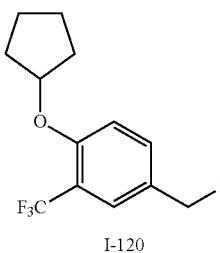

I-120

Intermediate I-119 (100 mg, 0.384 mmol) and 48% hydrobromic acid aqueous solution (1 mL) were mixed in toluene (1 mL), and the reaction mixture was stirred at 100° C. for one hour. The reaction solution was cooled to 10° C., added with water (20 mL), and extracted with petroleum ether (10 mL×3). The organic phases were combined, washed with saturated saline (10 mL), dried with anhydrous sodium sulfate, filtered, and the filtrate was concentrated under reduced pressure to remove the organic solvent to obtain intermediate I-120. The crude product was directly used in the next reaction without purification.

$^1$H NMR (400 MHz, Chloroform-d) δ 7.57 (d, J=2.4 Hz, 1H), 7.48 (dd, J=8.6, 2.4 Hz, 1H), 6.95 (d, J=8.5 Hz, 1H), 4.90-4.83 (m, 1H), 4.48 (s, 2H), 1.97-1.86 (m, 4H), 1.85-1.77 (m, 2H), 1.69-1.59 (m, 2H).

Reference Embodiment 119: Preparation of Intermediate I-121

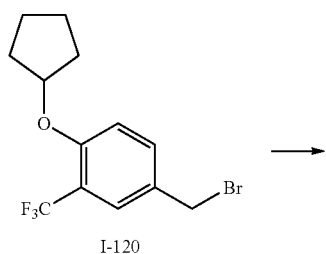

I-120

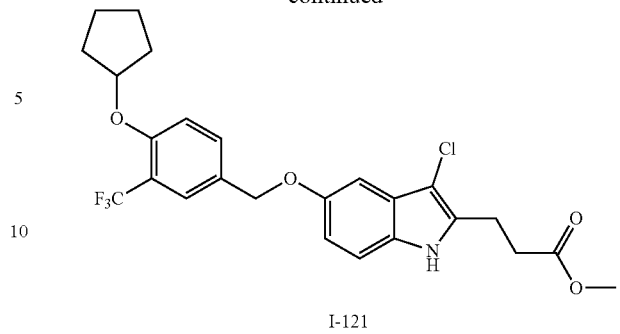

I-121

Intermediate I-120 (70.1 mg, 0.217 mmol) and intermediate I-107 (50.0 mg, 0.197 mmol) were dissolved in acetonitrile (5 mL), and cesium carbonate (128 mg, 0.394 mmol) was added at 10° C. The reaction mixture was stirred at 10° C. overnight. The reaction solution was filtered, and the filtrate was concentrated under reduced pressure to remove the organic solvent to obtain a crude product. The crude product was separated and purified by silica gel chromatography to obtain intermediate I-121.

LC-MS (ESI) [M+H]$^+$ 496.2.

$^1$H NMR (400 MHz, Chloroform-d) δ 8.64 (s, 1H), 7.66 (d, J=2.2 Hz, 1H), 7.55 (dd, J=8.5, 2.2 Hz, 1H), 7.20 (d, J=8.8 Hz, 1H), 7.05 (d, J=2.4 Hz, 1H), 7.00 (d, J=8.5 Hz, 1H), 6.89 (dd, J=8.8, 2.4 Hz, 1H), 5.04 (s, 2H), 4.91-4.85 (m, 1H), 3.72 (s, 3H), 3.09 (d, J=6.3 Hz, 2H), 2.72 (d, J=6.3 Hz, 2H), 1.99-1.86 (m, 4H), 1.85-1.78 (m, 2H), 1.68-1.58 (m, 2H).

Reference Embodiment 120: Preparation of Intermediate I-122

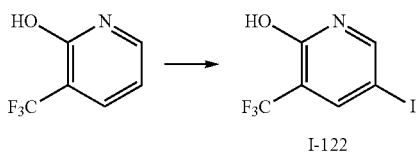 [SMILES: Oc1ncccc1C(F)(F)F ; Oc1ncc(I)cc1C(F)(F)F]

I-122

2-Hydroxy-3-trifluoromethylpyridine (5.00 g, 30.66 mmol) and NIS (6.90 g, 30.66 mmol) were dissolved in a mixed solvent of N,N-dimethylformamide and acetonitrile (60.0 mL, 1:1). The reaction mixture was heated to 80° C., and the reaction was stirred and reacted at this temperature for 3 hours. The reaction mixture was cooled to 25° C., added with sodium bicarbonate solution (35.0 mL, 1 M), and stirred for five minutes, and extracted with dichloromethane (500 mL×2). The organic phases were combined and concentrated under reduced pressure to remove the organic solvent to obtain a crude product. The crude product was stirred with water (25.0 mL) and filtered. The filter cake was dried in vacuum to obtain a crude product of intermediate I-122. The product was directly used for the next reaction without further purification.

Reference Embodiment 121: Preparation of Intermediate I-123

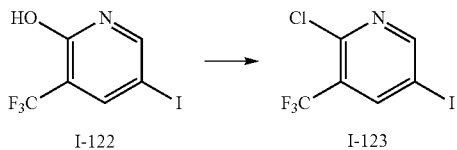 [SMILES: Oc1ncc(I)cc1C(F)(F)F ; FC(F)(F)c1cc(I)cnc1Cl]

Intermediate I-122 (6.3 g, 21.80 mmol) was dissolved in phosphorus oxychloride (15.0 mL). The reaction mixture was heated to 100° C., and the reaction was stirred at this temperature for 10 hours. After the reaction solution was cooled to room temperature, the solution was slowly added to ice water (200 mL), the pH of the solution was adjusted to neutral with sodium carbonate, and then extracted with ethyl acetate (400 mL×2). The organic phases were combined, dried with anhydrous sodium sulfate, filtered, and the filtrate was concentrated under reduced pressure to remove the organic solvent to obtain a crude product. The crude product was purified by silica gel column (PE:EA=100:1 to 10:1) to obtain intermediate I-123.

$^1$H NMR (400 MHz, CDCl$_3$) δ 8.78 (s, 1H), 8.28 (s, 1H).

Reference Embodiment 122: Preparation of Intermediate I-124

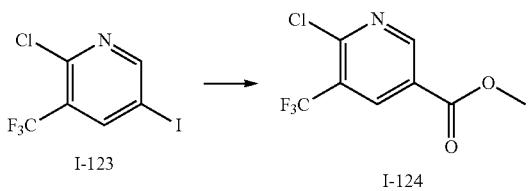

Intermediate I-123 (2.10 g, 6.83 mmol), sodium acetate (1.12 g, 13.66 mmol), palladium acetate (76.78 mg, 0.342 mmol) and 1,1'-bis (diphenylphosphine) ferrocene (114 mg, 0.205 mmol) were dissolved in anhydrous methanol (25.0 mL). The reaction mixture was heated to 80° C. and reacted at this temperature in CO atmosphere for 10 hours. The reaction solution was cooled to 25° C. and filtered with celite, and the filtrate was concentrated under reduced pressure to remove the organic solvent to obtain a crude product. The crude product was purified by silica gel chromatography to obtain intermediate I-124.

LC-MS (ESI) [M+H]$^+$ 240.1 [M+H+41]$^+$281.1.

$^1$H NMR (400 MHz, CD$_3$OD) δ 9.13 (d, J=1.8 Hz, 1H), 8.64 (d, J=1.8 Hz, 1H), 3.99 (s, 3H).

Reference Embodiment 123: Preparation of Intermediate I-125

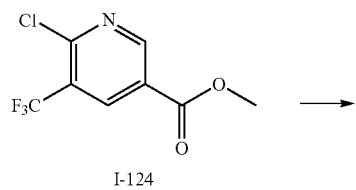

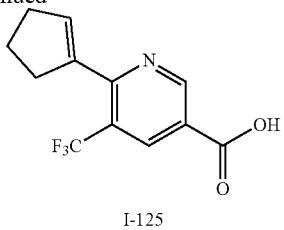

Intermediate I-124 (500 mg, 2.09 mmol), cyclopenten-1-ylboronic acid (281 mg, 2.51 mmol), tricyclohexylphosphine (58.6 mg, 0.209 mmol), cesium carbonate (2.04 g, 6.27 mmol) and Pd$_2$(dba)$_3$ were dissolved in a mixed solution of dioxane/acetonitrile/water (12.00 mL, 2.5:2.5:1), and the reaction solution was heated to 100° C. under the protection of nitrogen and reacted at this temperature for 8 hours. The reaction solution was cooled to room temperature and filtered with celite, and the filtrate was concentrated under reduced pressure to remove the organic solvent. The residue was diluted with ethyl acetate (30 mL), washed with water (15 mL) and saturated saline (30 mL), dried with anhydrous sodium sulfate and filtered. The filtrate was concentrated under reduced pressure to remove the organic solvent to obtain a crude product. The crude product was purified by silica gel chromatography to obtain intermediate I-125.

LC-MS (ESI) [M+H+41]$^+$299.2

Reference Embodiment 124: Preparation of Intermediate I-126

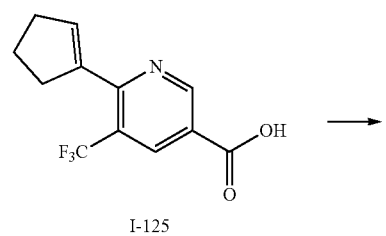

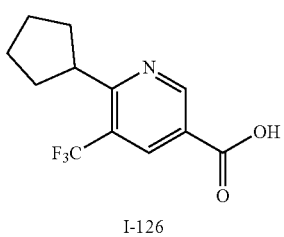

Intermediate I-125 (300 mg, 1.17 mmol) and PtO$_2$ (53.1 mg) was dissolved in ethyl acetate (10.0 mL). The reaction mixture was reacted at at 25° C. in hydrogen atmosphere for 10 hours. The reaction solution was filtered with celite, and the filtrate was concentrated under reduced pressure to remove the organic solvent to obtain intermediate I-126.

LC-MS (ESI) [M+H+41]$^+$301.2

Reference Embodiment 125: Preparation of Intermediate I-127

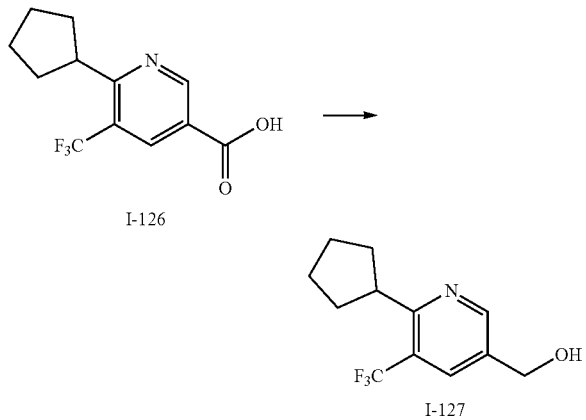

Intermediate I-126 (270 mg, 1.04 mmol) was dissolved in tetrahydrofuran (4.00 mL). The mixture was cooled to 0° C. and then BH$_3$ (3.12 mL, 1 M in THF, 3.12 mmol) was slowly added dropwise under the protection of nitrogen. The reaction was then raised to 25° C. and continuously reacted for 2 hours. The reaction solution was cooled to 0° C. again and then quenched with methanol (4.00 mL). The reaction solution was concentrated under reduced pressure to remove the organic solvent, and the residue was diluted with ethyl acetate (30.0 mL) and washed with water (15.0 mL). The organic phase was dried with anhydrous sodium sulfate and filtered. The filtrate was concentrated under reduced pressure to remove the organic solvent to obtain a crude product of intermediate I-127. The crude product was directly used in the next reaction without purification.

LC-MS (ESI) [M+H]$^+$ 246.1

Reference Embodiment 126: Preparation of Intermediate I-128

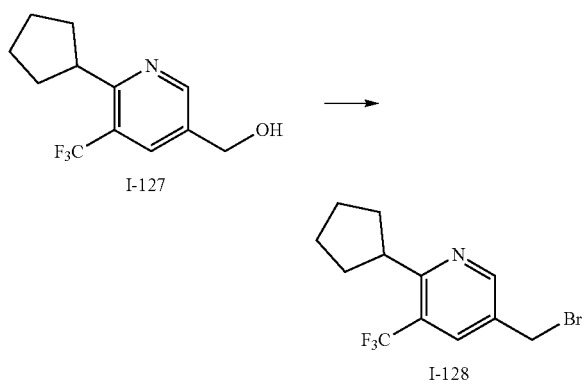

Intermediate I-127 (90 mg, 0.367 mmol) was dissolved in hydrobromic acid (5 mL, 40% in H$_2$O) and heated to 100° C. The reaction mixture was stirred at 100° C. for 2 hours and then cooled to room temperature, poured into saturated sodium bicarbonate (15 mL), and extracted with ethyl acetate (10 mL×3). The organic phases were combined, washed with saturated saline (10 mL), dried with anhydrous sodium sulfate, and filtered. The filtrate was concentrated under reduced pressure to remove the organic solvent to obtain a crude product. The crude product was separated and purified by silica gel chromatography to obtain intermediate I-128.

LC-MS (ESI) [M+H]$^+$ 307.9.

Reference Embodiment 127: Preparation of Intermediate I-129

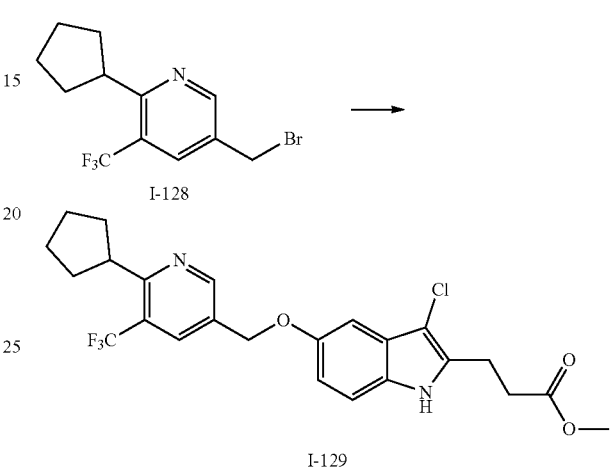

At 18° C., intermediate I-128 (60.0 mg, 0.195 mmol) was dissolved in N,N-dimethylformamide (2.5 mL). And intermediate I-107 (54.5 mg, 0.215 mmol) and cesium carbonate (191 mg, 0.585 mmol) were added successively. The reaction mixture was stirred at 30° C. for 8 hours and then the reaction system was poured into water (10 mL) and extracted with ethyl acetate (5 mL×3). The organic phases were combined, washed with saturated saline (5 mL), dried with anhydrous sodium sulfate, and filtered. The filtrate was concentrated under reduced pressure to remove the organic solvent to obtain a crude product. The crude product was separated and purified by silica gel chromatography to obtain intermediate I-129.

LC-MS (ESI) [M+H]$^+$ 481.1.

Reference Embodiment 128: Preparation of Intermediate I-130

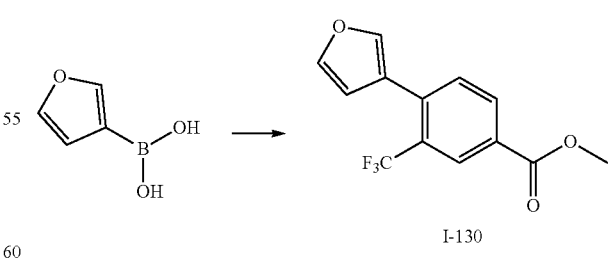

Compound 3-furanboronic acid (1.97 g, 17.61 mmol) was dissolved in DMF (30.0 mL) and methyl 3-(trifluoromethyl)-4-bromobenzoate (3.84 g, 13.57 mmol), cesium carbonate (8.83 g, 27.10 mmol) and 1,1'-bis(diphenylphosphino)ferrocenepalladium(II)dichloride dichloromethane complex (335 mg, 0.410 mmol) were added successively.

The reaction solution was heated to 90° C. under the protection of argon, stirred and reacted for 16 hours. Water (60 mL) and ethyl acetate (60 mL) were added to the reaction solution, and the aqueous phase was extracted with ethyl acetate (60 mL×2). The organic phases were combined, washed with saturated saline (10 mL), dried with anhydrous sodium sulfate and filtered. The filtrate was concentrated to dryness under reduced pressure, and the crude product was separated and purified by silica gel chromatography to obtain intermediate I-130.

$^1$H NMR (400 MHz, Chloroform-d) δ 8.42 (d, J=1.7 Hz, 1H), 8.19 (dd, J=8.0, 1.7 Hz, 1H), 7.60 (d, J=1.5 Hz, 1H), 7.54-7.48 (m, 2H), 6.62-6.56 (m, 1H), 3.97 (s, 3H).

Reference Embodiment 129: Preparation of Intermediate I-131

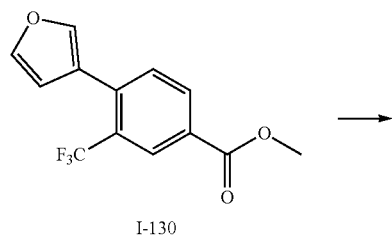

I-130

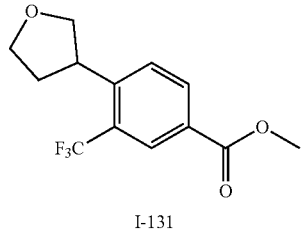

I-131

Intermediate I-130 (3.11 g, 11.51 mmol) was dissolved in methanol (100 mL), Pd/C (500 mg, 10% w/w) was added, and the reaction mixture was stirred at room temperature for 16 hours under hydrogen atmosphere. The reaction solution was filtered and the filtrate was concentrated to dryness. The crude product was separated and purified by silica gel chromatography to obtain intermediate I-131.

$^1$H NMR (400 MHz, Chloroform-d) δ 8.30 (d, J=1.8 Hz, 1H), 8.20-8.15 (m, 1H), 7.62 (d, J=8.3 Hz, 1H), 4.18-4.04 (m, 2H), 3.94 (s, 3H), 3.92-3.82 (m, 3H), 2.53-2.40 (m, 1H), 2.02-1.91 (m, 1H).

Reference Embodiment 130: Preparation of Intermediate I-132

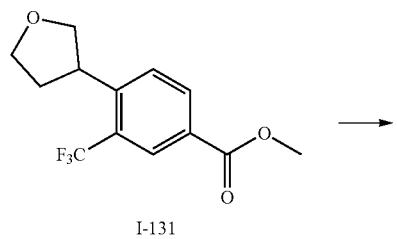

I-131

-continued

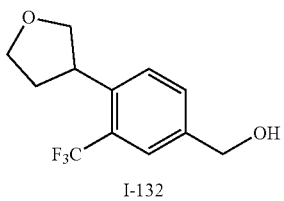

I-132

Intermediate I-131 (1.00 g, 3.65 mmol) was dissolved in anhydrous tetrahydrofuran (25 mL), cooled to −40° C., and a solution of diisobutylaluminium hydride in toluene (1.5 M, 9.73 mL, 14.60 mmol) was slowly added dropwise under the protection of argon, and the mixture was raised to room temperature and stirred for 2 hours after the dropwise addition. The reaction was quenched by adding with water (100 mL), then the mixture was added with ethyl acetate (50 mL), separated. The aqueous phase was extracted with ethyl acetate (50 mL×2). The organic phases were combined, washed with saline (20 mL×2), dried with anhydrous sodium sulfate, and filtered. The filtrate was concentrated under reduced pressure to remove the organic solvent, and the crude product was separated and purified by silica gel chromatography to obtain intermediate I-132.

LC-MS(ESI) [M−H]$^+$245.0.

Reference Embodiment 131: Preparation of Intermediate I-133

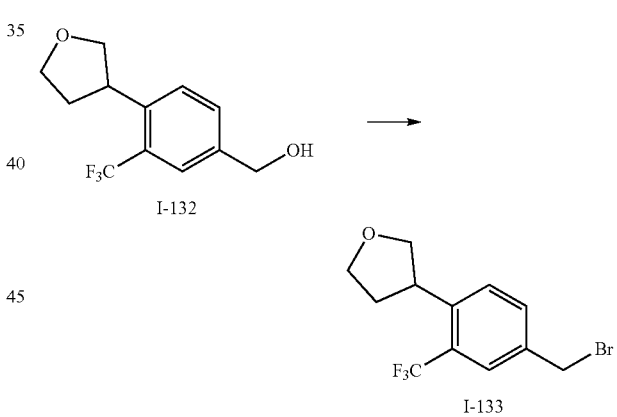

Hydrobromic acid aqueous solution (3.00 mL, 40% w/w) was added to the intermediate I-132 (150 mg, 0.609 mmol), and the reaction mixture was heated to 100° C. and stirred for 2 hours. After the reaction solution was cooled to room temperature, it was extracted with ethyl acetate (15 mL×3), the organic phases were combined, washed with saturated saline (15 mL), dried with anhydrous sodium sulfate, and filtered. The filtrate was concentrated under reduced pressure, and the crude product was separated and purified by silica gel chromatography to obtain intermediate I-133.

$^1$H NMR (400 MHz, Chloroform-d) δ 7.63 (s, 1H), 7.56 (d, J=8.2 Hz, 1H), 7.52 (d, J=8.2 Hz, 1H), 4.49 (s, 2H), 4.15-4.08 (m, 1H), 4.08-4.02 (m, 1H), 3.95-3.86 (m, 1H), 3.85-3.75 (m, 2H), 2.53-2.34 (m, 1H), 2.05-1.86 (m, 1H).

Reference Embodiment 132: Preparation of Intermediate I-134

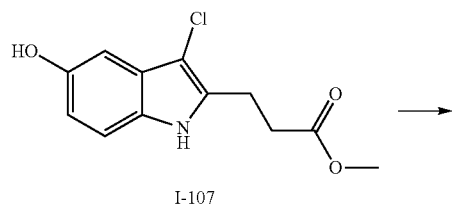

Intermediate I-133 (87.0 mg, 0.281 mmol) was dissolved in acetonitrile (3.00 mL), and intermediate I-107 (71.3 mg, 0.281 mmol) and cesium carbonate (275 mg, 0.843 mmol) were added successively. The reaction solution was heated to 30° C., stirred and reacted for 2 hours, then filtered, and the filtrate was concentrated to dryness under vacuum and reduced pressure. The residue was separated and purified by silica gel chromatography to obtain intermediate I-134.
LC-MS (ESI) [M+H]$^+$ 482.2.

Reference Embodiment 133: Preparation of Intermediate I-135

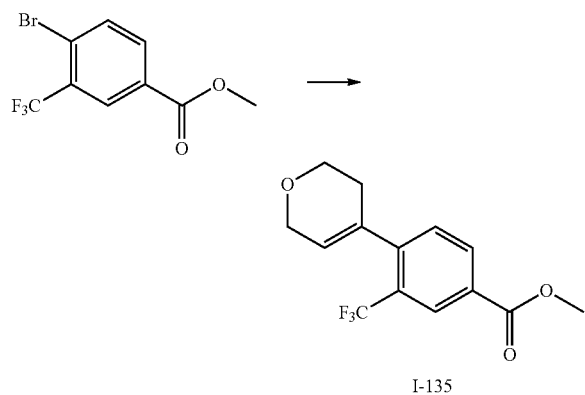

At 10° C., methyl 4-bromo-3-(trifluoromethyl)benzoate (3.5 g, 12.37 mmol) and 3,6-dihydro-2H-pyran-4-boronic acid pinacol ester (3.11 g, 14.8 mmol) was dissolved in dioxane/water (50 mL, volume ratio 4/1), and then tetrakis (triphenylphosphine)palladium (710 mg, 0.614 mmol) and potassium carbonate (5.1 g, 36.9 mmol) were added. The reaction mixture was stirred at 110° C. for 3 hours under the protection of argon. The reaction solution was added with water (200 mL), and extracted with petroleum ether (50 mL×4). The organic phases were combined, and washed with saturated saline (50 mL), dried with anhydrous sodium sulfate, and filtered. The filtrate was concentrated under reduced pressure to remove the organic solvent to obtain a crude product of intermediate I-135. The crude product was directly used in the next reaction without purification.

$^1$H NMR (400 MHz, CDCl$_3$) δ 8.34 (d, 1.4 Hz, 1H), 8.16 (dd, J=8.0, 1.4 Hz, 1H), 7.35 (t, J=6.6 Hz, 1H), 5.69 (s, 1H), 4.28 (q, J=2.7 Hz, 2H), 3.95 (s, 3H), 3.92 (t, J=5.4 Hz, 2H), 2.36 (dt, J=7.2, 2.5 Hz, 2H).

Reference Embodiment 134: Preparation of Intermediate I-136

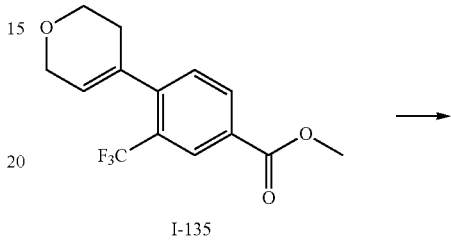

At 18° C., intermediate I-135 (3.5 g) was dissolved in ethanol (80 mL), and palladium carbon (100 mg, 10% w/w) was slowly added. The reaction mixture was stirred at 60° C. and 10 atm for 72 hours. After the reaction solution was cooled to room temperature, palladium carbon in the mixture was removed by filtration, and the filtrate was concentrated under reduced pressure to obtain a crude product. The crude product was separated and purified by silica gel chromatography to obtain intermediate I-136.

$^1$H NMR (400 MHz, CDCl$_3$) δ 8.31 (s, 1H), 8.19 (d, J=8.2 Hz, 1H), 7.57 (d, J=8.2 Hz, 1H), 4.10 (dd, J=11.5, 4.1 Hz, 2H), 3.94 (s, 3H), 3.56 (td, J=11.8, 1.7 Hz, 2H), 3.25 (t, J=11.8 Hz, 1H), 1.88 (dd, J=12.6, 4.2 Hz, 2H), 1.75-1.67 (m, 2H).

Reference Embodiment 135: Preparation of Intermediate I-137

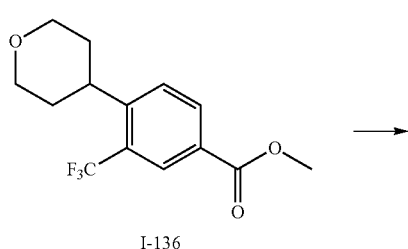

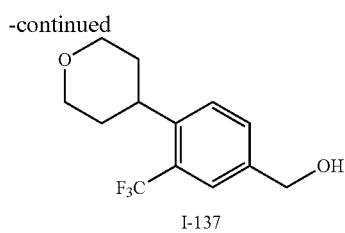

I-137

Intermediate I-136 (2.0 g, 6.94 mmol) was dissolved in tetrahydrofuran, and diisobutyl aluminum hydride solution (13.9 mL, 1.5 MIL toluene solution) was slowly added dropwise to the above mixture at −60° C. The reaction mixture was stirred at −30° C. for 3 hours and then the reaction system was poured into dilute hydrochloric acid (100 mL) and extracted with ethyl acetate (50 mL×3). The organic phases were combined, washed with saturated sodium bicarbonate (30 mL), and then washed with saturated saline (50 mL), dried with anhydrous sodium sulfate, and filtered. The filtrate was concentrated under reduced pressure to remove the organic solvent to obtain a crude product. The crude product was separated and purified by silica gel chromatography to obtain intermediate I-137.

$^1$H NMR (400 MHz, CDCl$_3$) δ 7.64 (s, 1H), 7.53 (d, J=8.2 Hz, 1H), 7.46 (d, J=8.1 Hz, 1H), 4.71 (s, 2H), 4.07 (dd, J=11.5, 4.2 Hz, 2H), 3.54 (td, J=11.9, 1.6 Hz, 2H), 3.18 (t, J=11.8 Hz, 1H), 2.03 (d, J=4.8 Hz, 1H), 1.85 (qd, J=12.4, 4.3 Hz, 2H), 1.69 (d, J=10.6 Hz, 2H).

Reference Embodiment 136: Preparation of Intermediate I-138

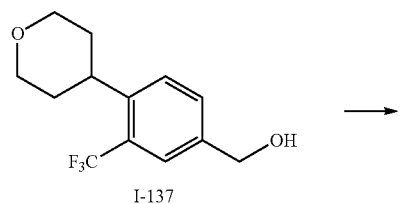

Compound I-137 (100 mg, 0.384 mmol) was dissolved in hydrobromic acid (5 mL, 40% aq.) and heated to 100° C. The reaction mixture was stirred at 100° C. for 3 hours and then cooled to room temperature, and extracted with ethyl acetate (5 mL×4). The organic phases were combined, washed with saturated sodium bicarbonate (10 mL) and saturated saline (10 mL), dried with anhydrous sodium sulfate, and filtered. The filtrate was concentrated under reduced pressure to remove the organic solvent to obtain a crude product. The crude product was separated and purified by silica gel chromatography to obtain intermediate I-138.

$^1$H NMR (400 MHz, CDCl$_3$) δ 7.64 (d, J=1.5 Hz, 1H), 7.58-7.54 (m, 1H), 7.46 (d, J=8.1 Hz, 1H), 4.49 (s, 2H), 4.08 (dd, J=11.6, 4.3 Hz, 2H), 3.54 (td, J=11.9, 1.9 Hz, 2H), 3.23-3.13 (m, 1H), 1.85 (dd, J=12.6, 4.2 Hz, 2H), 1.69 (dd, J=12.9, 1.9 Hz, 2H).

Reference Embodiment 137: Preparation of Intermediate I-139

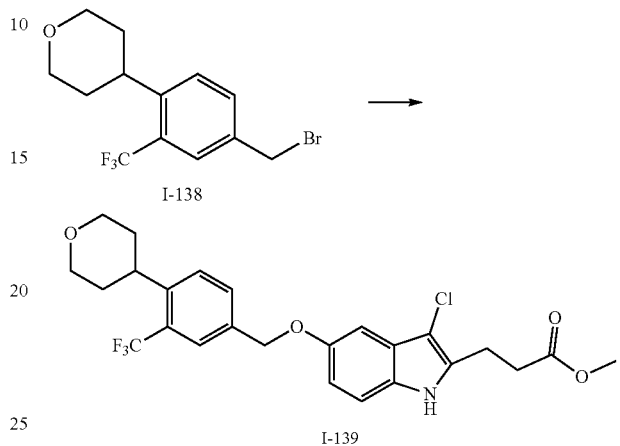

At 10° C., intermediate I-138 (60.0 mg, 0.186 mmol) was dissolved in N,N-dimethylformamide (2.5 mL). And intermediate I-107 (47.2 mg, 0.186 mmol) and cesium carbonate (182 mg, 0.558 mmol) were added successively. The reaction mixture was stirred at 30° C. for 8 hours and then the reaction system was poured into water (10 mL) and extracted with ethyl acetate (3 mL×4). The organic phases were combined, washed with saturated saline (5 mL), dried with anhydrous sodium sulfate, and filtered. The filtrate was concentrated under reduced pressure to remove the organic solvent to obtain a crude product. The crude product was separated and purified by silica gel chromatography to obtain intermediate I-139.

LC-MS (ESI) [M−H]$^-$ 494.1.

Reference Embodiment 138: Preparation of Intermediate I-140

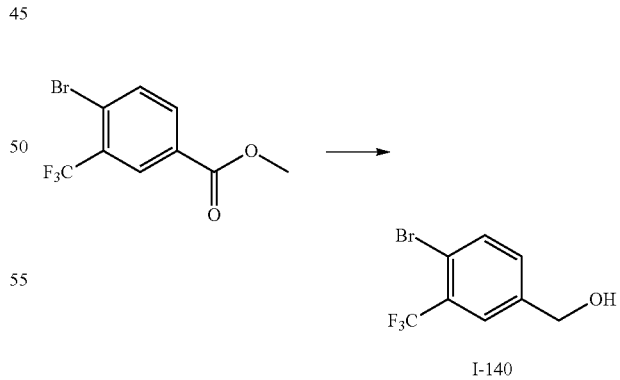

At 0° C., a solution of methyl 3-trifluoromethyl-4-bromobenzoate (1.50 g, 5.30 mmol) in anhydrous tetrahydrofuran (10 mL) was added dropwise to a solution of lithium aluminum hydride in tetrahydrofuran (10.6 mL, 1.0 M, 10.6 mmol). The reaction mixture was stirred at 0° C. for one hour. The reaction solution was quenched with saturated sodium bicarbonate solution (30 mL) at 0° C. and then filtered, and the filtrate was extracted with ethyl acetate (30 mL×3). The organic phases were combined, washed with saturated saline (30 mL), dried with anhydrous sodium sulfate, and filtered. The filtrate was concentrated under reduced pressure to remove the organic solvent to obtain a crude product. The crude product was separated and purified by silica gel chromatography to obtain intermediate I-140.

¹H NMR (400 MHz, CDCl₃) δ 7.70 (s, 1H), 7.68 (s, 1H), 7.39 (dd, J=8.2, 1.4 Hz, 1H), 4.72 (s, 1H).

Reference Embodiment 139: Preparation of Intermediate I-141

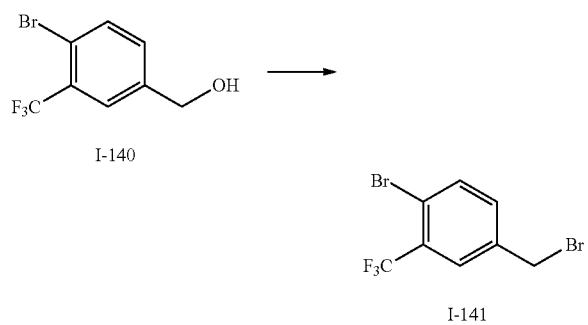

At room temperature, intermediate I-140 (305 mg, 1.20 mmol) was dissolved in hydrobromic acid (3 mL, 40 wt % aqueous solution). The reaction mixture was stirred at 100° C. for 2 hours. The reaction mixture was cooled to room temperature, diluted with water (30 mL), and then extracted with ethyl acetate (20 mL×3). The organic phases were combined, washed with saturated saline (10 mL), dried with anhydrous sodium sulfate, and filtered. The filtrate was concentrated under reduced pressure to remove the organic solvent to obtain a crude product. The crude product was separated and purified by silica gel chromatography to obtain intermediate I-141.

¹H NMR (400 MHz, CDCl₃) δ 7.70 (s, 1H), 7.68 (s, 1H), 7.42 (dd, J=8.2, 2.1 Hz, 1H), 4.45 (s, 2H).

Reference Embodiment 140: Preparation of Intermediate I-142

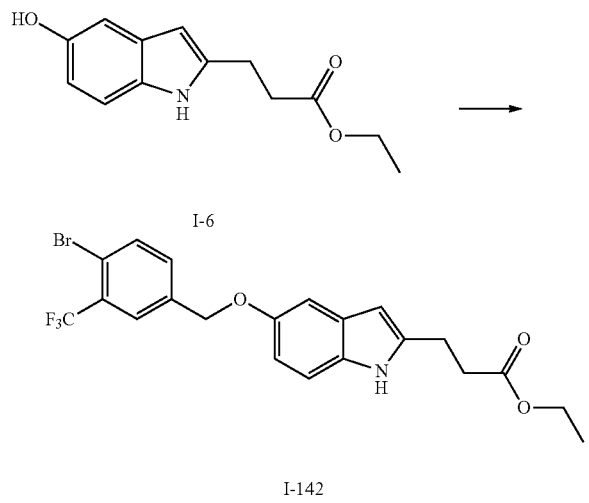

At room temperature, intermediate I-141 (240 mg, 0.755 mmol) was dissolved in acetonitrile (10 mL). Intermediate I-6 (176 mg, 0.754 mmol) and cesium carbonate (738 mg, 2.27 mmol) were added successively. After the addition, the reaction mixture was stirred at 30° C. for one hour. The reaction solution was filtered, the filtrate was concentrated under reduced pressure to remove the organic solvent to obtain a crude product. The crude product was separated and purified by silica gel method to obtain intermediate I-142.

Reference Embodiment 141: Preparation of Intermediate I-143

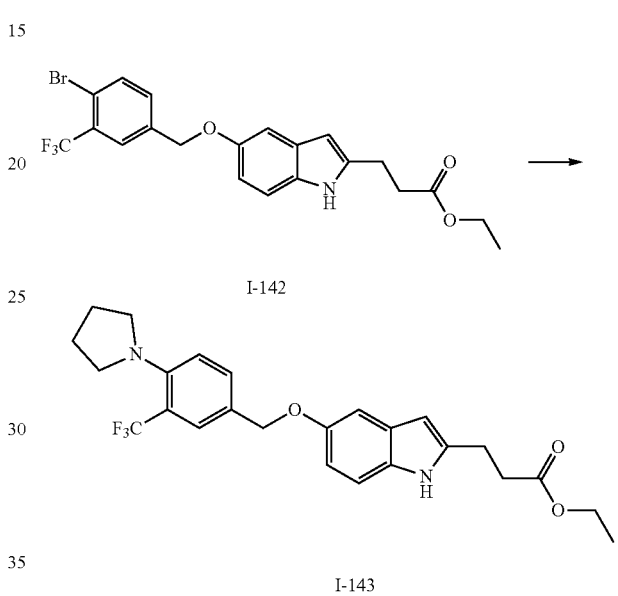

At room temperature, intermediate I-142 (57.0 mg, 0.121 mmol) was dissolved in toluene (2 mL, and pyrrolidine (17.8 mg, 0.250 mmol), palladium acetate (2.92 mg, 0.0130 mmol), cesium carbonate (122 mg, 0.374 mmol) and 1,1'-binaphthyl-2.2'-diphemyl phosphine (15.6 mg, 0.0250 mmol) were added successively. The reaction mixture was stirred and reacted at 110° C. for 16 hours under the protection of nitrogen. The reaction mixture was concentrated under reduced pressure to remove the organic solvent to obtain a crude product. The crude product was separated and purified by silica gel chromatography to obtain intermediate I-143.

LC-MS (ESI) [M+H]⁺ 461.2.

Reference Embodiment 142: Preparation of Intermediate I-144

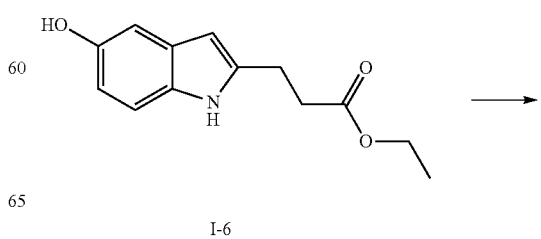

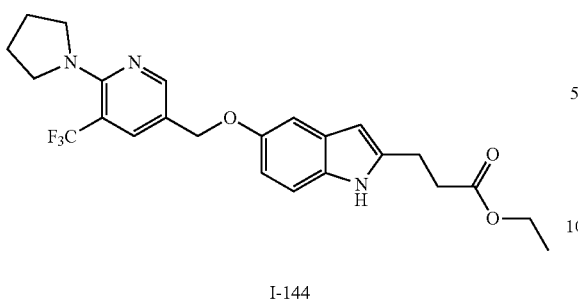

I-144

At room temperature, intermediate I-6 (233 mg, 1.00 mmol) and intermediate I-128 (308 mg, 1.00 mmol) were dissolved in acetonitrile (3 mL), and cesium carbonate (977 mg, 3.00 mmol) was added. The reaction solution was stirred at 25° C. for 2 hours. The reaction solution was filtered, the filtrate was concentrated under reduced pressure to remove the organic solvent. The residue was separated and purified by silica gel chromatography to obtain intermediate I-144.

LC-MS (ESI) [M+H]$^+$ 461.2.

Reference Embodiment 143: Preparation of Intermediate I-145

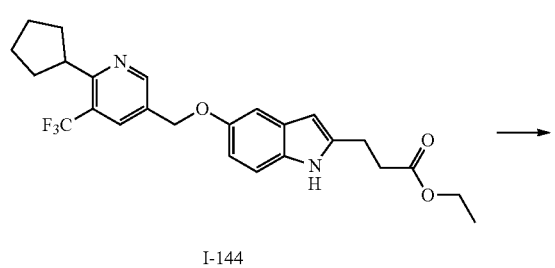

I-144

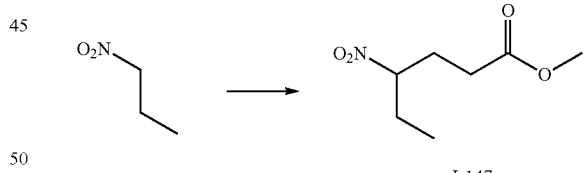

I-145

Intermediate I-144 (100 mg, 0.217 mmol) was dissolved in acetonitrile (2 mL) at room temperature, after cooling to 0° C., a solution of Selectfluor (92.2 mg, 0.260 mmol) in water (1 mL) was added, and the reaction solution was stirred at 0° C. for 40 minutes. The reaction solution was extracted with ethyl acetate (20 mL×3). The organic phases were combined, washed with saturated saline (5 mL), the organic phase was separated and concentrated under reduced pressure. The residue was separated and purified by silica gel chromatography to obtain intermediate I-145.

LC-MS (ESI) [M+H]$^+$ 479.2.

Reference Embodiment 144: Preparation of Intermediate I-146

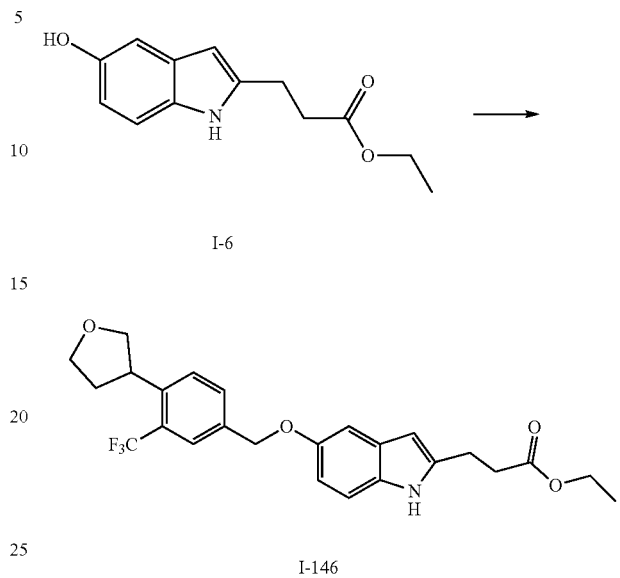

I-146

At room temperature, intermediate I-6 (467 mg, 2.00 mmol) and intermediate I-133 (618 mg, 2.00 mmol) were dissolved in acetonitrile (5 mL), and cesium carbonate (1.95 g, 6.00 mmol) was added, and the reaction solution was stirred at 25° C. for 3 hours. The reaction solution was filtered, the filtrate was concentrated under reduced pressure to remove the organic solvent. The residue was separated and purified by silica gel chromatography to obtain intermediate I-146.

Reference Embodiment 145: Preparation of Intermediate I-147

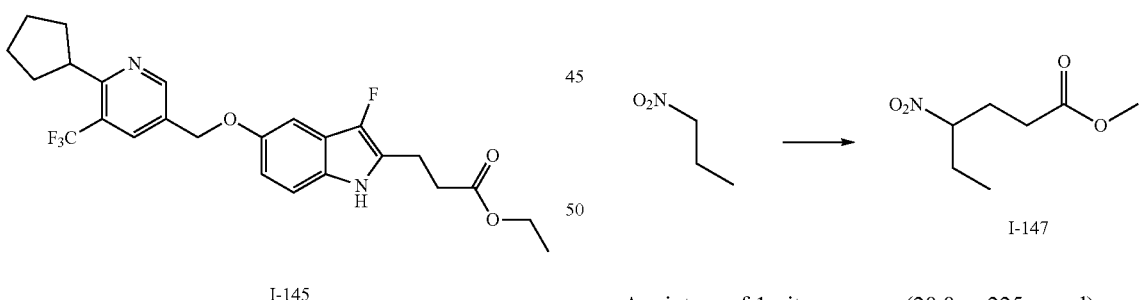

I-147

A mixture of 1-nitropropane (20.0 g, 225 mmol), methyl acrylate (19.4 g, 225 mmol) and potassium carbonate (9.33 g, 67.5 mmol) were reacted at room temperature for 24 hours. The reaction solution was filtered, and the filtrate was diluted with ethyl acetate (150 mL) and washed with water (50 mL) and saturated saline (50 mL) successively, dried with anhydrous sodium sulfate, and filtered. The filtrate was concentrated under reduced pressure to obtain a crude product. The crude product was purified by silica gel chromatography to obtain intermediate I-147.

$^1$H NMR (400 MHz, CDCl$_3$) δ 4.52-4.42 (m, 1H), 3.68 (s, 3H), 2.44-2.28 (m, 2H), 2.27-2.16 (m, 1H), 2.15-2.04 (m, 1H), 2.01-1.92 (m, 1H), 1.84-1.75 (m, 1H), 0.96 (t, J=7.1 Hz, 3H).

Reference Embodiment 146: Preparation of Intermediate I-148

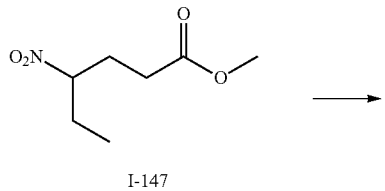

I-147

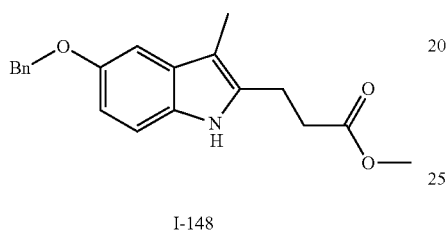

I-148

Under the protection of argon, sodium methanolate (2.87 g, 30% methanol solution, 16.0 mmol) was added to a solution of 4-benzyloxyphenylhydrazine hydrochloride (2.00 g, 7.98 mmol) in methanol (35 mL) at room temperature. Intermediate I-147 (1.54 g, 8.79 mmol) was added, and the reaction mixture was stirred at room temperature for 2 hours. The mixture was cooled to 0° C., acidified with $H_2SO_4$ (1.57 g, 16.0 mmol), and then heated to 90° C. and reacted for 3 hours. After the reaction mixture was cooled to room temperature, most of the methanol was removed by vacuum concentration, then the mixture was diluted with water (20 mL), and extracted with ethyl acetate (20 mL×3). The organic phases were combined, washed with saturated saline (50 mL), dried with anhydrous sodium sulfate, and filtered. The filtrate was concentrated under reduced pressure to obtain a crude product, which was purified by chromatography to obtain intermediate I-148.

$^1$H NMR (400 MHz, DMSO) δ 10.72 (s, 1H), 7.50-7.42 (m, 2H), 7.42-7.35 (m, 2H), 7.34-7.27 (m, 1H), 7.15 (d, J=8.7 Hz, 1H), 6.98 (t, J=4.3 Hz, 1H), 6.72 (dt, J=8.5, 4.2 Hz, 1H), 5.09 (d, J=6.3 Hz, 2H), 3.59 (s, 3H), 2.92 (q, J=7.6 Hz, 2H), 2.67 (q, J=7.6 Hz, 2H), 2.12 (s, 3H).

Reference Embodiment 147: Preparation of Intermediate I-149

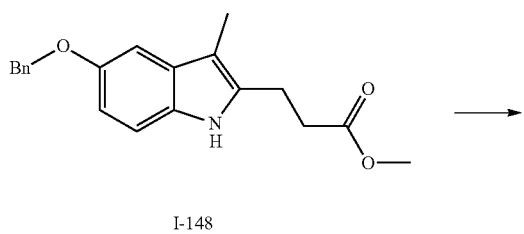

I-148

-continued

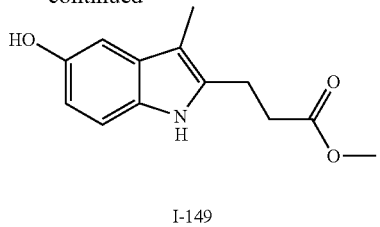

I-149

A reaction mixture of intermediate I-148 (680 mg, 2.10 mmol) and Pd/C (50.0 mg) in methanol (20 mL) was reacted at room temperature for 16 hours under hydrogen atmosphere. The reaction solution was filtered, and the filtrate was concentrated to obtain a crude product. The crude product was purified by silica gel chromatography to obtain intermediate I-149.

LC-MS (ESI) [M+H]$^+$ 234.2.

Reference Embodiment 148: Preparation of Intermediate I-150

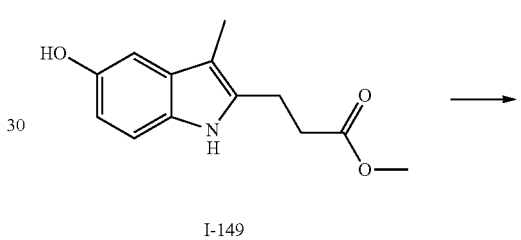

I-149

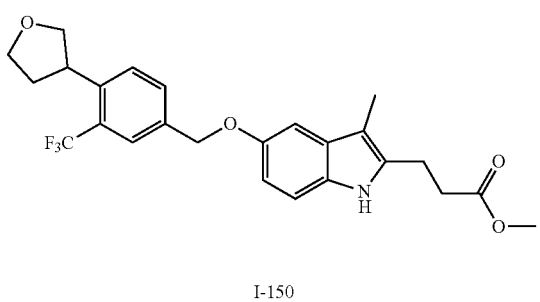

I-150

At room temperature, cesium carbonate (190 mg, 0.583 mmol) was added to a solution of intermediate I-149 (68.0 mg, 0.292 mmol) and intermediate I-133 (99.3 mg, 0.321 mmol) in acetonitrile. The reaction mixture was stirred at room temperature for 2 hours. The reaction mixture was diluted with water (25 mL), extracted with ethyl acetate (20 mL×3), and the organic phases were combined. The organic phases were washed with saturated saline (30 mL), dried with anhydrous sodium sulfate, and filtered. The filtrate was concentrated under reduced pressure to remove the organic solvent to obtain a crude product. The crude product was separated and purified by silica gel chromatography to obtain intermediate I-150.

LC-MS (ESI) [M+H]$^+$ 462.3.

Reference Embodiment 149: Preparation of Intermediate I-151

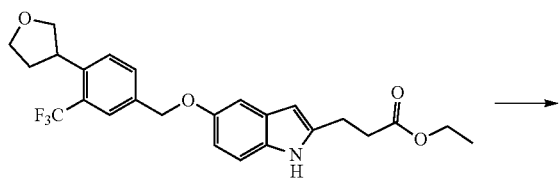

I-146

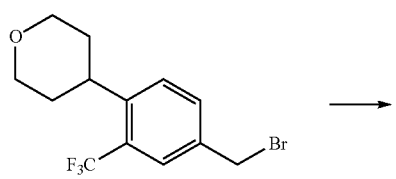

I-151

Intermediate I-146 (176 mg, 0.381 mmol) was dissolved in acetonitrile (12 mL) at room temperature, after cooling to 0° C., a solution of Selectfluor (162 mg, 0.457 mmol) in water (3 mL) was added, and the reaction solution was stirred at room temperature for one hour. The reaction mixture was added with water (20 mL), extracted with ethyl acetate (20 mL×3), and the organic phase was separated and concentrated under reduced pressure. The residue was separated and purified by silica gel chromatography to obtain intermediate I-151.

LC-MS (ESI) [M+H]$^+$ 480.3.

Reference Embodiment 150: Preparation of Intermediate I-152

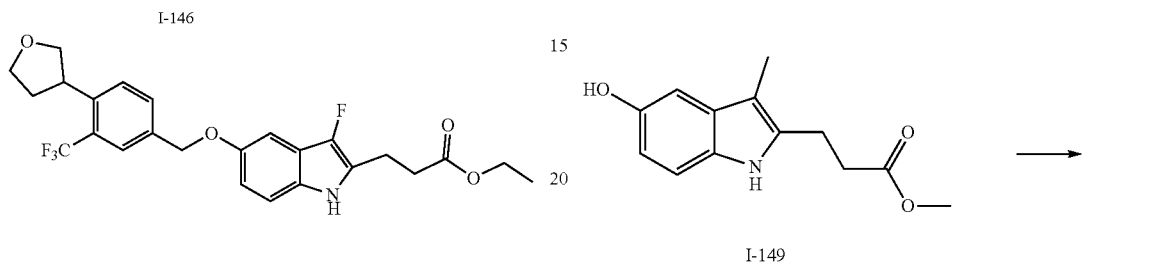

Intermediate I-138 (140 mg, 0.433 mmol) and intermediate I-6 (106.14 mg, 0.455 mmol) were dissolved in hexanitrile (5.00 mL), and then cesium carbonate (423.24 mg, 1.299 mmol) was added. The reaction was stirred at 25° C. for one hour. The mixture was added with water (20 mL), extracted with ethyl acetate (20 mL). The organic phase was separated, and the organic solvent was removed by concentration under reduced pressure to obtain a crude product. The crude product was separated and purified by silica gel chromatography to obtain intermediate I-152.

LC-MS (ESI) [M+H]$^+$ 476.2.

Reference Embodiment 151: Preparation of Intermediate I-153

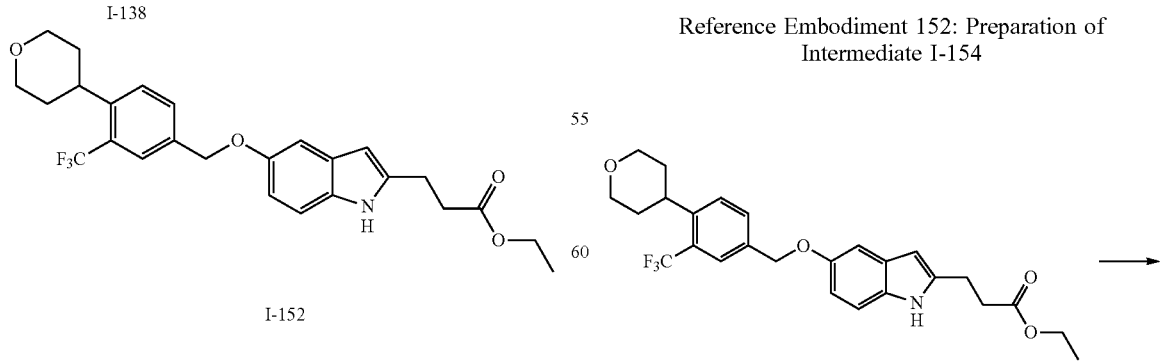

At room temperature, intermediate I-149 (33.1 mg, 0.142 mmol) and intermediate I-138 (46.0 mg, 0.142 mmol) were dissolved in acetonitrile (5 mL), and cesium carbonate (139 mg, 0.426 mmol) was added, and the reaction solution was stirred at room temperature for 16 hours. The reaction solution was filtered, the filtrate was concentrated under reduced pressure. The residue was separated and purified by silica gel chromatography to obtain intermediate I-153.

LC-MS (ESI) [M+H]$^+$ 476.3.

Reference Embodiment 152: Preparation of Intermediate I-154

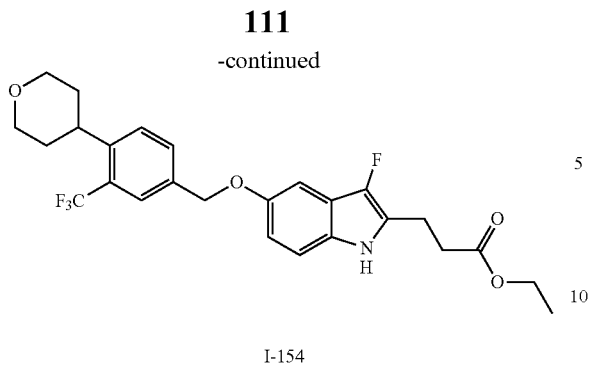

I-154

Intermediate I-152 (70 mg, 147.21 μmol) was dissolved in hexanitrile (3.00 mL) and water (0.500 mL), then the mixture was cooled to 0° C., and Selectfluor (52.15 mg, 147.21 μmol) was added slowly. The reaction mixture was stirred at 0° C. for 10 minutes. The mixture was added with water (6.00 mL), extracted with ethyl acetate (8.00 mL). The organic phase was separated, dried with anhydrous sodium sulfate and filtered. The filtrate was concentrated under reduced pressure to remove organic solvent to obtain intermediate I-154.

Reference Embodiment 153: Preparation of Intermediate I-155

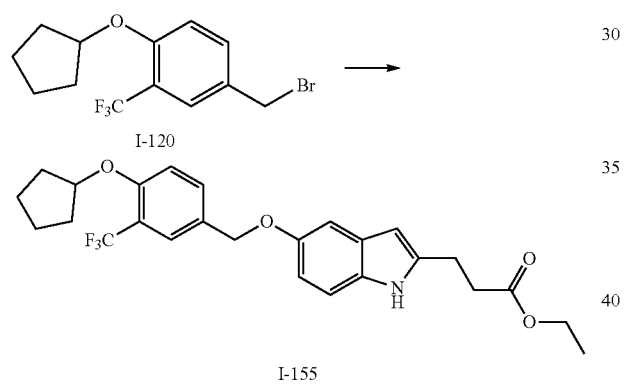

I-120

I-155

Intermediate I-120 (300 mg, 0.928 mmol) and intermediate I-6 (216 mg, 0.928 mmol) were dissolved in acetonitrile (15 mL), and cesium carbonate (606 mg, 1.86 mmol) was added under stirring. The reaction mixture was stirred at room temperature overnight. The mixture was filtered, and the filtrate was concentrated under reduced pressure to remove the organic solvent to obtain a crude product. The crude product was separated and purified by silica gel chromatography to obtain intermediate I-155.

LC-MS (ESI) [M+H]$^+$ 476.2.

Reference Embodiment 154: Preparation of Intermediate I-156

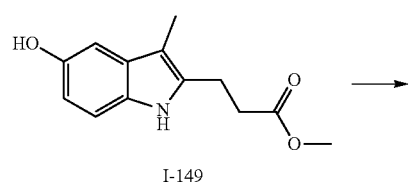

I-149

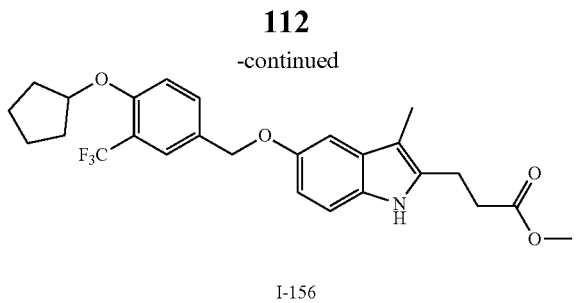

I-156

Intermediate I-149 (72.1 mg, 0.309 mmol) and intermediate I-120 (100.0 mg, 0.309 mmol) were dissolved in acetonitrile (5 mL), and cesium carbonate (201 mg, 0.618 mmol) was added at room temperature. The reaction mixture was stirred at room temperature for one hour. The reaction solution was filtered, and the filtrate was concentrated under reduced pressure to remove the organic solvent to obtain a crude product. The crude product was separated and purified by silica gel chromatography to obtain intermediate I-156.

LC-MS (ESI) [M+H]$^+$ 476.3.

Reference Embodiment 155: Preparation of Intermediate I-157

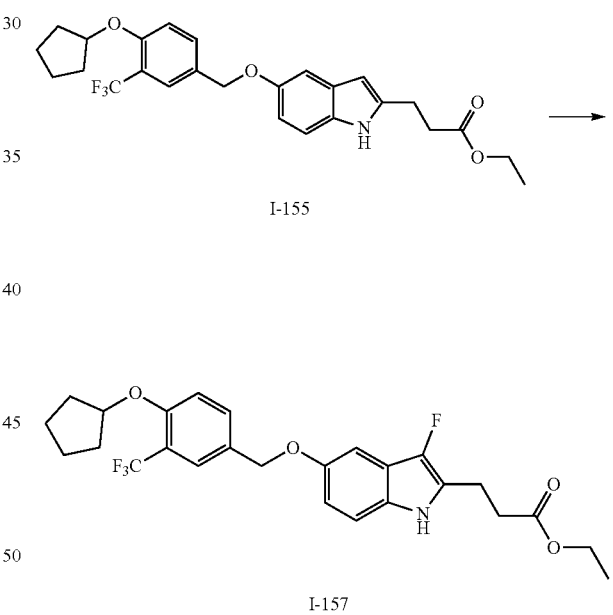

I-155

I-157

Intermediate I-155 (170 mg, 0.358 mmol) was dissolved in acetonitrile (10 mL). At 0° C., a solution of Selectfluor (127 mg, 0.358 mmol) in water (2 mL) was added to the solution. The reaction mixture was stirred at 0° C. for half an hour. The mixture was poured into water (100 mL) and extracted with ethyl acetate (20 mL×2). The organic phases were combined, washed with saturated saline (50 mL), dried with anhydrous sodium sulfate, and filtered. The filtrate was concentrated under reduced pressure to remove the organic solvent to obtain a crude product. The crude product was separated and purified by silica gel chromatography to obtain intermediate I-157.

LC-MS (ESI) [M+H]$^+$ 494.2.

Reference Embodiment 156: Preparation of Intermediate I-158

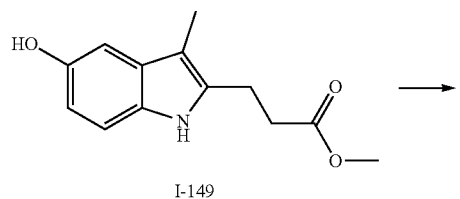

I-149

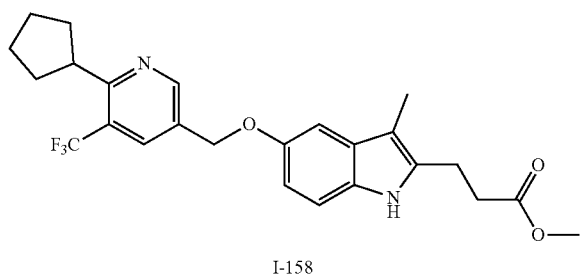

I-158

Intermediate I-149 (50.0 mg, 0.214 mmol) was dissolved in acetonitrile (10.0 mL). Cesium carbonate (139 mg, 0.428 mmol) and 1-128 (79.2 mg, 0.257 mmol) were added to the reaction system successively. The reaction mixture was stirred at room temperature for 2 hours. The reaction mixture was diluted with water (20 mL), extracted with ethyl acetate (10 mL×3). The organic phases were combined, and washed with saturated saline, dried with anhydrous sodium sulfate, and filtered. The filtrate was concentrated under reduced pressure to obtain a crude product, the crude product was separated and purified by silica gel chromatography to obtain compound 1-158.

LC-MS (ESI) [M+H]$^+$ 461.7.

$^1$H NMR (400 MHz, DMSO-d$_6$) δ 10.53 (s, 1H), 8.91 (d, J=1.7 Hz, 1H), 8.16 (d, 7=2.0 Hz, 1H), 7.15 (d, J=8.8 Hz, 1H), 7.02 (d, J=2.4 Hz, 1H), 6.75 (dd, J=8.7, 2.4 Hz, 1H), 5.20 (s, 2H), 3.59 (s, 3H), 3.43-3.40 (m, 1H), 2.93 (t, J=7.7 Hz, 2H), 2.67 (t, J=7.7 Hz, 2H), 2.13 (s, 3H), 1.98-1.93 (m, 2H), 1.87-1.76 (m, 4H), 1.70-1.66 (m, 2H).

Embodiment 1: Preparation of Compound 1

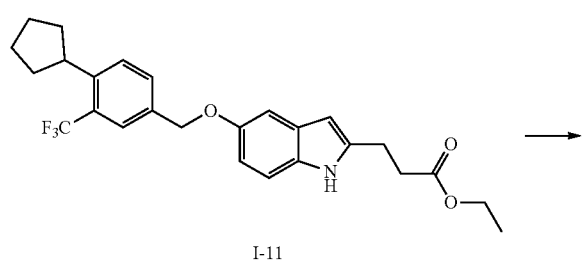

I-11

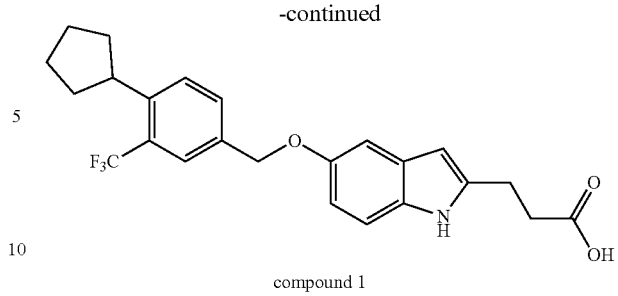

compound 1

Lithium hydroxide monohydrate (20 mg, 0.48 mmol) was added to a mixed solution of intermediate I-11 (73 mg, 0.16 mmol) in tetrahydrofuran/ethanol/water (5 mL, 2:2:1), and the reaction solution was stirred at room temperature for one hour. The pH of the reaction solution was adjusted to 6 with hydrochloric acid (1 N), and the organic solvent was evaporated under reduced pressure. 20 mL of water and 5 mL of ethyl acetate were added to the residue, the organic layer was separated by extraction, and the aqueous layer was continuously extracted with ethyl acetate (5 mL×2). The combined organic layers were washed with saturated saline, dried with anhydrous sodium sulfate, then filtered and concentrated to obtain a residue. The residue was purified by preparative HPLC to obtain compound 1.

LC-MS (ESI) [M+H]$^+$ 432.1.

$^1$H NMR (400 MHZ, DMSO-d$_6$) δ 12.20 (brs, 1H), 10.78 (s, 1H), 7.75-7.66 (m, 2H), 7.65-7.60 (m, 1H), 7.16 (d, J=8.7 Hz, 1H), 7.04-6.99 (m, 1H), 6.74-6.69 (m, 1H), 6.05 (s, 1H), 5.11 (s, 2H), 3.27-3.21 (m, 1H), 2.91 (t, J=7.4 Hz, 2H), 2.62 (t, J=7.6 Hz, 2H), 2.03-1.95 (m, 2H), 1.88-1.79 (m, 2H), 1.71-1.55 (m, 4H).

Embodiment 2: Preparation of Compound 2

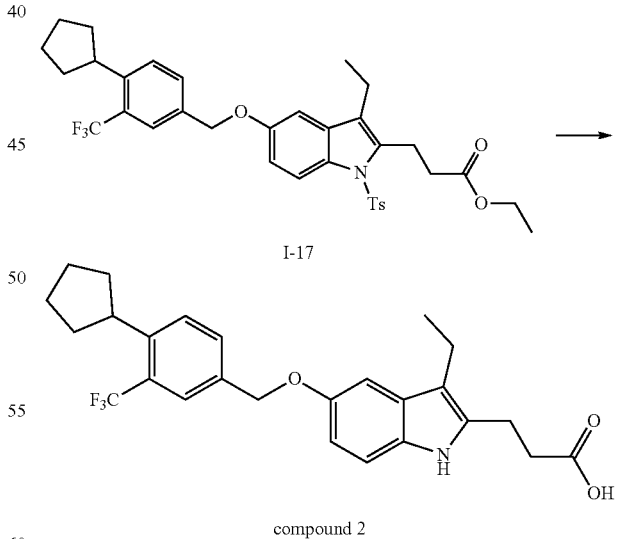

compound 2

Sodium hydroxide (23.4 mg, 0.59 mmol) was added to a mixed solution of intermediate I-17 (25.0 mg, 0.04 mmol) in ethanol (2 mL)/water (2 mL), and the reaction solution was stirred at 100° C. for 2 days. The pH of the reaction solution was adjusted to 6 with hydrochloric acid aqueous solution (1 N), and the solution was evaporated under reduced pressure to obtain a residue. The residue was purified by preparative HPLC to obtain compound 2.

LC-MS (ESI) [M+H]+ 460.1.

$^1$H NMR (400 MHz, MeOH-d$_4$) δ 7.71 (s, 1H), 7.66 (d, J=8.2 Hz, 1H), 7.56 (d, J=8.1 Hz, 1H), 7.14 (d, J=8.7 Hz, 1H), 7.00 (d, J=2.3 Hz, 1H), 6.76 (dd, J=8.7, 2.4 Hz, 1H), 5.10 (s, 2H), 3.39-3.34 (m, 1H), 2.99 (t, J=7.7 Hz, 2H), 2.73-2.57 (m, 4H), 2.10-2.00 (m, 2H), 1.95-1.84 (m, 2H), 1.76-1.58 (m, 4H), 1.17 (t, J=7.5 Hz, 3H).

Embodiment 3: Preparation of Compound 3

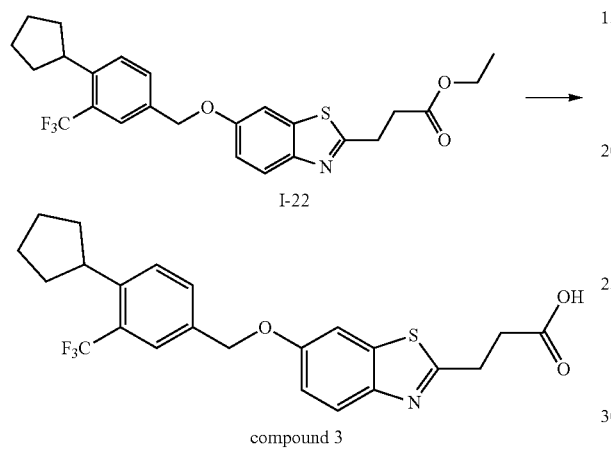

Lithium hydroxide monohydrate (19 mg, 0.44 mmol) was added to a mixed solution of intermediate I-22 (70.0 mg, 0.15 mmol) in methanol/tetrahydrofuran/water (3:1:1, 5 mL), and the reaction solution was stirred at room temperature for one hour. The pH of the reaction solution was adjusted to 2 with hydrochloric acid aqueous solution (2 N), and the solution was evaporated under reduced pressure to obtain a residue. The residue was purified by preparative HPLC to obtain compound 3.

LC-MS (ESI) [M+H]+ 450.1.

$^1$H NMR (400 MHz, MeOH-d$_4$) δ 7.80 (d, J=8.9 Hz, 1H), 7.73-7.69 (s, 1H), 7.69-7.64 (m, 1H), 7.61-7.57 (m, 1H), 7.56 (d, J=2.5 Hz, 1H), 7.18 (dd, J=8.9, 2.5 Hz, 1H), 5.17 (s, 2H), 3.40-3.32 (m, 3H), 2.89 (t, J=7.2 Hz, 2H), 2.12-2.03 (m, 2H), 1.95-1.86 (m, 2H), 1.77-1.60 (m, 4H).

Embodiment 4, Embodiment 5: Preparation of Compound 4 and Compound 5

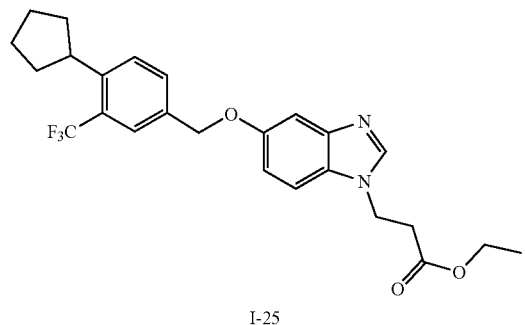

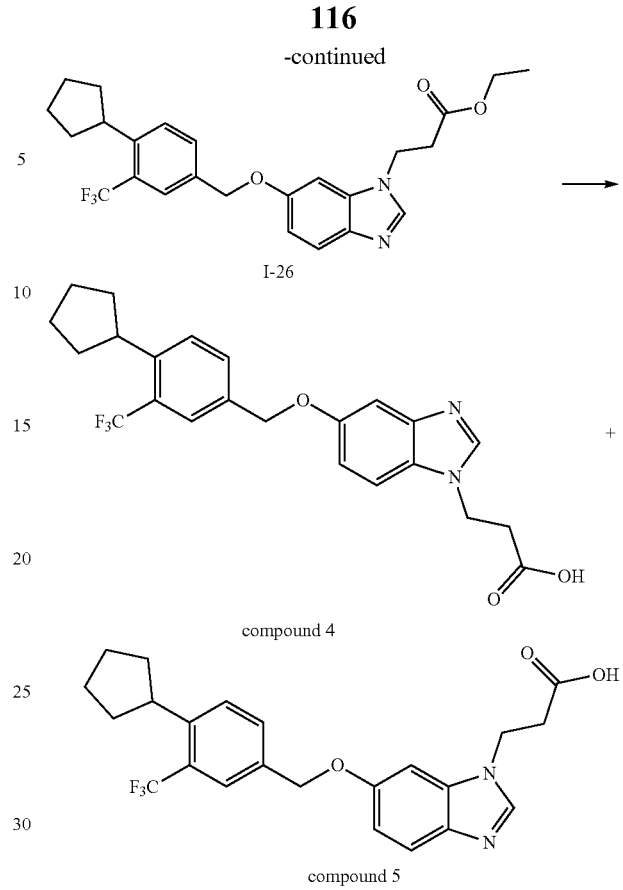

Lithium hydroxide monohydrate (54 mg, 1.30 mmol) was added to a mixed solution of intermediate I-25 and intermediate I-26 (200.0 mg, 0.43 mmol) in ethanol/water (1:1.6 mL), and the reaction solution was stirred at room temperature for 3 hours. The pH of the reaction solution was adjusted to 7-8 with hydrochloric acid aqueous solution (1 N), and the solution was evaporated under reduced pressure to obtain a residue. The residue was purified by SFC to obtain compound 4 and compound 5.

Compound 4

Chiral HPLC analysis conditions: (CO$_2$/MeOH 70/30 2.8 mL/min OD, 5 μm, 4.6*250 (Daicel), 15 min; retention time: 4.366 min).

LC-MS (ESI) [M+H]+ 433.5.

$^1$H NMR (400 MHz, DMSO-d$_6$) δ 8.11 (s, 1H), 7.78-7.68 (m, 2H), 7.64 (d, J=8.1 Hz, 1H), 7.53 (d, J=8.8 Hz, 1H), 7.25 (d, J=1.9 Hz, 1H), 6.98 (dd, J=8.8, 2.1 Hz, 1H), 5.19 (s, 2H), 4.41 (t, J=6.6 Hz, 2H), 3.27-3.21 (m, 1H), 2.79 (t, J=6.6 Hz, 2H), 2.06-1.92 (m, 2H), 1.90-1.76 (m, 2H), 1.73-1.54 (m, 4H).

Compound 5

Chiral HPLC analysis conditions: (CO$_2$/MeOH 70/30 2.8 mL/min OD, 5 μm, 4.6*250 (Daicel), 15 min; retention time: 3.675 min).

LC-MS (ESI) [M+H]+ 433.5.

$^1$H NMR (400 MHz, DMSO-d$_6$) δ 12.46 (s, 1H), 8.06 (s, 1H), 7.80-7.72 (m, 2H), 7.65 (d, J=8.1 Hz, 1H), 7.52 (d, J=8.8 Hz, 1H), 7.34 (d, J=2.3 Hz, 1H), 6.90 (dd, J=8.8, 2.4

Hz, 1H), 5.21 (s, 2H), 4.41 (t, J=6.8 Hz, 2H), 3.29-3.21 (m, 1H), 2.80 (t, J=6.8 Hz, 2H), 2.06-1.95 (m, 2H), 1.89-1.78 (m, 2H), 1.73-1.56 (m, 4H).

Embodiment 6: Preparation of Compound 6

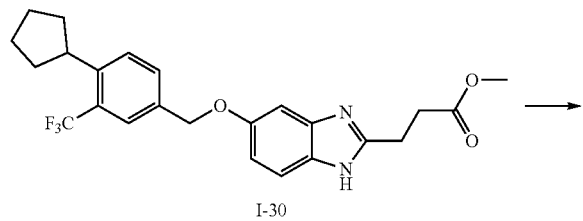
I-30

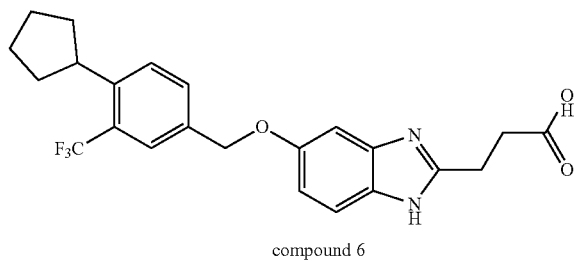
compound 6

Lithium hydroxide monohydrate (12 mg, 0.29 mmol) was added to a mixed solution of intermediate I-30 (43 mg, 0.096 mmol) in tetrahydrofuran/water (2:1, 3 mL), and the reaction solution was stirred at room temperature for one hour. The reaction solution was concentrated under reduced pressure, and the pH of the reaction solution was adjusted to 2-3 with aqueous hydrochloric acid (1 N), and then the mixture was extracted with ethyl acetate (5 mL×2). The combined organic layers were washed with saturated saline, dried with anhydrous sodium sulfate, then filtered and concentrated to obtain a residue. The residue was purified by preparative HPLC to obtain compound 6.

LC-MS (ESI) [M+H]$^+$ 433.5.

$^1$H NMR (400 MHz, MeOH-d$_4$) δ 7.74-7.69 (m, 1H), 7.69-7.64 (m, 1H), 7.63-7.52 (m 2H), 7.23-7.12 (m, 2H), 5.20 (s, 2H), 3.41-3.33 (m, 1H), 3.30-3.24 (m, 2H), 2.97-2.87 (m, 2H), 2.12-2.01 (m, 2H), 1.96-1.84 (m, 2H), 1.79-1.56 (m, 4H).

Embodiment 7: Preparation of Compound 7

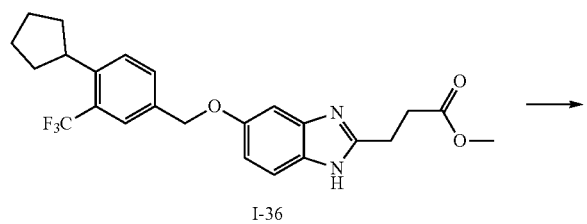
I-36

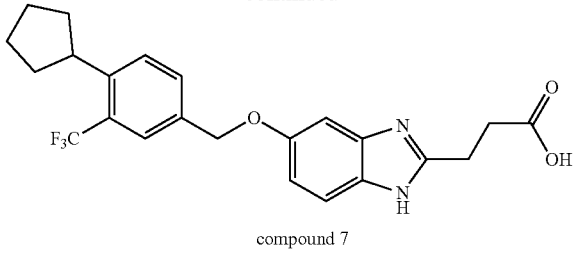
compound 7

Lithium hydroxide monohydrate (67.6 mg, 1.61 mmol) was added to a mixed solution of intermediate I-36 (240 mg, 0.53 mmol) in methanol/tetrahydrofuran/water (1:1:1, 9 mL), and the reaction solution was stirred at room temperature for 2 hours. The pH of the reaction solution was adjusted to 6 with hydrochloric acid aqueous solution (1 N), 10 mL of ethyl acetate was added and the organic phase was separated by extraction. The aqueous phase was continuously extracted with ethyl acetate (10 mL×2). The combined organic layer was washed with saturated saline, dried with anhydrous sodium sulfate, then filtered and concentrated to obtain a residue. The residue was purified by preparative HPLC to obtain compound 7.

LC-MS (ESI) [M+H]$^+$ 434.1.

$^1$H NMR (400 MHz, DMSO-d$_6$) δ 12.33 (s, 1H), 7.76-7.69 (m, 2H), 7.65 (d, J=8.1 Hz, 1H), 7.56 (d, J=8.7 Hz, 1H), 7.40 (d, J=2.4 Hz, 1H), 7.01 (dd, J=8.7, 2.4 Hz, 1H), 5.21 (s, 2H), 3.28-3.22 (m, 1H), 3.10 (t, J=6.9 Hz, 2H), 2.79 (t, J=7.0 Hz, 2H), 2.05-1.95 (m, 2H), 1.89-1.79 (m, 2H), 1.72-1.56 (m, 4H).

Embodiment 8: Preparation of Compound 8

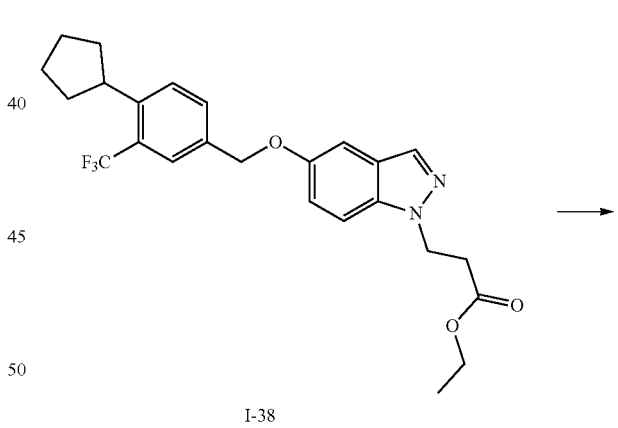
I-38

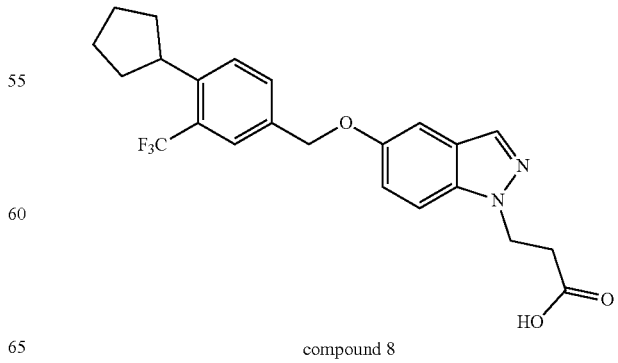
compound 8

Lithium hydroxide (15.60 mg, 0.65 mmol) was added to a mixed solution of intermediate I-38 (100 mg, 0.22 mmol) in tetrahydrofuran (3 mL)/water (0.5 mL), and the reaction solution was stirred at room temperature for 10 hours. The reaction solution was diluted with 3 mL of water and the pH of the reaction solution was adjusted to 5-6 with aqueous hydrochloric acid (1 N), and then the mixture was extracted with ethyl acetate (10 mL). The combined organic layers were dried with anhydrous sodium sulfate, then filtered and concentrated to obtain a residue. The residue was purified by preparative HPLC to obtain compound 8.

LC-MS (ESI) [M+H]+ 433.1.

$^1$H NMR (400 MHz, MeOH-$d_4$) δ 7.90 (s, 1H), 7.73-7.64 (m, 2H), 7.61-7.51 (m, 2H), 7.23 (d, J=2.0 Hz, 1H), 7.17 (dd, J=9.1, 2.3 Hz, 1H), 5.13 (s, 2H), 4.63 (t, J=6.8 Hz, 2H), 3.41-3.35 (m, 1H), 2.89 (t, J=6.7 Hz, 2H), 2.12-2.02 (m, 2H), 1.95-1.84 (m, 2H), 1.79-1.60 (m, 4H).

Embodiment 9: Preparation of Compound 9

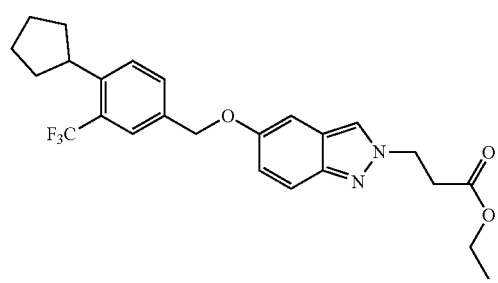

I-39

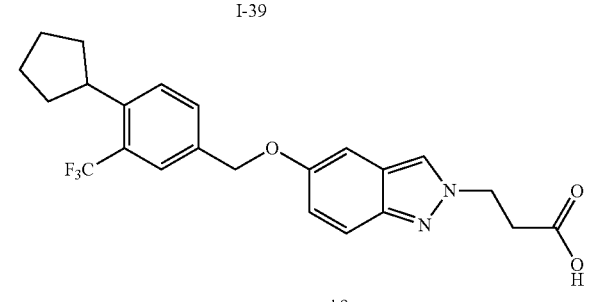

compound 9

Lithium hydroxide (23.40 mg, 0.98 mmol) was added to a mixed solution of intermediate I-39 (150 mg) in tetrahydrofuran (3 mL)/water (0.5 mL), and the reaction solution was stirred at 25° C. for 10 hours. The reaction solution was diluted with 3 mL of water and the pH of the reaction solution was adjusted to 5-6 with hydrochloric acid (1 N), and then the mixture was extracted with ethyl acetate (30 mL). The combined organic layers were dried with anhydrous sodium sulfate, then filtered and concentrated to obtain a residue. The residue was purified by preparative HPLC to obtain compound 9.

LC-MS (ESI) [M+H]+ 433.5.

$^1$H NMR (400 MHz, MeOH-$d_4$) δ 8.07 (s, 1H), 7.76-7.63 (m, 2H), 7.62-7.46 (m, 2H), 7.16-7.02 (m, 2H), 5.10 (s, 2H), 4.65 (t, J=6.7 Hz, 2H), 3.41-3.35 (m, 1H), 2.99 (t, J=6.7 Hz, 2H), 2.14-2.02 (m, 2H), 1.96-1.84 (m, 2H), 1.79-1.57 (m, 4H).

Embodiment 10: Preparation of Compound 10

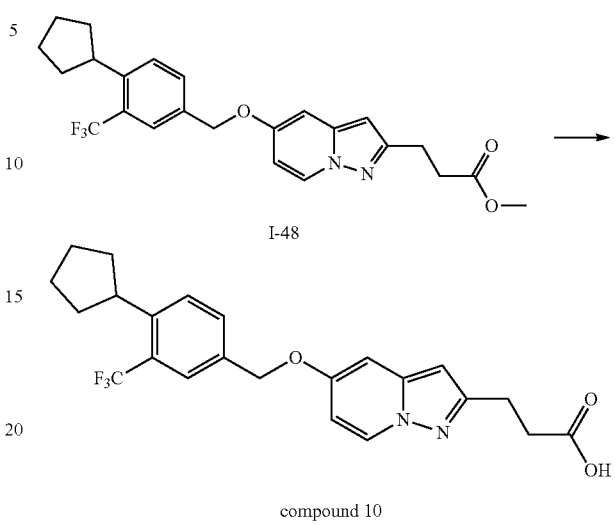

I-48 compound 10

Lithium hydroxide monohydrate (6.2 mg, 0.14 mmol) was added to a mixed solution of intermediate I-48 (35 mg) in methanol (2 mL)/water (1 mL), and the reaction solution was stirred at room temperature for 24 hours. The pH of the reaction solution was adjusted to 3 with hydrochloric acid (1 N), and the organic solvent was evaporated under reduced pressure to obtain a residue. The residue was purified by preparative HPLC to obtain compound 10.

LC-MS (ESI) [M+H]+ 433.2.

$^1$H NMR (400 MHz, MeOH-$d_4$) δ 8.26 (d, J=7.6 Hz, 1H), 7.71 (s, 1H), 7.68-7.66 (m, 1H), 7.60 (d, J=8.2 Hz, 1H), 6.96 (d, J=2.6 Hz, 1H), 6.58 (dd, J=7.6, 2.7 Hz, 1H), 6.24 (s, 1H), 5.15 (s, 2H), 3.41-3.34 (m, 1H), 3.04 (t, J=7.6 Hz, 2H), 2.73 (t, J=7.6 Hz, 2H), 2.12-2.03 (m, 2H), 1.95-1.86 (m, 2H), 1.80-1.71 (m, 2H), 1.70-1.61 (m, 2H).

Embodiment 11: Preparation of Compound 11

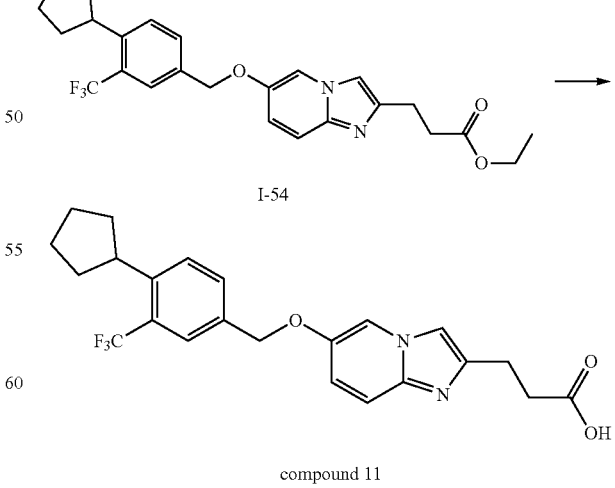

I-54 compound 11

Lithium hydroxide (4.68 mg, 0.195 mmol) was added to a mixed solution of intermediate I-54 (30 mg, 0.065 mmol)

in tetrahydrofuran (1 mL)/water (0.2 mL), and the reaction solution was stirred at room temperature for 10 hours. The reaction solution was diluted with 6 mL of water, and extracted with 10 mL of ethyl acetate. The pH of the aqueous phase was adjusted to 5-6 with hydrochloric acid aqueous solution (1 N), 10 mL of ethyl acetate was added for extraction, and the combined organic layers were dried and concentrated to obtain a residue. The residue was purified by preparative HPLC to obtain compound 11 (because the mobile phase of preparative HPLC contains formic acid, the product was separated and purified in the form of formate).

LC-MS (ESI) [M+H]+ 433.5.

$^1$H NMR (400 MHz, MeOH-d$_4$) δ 8.26 (d, J=1.9 Hz, 1H), 8.20 (s, 1H) 7.79-7.65 (m, 3H), 7.61 (d, J=8.2 Hz, 1H), 7.52 (d, J=9.7 Hz, 1H), 7.37 (dd, J=9.7, 2.2 Hz, 1H), 5.14 (s, 2H), 3.41-3.36 (m, 1H), 3.06 (t, J=7.3 Hz, 2H), 2.74 (t, J=7.3 Hz, 2H), 2.12-2.02 (m, 2H), 1.96-1.84 (m, 2H), 1.80-1.60 (m, 4H).

Embodiment 12: Preparation of Compound 12

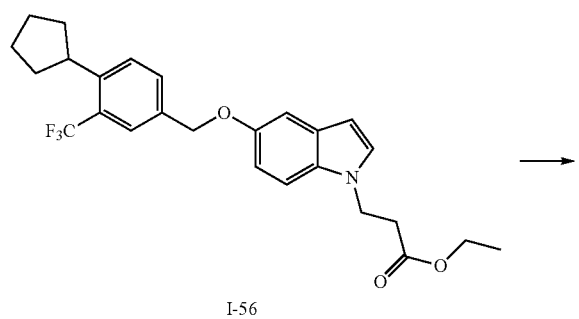

Lithium hydroxide monohydrate (37 mg, 0.88 mmol) and water (0.5 mL) were added to a solution of intermediate I-56 (200 mg, 0.44 mmol) in methanol (2 mL), and the reaction solution was stirred at room temperature for 4 hours. The reaction solution was purified by preparative HPLC to obtain compound 12.

LC-MS (ESI) [M+H]+ 432.2.

$^1$H NMR (400 MHz, DMSO-d$_6$) δ 7.74-7.67 (m, 2H), 7.63 (d, J=8.0 Hz, 1H), 7.39 (d, J=8.9 Hz, 1H), 7.30 (d, J=3.0 Hz, 1H), 7.13 (d, J=2.3 Hz, 1H), 6.86 (dd, J=8.9, 2.3 Hz, 1H), 6.31 (d, J=3.0 Hz, 1H), 5.14 (s, 2H), 4.34 (t, J=6.8 Hz, 2H), 3.28-3.23 (m, 1H), 2.71 (t, J=6.8 Hz, 2H), 2.04-1.95 (m, 2H), 1.88-1.79 (m, 2H), 1.72-1.55 (m, 4H).

Embodiment 13: Preparation of Compound 13

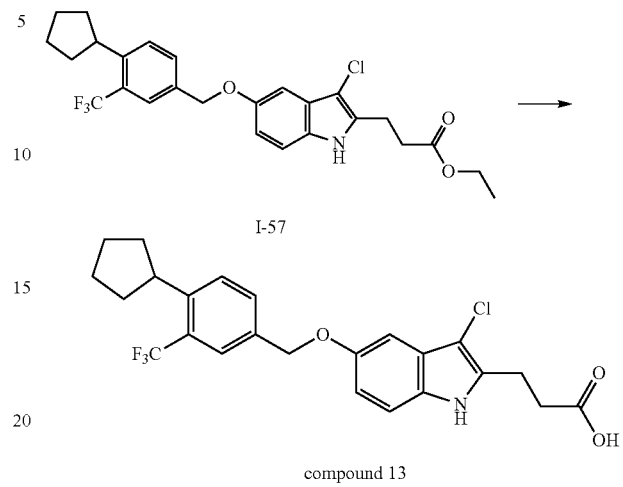

At room temperature, intermediate I-57 (90 mg, 0.18 mmol) was dissolved in tetrahydrofuran (5 mL) and water (1 mL), and lithium hydroxide monohydrate (38 mg, 0.91 mmol) was added to the reaction system. The reaction mixture was stirred at room temperature overnight. The reaction solution was concentrated under reduced pressure to obtain a crude product. The crude product was purified by preparative HPLC to obtain compound 13.

LC-MS (ESI) [M+H]+ 466.1.

$^1$H NMR (400 MHz, MeOH-d$_4$) δ 8.45 (s, 1H), 7.71 (s, 1H), 7.67 (d, J=8.1 Hz, 1H), 7.57 (d, J=8.2 Hz, 1H), 7.20 (d, J=8.8 Hz, 1H), 6.98 (d, J=2.4 Hz, 1H), 6.84 (dd, J=8.8, 2.4 Hz, 1H), 5.12 (s, 2H), 3.40-3.35 (m, 1H), 3.05 (t, J=7.8 Hz, 2H), 2.64 (t, J=7.6 Hz, 2H), 2.12-2.03 (m, 2H), 1.96-1.85 (m, 2H), 1.77-1.61 (m, 4H).

Embodiment 14: Preparation of Compound 14

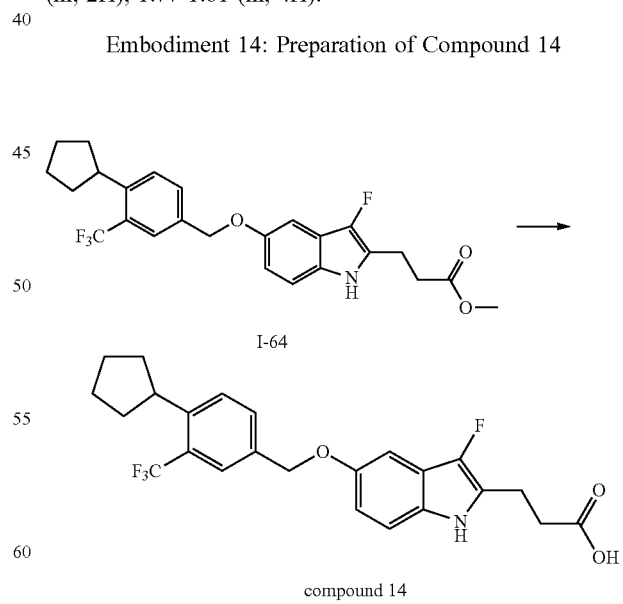

At room temperature, intermediate I-64 (0.18 mmol) was dissolved in a mixed solvent of tetrahydrofuran (3 mL) and water (1 mL), and lithium hydroxide monohydrate (23 mg, 0.54 mmol) was added. The reaction solution was stirred at room temperature for 3 hours. The reaction solution was concentrated under reduced pressure to remove the organic solvent, and added with water (5 mL). The pH of the mixture was adjusted to 2 with dilute hydrochloric acid (IN), ethyl acetate (5 mL) was added to separate by extraction, and the aqueous phase was extracted with ethyl acetate (5 mL). The organic phases were combined, washed with saturated saline (5 mL), dried with anhydrous sodium sulfate, filtered, and the filtrate was concentrated under reduced pressure to obtain a residue. The crude product was purified by preparative HPLC to obtain compound 14.

LC-MS (ESI) [M+H]$^+$ 450.1.

$^1$H NMR (400 MHz, MeOH-d$_4$) δ 9.93 (s, 1H), 7.70 (s, 1H), 7.65 (d, J=8.3 Hz, 1H), 7.57 (d, J=8.1 Hz, 1H), 7.15 (dd, J=8.8, 2.5 Hz, 1H), 6.99 (d, J=2.3 Hz, 1H), 6.81 (dd, J=8.8, 2.4 Hz, 1H), 5.09 (s, 2H), 3.42-3.34 (m, 1H), 3.02 (t, J=7.6 Hz, 2H), 2.70 (t, J=7.6 Hz, 2H), 2.11-2.03 (m, 2H), 1.95-1.84 (m, 2H), 1.79-1.45 (m, 4H).

Embodiment 15: Preparation of Compound 15

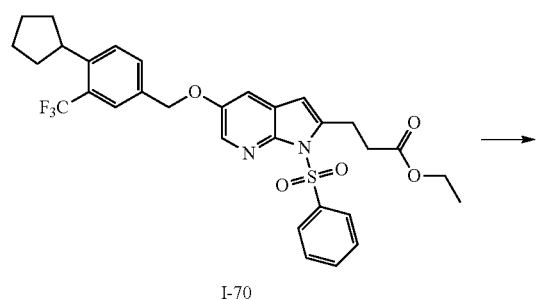

Intermediate I-70 (100 mg, 0.17 mmol) was dissolved in a mixed solvent of water/methanol (3/3 mL). At 10° C., sodium hydroxide (600 mg, 15 mmol) was added. The reaction mixture was stirred at 60° C. for 3 hours, and then dilute hydrochloric acid (3 M) was added to adjust the pH of the reaction mixture to 7-8. The reaction mixture was extracted with dichloromethane (1 mL×5). The organic phases were combined, washed with saturated saline, dried with anhydrous sodium sulfate, filtered, and the filtrate was concentrated under reduced pressure to obtain a residue. The residue was separated and purified by preparative liquid chromatography to obtain compound 15.

LC-MS (ESI) [M+H]$^+$ 433.1.

$^1$H NMR (400 MHz, DMSO-d$_6$) δ 11.35 (s, 1H), 7.92 (d, J=2.7 Hz, 1H), 7.75-7.68 (m, 2H), 7.64 (d, J=8.0 Hz, 1H), 7.50 (d, J=2.6 Hz, 1H), 6.08 (s, 1H), 5.18 (s, 2H), 3.26-3.23 (m, 1H), 2.92 (t, J=7.6 Hz, 2H), 2.64 (t, J=7.6 Hz, 2H), 2.04-1.95 (m, 2H), 1.89-1.78 (m, 2H), 1.72-1.55 (m, 4H).

Embodiment 16: Preparation of Compound 16

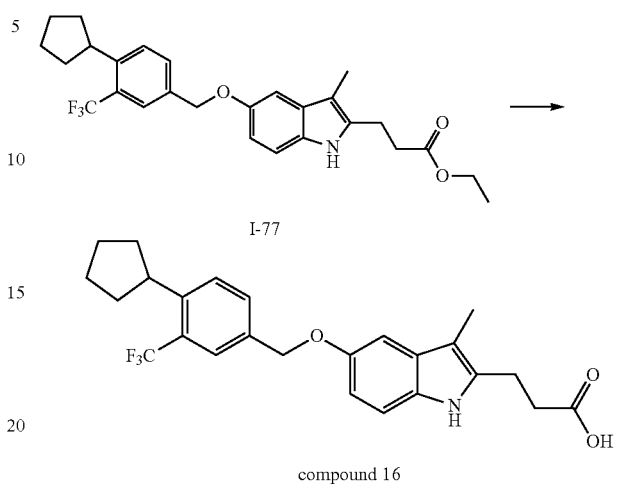

Intermediate I-77 (110 mg) was dissolved in tetrahydrofuran (2 mL), and lithium hydroxide monohydrate (29 mg, 0.70 mmol) and water (0.5 mL) were added. After the reaction was stirred at room temperature for 3 hours, the reaction solution was separated and purified by preparative liquid chromatography to obtain compound 16.

LC-MS (ESI) [M−H]$^-$ 444.1.

$^1$H NMR (400 MHz, MeOH-d$_4$) δ 7.71 (s, 1H), 7.66 (d, J=8.2 Hz, 1H), 7.57 (d, J=8.2 Hz, 1H), 7.13 (d, J=8.7 Hz, 1H), 6.98 (d, J=2.3 Hz, 1H), 6.76 (dd, J=8.7, 2.4 Hz, 1H), 5.10 (s, 2H), 3.41-3.35 (m, 1H), 3.00 (t, J=7.7 Hz, 2H), 2.63 (t, J=7.7 Hz, 2H), 2.18 (s, 3H), 2.10-2.02 (m, 2H), 1.95-1.86 (m, 2H), 1.78-1.60 (m, 4H).

Embodiment 17: Preparation of Compound 17

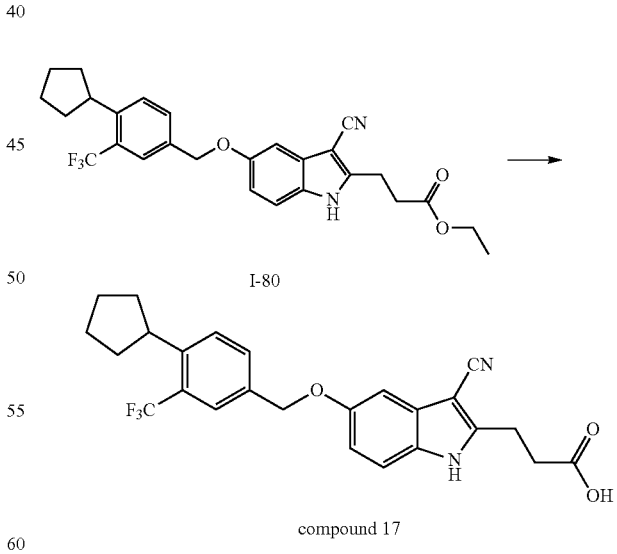

Intermediate I-80 (130 mg, 0.27 mmol) was dissolved in a mixed solvent of tetrahydrofuran (1 mL) and water (0.5 mL), and lithium hydroxide monohydrate (23 mg, 0.54 mmol) was added. The reaction mixture was stirred at room temperature for one hour, and the pH of the reaction solution was adjusted to 6.0 with IN dilute hydrochloric acid. Water (10 mL) and ethyl acetate (10 mL) were added to the reaction mixture. The organic phase was separated and the aqueous phase was extracted with ethyl acetate (10 mL×2). The organic phases were combined, washed with saturated saline (5 mL), dried with anhydrous sodium sulfate, filtered, and the filtrate was concentrated under reduced pressure to obtain a residue. The residue was separated and purified by preparative liquid chromatography to obtain compound 17.

LC-MS (ESI) [M−H]⁻ 455.0.

$^1$H NMR (400 MHz, MeOH-d$_4$) δ 7.71 (s, 1H), 7.67 (d, J=8.3 Hz, 1H), 7.58 (d, J=8.2 Hz, 1H), 7.32 (d, J=8.8 Hz, 1H), 7.12 (d, J=2.3 Hz, 1H), 6.95 (dd, J=8.8, 2.4 Hz, 1H), 5.14 (s, 2H), 3.40-3.34 (m, 1H), 3.19 (t, J=7.5 Hz, 2H), 2.80 (t, J=7.5 Hz, 2H), 2.11-2.02 (m, 2H), 1.95-1.86 (m, 2H), 1.79-1.60 (m, 4H).

Embodiment 18: Preparation of Compound 18

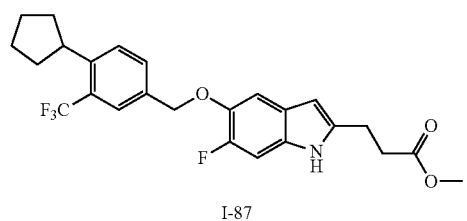

I-87

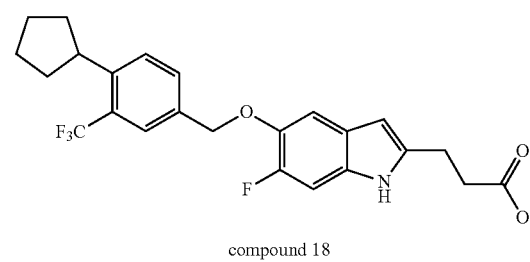

compound 18

Intermediate I-87 (68 mg, 0.15 mmol) was dissolved in tetrahydrofuran (4 mL) and methanol (1 mL), and a solution of lithium hydroxide monohydrate (13 mg, 0.31 mmol) in water (1 mL) were added. The reaction mixture was stirred at room temperature for one hour, and then diluted hydrochloric acid (1 M, 0.3 mL) was added to adjust the pH of the reaction mixture to 5. The reaction mixture was concentrated under reduced pressure to remove the organic solvent to obtain a residue. The residue was separated and purified by preparative liquid chromatography to obtain compound 18.

LC-MS (ESI) [M+H]⁺ 450.2.

$^1$H NMR (400 MHz, DMSO-d$_6$) δ 12.19 (s, 1H), 10.85 (s, 1H), 7.71 (s, 1H), 7.69 (d, J=8.4 Hz, 1H), 7.62 (d, J=8.2 Hz, 1H), 7.19 (d, J=8.4 Hz, 1H), 7.10 (d, J=11.6 Hz, 1H), 6.06 (s, 1H), 5.15 (s, 2H), 3.26-3.19 (m, 1H), 2.88 (t, J=7.5 Hz, 2H), 2.60 (t, J=7.6 Hz, 2H), 2.03-1.93 (m, 2H), 1.87-1.76 (m, 2H), 1.71-1.53 (m, 4H).

Embodiment 19: Preparation of Compound 19

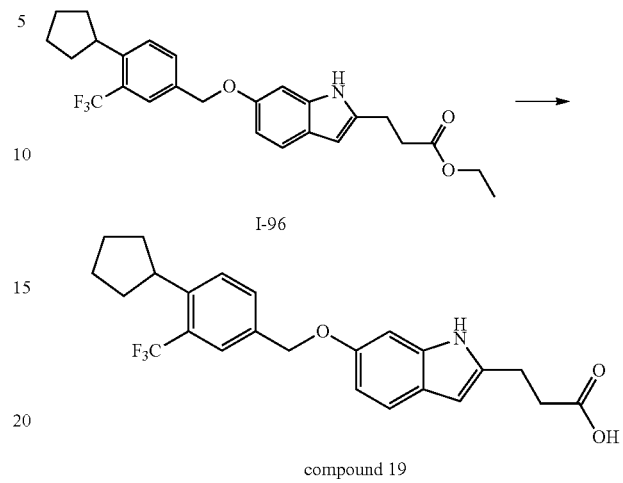

Intermediate I-96 (36 mg, 0.078 mmol) was dissolved in ethanol/water (5 mL/1 mL), and lithium hydroxide monohydrate (9.82 mg, 0.234 mmol) was added. The reaction mixture was stirred at room temperature for 3 hours. The organic solvent was removed by concentration under reduced pressure to obtain a crude product. The crude product was separated and purified by preparative HPLC to obtain compound 19.

LC-MS (ESI) [M+H]⁺ 432.1.

$^1$H NMR (400 MHz, CD$_3$OD) δ 10.11 (brs, 1H), 7.74-7.61 (m, 2H), 7.56 (d, J=8.1 Hz, 1H), 7.29 (d, J=8.5 Hz, 1H), 6.89 (s, 1H), 6.75-6.67 (m, 1H), 6.08 (s, 1H), 5.10 (s, 2H), 3.40-3.34 (m, 1H), 3.00 (t, J=7.5 Hz, 2H), 2.70 (t, J=7.5 Hz, 2H), 2.12-2.02 (m, 2H), 1.96-1.85 (m, 2H), 1.79-1.60 (m, 4H).

Embodiment 20: Preparation of Compound 20

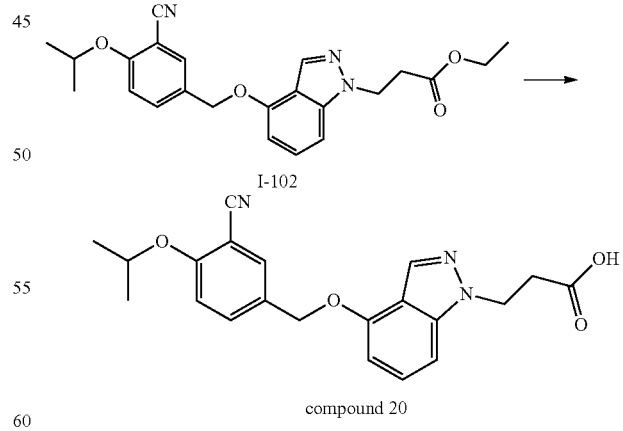

Intermediate I-102 (76 mg, 0.19 mmol) was dissolved in a mixed solution of tetrahydrofuran (3 mL)/water (1 mL), lithium hydroxide monohydrate (16 mg, 0.38 mmol) was added, and the reaction solution was stirred overnight at room temperature. The reaction solution was concentrated under reduced pressure, and the residue was acidified with IN hydrochloric acid and extracted with ethyl acetate (twice, 10 mL each). The organic phases were combined, dried with anhydrous sodium sulfate, filtered, and the filtrate was concentrated under reduced pressure to obtain a residue. The residue was separated and purified by preparative HPLC to obtain compound 20.

LC-MS (ESI) [M+H]$^+$ 380.2.

$^1$H NMR (400 MHz, DMSO-d$_6$) δ 12.32 (s, 1H), 8.06 (d, J=0.6 Hz, 1H), 7.86 (d, J=2.2 Hz, 1H), 7.77 (dd, J=8.8, 2.2 Hz, 1H), 7.36-7.20 (m, 3H), 6.66 (d, J=7.1 Hz, 1H), 5.21 (s, 2H), 4.85-4.76 (m, 1H), 4.55 (t, J=6.7 Hz, 2H), 2.83 (t, J=6.7 Hz, 2H), 1.32 (d, J=6.0 Hz, 6H).

Embodiment 21: Preparation of Compound 21

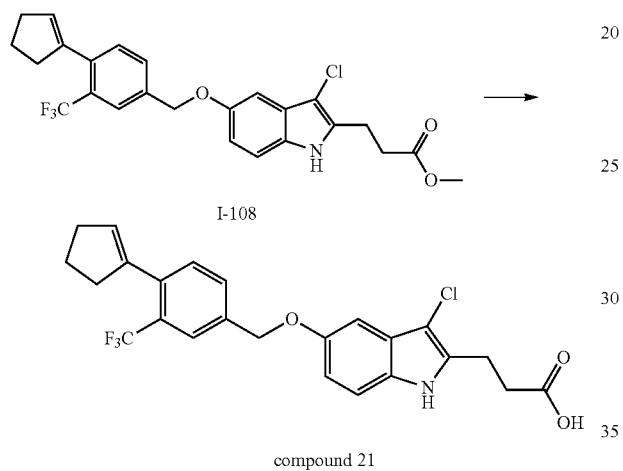

Intermediate I-108 (61.0 mg, 0.128 mmol) was dissolved in methanol (2.00 mL), and lithium hydroxide monohydrate (16.1 mg, 0.384 mmol) and water (0.500 mL) were added. The reaction mixture was stirred at 30° C. for 2 hours. The reaction solution was separated and purified by preparative HPLC to obtain compound 21.

LC-MS (ESI) [M+H]$^+$ 464.1.

$^1$H NMR (400 MHz, Methanol-d$_4$) δ 7.77 (d, J=1.8 Hz, 1H), 7.64 (dd, J=7.9, 1.8 Hz, 1H), 7.34 (d, J=7.9 Hz, 1H), 7.21 (d, J=8.8 Hz, 1H), 6.99 (d, J=2.4 Hz, 1H), 6.86 (dd, J=8.7, 2.5 Hz, 1H), 5.71 (t, J=2.3 Hz, 1H), 5.15 (s, 2H), 3.11-2.98 (m, 2H), 2.73-2.60 (m, 4H), 2.56-2.45 (m, 2H), 2.09-1.91 (m, 2H).

Embodiment 22: Preparation of Compound 22

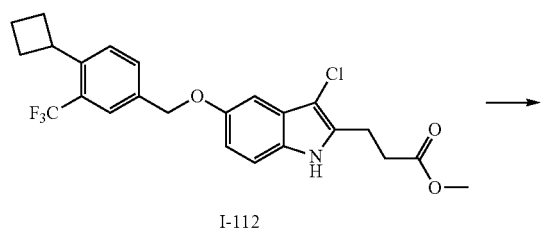

I-112

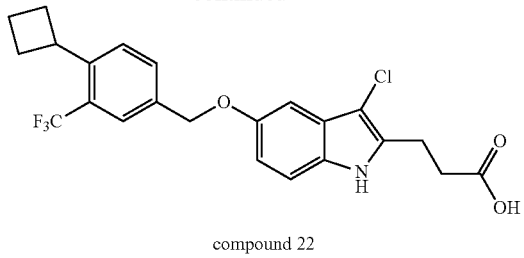

compound 22

At room temperature, intermediate I-112 (63.0 mg, 0.135 mmol) was dissolved in tetrahydrofuran (2 mL) and methanol (0.5 mL), and a solution of lithium hydroxide monohydrate (11.3 mg, 0.269 mmol) in water (0.5 mL) was added. The reaction mixture was stirred at room temperature for one hour, and then diluted hydrochloric acid (1 M) was added to adjust the pH of the reaction mixture to 5. The reaction mixture was concentrated under reduced pressure to remove the organic solvent to obtain a crude product. The crude product was separated and purified by preparative HPLC to obtain compound 22.

LC-MS (ESI) [M+H]$^+$ 452.1.

$^1$H NMR (400 MHz, DMSO-γ$_6$) δ 12.30 (s, 1H), 11.17 (s, 1H), 7.79-7.70 (m, 3H), 7.25 (d, J=8.7 Hz, 1H), 6.94 (d, J=2.3 Hz, 1H), 6.83 (dd, J=8.8, 2.4 Hz, 1H), 5.18 (s, 2H), 3.84-3.73 (m, 1H), 2.95 (t, J=7.8 Hz, 2H), 2.62 (t, J=7.8 Hz, 2H), 2.30-2.14 (m, 4H), 2.03-1.94 (m, 1H), 1.87-1.77 (m, 1H).

Embodiment 23: Preparation of Compound 23

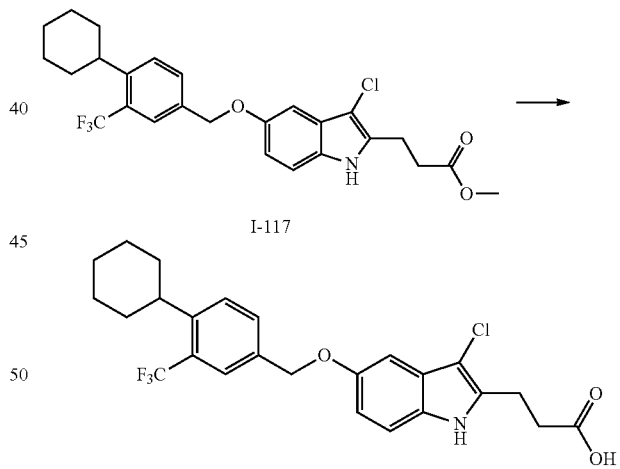

Intermediate I-117 (30.0 mg, 0.0607 mmol) was mixed with tetrahydrofuran (0.5 mL) and water (0.1 mL), and lithium hydroxide monohydrate (5.08 mg, 0.121 mmol) was added at 10° C. The reaction mixture was stirred at 10° C. overnight. The reaction mixture was concentrated under reduced pressure to remove the organic solvent, and then the pH was adjusted to 1 with IN dilute hydrochloric acid, and the mixture was extracted with ethyl acetate (5 mL×2). The organic phases were combined, washed with saturated saline (5 mL), dried with anhydrous sodium sulfate, and filtered. The filtrate was concentrated under reduced pressure to remove the organic solvent to obtain a crude product. The crude product was separated and purified by preparative HPLC to obtain compound 23.

LC-MS (ESI) [M+H]$^+$ 480.3

$^1$H NMR (400 MHz, Methanol-d$_4$) δ 10.50 (s, 1H), 7.72 (s, 1H), 7.66 (d, J=8.2 Hz, 1H), 7.56 (d, J=8.1 Hz, 1H), 7.21 (d, J=8.8 Hz, 1H), 6.99 (d, J=2.4 Hz, 1H), 6.85 (dd, J=8.8, 2.4 Hz, 1H), 5.12 (s, 2H), 3.06 (t, J=7.8 Hz, 2H), 2.98-2.89 (m, 1H), 2.69 (t, J=7.8 Hz, 2H), 1.93-1.75 (m, 5H), 1.60-1.33 (m, 5H).

Embodiment 24: Preparation of Compound 24

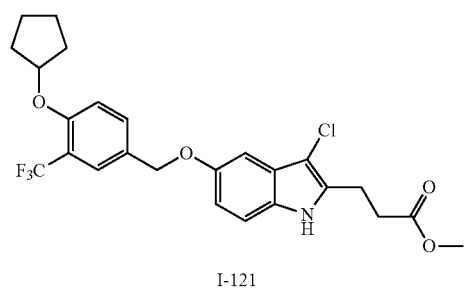

I-121

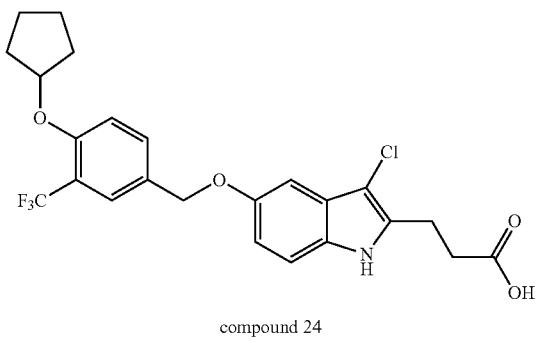

compound 24

Intermediate I-121 (90 mg, 0.181 mmol) was dissolved in tetrahydrofuran (5 mL) and water (1 mL), and lithium hydroxide monohydrate (22.8 mg, 0.543 mmol) was added. The reaction mixture was stirred at 10° C. for one hour. The reaction mixture was concentrated under reduced pressure to remove the organic solvent, and then the pH of the concentrate was adjusted to 1 with 1N dilute hydrochloric acid, and the mixture was extracted with ethyl acetate (5 mL×2). The organic phases were combined, dried with anhydrous sodium sulfate and filtered. The filtrate was concentrated under reduced pressure to remove the organic solvent to obtain a crude product. The crude product was separated and purified by preparative HPLC to obtain compound 24.

LC-MS (ESI) [M+H]$^+$ 482.2.

$^1$H NMR (400 MHz, Methanol-d$_4$) δ 7.65 (d, J=2.2 Hz, 1H), 7.62 (dd, J=8.5, 2.2 Hz, 1H), 7.20 (d, J=8.8 Hz, 1H), 7.15 (d, J=8.5 Hz, 1H), 6.98 (d, J=2.4 Hz, 1H), 6.83 (dd, J=8.8, 2.4 Hz, 1H), 5.04 (s, 2H), 4.99-4.94 (m, 1H), 3.06 (t, J=7.8 Hz, 2H), 2.68 (t, J=7.8 Hz, 2H), 1.98-1.75 (m, 6H), 1.72-1.61 (m, 2H).

Embodiment 25: Preparation of Compound 25

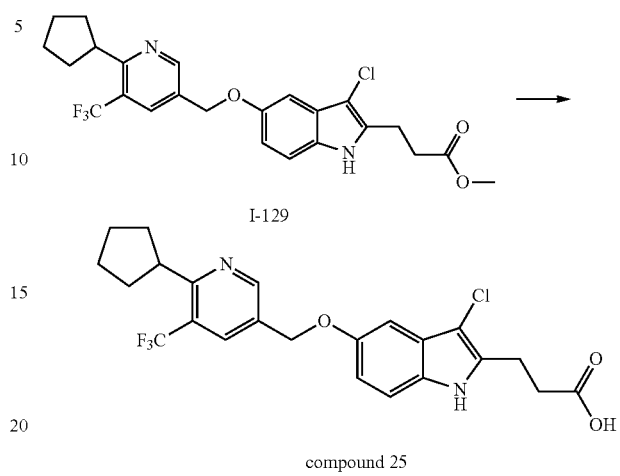

I-129 compound 25

At 15° C., intermediate I-129 (40.0 mg, 0.0832 mmol) was dissolved in methanol/water (1/1 mL), and lithium hydroxide monohydrate (6.97 mg, 0.166 mmol) was added, and the reaction mixture was stirred and reacted at 15° C. for 3 hours. The mixture was separated and purified by preparative HPLC to obtain compound 25.

LC-MS (ESI) [M+H]$^+$ 467.2.

$^1$H NMR (400 MHz, DMSO-d$_6$) δ 11.75 (brs, 1H), 8.92 (s, 1H), 8.17 (s, 1H), 7.25 (d, J=8.7 Hz, 1H), 6.97 (d, J=2.3 Hz, 1H), 6.83 (dd, J=8.7, 2.4 Hz, 1H), 5.22 (s, 2H), 3.44-3.39 (m, 1H), 2.89 (t, J=7.3 Hz, 2H), 2.03-1.92 (m, 4H), 1.88-1.79 (m, 3H), 1.71-1.62 (m, 2H), 1.48-1.42 (m, 1H).

Embodiment 26: Preparation of Compound 26

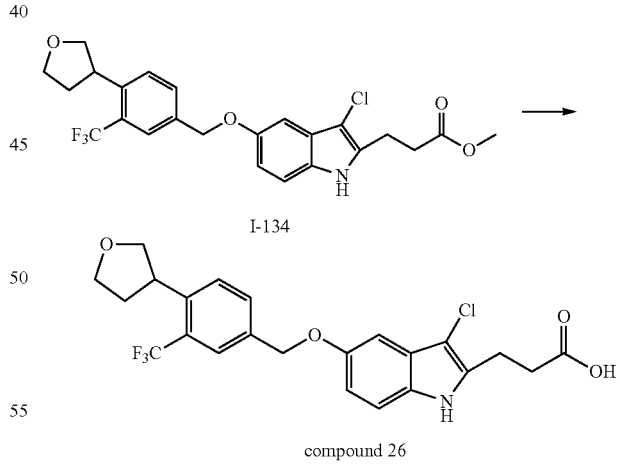

I-134 compound 26

Intermediate I-134 (105 mg, 0.218 mmol) was dissolved in methanol (3.00 mL), and lithium hydroxide monohydrate (27.4 mg, 0.654 mmol) and water (1.00 mL) were added. The reaction mixture was heated to 30° C., stirred and reacted for 2 hours. The reaction solution was separated and purified by preparative HPLC to obtain compound 26.

LC-MS (ESI) [M+H]$^+$ 468.2.

$^1$H NMR (400 MHz, Methanol-d$_4$) δ 10.50 (s, 1H), 7.76 (s, 1H), 7.71 (d, J=8.1 Hz, 1H), 7.62 (d, J=8.1 Hz, 1H), 7.21

(d, J=8.8 Hz, 1H), 6.98 (d, J=2.4 Hz, 1H), 6.85 (dd, J=8.8, 2.4 Hz, 1H), 5.14 (s, 2H), 4.19-3.99 (m, 2H), 3.94-3.87 (m, 1H), 3.84-3.74 (m, 2H), 3.06 (t, J=7.7 Hz, 2H), 2.68 (t, J=7.7 Hz, 2H), 2.48-2.37 (m, 1H), 2.09-1.93 (m, 1H).

Embodiment 27: Preparation of Compound 27

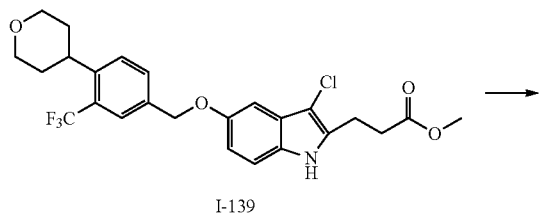

I-139

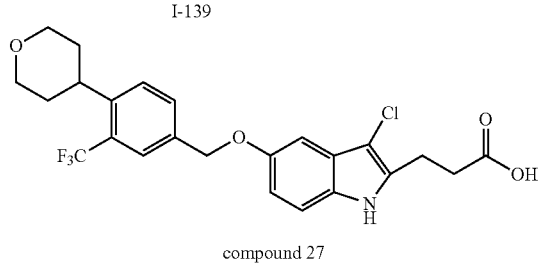

compound 27

At 15° C., intermediate I-139 (60.0 mg, 0.121 mmol) was dissolved in methanol/water (2 mL, 1:1), and lithium hydroxide monohydrate (10.2 mg, 0.242 mmol) was added, and the reaction mixture was stirred and reacted at 15° C. for 3 hours. The mixture was separated and purified by preparative HPLC to obtain compound 27.

LC-MS (ESI) [M+H]$^+$ 482.2.

$^1$H NMR (400 MHz, DMSO-d$_6$) δ 11.24 (s, 1H), 7.80-7.66 (m, 3H), 7.25 (d, J=8.8 Hz, 1H), 6.94 (d, J=2.3 Hz, 1H), 6.83 (dd, J=8.8, 2.4 Hz, 1H), 5.18 (s, 2H), 3.97 (dd, J=11.1, 3.8 Hz, 2H), 3.46-3.41 (m, 2H), 3.11-3.03 (m, 1H), 2.94 (t, J=7.7 Hz, 2H), 2.60 (t, J=7.7 Hz, 2H), 1.89-1.74 (m, 2H), 1.64-1.55 (m, 2H).

Embodiment 28: Preparation of Compound 28

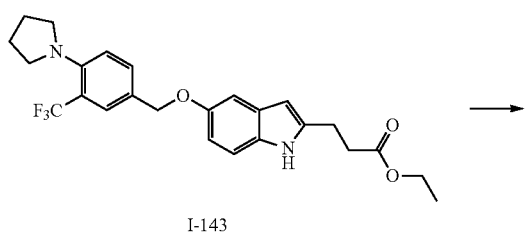

I-143

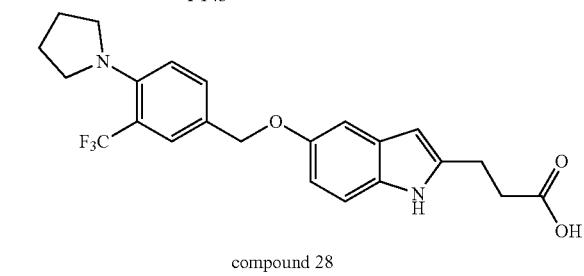

compound 28

At room temperature, intermediate I-143 (35.0 mg, 0.0760 mmol) was dissolved in tetrahydrofuran (2 mL) and methanol (0.5 mL), and a solution of lithium hydroxide monohydrate (6.38 mg, 0.152 mmol) in water (0.5 mL) was added. The reaction mixture was stirred at room temperature for one hour, and then dilute hydrochloric acid (1 M) was added to adjust the pH of the reaction mixture to 5. The reaction mixture was concentrated under reduced pressure to remove the organic solvent to obtain a crude product. The crude product was separated and purified by preparative HPLC to obtain compound 28.

LC-MS (ESI) [M+H]$^+$ 433.1.

$^1$H NMR (400 MHz, CDCl$_3$) δ 8.19 (s, 1H), 7.66 (d, J=1.7 Hz, 1H), 7.45 (d, J=8.5 Hz, 1H), 7.19 (d, J=8.6 Hz, 1H), 7.07 (d, J=1.8 Hz, 1H), 6.96 (d, J=8.6 Hz, 1H), 6.85 (dd, J=8.7, 2.1 Hz, 1H), 6.19 (s, 1H), 4.98 (s, 2H), 3.33 (t, J=6.1 Hz, 4H), 3.05 (t, J=6.4 Hz, 2H), 2.79 (t, J=6.4 Hz, 2H), 1.98-1.90 (m, 4H).

Embodiment 29: Preparation of Compound 29

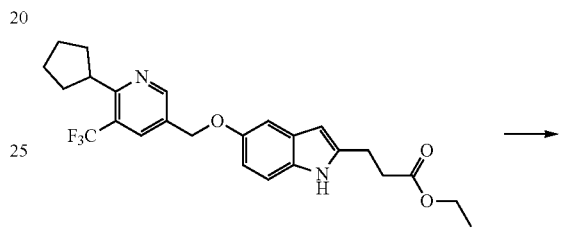

I-144

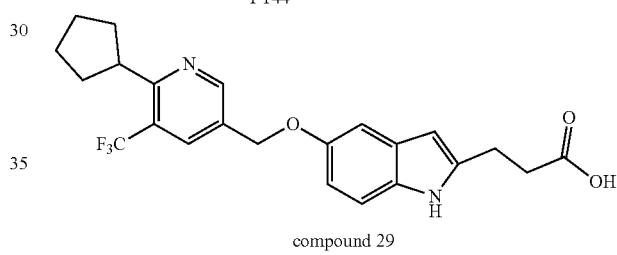

compound 29

Intermediate I-144 (46.1 mg, 0.100 mmol) was dissolved in methanol (2 mL), LiOH H$_2$O (12.6 mg, 0.300 mmol) and water (0.5 mL) were added, and the reaction solution was stirred at room temperature for 2 hours. The reaction solution was separated and purified by preparative HPLC to obtain compound 29.

LC-MS (ESI) [M+H]$^+$ 433.3.

$^1$H NMR (400 MHZ, DMSO-d$_6$) δ 10.83 (s, 1H), 8.89 (s, 1H), 8.13 (d, J=1.9 Hz, 1H), 7.17 (d, J=8.7 Hz, 1H), 7.05 (d, J=2.4 Hz, 1H), 6.73 (dd, J=8.7, 2.4 Hz, 1H), 6.06 (s, 1H), 5.17 (s, 2H), 3.43-3.39 (m, 1H), 2.91 (t, J=7.5 Hz, 2H), 2.60 (t, J=7.5 Hz, 2H), 1.99-1.92 (m, 2H), 1.90-1.78 (m, 4H), 1.72-1.62 (m, 2H).

Embodiment 30: Preparation of Compound 30

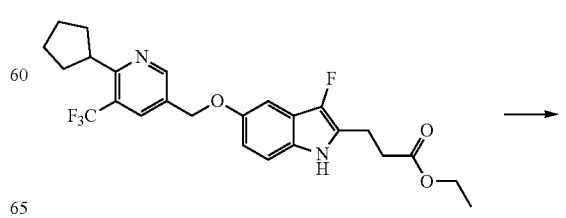

I-145

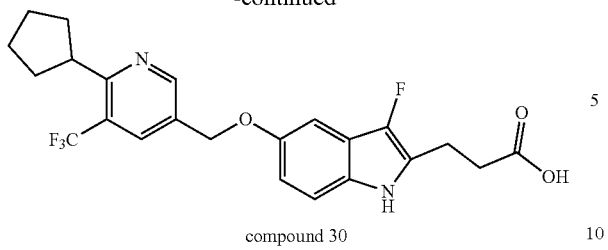

compound 30

Intermediate I-145 (35.2 mg, 0.0736 mmol) was dissolved in methanol (2 mL), LiOH H$_2$O (9.27 mg, 0.221 mmol) and water (0.5 mL) were added, and the reaction solution was stirred and reacted at room temperature for 2 hours. The reaction solution was separated and purified by preparative HPLC to obtain compound 30.

LC-MS (ESI) [M+H]$^+$ 451.1.

$^1$H NMR (400 MHz, DMSO-d$_6$) δ 12.18 (s, 1H), 10.65 (s, 1H), 8.90 (s, 1H), 8.15 (s, 1H), 7.19 (d, J=8.5 Hz, 1H), 7.03 (s, 1H), 6.81 (d, J=8.6 Hz, 1H), 5.21 (s, 2H), 3.45-3.39 (m, 1H), 2.92 (t, J=7.1 Hz, 2H), 2.64 (t, J=7.2 Hz, 2H), 2.00-1.50 (m, 8H).

Embodiment 31: Preparation of Compound 31

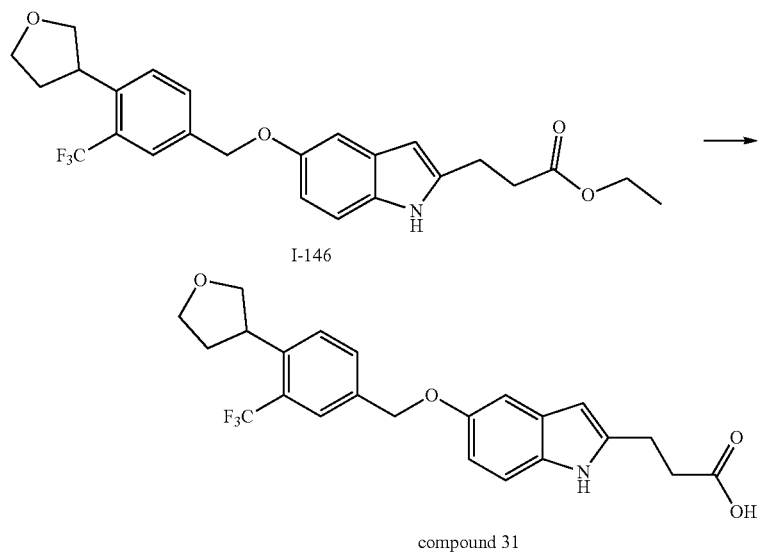

I-146 compound 31

Intermediate I-146 (100 mg, 0.217 mmol) was dissolved in tetrahydrofuran (5 mL), LiOH H$_2$O (27.3 mg, 0.651 mmol) and water (1 mL) were added, and the reaction solution was stirred at 25° C. for one hour. The reaction solution was separated and purified by preparative HPLC to obtain compound 31.

LC-MS (ESI) [M+H]$^+$ 434.2.

$^1$H NMR (400 MHz, DMSO-d$_6$) δ 12.25 (brs, 1H), 10.79 (s, 1H), 7.74 (d, J=10.1 Hz, 2H), 7.64 (d, J=8.0 Hz, 1H), 7.16 (d, J=8.7 Hz, 1H), 7.01 (d, J=2.4 Hz, 1H), 6.72 (dd, J=8.7, 2.4 Hz, 1H), 6.05 (s, 1H), 5.13 (s, 2H), 4.05-3.94 (m, 2H), 3.85-3.78 (m, 1H), 3.69-3.61 (m, 2H), 2.91 (t, J=7.6 Hz, 2H), 2.61 (t, J=7.6 Hz, 2H), 2.38-2.31 (m, 1H), 1.99-1.91 (m, 1H).

Embodiment 32: Preparation of Compound 32

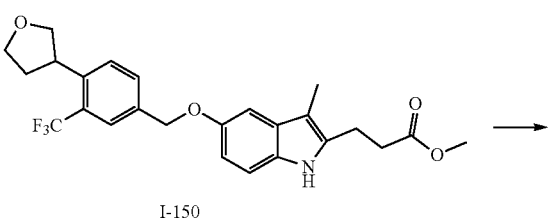

I-150

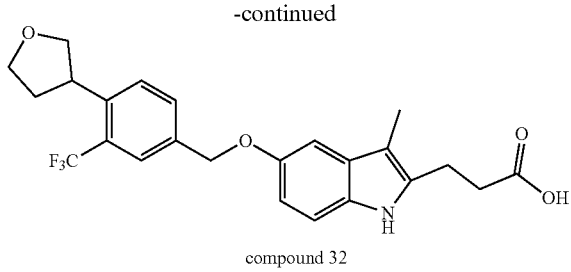

compound 32

At room temperature, a solution of lithium hydroxide monohydrate (21.8 mg, 0.520 mmol) in water (1 mL) was added to a solution of intermediate I-150 (80.0 mg, 0.173 mmol) in tetrahydrofuran (3 mL). The reaction mixture was stirred and reacted at room temperature for 5 hours and then the pH was adjusted to 1 with dilute hydrochloric acid (1 M). The reaction mixture was filtered with a membrane and purified by preparative HPLC to obtain compound 32.

LC-MS (ESI) [M+H]$^+$ 448.3.

$^1$H NMR (400 MHz, CD$_3$OD) δ 7.77 (s, 1H), 7.71 (d, J=8.3 Hz, 1H), 7.61 (d, J=8.1 Hz, 1H), 7.14 (d, J=8.7 Hz, 1H), 6.98 (d, J=2.3 Hz, 1H), 6.77 (dd, J=8.7, 2.4 Hz, 1H), 5.12 (s, 2H), 4.15-4.01 (m, 2H), 3.85-3.95 (m, 1H), 3.85-3.73 (m, 2H), 3.00 (t, J=7.7 Hz, 2H), 2.63 (t, J=7.7 Hz, 2H), 2.48-2.37 (m, 1H), 2.18 (s, 3H), 2.08-1.96 (m, 1H).

Embodiment 33: Preparation of Compound 33

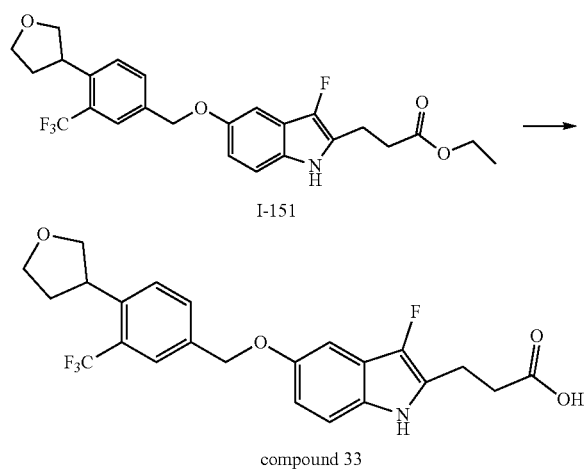

compound 33

Intermediate I-151 (100 mg, 0.209 mmol) was dissolved in tetrahydrofuran (4 mL), LiOH H$_2$O (26.3 mg, 0.627 mmol) and water (1 mL) were added, and the reaction solution was stirred at 25° C. for 2 hours. The reaction solution was separated and purified by preparative HPLC to obtain compound 33.

LC-MS (ESI) [M+H]$^+$ 452.2.

$^1$H NMR (400 MHZ, DMSO-d$_6$) δ 10.67 (S, 1H), 7.77 (S, 1H), 7.75 (d, J=8.0 HZ, 1H), 7.65 (d, J=8.0 Hz, 1H), 7.18 (dd, J=8.8, 2.6 Hz, 1H), 6.98 (d, J=2.4 Hz, 1H), 6.79 (dd, 7=8.8, 2.5 Hz, 1H), 5.17 (s, 2H), 4.09-3.92 (m, 2H), 3.81 (q, J=7.8 Hz, 1H), 3.66 (q, J=5.3, 4.7 Hz, 2H), 2.91 (t, J=7.6 Hz, 2H), 2.61 (t, J=7.6 Hz, 2H), 2.41-2.31 (m, 1H), 2.03-1.85 (m, 1H).

Embodiment 34: Preparation of Compound 34

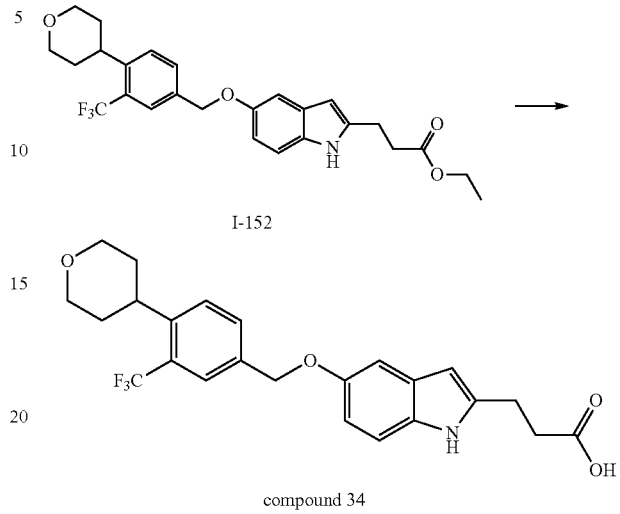

compound 34

Intermediate I-152 (40.0 mg, 84.12 μmol) and lithium hydroxide monohydrate (10.59 mg, 252.36 μmol) were dissolved in tetrahydrofuran (3.00 mL) and water (0.500 mL). The reaction mixture was stirred at 25° C. for 10 hours. The reaction solution was concentrated under reduced pressure to remove organic solvent and water to obtain a crude product. The crude product was separated and purified by preparative HPLC to obtain compound 34.

LC-MS (ESI) [M+H]$^+$ 448.2.

$^1$H NMR (400 MHz, CD$_3$OD) δ 7.75 (s, 1H), 7.69 (d, J=7.9 Hz, 1H), 7.59 (d, J=8.1 Hz, 1H), 7.18 (d, J=8.7 Hz, 1H), 7.03 (s, 1H), 6.78 (d, J=8.7 Hz, 1H), 6.11 (s, 1H), 5.11 (s, 2H), 4.12-4.00 (m, 2H), 3.56 (t, J=11.5 Hz, 2H), 3.26-3.13 (m, 1H), 3.03 (t, J=7.5 Hz, 2H), 2.71 (t, J=7.5 Hz, 2H), 1.99-1.83 (m, 2H), 1.74-1.62 (m, 2H).

Embodiment 35: Preparation of Compound 35

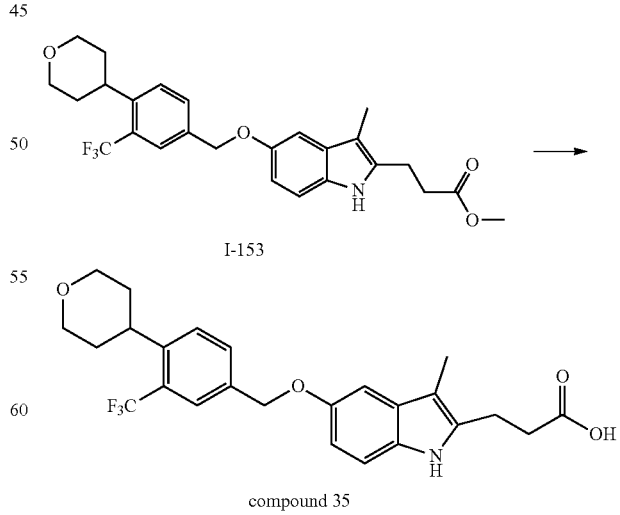

compound 35

Intermediate I-153 (35.2 mg, 0.0740 mmol) was dissolved in methanol (3 mL), LiOH H$_2$O (9.32 mg, 0.222 mmol) and water (0.5 mL) were added, and the reaction solution was stirred at room temperature for 3 hours. The reaction solution was separated and purified by preparative HPLC to obtain compound 35.

LC-MS (ESI) [M+H]⁺ 462.3.

¹H NMR (400 MHz, DMSO-d₆) δ 10.51 (s, 1H), 7.77 (s, 1H), 7.74 (d, J=8.4 Hz, 1H), 7.68 (d, J=8.1 Hz, 1H), 7.13 (d, J=8.6 Hz, 1H), 6.98 (d, J=2.3 Hz, 1H), 6.72 (dd, J=8.6, 2.4 Hz, 1H), 5.14 (s, 2H), 3.97 (m, 2H), 3.43 (m, 2H), 3.11-3.03 (m, 1H), 2.88 (t, J=7.7 Hz, 2H), 2.55 (t, J=8.0 Hz, 2H), 2.10 (s, 3H), 1.87-1.76 (m, 2H), 1.63-1.54 (m, 2H).

Embodiment 36: Preparation of Compound 36

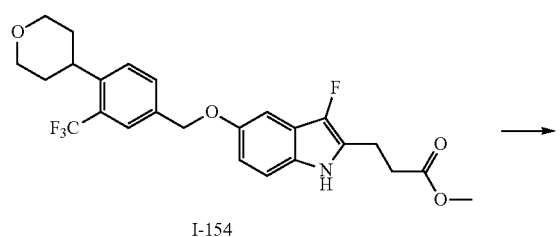

I-154

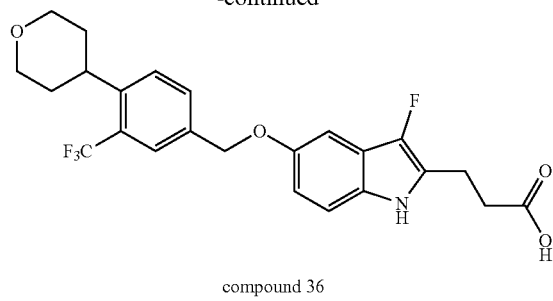

compound 36

Intermediate I-154 (30.0 mg, crude product) and lithium hydroxide monohydrate (4.06 mg, 96.66 μmol) were dissolved in tetrahydrofuran (2.00 mL) and water (0.500 mL). The reaction mixture was stirred at 25° C. for 10 hours. The reaction solution was concentrated under reduced pressure to remove organic solvent and water to obtain a crude product. The crude product was separated and purified by preparative HPLC to obtain compound 36.

LC-MS (ESI) [M+H]⁺ 466.2.

¹H NMR (400 MHz, CD₃OD) δ 7.75 (s, 1H), 7.70 (d, J=8.2 Hz, 1H), 7.60 (d, J=8.1 Hz, 1H), 7.15 (dd, J=8.8, 2.5 Hz, 1H), 6.98 (d, J=2.3 Hz, 1H), 6.81 (dd, J=8.8, 2.4 Hz, 1H), 5.12 (s, 2H), 4.13-4.00 (m, 2H), 3.62-3.49 (m, 2H), 3.21 (m, 1H), 3.02 (t, J=7.6 Hz, 2H), 2.68 (t, J=7.6 Hz, 2H), 1.97-1.84 (m, 2H), 1.77-1.65 (m, 2H).

Embodiment 37: Preparation of Compound 37

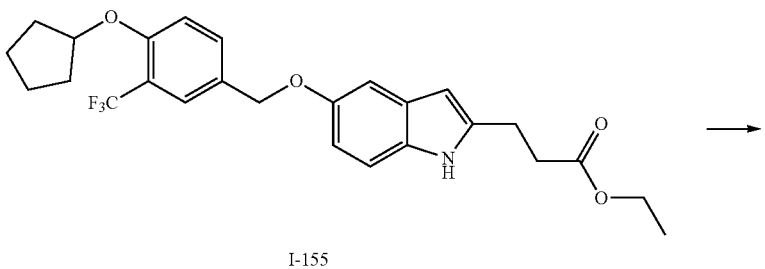

I-155

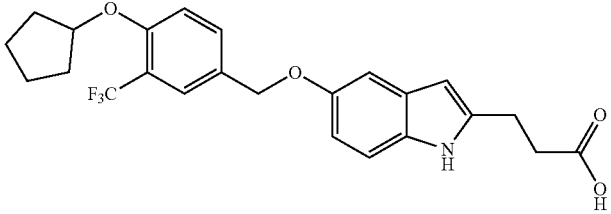

compound 37

Intermediate I-155 (50 mg, 0.105 mmol) was dissolved in tetrahydrofuran (3 mL) and water (0.5 mL), and lithium hydroxide monohydrate (22.0 mg, 0.525 mmol) was added at room temperature. The reaction mixture was stirred at room temperature overnight. The reaction mixture was concentrated under reduced pressure to remove the organic solvent, and then the pH of the concentrate was adjusted to 1 with 1N dilute hydrochloric acid, and the mixture was extracted with ethyl acetate (5 mL×2). The organic phases were combined, washed with saturated saline (5 mL), dried with anhydrous sodium sulfate and filtered. The filtrate was concentrated under reduced pressure to remove the organic solvent to obtain a crude product. The crude product was separated and purified by preparative HPLC to obtain compound 37.

LC-MS (ESI) [M+H]+ 448.3.

$^1$H NMR (400 MHz, Methanol-$d_4$) δ 10.16 (s, 1H), 7.63 (s, 1H), 7.60 (d, 2H), J=8.6 Hz, 7.19-7.11 (m, 2H), 7.03 (d, J=2.4 Hz, 1H), 6.75 (dd, J=8.7, 2.4 Hz, 1H), 6.11 (s, 1H), 5.01 (s, 2H), 4.99-4.93 (m, 1H), 3.02 (t, J=7.6 Hz, 2H), 2.71 (t, J=7.6 Hz, 2H), 1.98-1.75 (m, 6H), 1.72-1.61 (m, 2H).

Embodiment 38: Preparation of Compound 38

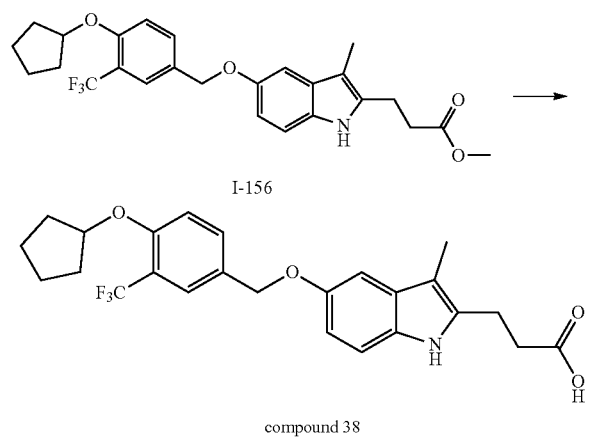

Intermediate I-156 (100 mg, 0.210 mmol) was dissolved in tetrahydrofuran (5 mL) and water (1 mL), and lithium hydroxide monohydrate (44.1 mg, 1.05 mmol) was added at room temperature. The reaction mixture was stirred at room temperature overnight. The reaction mixture was concentrated under reduced pressure to remove the organic solvent, and then the pH of the concentrate was adjusted to 1 with 1N dilute hydrochloric acid, and the mixture was extracted with ethyl acetate (5 mL×2). The organic phases were combined, dried with anhydrous sodium sulfate and filtered. The filtrate was concentrated under reduced pressure to remove the organic solvent to obtain a crude product. The crude product was separated and purified by preparative HPLC to obtain compound 38.

LC-MS (ESI) [M+H]+ 462.3.

$^1$H NMR (400 MHz, Methanol-$d_4$) δ 7.65 (d, J=2.2 Hz, 1H), 7.61 (dd, J=8.5, 2.2 Hz, 1H), 7.14 (dd, J=8.6, 4.1 Hz, 2H), 6.98 (d, J=2.4 Hz, 1H), 6.75 (dd, J=8.7, 2.4 Hz, 1H), 5.03 (s, 2H), 4.99-4.94 (m, 1H), 3.01 (t, J=7.6 Hz, 2H), 2.63 (t, J=7.7 Hz, 2H), 2.19 (s, 3H), 1.98-1.85 (m, 4H), 1.84-1.76 (m, 2H), 1.72-1.61 (m, 2H).

Embodiment 39: Preparation of Compound 39

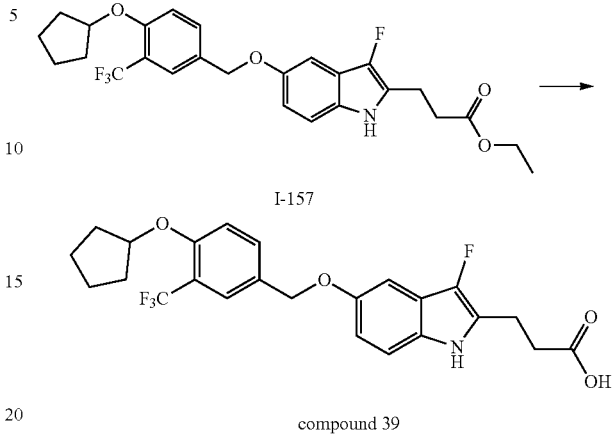

Intermediate I-157 (57 mg, 0.116 mmol) was dissolved in tetrahydrofuran (5 mL) and water (0.5 mL), and lithium hydroxide monohydrate (24.3 mg, 0.580 mmol) was added at room temperature. The reaction mixture was stirred at room temperature for 4 hours. The reaction mixture was concentrated under reduced pressure to remove the organic solvent, and then the pH of the concentrate was adjusted to 1 with 1N dilute hydrochloric acid, and the mixture was extracted with ethyl acetate (5 mL×2). The organic phases were combined, washed with saturated saline (5 mL), dried with anhydrous sodium sulfate and filtered. The filtrate was concentrated under reduced pressure to remove the organic solvent to obtain a crude product. The crude product was separated and purified by preparative HPLC to obtain compound 39.

LC-MS (ESI) [M+H]+ 466.2.

$^1$H NMR (400 MHz, Methanol-$d_4$) δ 7.68-7.58 (m, 2H), 7.19-7.11 (m, 2H), 6.99 (d, J=2.3 Hz, 1H), 6.80 (dd, J=8.8, 2.4 Hz, 1H), 5.03 (s, 2H), 4.99-4.94 (m, 1H), 3.03 (t, J=7.6 Hz, 2H), 2.70 (t, J=7.6 Hz, 2H), 1.99-1.75 (m, 6H), 1.73-1.61 (m, 2H).

Embodiment 40: Preparation of Compound 40

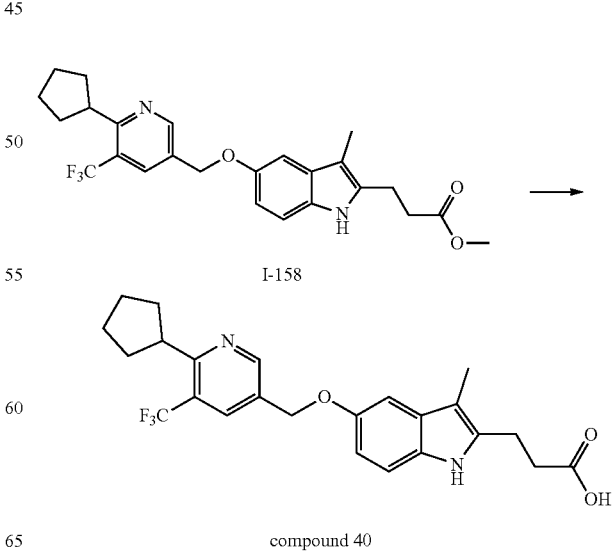

Intermediate I-158 (60.0 mg, 0.130 mmol) was dissolved in anhydrous methanol (1.00 mL), and a solution of lithium hydroxide monohydrate (16.4 mg, 0.390 mmol) in water (1.00 mL) was added. The reaction mixture was stirred at room temperature for one hour, and then dilute hydrochloric acid (0.05 M) was added to adjust the pH of the reaction mixture to 6.0. The reaction mixture was concentrated under reduced pressure to remove the organic solvent to obtain a crude product. The crude product was separated and purified by preparative HPLC to obtain compound 40.

LC-MS (ESI) [M+H]$^+$ 447.3.

$^1$H NMR (400 MHz, DMSO-d$_6$) δ 12.03 (s, 1H), 10.51 (s, 1H), 8.90 (s, 1H), 8.15 (d, J=1.7 Hz, 1H), 7.14 (d, J=8.6 Hz, 1H), 7.01 (d, J=2.4 Hz, 1H), 6.73 (dd, J=8.6, 2.4 Hz, 1H), 5.19 (s, 2H), 3.46-3.39 (m, 1H), 2.89 (t, J=8.0 Hz, 2H), 2.56 (t, J=8.0 Hz, 2H), 2.13 (s, 3H), 2.01-1.90 (m, 2H), 1.74-1.89 (m, 4H), 1.73-1.60 (m, 2H).

Experimental Embodiment 1: Inhibitory Effect Mediated by S1P1

The cell line used in the test was PathHunter® CHO-K1 EDG1 β-Arrestin Cell Line, supplier: DiscoverX, catalog number: 93-0207C2. The inhibitory effect of compounds on S1P1 mediated forskolin induced cAMP activity was evaluated.

Different concentrations of compounds and a final concentration of 0.6 μM forskolin were added to the test plate wells for each test, and the mixture was centrifuged at 1000 rpm for 10 seconds. A frozen cell was taken, washed twice with HBSS buffer and resuspended. 5000 cells were added to test plates per well, the mixture was shaked for 20 seconds, centrifuged at 1000 rpm for 10 seconds, and incubated at room temperature for 60 minutes. Anti-cAMP-Eu$^{2+}$-Cryptate and cAMP-d2 were added. Then the mixture was shaked for 20 seconds, centrifuged at 1000 rpm for 10 seconds, incubated at room temperature for 60 minutes, and the plate was read on an Envision plate reader. The data was analyzed by nonlinear regression to determine the EC$_{50}$ of the compounds for the inhibition of cAMP induced by forskolin. The experimental results are shown in Table 1.

TABLE 1

| Activation of S1P1 receptor mediated cAMP inhibitory effect by compounds | |
|---|---|
| Compound number | S1P1 cAMP EC$_{50}$ (nM) |
| Compound 1 | <0.05 |
| Compound 2 | 0.07 |
| Compound 4 | 0.50 |
| Compound 6 | 0.16 |
| Compound 12 | 0.65 |
| Compound 13 | 0.08 |
| Compound 14 | 0.07 |
| Compound 16 | 0.18 |
| Compound 17 | 0.21 |
| Compound 18 | 0.08 |
| Compound 21 | 0.035 |
| Compound 22 | 0.11 |
| Compound 23 | 0.032 |
| Compound 26 | 0.0041 |
| Compound 24 | 0.0072 |
| Compound 25 | 0.0017 |
| Compound 27 | 0.0021 |
| Compound 30 | 0.15 |
| Compound 31 | 0.18 |
| Compound 32 | 0.56 |
| Compound 33 | 0.057 |
| Compound 35 | 0.34 |

TABLE 1-continued

| Activation of S1P1 receptor mediated cAMP inhibitory effect by compounds | |
|---|---|
| Compound number | S1P1 cAMP EC$_{50}$ (nM) |
| Compound 36 | 0.30 |
| Compound 37 | 0.20 |
| Compound 39 | 0.027 |
| APD334 | 2.07 |

Experimental data shows that the compound of the present disclosure has good activation characteristics for S1P1 mediated cAMP inhibitory effect.

Experimental embodiment 2: Activation effect of β-Arrestin reporter gene mediated by S1P1

The cell line used in the test was PathHunter® CHO-K1 EDG1 β-Arrestin Cell Line, supplier: DiscoverX, catalog number: 93-0207C2. According to the supplier's instructions, the cells were added to the test plate according to 25 μL cell suspension containing 5000 cells per well, and cultured at 37° C. for 20 hours. Compounds of 10 concentrations diluted 4 times were added to the cell culture medium and incubated at 37° C. for 90 minutes. The detection solution was prepared, 12 μL per well, incubated at room temperature for 60 minutes, the plate was read on an Envision plate reader. The data was analyzed by nonlinear regression to determine the EC$_{50}$ of β-arrestin activity. The experimental results are shown in Table 2.

TABLE 2

| Activation of S1P1 receptor mediated β-arrestin activity by compounds | |
|---|---|
| Compound number | S1P1 β-arrestin EC$_{50}$ (nM) |
| Compound 1 | 0.95 |
| Compound 2 | 1.62 |
| Compound 12 | 1.96 |
| Compound 13 | 1.83 |
| Compound 14 | 1.86 |
| Compound 16 | 1.13 |
| Compound 17 | 1.78 |
| Compound 18 | 1.10 |
| Compound 21 | 2.26 |
| Compound 22 | 1.65 |
| Compound 23 | 3.82 |
| Compound 24 | 1.73 |
| Compound 25 | 1.23 |
| Compound 26 | 1.11 |
| Compound 27 | 1.03 |
| Compound 28 | 2.08 |
| Compound 29 | 2.15 |
| Compound 30 | 0.62 |
| Compound 31 | 2.63 |
| Compound 32 | 1.47 |
| Compound 33 | 1.10 |
| Compound 34 | 5.35 |
| Compound 35 | 0.88 |
| Compound 36 | 0.85 |
| Compound 37 | 1.72 |
| Compound 38 | 1.11 |
| Compound 39 | 0.76 |
| Compound 40 | 1.18 |

Experimental data shows that the compounds of the present disclosure exhibit a good activation effect on S1P1 mediated β-arrestin.

Experimental Embodiment 3: Internalization Effect Experiment of S1P1 Receptor of the Compound of the Present Disclosure 1. CHO-K1 DEG1 cells (PathHunter® CHO-K1 EDG1 β-Arrestin Cell Line, supplier: DiscoverX, catalog number: 93-0207C2), and culture medium was removed (F12 medium 1000 mL, 10% FBS, 800 μg/mL G418, 300 μg/mL Hygromycin, 1% Glutamax and 1% Pen/Strep), the cells were washed with 2 mL of DPBS, 5 mL of cell dispersion (Invitrogen-13151014) was added to disperse the cells, the cells were incubated in an incubator at 37° C. for 1-2 minutes. The flask was gently patted to make the cells fall off. 5 mL of growth medium was added, and pipette was gently blown to suspend the cells. Cell counting was performed using Vi-Cell. The mixture was centrifuged at 1000 rpm for 5 minutes at room temperature, the supernatant was gently poured out, and the cells in FACS buffer were resuspended to a concentration of 1.5e6 cells per mL. 2. S1P and compounds were diluted with DMSO in a 384-well plate, and a volume of 500 nL was transferred to a 96 V-well plate (Cat #Axygen-WIPP02280). 3. 50 μL of cells were added to a 96-well plate; 4. The 96-well plate was incubated in a 37° C. 5% $CO_2$ incubator for 2 hours. 5. The cells were centrifuged at room temperature at 1500 rpm for 5 minutes to remove the supernatant. 6. 100 μL of FACS buffer was added to the resuspended cells, centrifuged at 1500 rpm for 5 minutes, and the supernatant was removed. 7. The anti-human S1P1/EDG-1-Alex647 (R&D-FAB1864R) and anti-IgG2B-Alex647 (R&D-IC0041R) antibodies were diluted 200 times with FACS buffer. 8. 50 μL of antibody was added to 96 wells, and the plates were transferred to 4° C. for 30 minutes. 9. The cells were centrifuged at room temperature at 1500 rpm for 5 minutes to remove the supernatant. 10. 100 μL of FACS buffer was added to the resuspended cells. 11. The cells were centrifuged at 4° C. at 1500 rpm for 5 minutes to remove the supernatant. 12. After washing, the cells were resuspended in 50 μL of FACS buffer per well. 13. Cell samples were read using iQue Screener PLUS-VBR. The experimental results are shown in Table 3.

TABLE 3

Internalization effect experiment of compounds against S1P1 receptor

| Compound number | S1P1 internalized $EC_{50}$ (nM) |
|---|---|
| Compound 2 | 0.32 |
| Compound 13 | 0.18 |
| Compound 14 | 0.14 |
| Compound 16 | 0.015 |
| Compound 18 | 0.69 |
| APD334 | 6.26 |

Experimental data shows that the compounds of the present disclosure exhibit good activation internalization against S1P1 receptor.

Experimental Embodiment 4: Determination of Agonist Activity Against S1P3 Receptor The cells, culture conditions and cell collection conditions used in this experiment were the same as those in experimental embodiment 3.

(1) 25 μL (5000 cells) of cell suspension was added to each well of the assay plate and incubated at 37° C. for 20 hours. (2) 10 doses were obtained by diluting four times of the compound, and incubated at 37° C. for 90 minutes. (3) 12 μL of detection reagent was added to each well of the detection plate, and incubated at 23° C. for 60 minutes. (4) The plate was read on an Envision plate reader. The experimental results are shown in Table 4.

TABLE 4

Determination of agonist activity against S1P3 receptor

| Compound | β-arrestin $EC_{50}$ (nM) | |
|---|---|---|
| number | S1P1 | S1P3 |
| Compound 13 | 1.17 | 712 |
| Compound 16 | 0.75 | 3497 |

Experimental data shows that the compounds of the present disclosure exhibit good selectivity against S1P3 receptor.

Experimental Embodiment 5: In Vivo Pharmacokinetic Experiment of the Compounds of the Present Disclosure In this experimental embodiment, in vivo pharmacokinetic evaluation was performed in rats by intravenous injection and oral administration.

Experimental methods and conditions: male Sprague Dawley rats were given the test compounds 1 mg/kg (solvent 5% DMSO/15% Solutol/80% Saline) by intravenous injection and 1 mg/kg (solvent 0.5% MC) by oral gavage respectively. 5 min, 15 min, 30 min, 1 hr, 2 hr, 4 hr, 6 hr, 8 hr, 24 hr after administration, blood was collected from submandibular vein, each sample was collected about 0.20 mL, and heparin sodium was used for anti coagulation. After collection, the sample was placed on ice, and the blood was centrifuged to be measured within one hour. Blood drug concentration in plasma was detected by liquid chromatography tandem mass spectrometry (LC/MS/MS), and the pharmacokinetic parameters were calculated by Phoenix WinNonlin software. The experimental results are shown in Tables 5 and 6.

TABLE 5

Pharmacokinetics of oral administration (1 mg/kg)

| Compound | $T_{1/2}$ (hr) | $C_{max}$ (ng/mL) | $AUC_{inf}$ (ng*hr/mL) | F (%) |
|---|---|---|---|---|
| Compound 13 | 3.9 | 184 | 1194 | 17.4 |
| Compound 14 | 4.0 | 258 | 2338 | 21.3 |
| Compound 16 | 2.9 | 162 | 649 | 13.3 |
| APD334 | 5.5 | 341 | 4442 | 46.3 |

TABLE 6

Pharmacokinetics of intravenous administration (1 mg/kg)

| Compound | $T_{1/2}$ (hr) | $AUC_{inf}$ (ng*hr/mL) | Cl (L/hr/kg) |
|---|---|---|---|
| Compound 13 | 2.8 | 4753 | 0.21 |
| Compound 14 | 4.1 | 10842 | 0.093 |
| Compound 16 | 1.4 | 4145 | 0.25 |
| APD334 | 5.2 | 9414 | 0.11 |

Experimental data shows that the compounds of the present disclosure exhibit short half-life in vivo ($T_{1/2}$) in rats.

Experimental Embodiment 6: The Effect of the Compounds of the Present Disclosure in the Determination of Peripheral Lymphocyte Lowering (PLL)

PLL Determination:

Mice: SPF female C57BL/6j mice, weighing 19-22 g. Rats: Male Sprague-Dawley rats, weighing 200-220 g. Feeding environment: the temperature was 23±2° C., the relative humidity was 40-70%, and the lighting time was at 7:00 in the morning to 7:00 in the evening; animals were freely fed with common feed and sterilized drinking water. All animal experiments were approved by the animal ethics committee; all animal experiments were carried out in accordance with the relevant SOP requirements of animal room. Animals were reared adaptively for one week before the experiment.

Animals were administered orally with a volume of 10 mL/kg. The vehicle for administration was 0.5% DMSO+ 0.5% MC. Animals were anesthetized with isoflurane 5 hours after administration, and 100-150 µL of peripheral blood was collected through the eye socket in EP tubes, placed on ice. The lymphocyte count of blood analysis was detected by XT-2000i automated hematology analyzer within 30 minutes. Another 20 µL of whole blood was diluted with 40 µL of DDW, and snap frozen in liquid nitrogen, the concentration of the compounds in blood was detected.

Figure 2:
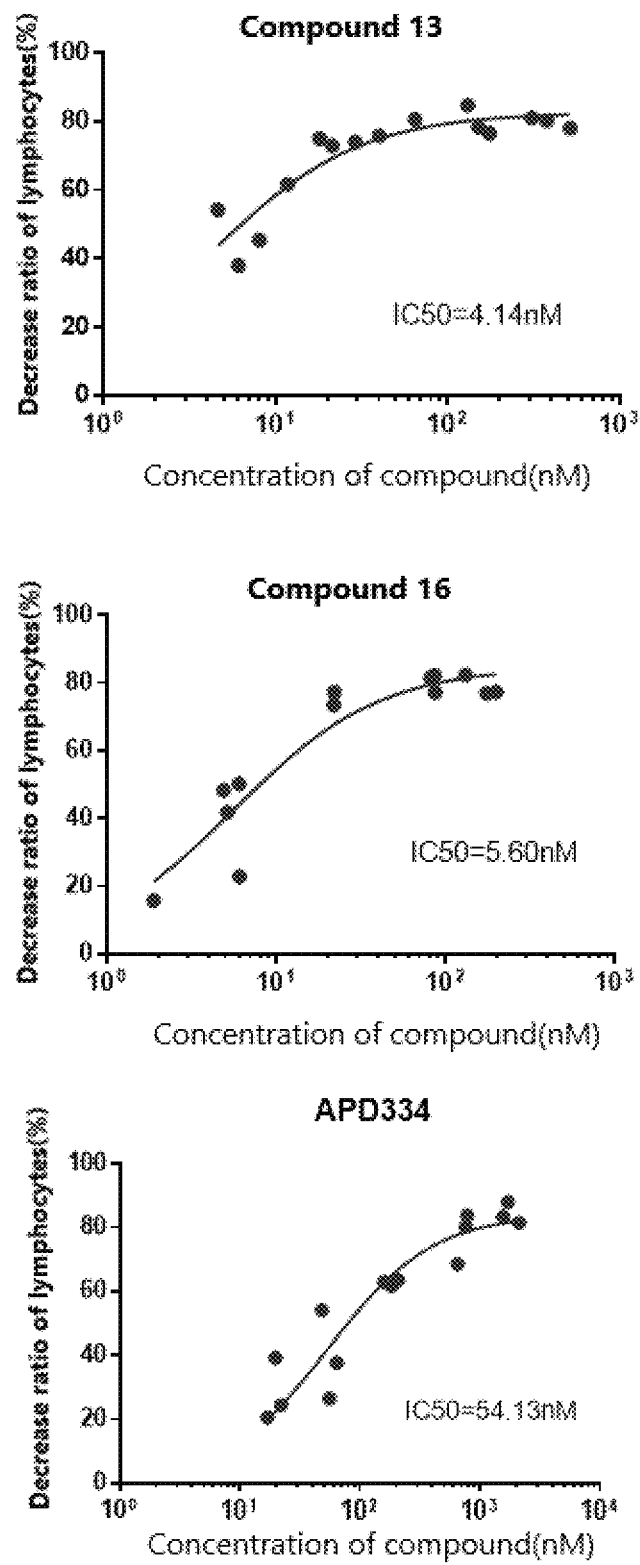
FIG. 2 shows the effects of compounds 13 and 16 in the peripheral blood lymphocyte (PBL) reduction test in rats.

The results show that compounds 13 and 16 decrease the peripheral blood lymphocyte (PBL) count of mice 5 hours after administration, and the $IC_{50}$ values are 18.49 nm (compound 13) and 24.68 nm (compound 16), respectively, the experimental results are shown in FIG. 1. 5 hours after administration, compounds 13 and 16 decrease peripheral blood lymphocyte (PBL) count of rats, and the $IC_{50}$ values are 4.1 nm (compound 13) and 5.3 nm (compound 16), respectively, the experimental results are shown in FIG. 2.

Figure 3:
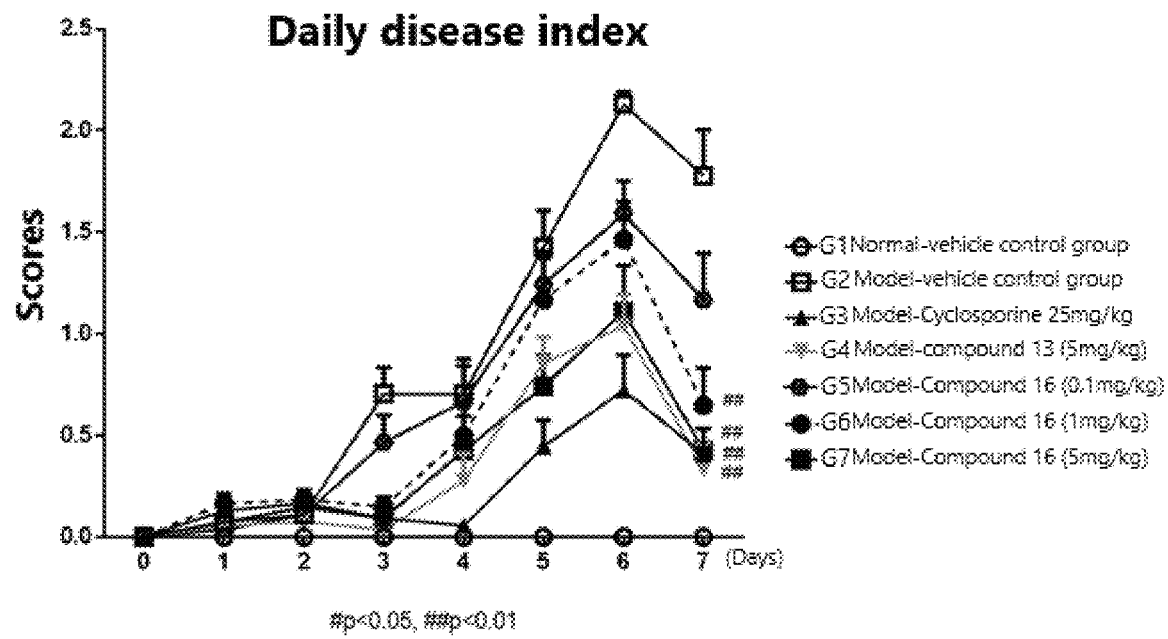
FIG. 3 shows the effects of compounds 13 and 16 in a mouse colitis model induced by DSS.

Experimental Embodiment 7: Effect of the Compound of the Present Disclosure on Colitis Animal enteritis model proved that the compounds of the present disclosure had therapeutic effect on colitis. Dextran sodium sulfate (DSS) was dissolved in drinking water and fed to mice, rats, hamsters, or guinea pigs to induced colitis, which resulted in hematochezia, weight loss, shortened intestinal length, mucosal ulcer, and neutrophil infiltration. Histopathological analysis showed that the intestinal tissue had a large number of crypts, epithelial cell ulcers and tissue edema, and activate the natural immune system, which was similar to human gastrointestinal inflammatory bowel disease (IBD). The test animal was C57BL/6, female, 6-8 weeks old/18-20 g. The animals were kept in SPF room with a room temperature of 20-26° C., a humidity of 40-70%, fluorescent lamp lighting, 12 hours of lighting (08:00-20:00) and 12 hours of no lighting, with 2-5 animals in each cage (same administration group). Experimental mice can obtain unlimited amount of special mice food and water. On the first day, the animals were divided into 7 groups with 13-18 animals in each group. From 9:00 on day 0 to 9:00 on day 6, mice in groups 2 to 7 were given aqueous solution containing 2% DSS for 6 days (from day 0 to day 6), after which the mice were given free access to normal water for 1 day (from 9:00 on day 6 to before anatomical examination on day 7). The day of modeling was counted as 0 day. The mice in group 1 were given free access to normal water for 7 days. The animals in group 1 were given 0.5% methylcellulose; other groups of model animals were given 0.5% methylcellulose or different test subjects, respectively. Body weight was observed once a day and daily disease index was recorded once a day, which was rated as 4 classes according to the following criteria: weight change (0, ≤1%; 1, 1-5%; 2, 5-10%; 3, 10-15%; 4, >15%); blood stool (0, negative; 4, positive); and stool score (0, normal; 2, loose stool; 4, diarrhea). The scores of the above three parts were added and divided by 3 to get the daily disease index value. The experimental results are shown in FIG. 3.

The results show that test compounds 13 and 16 significantly reduce the daily disease index of animals at the end of the experiment (7th day).

The Wistar rat ulcerative enteritis model induced by DNBS (2, 4-dinitrobenzenesulfonic acid) is also one of the commonly used models for development of enteritis drugs. DNBS combines with intestinal tissue protein to form complete antigen, which increases vascular permeability, activates inflammatory transmitters, increases fibrinolytic activity, and makes the body produce immune response against intestinal mucosa, resulting in persistent ulcer and inflammation of intestinal mucosa in rats.

The experimental animals were Wistar rats, male, 5-6 weeks old, 140-160 g. The animals were kept in SPF room with a room temperature of 20-26° C., a humidity of 40-70%, fluorescent lamp lighting, 12 hours of lighting (08:00-20:00) and 12 hours of no lighting, with 2-5 animals in each cage (same administration group). The rats were fasted for 40 hours before the experiment and were given a subcutaneous injection of 5% glucose saline (10 mL) during the fasting period. On the first day of the experiment, fasting rats were anesthetized by intraperitoneal injection of Shutai (25 mg/kg Tiletamine and 25 mg/kg Zolazepam) and 5 mg/kg xylazine. In the other group, a hose was extended from anus to the left bend of colon (about 8 cm from anus), and DNBS (50 mg/mL, DNBS dissolved in 30% ethanol) was used for enema (0.5 mL/rat) to induce colitis in rats. The normal control group was enema with 30% ethanol in the same way. The enema animals kept their heads down for 15 minutes, then kept the Trendelenburg position until the animals woke up to avoid the reflux of enema fluid.

Figure 4:
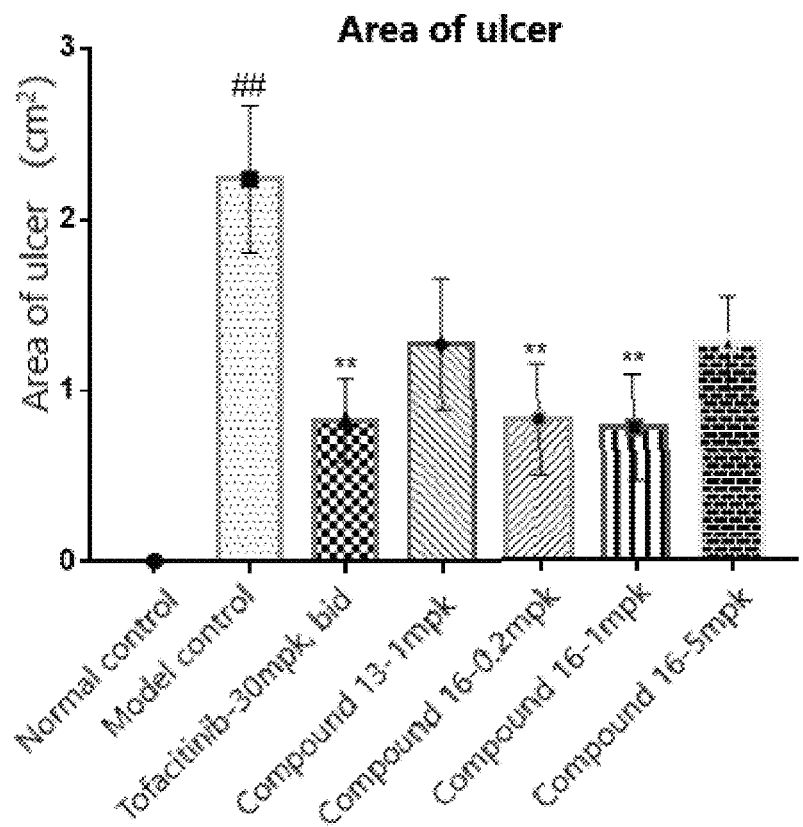
FIG. 4 shows the effects of compounds 16 in a rat colitis model induced by DNBS.

Drug treatment: 4 hours after modeling, animals were given with different concentrations of drugs or 0.5% methylcellulose by gavage, 10 mL/kg, once a day for 7 consecutive days. During the administration period, the changes of animal body weight and fecal traits were observed every day. After administration, the animals were euthanized, colon tissues were collected, colon length, colon weight and ulcer area were measured, and colon injury in rats was evaluated macroscopically, so as to evaluate the therapeutic effect of the tested drugs on DNBS-induced inflammatory colitis model in rats. The experimental results are shown in FIG. 4.

The results show that compound 16 at 0.2 mg/kg and 1 mg/kg can significantly reduce the area of colonic ulcer in animals.

Experimental Embodiment 8: Effect of the Compounds of the Present Disclosure on Experimental Autoimmune Encephalomyelitis (EAE)

Female C57BL/6J mice were immunized with MOG35-55 antigen emulsion. 2 hours after immunization, each animal was injected with 200 ng/100 µL PTX solution intraperitoneally. After 24 hours (the second day), the same dose of PTX solution was injected once again. On the fifth day, the animals in each group began to administer the drug, and each group was given the drug by gavage, with a dosage of 10 mL/kg, once a day for 33 consecutive days (days 5-37). During the experiment, general clinical observation was carried out twice a day, and the weight and EAE clinical scores were measured once a day after administration. The score was divided into five grades: (0. normal mice, no obvious disease; 1. tail weakness or hind limb weakness; 2. tail weakness and hind limb weakness; 3. hemiplegia of hind limbs; 4. complete paralysis of hind limbs; 5, died of EAE or euthanasia in near-death state).

Figure 5:
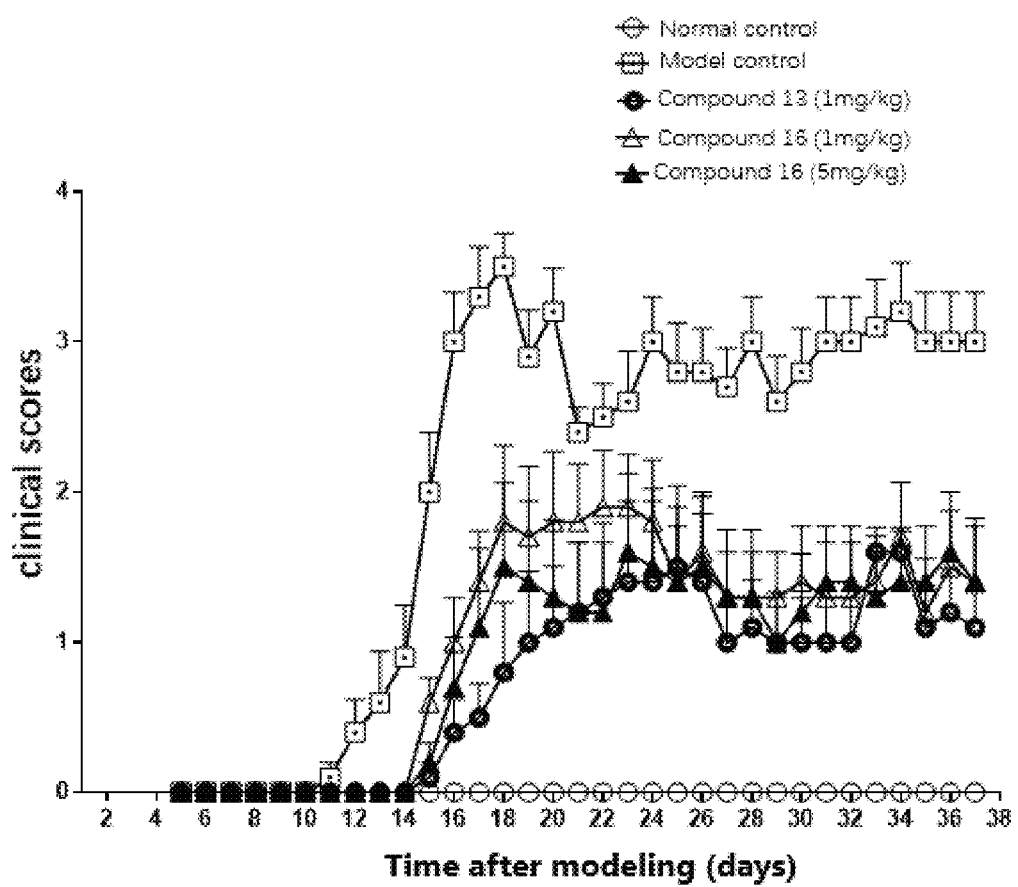
FIG. 5 shows the effects of compounds 13 and 16 on experimental autoimmune encephalomyelitis (EAE).

The results show that compound 13 (1 mg/kg) and compound 16 (1 mg/kg and 5 mg/kg) can significantly reduce the disease symptoms of model animals. The mice administrated with compound 13 (1 mg/kg) show slight symptoms from the 15th day, and then the symptoms are slightly enhanced, which are significantly lower than that of the model control group during the 14th to 21st, 24th and 26th to 37th days. The mice administrated with compound 16 (1 mg/kg and 5 mg/kg) show slight symptoms from the 15th day, and then the symptoms are slightly enhanced, which are significantly lower than that of the model control group during the 24th to 37th day. The experimental results are shown in FIG. 5.

What is claimed is:

1. A compound of formula (I) or a pharmaceutically acceptable salt thereof,

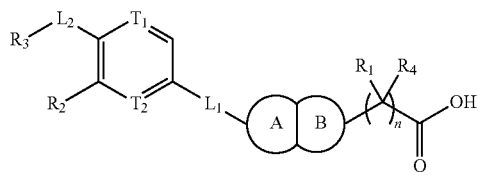

(I)

wherein, n is selected from 1, 2 or 3;

$R_1$ is independently selected from H, $CH_3$, or $CH_2CH_3$;

$R_4$ is independently selected from H, $CH_3$, or $CH_2CH_3$;

$R_2$ is selected from H, halogen, CN or $C_{1-3}$ alkyl, the $C_{1-3}$ alkyl is optionally substituted by one, two or three R;

$R_3$ is $C_{3-7}$ cycloalkyl;

the moiety

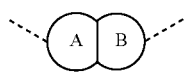

is selected from the group consisting of

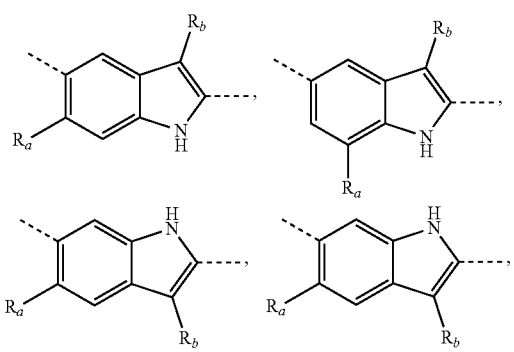

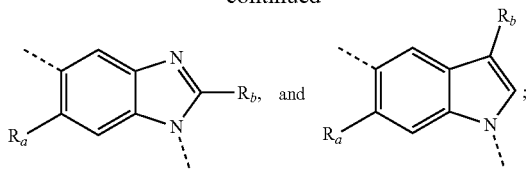

$R_a$ is independently selected from H, halogen, CN or $C_{1-3}$ alkyl, the $C_{1-3}$ alkyl is optionally substituted by one, two or three R;

$R_b$ is selected from H, halogen, CN or $C_{1-3}$ alkyl, the $C_{1-3}$ alkyl is optionally substituted by one, two or three R;

R is independently selected from F, Cl, Br, CN, or $C_{1-3}$ alkyl;

$T_1$ is selected from N or CH;

$T_2$ is selected from N or CH;

$L_1$ is

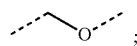

and $L_2$ is selected from single bond, O or S.

2. The compound or the pharmaceutically acceptable salt thereof according to claim 1, wherein, $R_2$ is selected from H, F, Cl, Br, CN, $CH_3$ and $CH_2CH_3$, the $CH_3$ or $CH_2CH_3$ is optionally substituted by one, two or three R;

or, $R_a$ is selected from H, F, Cl, Br, CN, $CH_3$ or $CH_2CH_3$, the $CH_3$ or $CH_2CH_3$ is optionally substituted by one, two or three R.

3. The compound or the pharmaceutically acceptable salt thereof according to claim 2, wherein, $R_2$ is selected from H, F, Cl, Br, CN, $CH_3$, $CH_2CH_3$ or $CF_3$;

or, $R_a$ is selected from H, F, Cl, Br, CN, $CH_3$, $CH_2CH_3$ or $CF_3$;

or, $R_b$ is selected from H, F, Cl, Br, CN, $CH_3$, $CH_2CH_3$ or $CF_3$.

4. The compound or the pharmaceutically acceptable salt thereof according to claim 1, wherein, $R_3$ is selected from

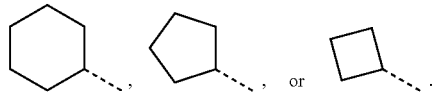

5. The compound or the pharmaceutically acceptable salt thereof according to claim 1, wherein, the moiety

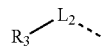

is selected from

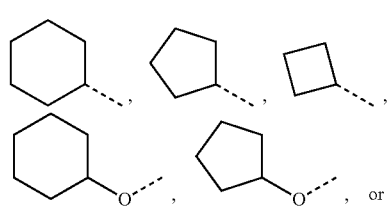

-continued

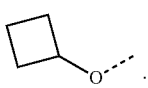

6. The compound or the pharmaceutically acceptable salt thereof according to claim 1, wherein, the moiety

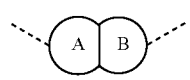

is selected from

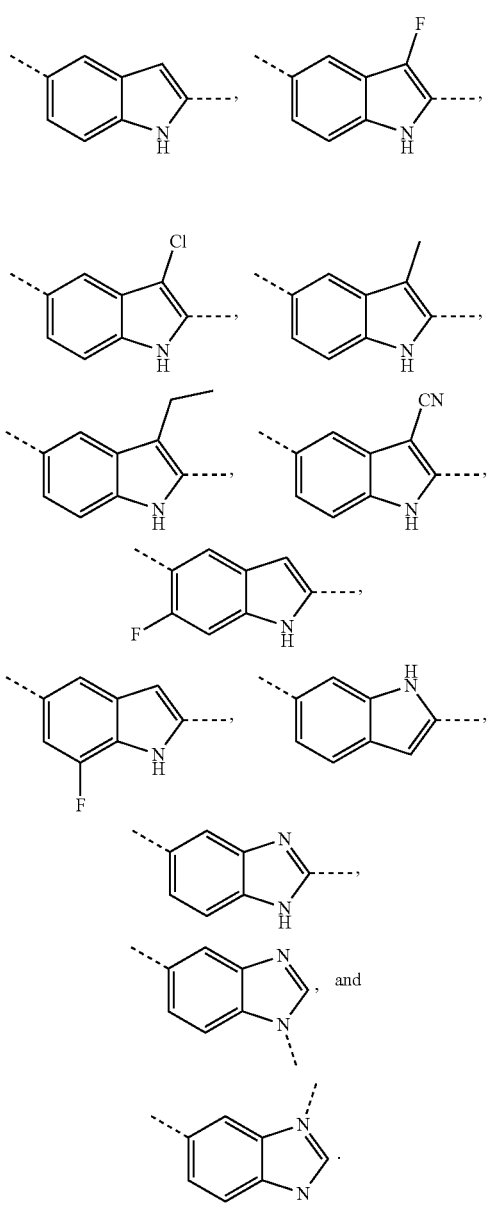

7. The compound or the pharmaceutically acceptable salt thereof according to claim 1, wherein, the moiety

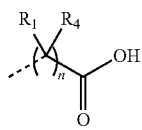

is

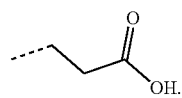

8. The compound or the pharmaceutically acceptable salt thereof according to claim 1, wherein the compound or salt is, (I-1)

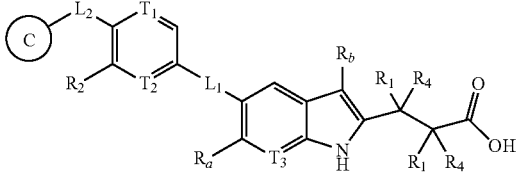

wherein, $T_1$, $T_2$, $L_1$, $L_2$, $R_1$, $R_4$, $R_2$, $R_a$ and $R_b$ are as defined in claim 1;

$T_3$ is selected from N or $C(R_a)$;

ring C is $C_{3-6}$ cycloalkyl.

9. A compound of formula (I-1A) or a pharmaceutically acceptable salt thereof (I-1A)

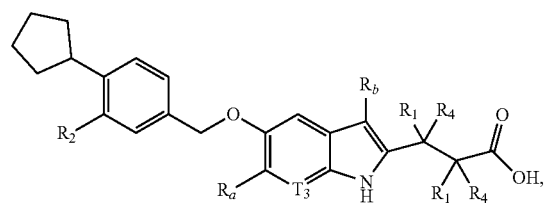

wherein, $T_3$ is selected from N and $C(R_a)$;

$R_a$ is independently selected from H, halogen, CN or $C_{1-3}$ alkyl, the $C_{1-3}$ alkyl is optionally substituted by one, two or three R;

$R_b$ is selected from H, halogen, CN or $C_{1-3}$ alkyl, the $C_{1-3}$ alkyl is optionally substituted by one, two or three R;

$R_1$ is independently selected from H, $CH_3$ or $CH_2CH_3$;

$R_4$ is independently selected from H, $CH_3$ or $CH_2CH_3$;

$R_2$ is selected from H, halogen, CN or $C_{1-3}$ alkyl, the $C_{1-3}$ alkyl is optionally substituted by one, two or three R; and R is independently selected from F, Cl, Br, CN, or $C_{1-3}$ alkyl.

10. A compound of the following formula or a pharmaceutically acceptable salt thereof, 153
-continued
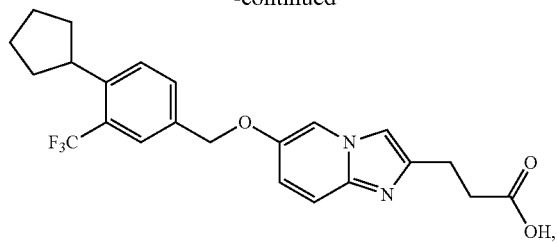
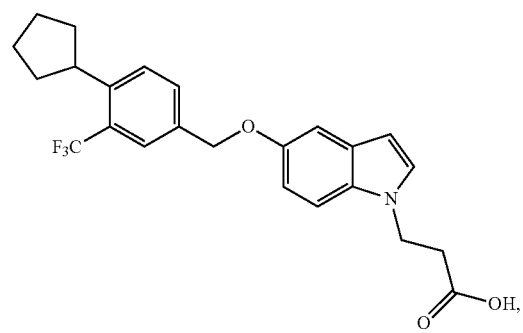
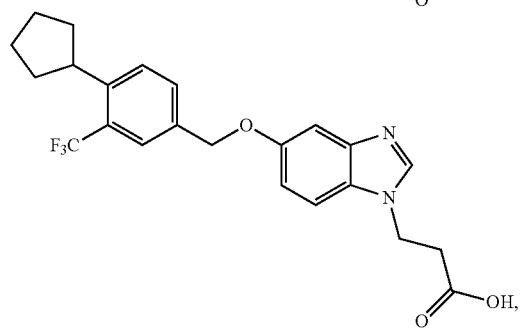
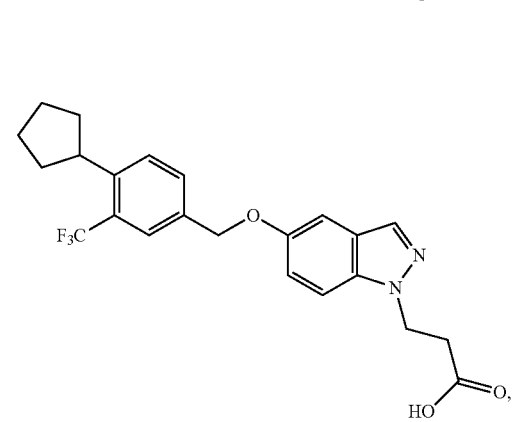
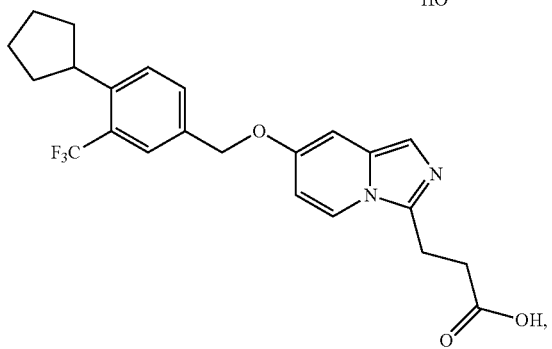
154
-continued
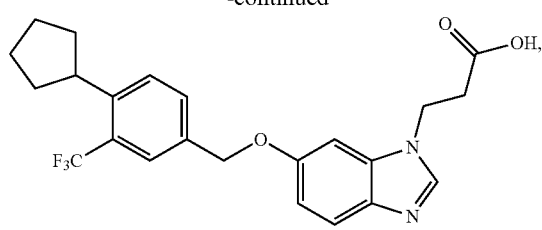
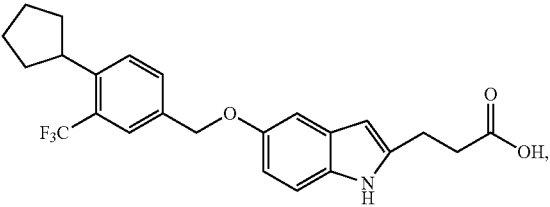
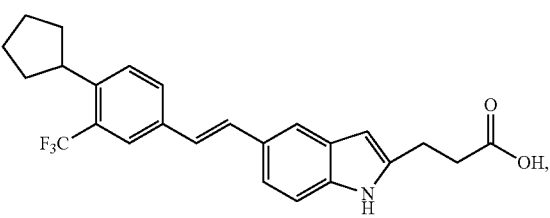
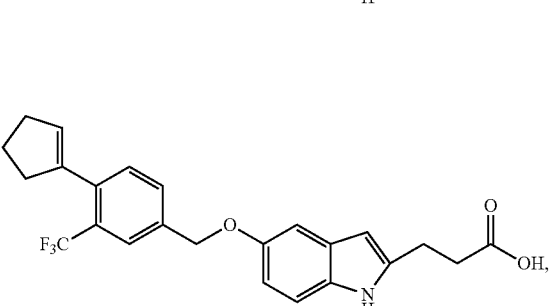
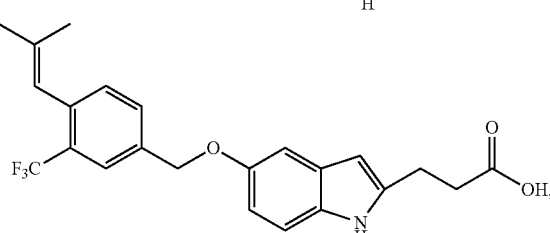
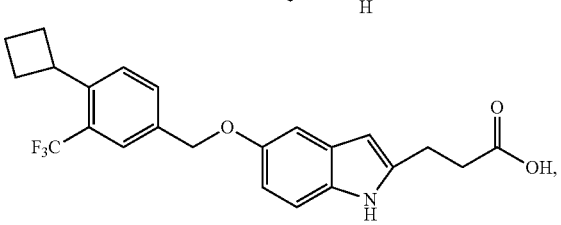
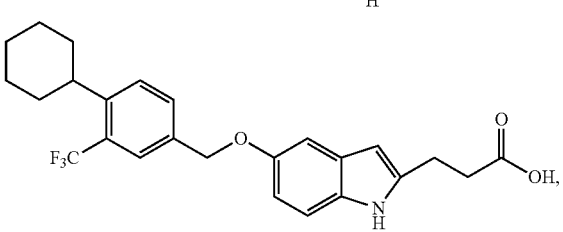

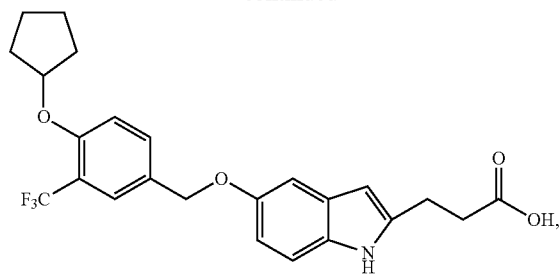
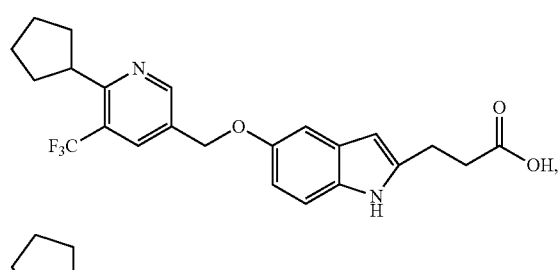
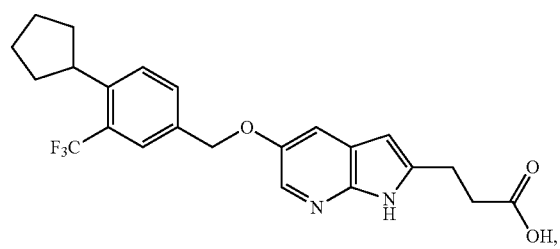
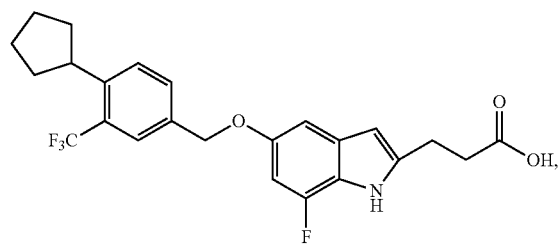
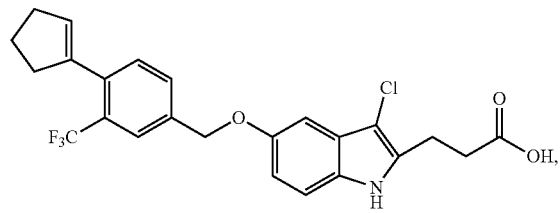
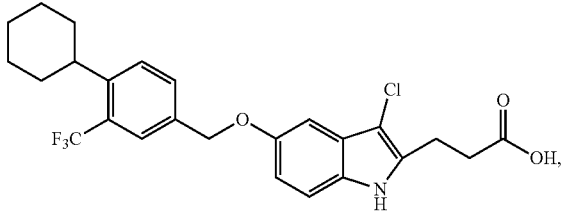
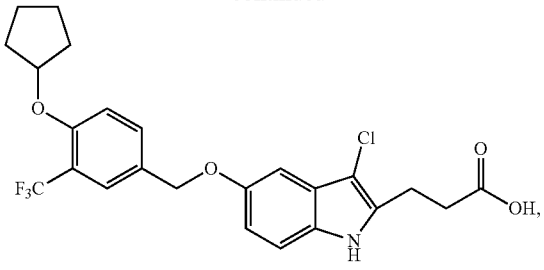
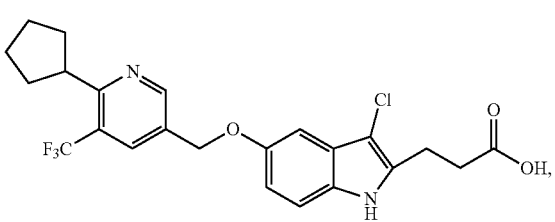
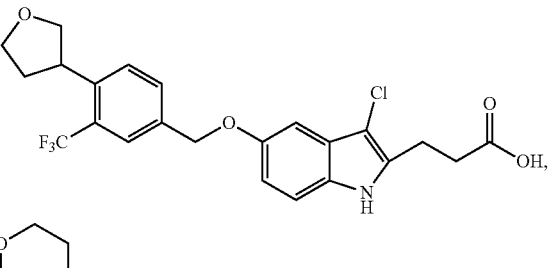
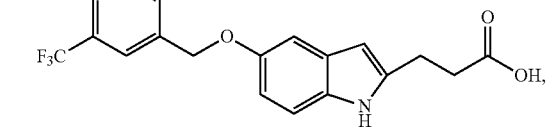
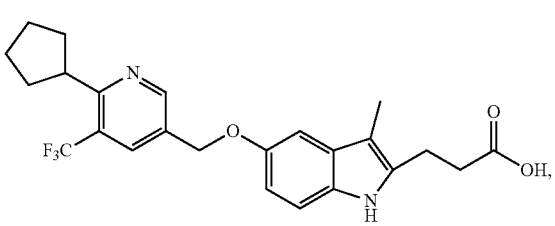
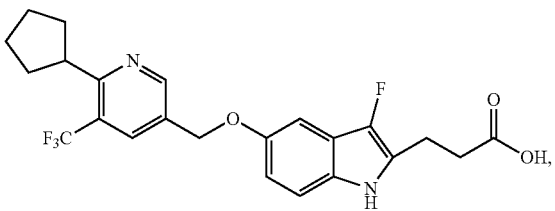

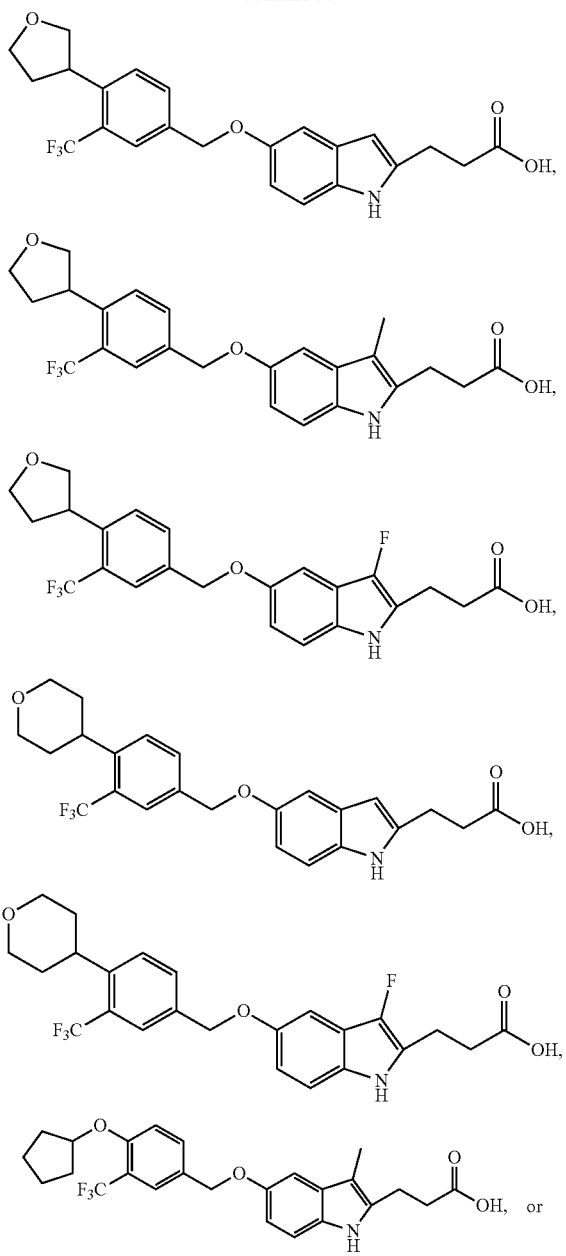

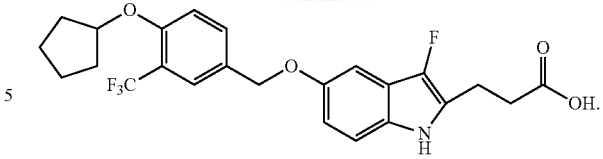

11. A pharmaceutical composition, comprising the compound or the pharmaceutically acceptable salt thereof as defined in claim 1 and one or more pharmaceutically acceptable carriers, diluents or excipients.

12. A method for treating S1P1 receptor-related diseases in a subject in need thereof, comprising administering a therapeutically effective amount of the compound or the pharmaceutically acceptable salt thereof as defined in claim 1 to the subject.

13. The method for treating S1P1 receptor-related diseases according to claim 12, wherein, the S1P1 receptor-related diseases are selected from Ulcerative colitis, Crohn's disease, Multiple sclerosis, Systemic lupus erythematosus, Lupus nephritis, Rheumatoid arthritis, Primary Biliary Cholangitis, Atopic Dermatitis, Intracerebral hemorrhage, Graft versus Host Disease, Psoriasis, Type I diabetes, Acne, microbial infections or microbial diseases or viral infections or viral diseases.

14. A method for treating S1P1 receptor-related diseases in a subject in need thereof, comprising administering a therapeutically effective amount of the pharmaceutical composition as defined in claim 11 to the subject.

15. The method for treating S1P1 receptor-related diseases according to claim 14, wherein, the S1P1 receptor-related diseases are selected from Ulcerative colitis, Crohn's disease, Multiple sclerosis, Systemic lupus erythematosus, Lupus nephritis, Rheumatoid arthritis, Primary Biliary Cholangitis, Atopic Dermatitis, Intracerebral hemorrhage, Graft versus Host Disease, Psoriasis, Type I diabetes, Acne, microbial infections or microbial diseases or viral infections or viral diseases.

16. The compound or the pharmaceutically acceptable salt thereof according to claim 8, wherein, the ring C is selected from

* * * * *